US006197973B1

(12) United States Patent
Zagar et al.

(10) Patent No.: US 6,197,973 B1
(45) Date of Patent: Mar. 6, 2001

(54) SUBSTITUTED 3-PHENYLPYRAZOLES

(75) Inventors: Cyrill Zagar, Ludwigshafen; Gerhard Hamprecht, Weinheim; Markus Menges, Mannheim; Olaf Menke, Altleiningen; Peter Schäfer, Ottersheim; Karl-Otto Westphalen, Speyer; Ulf Misslitz, Neustadt; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/230,838

(22) PCT Filed: Jul. 21, 1997

(86) PCT No.: PCT/EP97/03901

§ 371 Date: Feb. 1, 1999

§ 102(e) Date: Feb. 1, 1999

(87) PCT Pub. No.: WO98/05649

PCT Pub. Date: Feb. 12, 1998

(30) Foreign Application Priority Data

Aug. 1, 1996 (DE) ........................................ 196 31 008

(51) Int. Cl.[7] ........................ C07D 231/14; A01N 43/56

(52) U.S. Cl. .................... 548/336.1; 504/139; 548/337.1

(58) Field of Search ............................ 548/336.1, 337.1; 514/399, 400; 504/139

(56) References Cited

U.S. PATENT DOCUMENTS

| | | | | |
|---|---|---|---|---|
| 4,337,268 | * | 6/1982 | Stetter et al. | 424/285 |
| 4,550,175 | * | 10/1985 | Mixich et al. | 548/336.1 |
| 4,798,845 | * | 1/1989 | Pettman et al. | 514/400 |
| 5,281,571 | | 1/1994 | Woodard et al. | 504/225 |

FOREIGN PATENT DOCUMENTS

| | | | | |
|---|---|---|---|---|
| 0254364 | * | 1/1988 | (EP) | 548/336.1 |
| 443059 | | 8/1991 | (EP) . | |
| 3151367 | | 11/1989 | (JP) . | |
| 92/02509 | | 2/1992 | (WO) . | |
| 92/06962 | | 4/1992 | (WO) . | |
| 95/32188 | | 11/1995 | (WO) . | |
| 95/33728 | | 12/1995 | (WO) . | |
| 96/01254 | | 1/1996 | (WO) . | |
| 96/02518 | | 2/1996 | (WO) . | |
| 96/15115 | | 5/1996 | (WO) . | |
| 96/40643 | | 12/1996 | (WO) . | |

* cited by examiner

*Primary Examiner*—Floyd D. Higel
(74) *Attorney, Agent, or Firm*—Keil & Weinkauf

(57) ABSTRACT

3-phenylpyrazoles of formula I

I

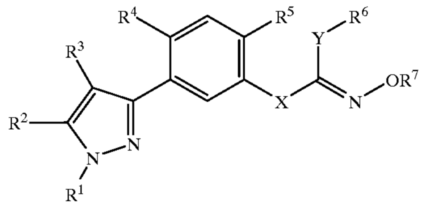

wherein $R^1$ is cyano, alkyl or haloalkyl;

$R^2$ is cyano or is optionally halogenated alkyl, alkoxy, alkylthio, alkylsulfinyl or alkylsulfonyl;

$R^3$ is hydrogen, cyano, halogen, alkyl or haloalkyl;

$R^4$ is hydrogen or halogen;

$R^5$ is cyano, halogen, or is optionally halogenated alkyl or alkoxy;

$R^6$, $R^7$ independently of one another are optionally substituted alkyl, alkenyl, alkynyl, cycloalkyl, heterocyclyl or phenyl, optionally substituted alkylcarbonyl, alkoxycarbonyl, aminocarbonyl, alkylaminocarbonyl, dialkylaminocarbonyl or optionally halogenated alkylsulfonyl;

X is a chemical bond, $-C{\equiv}C-$, $-CH_2-CH(R^8)-$ or $-CH{=}C(R^8)-$, wherein $R^8$ is hydrogen, cyano, nitro, halogen, alkyl or haloalkyl;

Y is oxygen or sulfur;

their preparation and their use for controlling undesirable vegetation.

20 Claims, No Drawings

SUBSTITUTED 3-PHENYLPYRAZOLES

The present invention relates to novel substituted 3-phenylpyrazoles of the formula I

I

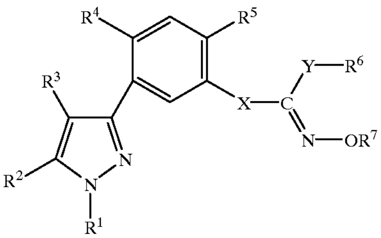

in which the variables have the following meanings:

$R^1$ is $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-haloalkylsulfonyl;

$R^3$ is hydrogen, cyano, halogen, $C_1$–$C_4$-alkyl or $C_1$–$C_4$-haloalkyl;

$R^4$ is hydrogen or halogen;

$R^5$ is cyano, halogen, $C_1$–$C_4$-alkyl, $C_1$–$C_4$-haloalkyl, $C_1$–$C_4$-alkoxy or $C_1$–$C_4$-haloalkoxy;

$R^6$, $R^7$ independently of one another are $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkyloxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkyl-sulfinyl-$C_1$–$C_4$-alkyl, $C_3$–$C_4$o-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, cyano-$C_3$–$C_6$-alkenyl, $C_3$–$C_6$-haloalkyl, $C_3$–$C_6$-alkynyl, cyano-$C_3$–$C_6$-alkynyl, $C_3$–$C_6$-haloalkynyl, ($C_1$–$C_4$-alkyl)-carbonyl, ($C_1$–$C_4$-haloalkyl)carbonyl, ($C_1$–$C_4$-alkoxy)carbonyl, aminocarbonyl, ($C_1$–$C_4$-alkyl)aminocarbonyl, di($C_1$–$C_4$-alkyl)aminocarbonyl, ($C_1$–$C_4$-alkoxy-$C_1$–$C_4$-alkyl)carbonyl, $C_1$–$C_4$-alkylsulfonyl, $C_1$–$C_4$-haloalkylsulfonyl, ($C_1$–$C_4$-alkyl)carbonyl-$C_1$–$C_4$-alkyl, ($C_1$–$C_4$-haloalkyl)carbonyl-$C_1$–$C_4$-alkyl, ($C_3$–$C_8$-cycloalkyl)carbonyl-$C_1$–$C_4$-alkyl, ($C_1$–$C_4$-alkoxy)imino-$C_1$–$C_4$-alkyl, ($C_3$–$C_4$-alkenyloxy) imino-$C_1$–$C_4$-alkyl, hydroxycarbonyl-$C_1$–$C_4$-alkyl, ($C_1$–$C_4$-alkoxy)carbonyl-$C_1$–$C_4$-alkyl which can have a ($C_1$–$C_4$-alkoxy)imino group attached to it, ($C_1$–$C_4$-haloalkoxy) carbonyl-$C_1$–$C_4$-alkyl, ($C_1$–$C_4$-alkylthio) carbonyl-$C_1$–$C_4$-alkyl, aminocarbonyl-$C_1$–$C_4$-alkyl, ($C_1$–$C_4$-alkylamino)carbonyl-$C_1$–$C_4$-alkyl, di($C_1$–$C_4$-alkylamino)carbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- to 7-membered heterocyclyl or heterocyclyl-$C_1$–$C_4$-alkyl, it being possible, if desired, for all cycloalkyl rings and heterocycles to contain a carbonyl or thiocarbonyl ring member, and it being possible for each cycloalkyl, phenyl or heterocyclyl ring to be unsubstituted or to have attached to it one to four substituents, in each case selected from the group consisting of cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino;

X is a chemical bond, a 1,2-ethynediyl group or a group *—$CH_2$—$CH(R^8)$— or *—$CH{=}C(R^8)$— which is bonded to the phenyl ring via the bond characterized with an asterisk, where $R^8$ is hydrogen, cyano, nitro, halogen, $C_1$–$C_4$-alkyl or $C_1$–$C_4$-haloalkyl;

Y is oxygen or sulfur;

and to the agriculturally useful salts of the compounds I.

Furthermore, the invention relates to the use of these compounds I as herbicides, herbicidal compositions which comprise the compounds I as active substances, processes for the preparation of the compounds I and of herbicidal compositions using the compounds I, and methods of controlling undesirable vegetation using the compounds I.

Herbicidally active 3-phenylpyrazoles have already been described in EP-A 443 059, WO 92/06 962, JP-A 03/151 367, WO 92/02 509, WO 96/15 115, WO 95/32 188, WO 95/33 728, WO 96/01 254, WO 96/02518 and WO 96 40 643.

However, the herbicidal properties of the known herbicides are not always entirely satisfactory with regard to the harmful plants.

It is an object of the present invention to provide novel herbicidally active compounds with which undesirable plants can be controlled better than was possible to date.

We have found that this object is achieved by the present substituted 3-phenylpyrazoles of the formula I and by their herbicidal activity.

We have furthermore found herbicidal compositions which comprise the compounds I and have a very good herbicidal activity. Moreover, we have found processes for the preparation of these compositions and methods of controlling undesirable vegetation using the compounds I.

Depending on the substitution pattern, the compounds of the formula I can contain one or more chiral centers, in which case they are present as enantiomer or diastereomer mixtures. Depending on the meaning of X, E/Z isomers are also possible. The invention relates both to the pure enantiomers or diastereomers and to mixtures of these.

Suitable amongst the agriculturally useful salts are mainly salts of those cations or the acid addition salts of those acids whose cations, or anions, respectively, do not adversely affect the herbicidal activity of the compounds I. Thus, especially suitable cations are the ions of the alkali metals, preferably sodium and potassium, of the alkaline earth metals, preferably calcium, magnesium and barium, and of the transition metals, preferably manganese, copper, zinc and iron, and the ammonium ion which, if desired, can have attached to it one to four $C_1$–$C_4$-alkyl substituents and/or a phenyl or benzyl substituent, preferably diisopropylammonium, tetramethylammonium, tetrabutylammonium, trimethylbenzylammonium, furthermore phosphonium ions, sulfonium ions, preferably tri ($C_1$–$C_4$-alkyl)sulfonium and sulfoxonium ions, preferably tri($C_1$–$C_4$-alkyl)sulfoxonium.

Anions of useful acid addition salts are principally chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$–$C_4$-alkanoic acids, preferably formate, acetate, propionate and butyrate.

The organic moieties mentioned for the substituents $R^1$ to $R^3$ and $R^5$ to $R^8$ or as radicals on cycloalkyl, phenyl or heterocyclyl rings are collective terms for individual enumerations of the individual group members. All carbon chains, ie. all alkyl, haloalkyl, alkoxy, haloalkoxy, alkylthio, haloalkylthio, alkylsulfinyl, haloalkylsulfinyl, alkylsulfonyl, haloalkylsulfonyl, cyanoalkyl, hydroxyalkyl, hydroxycarbonylalkyl, aminoalkyl, aminocarbonylalkyl, phenylalkyl, heterocyclylalkyl, alkylcarbonyl, haloalkylcarbonyl, alkylcarbonyloxy, haloalkylcarbonyloxy, alkoxycarbonyl, haloalkoxycarbonyl, alkylthiocarbonyl, alkylamino, alkenyl, haloalkenyl, cyanoalkenyl, alkynyl, haloalkynyl, cyanoalkynyl, alkenyloxy, alkynyloxy, alkenylthio, alkynylthio, alkenylsulfinyl, alkynylsulfinyl, alkenylsulfonyl, and alkynylsulfonyl moieties may be straight-chained or branched. Halogenated substituents preferably have attached to them one to five identical or different halogen atoms.

The meaning of halogen is in each case fluorine, chlorine, bromine or iodine, in particular fluorine or chlorine.

Other examples are:

$C_1$–$C_4$-alkyl: $CH_3$, $C_2H_5$, n-propyl, $CH(CH_3)_2$, n-butyl, 1-methyl-propyl, $CH_2$—$CH(CH_3)_2$ or $C(CH_3)_2$ or $C(CH_3)_3$, in particular $CH_3$ or $C_2H_5$;

$C_1$–$C_6$-alkyl: $C_1$–$C_4$-alkyl as mentioned above, or, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, in particular $CH_3$, $C_2H_5$, n-propyl, $CH(CH_3)_2$, n-butyl, $C(CH_3)_3$, n-pentyl or n-hexyl;

$C_1$–$C_4$: a $C_1$–$C_4$-alkyl radical as mentioned above which is partially or fully substituted by fluorine, chlorine, bromine and/or iodine, ie. $CH_2Cl$, $CH(Cl)_2$, $C(Cl)_3$, $CH_2F$, $CHF_2$, $CF_3$ CHFCl, $CF(Cl)_2$, $CF_2Cl$, $Cf_2Br$, 1-fluoroethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chlor-2,2-difluoroethyl, 2,2-dichloro-2-fluoroethyl, 1,2-dichloroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl, in particular chloromethyl, fluoromethyl, difluoromethyl, brifluoromethyl, 2-fluoroethyl, 2-chloroethyl, 1,2-dichloroethyl, 2,2,2-trifluoroethyl or pentafluoroethyl;

$C_1$–$C_6$-haloalkyl: $C_1$–$C_6$-alkyl as mentioned above which is partially or fully substituted by fluorine, chlorine and/or bromine, ie. one of the abovementioned $C_1$–$C_4$-haloalkyl radicals or 5-fluoropentyl, 5-chloropentyl, 5-bromopentyl, 5-iodopentyl, 5,5,5-trichloropentyl, undecafluoropentyl, 6-fluorohexyl, 6-chlorohexyl, 6-bromohexyl, 6-iodohexyl, 6,6,6-trichlorohexyl or dodecafluorohexyl, in particular fluoromethyl, difluoromethyl, trifluoromethyl, chloromethyl, 2-fluoroethyl, 2-chloroethyl or 2,2,2-trifluoroethyl;

$C_3$–$C_8$-cycloalkyl: cyclopropyl, cyclobutyl, cyclopentyl, cyclohexyl, cycloheptyl or cyclooctyl, in particular cyclopentyl or cyclohexyl;

$C_3$–$C_8$-cycloalkyl, which contains a carbonyl or thiocarbonyl ring member: for example cyclobutanon-2-yl, cyclobutanon-3-yl, cyclopentanon-2-yl, cyclopentanon-3-yl, cyclohexanon-2-yl, cyclohexanon-4-yl, cycloheptanon-2-yl, cyclooctanon-2yl, cyclobutanthion-2-yl, cyclobutanthion-2yl, cyclobutanthion-3-yl, cyclopentanthion-2-yl, cyclopentanthion-3-yl, cyclohexanthion-2-yl, cyclohexanthion-4-yl, cycloheptanthion-2-yl or cyclooctanthion-2-yl;

$C_1$–$C_4$-alkoxy: $OCH_3$, $OC_2H_5$, n-propoxy, $OCH(CH_3)_2$, n-butoxy, 1-methylpropoxy, 2-methylpropoxy or $OC(CH_3)_3$, in particular $OCH_3$, $OC_2H_5$, $OCH(CH_3)_2$ or $OC\ (CH_3)_3$;

$C_1$–$C_4$-haloalkoxy: $C_1$–$C_4$-alkoxy as mentioned above which is partially or fully substituted by fluorine, chlorine, bromine and/or iodine, ie. $OCH_2Cl$, $OCH(Cl)_2$, $OC(Cl)_3$, $OCH_2F$, $OCHF_2$, $OCF_3$, OCHFCl, $OCF(Cl)_2$, $OCF_2Cl$, $OCF_2Br$, 1-fluoroethoxy, 2-fluoroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 1,2-dichloroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or non-afluorobutoxy, in particular chloromethoxy, fluoromethoxy, difluoromethoxy, trifuloromethoxy, 2-fluoroethoxy, 2-chloroethoxy, 1,2-dichloroethoxy, 2,2,2-trifluoroethoxy or pentafluoroethoxy;

$C_1$–$C_4$-alkylthio: $SCH_3$, $SC_2H_5$, n-propylthio, $SCH(CH_3)_2$, n-butylthio, 1-methylpropylthio, 2-methylpropylthio or $SC(CH_3)_3$, in particular $SCH_3$ or $SC_2H_5$;

$C_1$–$C_4$-haloalkylthio: $C_1$–$C_4$-alkylthio as mentioned above which is partially or fully substituted by fluorine, chlorine, bromine and/or iodine, ie. $SCH_2Cl$, $SCH(Cl)_2$, $SC(Cl)_3$, $SCH_2F$, $SCHF_2$, $SCF_3$, SCHFCl, $SCF(Cl)_2$, $SCF_2Cl$, $SCF_2Br$, 1-fluoroethylthio, 2-fluoroethylthio, 2-chloroethylthio, 2-bromoethylthio, 2-iodoethylthio, 2,2-difluoroethylthio, 2,2,2-trifluoroethylthio, 1,2-dichloroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutoxy, in particular chloromethylthio, fluoromethylthio, difluoromethylthio, trifluoromethylthio, 2-fluoroethylthio, 2-chloroethylthio, 1,2-dichloroethylthio, 2,2,2-trifluoroethylthio or pentafluoroethylthio;

$C_1$–$C_4$-alkylsulfinyl: $SOCH_3$, $SOC_2H_5$, n-propylsulfinyl, $SOCH(CH_3)_2$, n-butylsulfinyl, 1-methylpropylsulfinyl, 2-methylpropylsulfinyl or $SOC(CH_3)_3$, in particular $SOCH_3$ or $SOC_2H_5$;

$C_1$–$C_4$-haloalkylsulfinyl: a $C_1$–$C_4$-alkylsulfinyl radical as mentioned above which is partially or fully substituted by fluorine, chlorine, bromine and/or iodine, ie. chloromethylsulfinyl, dichloromethylsulfinyl, trichloromethylsulfinyl, fluoromethylsulfinyl, difluoromethylsulfinyl, trifluoromethylsulfinyl, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 1,2-dichloroethylsulfinyl, 2,2,2-trichloroethylsulfinyl, pentafluoroethylsulfinyl, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromoethyl)-2-bromoethylsulfinyl, 4-fluorobutylsulfinyl, 4-chlorobutylsulfinyl, 4-bromobutylsulfinyl or nonafluorobutylsulfinyl, in particular chloromethylsulfinyl, fluoromethylsulfinyl, difluoromethylsulfinyl, trifluoromethylsulfinyl, 2-fluoroethylsulfinyl, 2-chloroethylsulfinyl, 1,2-dichloroethylsulfinyl, 2,2,2-trifluoroethylsulfinyl or pentafluoroethylsulfinyl;

$C_1$–$C_4$-alkylsulfonyl: $SO_2CH_3$, $SO_2C_2H_5$, n-propylsulfonyl, $SO_2CH(CH_3)_2$, n-butylsulfonyl, 1-methylpropylsulfonyl, 2-methylpropylsulfonyl or $SO_2C(CH_3)_3$, in particular $SO_2CH_3$ or $SO_2C_2H_5$;

$C_1$–$C_4$-haloalkylsulfonyl: a $C_1$–$C_4$-alkylsulfonyl radical as mentioned above which is partially or fully substituted by fluorine, chlorine, bromine and/or iodine, ie. chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 1,2-dichloroethylsulfonyl, 2,2,2-trichloroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromoethyl)-2-bromoethylsulfonyl, 4-fluorobutylsulfonyl, 4-chlorobutylsulfonyl, 4-bromobutylsulfonyl, or nonafluorobutylsulfonyl, in particular chloromethylsulfonyl, fluoromethylsulfonyl, difluoromethylsulfonyl, trifluoromethylsulfonyl, 2-fluoroethylsulfonyl, 2-chloroethylsulfonyl, 1,2-dichloroethylsulfonyl, 2,2,2-trifluoroethylsulfonyl or pentafluoroethylsulfonyl;

cyano-$C_1$–$C_4$-alkyl: for example $CH_2CN$, 1-cyanoethyl, 2-cyanoethyl, 1-cyanoprop-1-yl, 2-cyanprop-1-yl, 3-cyanoprop-1-yl, 1-cyanobut-1-yl, 2-cyanobut-1-yl, 3-cyanobut-1-yl, 4-cyanobut-1-yl, 1-cyanobut-2-yl, 2-cyanobut-2-yl, 3-cyanobut-2-yl, 4-cyanobut-2-yl, 1-($CH_2CN$)-eth-1-yl, 1-($CH_2CN$)-1-($CH_3$)-eth-1-yl or 1-($CH_2CN$)-prop-1-yl, in particular $CH_2CN$ or 2-cyanoethyl;

hydroxy-$C_1$–$C_4$-alkyl: for example $CH_2OH$, 1-hydroxyethyl, 2-hydroxyethyl, 1-hydroxyprop-1-yl, 2-hydroxyprop-1-yl, 3-hydroxyprop-1-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 3-hydroxybut-2-yl, 4-hydroxybut-2-yl, 1-($CH_2OH$)eth-1-yl, 1-($CH_2OH$)-1-($CH_3$)-eth-1-yl or 1-($CH_2OH$)prop-1-yl, in particular $CH_2OH$ or 2-hydroxyethyl;

hydroxycarbonyl-$C_1$–$C_4$-alkyl: for example $CH_2COOH$, 1-(COOH)ethyl, 2-(COOH)ethyl, 1-(COOH)prop-1-yl, 2-(COOH)prop-1-yl, 3-(COOH)prop-1-yl, 1-(COOH)but-1-yl, 2-(COOH)but-1-yl, 3-(COOH)but-1-yl, 4-(COOH)but-1-yl, 1-(COOH)but-2-yl, 2-(COOH)but-2-yl, 3-(COOH)but-2-yl, 4-(COOH)but-2-yl, 1-($CH_2COOH$)eth-1-yl, 1-($CH_2COOH$)-1-($CH_3$)-eth-1-yl or 1-($CH_2COOH$)prop-1-yl, in particular $CH_2$–COOH or 2-hydroxycarbonylethyl;

amino-$C_1$–$C_4$-alkyl: for example $CH_2NH_2$, 1-aminoethyl, 2-aminoethyl, 1-aminoprop-1-yl, 2-aminoprop-1-yl, 3-aminoprop-1-yl, 1-aminobut-1-yl, 2-aminobut-1-yl, 3-aminobut-1-yl, 4-aminobut-1-yl, 1-aminobut-2-yl, 2-aminobut-2-yl, 3-aminobut-2-yl, 4-aminobut-2-yl, 1($CH_2NH_2$)eth-1-yl, 1-($CH_2NH_2$)-1-($CH_3$)-eth-1-yl or 1-($CH_2NH_2$)prop-1-yl, in particular $CH_2NH_2$ or 2-aminoethyl;

aminocarbonyl-$C_1$–$C_4$-alkyl: for example $CH_2CONH_2$, 1-($CONH_2$)ethyl, 2-($CONH_2$)ethyl, 1-($CONH_2$)prop-1-yl, 2-($CONH_2$)prop-1-yl, 3-($CONH_2$)prop-1-yl, 1-($CONH_2$)but-1-yl, 2-($CONH_2$)but-1-yl, 3-($CONH_2$)but-1-yl, 4-($CONH_2$)but-1-yl, 1-($CONH_2$)but-2-yl, 2-($CONH_2$)but-2-yl, 3-($CONH_2$)but-2-yl, 4-($CONH_2$)but-2-yl, 1-($CH_2CONH_2$)eth-1-yl, 1-($CH_2CONH_2$)-1-($CH_3$)-eth-1-yl or 1-($CH_2CONH_2$)prop-1-yl, in particular $CH_2CONH_2$ or 2-aminocarbonylethyl;

phenyl-$C_1$–$C_4$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)eth-1-yl, 1-(phenylmethyl)-1-(methyl)eth-1-yl or 1-(phenylmethyl)prop-1-yl, in particular benzyl or 2-phenylethyl;

$C_3$–$C_8$-cycloalkyl-$C_1$–$C_4$-alkyl: cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropylbut-1-yl, 4-cyclopropylbut-1-yl, 1-cyclopropylbut-2-yl, 2-cyclopropylbut-2-yl, 3-cyclopropylbut-2-yl, 4-cyclopropylbut-2-yl, 1-(cyclopropylmethyl)eth-1-yl, 1-(cyclopropylmethyl)-1-($CH_3$)eth-1-yl, 1-(cyclopropylmethyl)prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-($CH_3$)eth-1-yl, 1-(cyclobutylmethyl)prop-1-yl, cyclopentylmethyl, 1-cyclopentyl-ethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 4-cyclopentylbut-2-yl, 1-(cyclopentylmethyl)eth-1-yl, 1-(cyclopentylmethyl)-1-($CH_3$)eth-1-yl, 1-(cyclopentylmethyl)prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexylbut-1-yl, 4-cyclohexylbut-1-yl, 1-cyclohexylbut-2-yl, 2-cyclohexylbut-2-yl, 3-cyclohexylbut-2-yl, 4-cyclohexylbut-2-yl, 1-(cyclohexylmethyl)eth-1-yl, 1-(cyclohexylmethyl)-1-($CH_3$)eth-1-yl, 1-(cyclohexylmethyl)prop-1-yl, cycloheptylmethyl, 1-cycloheptyl-ethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 4-cycloheptylbut-2-yl, 1-(cycloheptylmethyl)eth-1-yl, 1-(cycloheptylmethyl)-1-($CH_3$) eth-1-yl, 1-(cycloheptylmethyl) prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 4-cyclooctylbut-2-yl, 1-(cyclooctylmethyl)eth-1-yl, 1-(cyclooctylmethyl)-1-($CH_3$)eth-1-yl or 1-(cyclooctylmethyl)prop-1-yl, in particular $C_3$–$C_6$-cycloalkylmethyl;

$C_3$–$C_8$-cycloalkyl-$C_1$–$C_4$-alkyl, which contains a carbonyl or thiocarbonyl ring member: for example cyclobutanon-2-ylmethyl, cyclobutanon-3-ylmethyl, cyclopentanon-2-ylmethyl, cyclopentanon-3-ylmethyl, cyclohexanon-2-ylmethyl, cyclohexanon-4-ylmethyl, cycloheptanon-2-ylmethyl, cyclooctanon-2-ylmethyl, cyclobutanethion-2-ylmethyl, cyclobutanethion-3-ylmethyl, cyclopentanethion-2-ylmethyl, cyclopentanethion-3-ylmethyl, cyclohexanethion-2-ylmethyl, cyclohexanethion-4-ylmethyl, cycloheptanethion-2-ylmethyl, cyclooctanethion-2-ylmethyl, 1-(cyclobutanon-2-yl)ethyl, 1-(cyclobutanon-3-yl)ethyl, 1-(cyclopentanon-2-yl)ethyl, 1-(cyclopentanon-3-yl)ethyl, 1-(cyclohexanon-2-yl)ethyl, 1-(cyclohexanon-4-yl)ethyl, 1-(cycloheptanon-2-yl)ethyl, 1-(cyclooctanon-2-yl)ethyl, 1-(cyclobutanethion-2-yl)ethyl, 1-(cyclobutanethion-3-yl)ethyl, 1-(cyclopentanethion-2-yl)ethyl, 1-(cyclopentanethion-3-yl)ethyl, 1-(cyclohexanethion-2-yl)ethyl, 1-(cyclohexanethion-4-yl)ethyl, 1-(cycloheptanethion-2-yl)ethyl, 1-(cyclooctanethion-2-yl)ethyl, 2-(cyclobutanon-2-yl)ethyl, 2-(cyclobutanon-3-yl)ethyl, 2-(cyclopentanon-2-yl)ethyl, 2-(cyclopentanon-3-yl)ethyl, 2-(cyclohexanon-2-yl)ethyl, 2-(cyclohexanon-4-yl)ethyl, 2-(cycloheptanon-2-yl)ethyl, 2-(cyclooctanon-2-yl)ethyl, 2-(cyclobutanethion-2-yl)ethyl, 2-(cyclobutanethion-3-yl)ethyl, 2-(cyclopentanethion-2-yl)ethyl, 2-(cyclopentanethion-3-yl)ethyl, 2-(cyclohexanethion-2-yl)ethyl, 2-(cyclohexanethion-4-yl)ethyl, 2-(cycloheptanethion-2-yl)ethyl, 2-(cyclooctanethion-2-yl)ethyl, 3-(cyclobutanon-2-yl)propyl, 3-(cyclobutanon-3-yl)propyl, 3-(cyclopentanon-2-yl)propyl, 3-(cyclopentanon-3-yl)propyl, 3-(cyclohexanon-2-yl)propyl, 3-(cyclohexanon-4-yl)propyl, 3-(cycloheptanon-2-yl)propyl, 3-(cyclooctanon-2-yl)propyl, 3-(cyclobutanethion-2-yl)propyl, 3-(cyclobutanethion-3-yl)propyl, 3-(cyclopentanethion-2-yl)propyl, 3-(cyclopentanethion-3-yl)propyl, 3-(cyclohexanethion-2-yl)propyl, 3-(cyclohexanethion-4-yl)propyl, 3-(cycloheptanethion-2-yl)propyl, 3-(cyclooctanethion-2-yl)propyl, 4-(cyclobutanon-2-yl)butyl, 4-(cyclobutanon-3-yl)butyl, 4-(cyclopentanon-2-yl)butyl, 4-(cyclopentanon-3-yl)butyl, 4-(cyclohexanon-2-yl)butyl, 4-(cyclohexanon-4-yl)butyl, 4-(cycloheptanon-2-yl)butyl, 4-(cyclooctanon-2-yl)butyl, 4-(cyclobutanethion-2-yl)butyl, 4-(cyclobutanethion-3-yl)butyl, 4-(cyclopentanethion-2-yl)butyl, 4-(cyclopentanethion-3-yl)butyl, 4-(cyclohexanethion-2-yl)butyl, 4-(cyclohexanethion-4-yl)butyl, 4-(cycloheptanethion-2-yl)butyl or 4-(cyclooctanethion-2-yl)butyl;

heterocyclyl-$C_1$–$C_4$-alkyl: heterocyclylmethyl, 1-(heterocyclyl)ethyl, 2-(heterocyclyl)ethyl, 1-(heterocyclyl)prop-1-yl, 2-(heterocyclyl)prop-1-yl, 3-(heterocyclyl)prop-1-yl, 1-(heterocyclyl)but-1-yl, 2-(heterocyclyl)but-1-yl, 3-(heterocyclyl)but-1-yl, 4-(heterocyclyl)but-1-yl, 1-(heterocyclyl)but-2-yl, 2-(heterocyclyl)but-2-yl, 3-(heterocyclyl)but-2-yl, 4-(heterocyclyl)but-2-yl, 1-(heterocyclylmethyl)eth-1-yl, 1-(heterocyclylmethyl)-1-($CH_3$)eth-1-yl or 1-(heterocyclylmethyl)prop-1-yl, in particular heterocyclylmethyl or 2-(heterocyclyl)ethyl;

$C_1$–$C_4$-alkoxy-$C_1$–$C_4$-alkyl and the alkoxyalkyl moiety of ($C_1$–$C_4$-alkoxy-$C_1C_4$-alkyl)carbonyl: $C_1$–$C_4$-alkyl which is substituted by $C_1$–$C_4$-alkoxy as mentioned above, i.e. $CH_2OCH_3$, $CH_2OC_2H_5$, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-($OCH_3$)propyl, 2-($OC_2H_5$)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1- dimethylethoxy)propyl, 3-($OCH_3$)propyl, 3-($OC_2H_5$) propyl, 3-(n-propoxy)propyl, 3-(1-methylethoxy) propyl, 3-(n-butoxy)propyl, 3-(1-methylpropoxy) propyl, 3-(2-methylpropoxy)propyl, 3-(1,1-dimethylethoxy)propyl, 2-($OCH_3$)butyl, 2-($OC_2H_5$) butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-($OCH_3$)butyl, 3-($OC_2H_5$)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1, 1-dimethylethoxy)butyl, 4-($OCH_3$)butyl, 4-($OC_2H_5$) butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

($C_1$–$C_4$-alkoxy)imino-$C_1$–$C_4$-alkyl: $C_1$–$C_4$-alkyl which is substituted by $C_1$–$C_4$-alkoxyimino, such as methoxyimino, ethoxyimino, n-propoxyimino, 1-methylethoxyimino, n-butoxyimino, 1-methylpropoxyimino, 2-methylpropoxyimino or 1,1-dimethylethoxyimino, in particular methoxyimino or ethoxyimino, i.e. 2-(methoxyimino)ethyl, 2-(ethoxyimino)ethyl, 2-(n-propoxyimino)ethyl, 2-(1-methylethoxyimino)ethyl, 2-(n-butoxyimino)ethyl, 2-(1-methylpropoxyimino)ethyl, 2-(2-methylpropoxyimino)ethyl, 2-(1,1-dimethylethoxyimino)ethyl, 2-(methoxyimino)propyl, 2-(ethoxyimino)propyl, 2-(n-propoxyimino)propyl, 2-(1-methylethoxyimino)propyl, 2-(n-butoxyimino) propyl, 2-(1-methylpropoxyimino)propyl, 2-(2-methylpropoxyimino)propyl, 2-(1,1-dimethylethoxyimino)propyl, 3-(methoxyimino) propyl, 3-(ethoxyimino)propyl, 3-(n-propoxyimino) propyl, 3-(1-methylethoxyimino)propyl, 3-(n-butoxyimino)propyl, 3-(1-methylpropoxyimino) propyl, 3-(2-methylpropoxyimino)propyl, 3-(1,1-dimethylethoxyimino)propyl, 2-(methoxyimino)butyl, 2-(ethoxyimino)butyl, 2-(n-propoxyimino)butyl, 2-(1-methylethoxyimino)butyl, 2-(n-butoxyimino)butyl, 2-(1-methylpropoxyimino)butyl, 2-(2-methylpropoxyimino)butyl, 2-(1,1-dimethylethoxyimino)butyl, 3-(methoxyimino)butyl, 3-(ethoxyimino)butyl, 3-(n-propoxyimino)butyl, 3-(1-methylethoxyimino)butyl, 3-(n-butoxyimino)butyl, 3-(1-methylpropoxyimino)butyl, 3-(2-methylpropoxyimino)butyl, 3-(1,1-dimethylethoxyimino)butyl, 4-(methoxy)butyl, 4-(ethoxyimino)butyl, 4-(n-propoxyimino)butyl, 4-(1-methylethoxyimino)butyl, 4-(n-butoxyimino)butyl, 4-(1-methylpropoxyimino)butyl, 4-(2-methylpropoxyimino)butyl or 4-(1,1-dimethylethoxyimino)butyl, in particular 2-(methoxyimino)ethyl or 2-(ethoxyimino)ethyl;

$C_1$–$C_4$-haloalkoxy-$C_1$–$C_4$-alkyl: $C_1$–$C_4$-alkyl which is substituted by $C_1$–$C_4$-haloalkoxy as mentioned above, e.g. 2-difluoromethoxy)ethyl, 2-(trifluoromethoxy) ethyl or 2-(pentafluoroethoxy)ethyl;

$C_3$–$C_8$-cycloalkyloxy-$C_1$–$C_4$-alkyl: cyclopropyloxymethyl, 1-cyclopropyloxyethyl, 2-cyclopropyloxyethyl, 1-cyclopropyloxyprop-1-yl, 2-cyclopropyloxyprop-1-yl, 3-cyclopropyloxyprop-1-yl, 1-cyclopropyloxybut-1-yl, 2-cyclopropyloxybut-1-yl, 3-cyclopropyloxybut-1-yl, 4-cyclopropyloxybut-1-yl, 1-cyclopropyloxybut-2-yl, 2-cyclopropyloxybut-2-yl, 3-cyclopropyloxybut-2-yl, 3-cyclopropyloxybut-2-yl, 4-cyclopropyloxybut-2-yl, 1-(cyclopropyloxymethyl)eth-1-yl, 1-(cyclopropyloxymethyl)-1-($CH_3$)eth-1-yl, 1-(cyclopropylmethyloxy)prop-1-yl, cyclobutyloxymethyl, 1-cyclobutyloxyethyl, 2-cyclobutyloxyethyl, 1-cyclobutyloxyprop-1-yl, 2-cyclobutyloxyprop-1-yl, 3-cyclobutyloxyprop-1-yl, 1-cyclobutyloxybut-1-yl, 2-cyclobutyloxybut-1-yl, 3-cyclobutyloxybut-1-yl, 4-cyclobutyloxybut-1-yl, 1-cyclobutyloxybut-2-yl, 2-cyclobutyloxybut-2-yl, 3-cyclobutyloxybut-2-yl, 4-cyclobutyloxybut-2-yl, 1-(cyclobutyloxymethyl)eth-1-yl, 1-(cyclobutyloxymethyl)- 1-($CH_3$)eth-1-yl, 1-(cyclobutyloxymethyl)prop-1-yl, cyclopentyloxymethyl, 1-cyclopentyloxyethyl, 2-cyclopentyloxyethyl, 1-cyclopentyloxy-prop-1-yl, 2-cyclopentyloxyprop-1-yl, 3-cyclopentyloxyprop-1-yl, 1-cyclopentyloxybut-1-yl, 2-cyclopentyloxybut-1-yl, 3-cyclopentyloxybut-1-yl, 4-cyclopentyloxybut-1-yl, 1-cyclopentyloxybut-2-yl, 2-cyclopentyloxybut-2-yl, 3-cyclopentyloxybut-2-yl, 4-cyclopentyloxybut-2-yl, 1-(cyclopentyloxymethyl)eth-1-yl, 1-(cyclopentyloxymethyl)-1-($CH_3$)eth-1-yl, 1-(cyclopentyloxymethyl)prop-1-yl, cyclohexyloxymethyl, 1-cyclohexyloxyethyl, 2-cyclohexyloxyethyl, 1-cyclohexyloxyprop-1-yl, 2-cyclohexyloxyprop-1-yl, 3-cyclohexyloxyprop-1-yl, 1-cyclohexyloxybut-1-yl, 2-cyclohexyloxybut-1-yl, 3-cyclohexyloxybut-1-yl, 4-cyclohexyloxybut-1-yl, 1-cyclohexyloxybut-2-yl, 2-cyclohexyloxybut-2-yl, 3-cyclohexyloxybut-2-yl, 4-cyclohexyloxybut-2-yl, 1-(cyclohexyloxymethyl)eth-1-yl, 1-(cyclohexyloxymethyl)-1-($CH_3$)eth-1-yl, 1-(cyclohexyloxymethyl)prop-1-yl, cycloheptyloxymethyl, 1-cycloheptyloxyethyl, 2-cycloheptyloxyethyl, 1-cycloheptyloxyprop-1-yl, 2-cycloheptyloxyprop-1-yl, 3-cycloheptyloxyprop-1-yl, 1-cycloheptyloxybut-1-yl, 2-cycloheptyloxybut-1-yl, 3-cycloheptyloxybut-1-yl, 4-cycloheptyloxybut-1-yl, 1-cycloheptyloxybut-2-yl, 2-cycloheptyloxybut-2-yl, 3-cycloheptyloxybut-2-yl, 4-cycloheptyloxybut-2-yl, 1-(cycloheptyloxymethyl)eth-1-yl, 1-(cycloheptyloxymethyl)-1-($CH_3$)eth-1-yl, 1-(cycloheptyloxymethyl)prop-1-yl, cyclooctyloxymethyl, 1-cyclooctyloxyethyl, 2-cyclooctyloxyethyl, 1-cyclooctyloxyprop-1-yl, 2-cyclooctyloxyprop-1-yl, 3-cyclooctyloxyprop-1-yl, 1-cyclooctyloxybut-1-yl, 2-cyclooctyloxybut-1-yl, 3-cyclooctyloxybut-1-yl, 4-cyclooctyloxybut-1-yl, 1-cyclooctyloxybut-2-yl, 2-cyclooctyloxybut-2-yl, 3-cyclooctyloxybut-2-yl, 4-cyclooctyloxybut-2-yl, 1-(cyclooctyloxymethyl)eth-1-yl, 1-(cyclooctyloxymethyl)-1-($CH_3$)eth-1-yl or 1-(cyclooctyloxymethyl)prop-1-yl, in particular $C_3$–$C_6$-cycloalkoxymethyl or 2-($C_3$–$C_6$-cycloalkoxy) ethyl;

$C_1$–$C_4$-alkylthio-$C_1$–$C_4$-alkyl: $C_1$–$C_4$-alkyl which is substituted by $C_1$–$C_4$-alkylthio as mentioned above, i.e. $CH_2SCH_3$, $CH_2SC_2H_5$, n-propylthiomethyl, $CH_2SCH(CH_3)_2$, n-butylthiomethyl, (1-methylpropylthio) methyl, (2-methylpropylthio)methyl, $CH_2SC(CH_3)_3$, 2-methylthioethyl, 2-ethylthioethyl, 2-(n-propylthio) ethyl, 2-(1-methylethylthio)ethyl, 2-(n-butylthio)ethyl, 2-(1-methylpropylthio)ethyl, 2-(2-methylpropylthio) ethyl, 2-(1,1-dimethylethylthio)ethyl, 2-($SCH_3$)propyl, 3-($SCH_3$)propyl, 2-($SC_2H_5$)propyl, 3-($SC_2H_5$)propyl, 3-(propylthio)propyl, 3-(butylthio)propyl, 4-($SCH_3$) butyl, 4-($SC_2H_5$)butyl, 4-(n-propylthio)butyl or 4-(n- butylthio)butyl, in particular $CH_2SCH_3$ or 2-(methylthio)ethyl;

$C_1$–$C_4$-haloalkylthio-$C_1$–$C_4$-alkyl: $C_1$–$C_4$-alkyl which is substituted by $C_1$–$C_4$-haloalkylthio as mentioned above, i.e. 2-(difluoromethylthio)ethyl, 2-(trifluoromethylthio)ethyl or 2-(pentafluoroethylthio)ethyl;

$C_1$–$C_4$-alkylsulfinyl-$C_1$–$C_4$-alkyl: $C_1$–$C_4$-alkyl which is substituted by $C_1$–$C_4$-alkylsulfinyl as mentioned above, i.e. $CH_2SOCH_3$, $CH_2SOC_2H_5$, n-propylsulfinylmethyl, (1-methylethylsulfinyl)methyl, n-butylsulfinylmethyl, (1-methylpropylsulfinyl)methyl, (2-methylpropylsulfinyl)methyl, (1,1-dimethylethylsulfinyl)methyl, 2-methylsulfinylethyl, 2-ethylsulfinylethyl, 2-(n-propylsulfinyl)ethyl, 2-(1-methylethylsulfinyl)ethyl, 2-(n-butylsulfinyl)ethyl, 2-(1-methylpropylsulfinyl)ethyl, 2-(2-methylpropylsulfinyl)ethyl, 2-(1,1-dimethylethylsulfinyl)ethyl, 2-($SOCH_3$)propyl, 3-($SOCH_3$)propyl, 2-($SOC_2H_5$)propyl, 3-($SOC_2H_5$)propyl, 3-(propylsulfinyl)propyl, 3-(butylsulfinyl)propyl, 4-($SOCH_3$)butyl, 4-($SOC_2H_5$)butyl, 4-(n-propylsulfinyl)butyl or 4-(n-butylsulfinyl)butyl, in particular 2-($SOCH_3$)ethyl;

$C_1$–$C_4$-haloalkylsulfinyl-$C_1$–$C_4$-alkyl: $C_1$–$C_4$-alkyl which is substituted by $C_1$–$C_4$-haloalkylsulfinyl as mentioned above, i.e. 2-(2,2,2-trifluoroethylsulfinyl)ethyl;

$C_1$–$C_4$-alkylsulfonyl-$C_1$–$C_4$-alkyl: $C_1$–$C_4$-alkyl which is substituted by $C_1$–$C_4$-alkylsulfonyl as mentioned above, i.e. $CH_2SO_2CH_3$, $CH_2SO_2C_2H_5$, n-propylsulfonylmethyl, (1-methylethylsulfonyl)methyl, n-butylsulfonylmethyl, (1-methylpropylsulfonyl)methyl, (2-methylpropylsulfonyl)methyl, (1,1-dimethylethylsulfonyl)methyl, 2-methylsulfonylethyl, 2-ethylsulfonylethyl, 2-(n-propylsulfonyl)ethyl, 2-(1-methylethylsulfonyl)ethyl, 2-(n-butylsulfonyl)ethyl, 2-(1-methylpropylsulfonyl)ethyl, 2-(2-methylpropylsulfonyl)ethyl, 2-(1,1-dimethylethylsulfonyl)ethyl, 2-($SO_2CH_3$)propyl, 3-($SO_2CH_3$)propyl, 2-($SO_2C_2H_5$)propyl, 3-($SO_2C_2H_5$)propyl, 3-(propylsulfonyl)propyl, 3-(butylsulfonyl)propyl, 4-($SO_2CH_3$)butyl, 4-($SO_2C_2H_5$)butyl, 4-(n-propylsulfonyl)butyl or 4-(n-butylsulfonyl)butyl, in particular 2-($SO_2CH_3$)ethyl or 2-($SO_2C_2H_5$)ethyl;

$C_1$–$C_4$-haloalkylsulfonyl-$C_1$–$C_4$-alkyl: $C_1$–$C_4$-alkyl which is substituted by $C_1$–$C_4$-haloalkylsulfonyl as mentioned above, i.e. 2-(2,2,2-trifluoroethylsulfonyl)ethyl;

($C_1$–$C_4$-alkyl)carbonyl: $COCH_3$, $COC_2H_5$, n-propylcarbonyl, $COCH(CH_3)_2$, n-butylcarbonyl, 1-methylpropylcarbonyl, 2-methylpropylcarbonyl or $COC(CH_3)_3$, in particular $COCH_3$, $COC_2H_5$ or $COC(CH_3)_3$;

($C_1$–$C_4$-haloalkyl)carbonyl: ($C_1$–$C_4$-alkyl)carbonyl as mentioned above which is partially or fully substituted by fluorine, chlorine, bromine and/or iodine, i.e. $COCH_2Cl$, $COCH(Cl)_2$, $COC(Cl)_3$, $COCH_2F$, $COCHF_2$, $COCF_3$, COCHFCl, $COCF(Cl)_2$, $COCF_2Cl$, $COCF_2Br$, 1-fluoroethylcarbonyl, 2-fluoroethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 1,2-dichloroethylcarbonyl, 2,2,2-trichloroethylcarbonyl, $COC_2F_5$, 3-chloropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl or nonafluorobutylcarbonyl, in particular $COCH_2Cl$, $COCH_2F$, $COCHF_2$, $COCF_3$, 2-fluoroethylcarbonyl, 2-chloroethylcarbonyl, 1,2-dichloroethylcarbonyl, 2,2,2-trifluoroethylcarbonyl or $COC_2F_5$;

($C_1$–$C_4$-alkyl)carbonyl-$C_1$–$C_4$-alkyl: $C_1$–$C_4$-alkyl which is substituted by ($C_1$–$C_4$-Alkyl)carbonyl as mentioned above, i.e. $CH_2COCH_3$, $CH_2COC_2H_5$ or $CH_2COC(CH_3)_3$;

($C_1$–$C_4$-haloalkyl)carbonyl-$C_1$–$C_4$-alkyl: $C_1$–$C_4$-alkyl which is substituted by ($C_1$–$C_4$-haloalkyl)carbonyl as mentioned above, i.e. $CH_2COCF_3$ or $CH_2COCH_2Cl$;

($C_3$–$C_8$-cycloalkyl)carbonyl-$C_1$–$C_4$-alkyl: cyclopropyl-CO-$CH_2$-, 1-(cyclopropyl-CO-)ethyl, 2-(cyclopropyl-CO-)ethyl, 1-(cyclopropyl-CO-)prop-1-yl, 2-(cyclopropyl-CO-)prop-1-yl, 3-(cyclopropyl-CO-)prop-1-yl, 1-(cyclopropyl-CO-)but-1-yl, 2-(cyclopropyl-CO-)but-1-yl, 3-(cyclopropyl-CO-)but-1-yl, 4-(cyclopropyl-CO-)but-1-yl, 1-(cyclopropyl-CO-)but-2-yl, 2-(cyclopropyl-CO-)but-2-yl, 3-(cyclopropyl-CO-)but-2-yl, 4-(cyclopropyl-CO-)but-2-yl, 1-(cyclopropyl-CO-$CH_2$-)eth-1-yl, 1-(cyclopropyl-CO-$CH_2$-)-1-($CH_3$)eth-1-yl, 1-(cyclopropyl-CO-$CH_2$-)prop-1-yl, cyclobutyl-CO-$CH_2$-, 1-(cyclobutyl-CO-)ethyl, 2-(cyclobutyl-CO-)ethyl, 1-(cyclobutyl-CO-)prop-1-yl, 2-(cyclobutyl-CO-)prop-1-yl, 3-(cyclobutyl-CO-)prop-1-yl, 1-(cyclobutyl-CO-)but-1-yl, 2-(cyclobutyl-CO-)but-1-yl, 3-(cyclobutyl-CO-)but-1-yl, 4-(cyclobutyl-CO-)but-1-yl, 1-(cyclobutyl-CO-)but-2-yl, 2-(cyclobutyl-CO-)but-2-yl, 3-(cyclobutyl-CO-)but-2-yl, 4-(cyclobutyl-CO-)but-2-yl, 1-(cyclobutyl-CO-$CH_2$-)eth-1-yl, 1-(cyclobutyl-CO-$CH_2$-)-1-($CH_3$)eth-1-yl, 1-(cyclobutyl-CO-$CH_2$-)prop-1-yl, cyclopentyl-CO-$CH_2$-, 1-(cyclopentyl-CO-)ethyl, 2-(cyclopentyl-CO-)ethyl, 1-(cyclopentyl-CO-)prop-1-yl, 2-(cyclopentyl-CO-)prop-1-yl, 3-(cyclopentyl-CO-)prop-1-yl, 1-(cyclopentyl-CO-)but-1-yl, 2-(cyclopentyl-CO-)but-1-yl, 3-(cyclopentyl-CO-)but-1-yl, 4-(cyclopentyl-CO-)but-1-yl, 1-(cyclopentyl-CO-)but-2-yl, 2-(cyclopentyl-CO-)but-2-yl, 3-(cyclopentyl-CO-)but-2-yl, 4-(cyclopentyl-CO-)but-2-yl, 1-(cyclopentyl-CO-$CH_2$-)eth-1-yl, 1-(cyclopentyl-CO-$CH_2$-)-1-($CH_3$)-eth-1-yl, 1-(cyclopentyl-CO-$CH_2$-)prop-1-yl, cyclohexyl-CO-$CH_2$-, 1-(cyclohexyl-CO-)ethyl, 2-(cyclohexyl-CO-)ethyl, 1-(cyclohexyl-CO-)prop-1-yl, 2-(cyclohexyl-CO-)prop-1-yl, 3-(cyclohexyl-CO-)prop-1-yl, 1-cyclohexyl-CO-)but-1-yl, 2-(cyclohexyl-CO-)but-1-yl, 3-(cyclohexyl-CO-)but-1-yl, 4-(cyclohexyl-CO-)but-1-yl, 1-(cyclohexyl-CO-)but-2-yl, 2-(cyclohexyl-CO-)but-2-yl, 3-(cyclohexyl-CO-)but-2-yl, 4-(cyclohexyl-CO-)but-2-yl, 1-(cyclohexyl-CO-$CH_2$-)eth-1-yl, 1-(cyclohexyl-CO-$CH_2$-)-1-($CH_3$)eth-1-yl, 1-(cyclohexyl-CO-$CH_2$-)prop-1-yl, cycloheptyl-CO-$CH_2$-, 1-(cycloheptyl-CO-)ethyl, 2-(cycloheptyl-CO-)ethyl, 1-(cycloheptyl-CO-)prop-1-yl, 2-(cycloheptyl-CO-)prop-1-yl, 3-(cycloheptyl-CO-)prop-1-yl, 1-(cycloheptyl-CO-)but-1-yl, 2-(cycloheptyl-CO-)but-1-yl, 3-(cycloheptyl-CO-)but-1-yl, 4-(cycloheptyl-CO-)but-1-yl, 1-(cycloheptyl-CO-)but-2-yl, 2-(cycloheptyl-CO-)but-2-yl, 3-(cycloheptyl-CO-)but-2-yl, 4-(cycloheptyl-CO-)but-2-yl, 1-(cycloheptyl-CO-$CH_2$-)eth-1-yl, 1-(cycloheptyl-CO-$CH_2$-)-1-($CH_3$)eth-1-yl, 1-(cycloheptyl-CO-$CH_2$-)prop-1-yl, cyclooctyl-CO-$CH_2$-, 1-(cyclooctyl-CO-)ethyl, 2-(cyclooctyl-CO-)ethyl, 1-(cyclooctyl-CO-)prop-1-yl, 2-(cyclooctyl-CO-)prop-1-yl, 3-(cyclooctyl-CO-)prop-1-yl, 1-(cyclooctyl-CO-)but-1-yl, 2-(cyclooctyl-CO-)but-1-yl, 3-(cyclooctyl-CO-)but-1-yl, 4-(cyclooctyl-CO-)but-1-yl, 1-(cyclooctyl-CO-)but-2-yl, 2-(cyclooctyl-CO-)but-2-yl, 3-(cyclooctyl-CO-)but-2-yl, 4-(cyclooctyl-CO-)but-2-yl, 1-(cyclooctyl-CO-$CH_2$-)eth-1-yl, 1-(cyclooctyl-CO-$CH_2$-)-1-($CH_3$)eth-1-yl or 1-(cyclooctyl-CO-$CH_2$)prop-1-yl, in particular ($C_3$–$C_6$-cycloalkyl)carbonylmethyl;

$C_1$–$C_4$-alkylcarbonyloxy: O—$COCH_3$, O—$COC_2H_5$, n-propylcarbonyloxy, O—$COCH(CH_3)_2$, n-butylcarbonyloxy, 1-methylpropylcarbonyloxy, 2-methylpropylcarbonyloxy or O—$COC(CH_3)_3$, in particular O—$COCH_3$, O—$COC_2H_5$ or O—COC$(CH_3)_3$;

($C_1$–$C_4$-haloalkyl)carbonyloxy: ($C_1$–$C_4$-alkyl)carbonyloxy as mentioned above which is partially or fully substituted by fluorine, chlorine, bromine and/or iodine, i.e. O—$COCH_2Cl$, O—$COCH(Cl)_2$, O—COC$(Cl)_3$, O—$COCH_2F$, O—$COCHF_2$, O—$COCF_3$, O—COCHFCl, O—$COCF(Cl)_2$, O—$COCF_2Cl$, O—$COCF_2Br$, 1-fluoroethylcarbonyloxy, 2-fluoroethylcarbonyloxy, 2,2-difluoroethylcarbonyloxy, 2,2,2-trifluoroethylcarbonyloxy, 2-chloro-2-fluoroethylcarbonyloxy, 2-chloro-2,2-difluoroethylcarbonyloxy, 2,2-dichloro-2-fluoroethylcarbonyloxy, 1,2-dichloroethylcarbonyloxy, 2,2,2-trichloroethylcarbonyloxy, O—$COC_2F_5$, 3-chloropropylcarbonyloxy, heptafluoropropylcarbonyloxy, 1-(fluoromethyl)-2-fluoroethylcarbonyloxy, 1-(chloromethyl)-2-chloroethylcarbonyloxy, 1-(bromomethyl)-2-bromoethylcarbonyloxy, 4-fluorobutylcarbonyloxy, 4-chlorobutylcarbonyloxy, 4-bromobutylcarbonyloxy or nonafluorobutylcarbonyloxy, in particular O—$COCH_2Cl$, O—$COCH_2F$, O—$COCHF_2$, O—$COCF_3$, 2-fluoroethylcarbonyloxy, 2-chloroethylcarbonyloxy, 1,2-dichloroethylcarbonyloxy, 2,2,2-trifluoroethylcarbonyloxy or O—$COC_2F_5$;

($C_1$–$C_4$-alkoxy)carbonyl: $COOCH_3$, $COOC_2H_5$, n-propoxycarbonyl, $COOCH(CH_3)_2$, n-butoxycarbonyl, 1-(methylpropoxy)carbonyl, 2-(methylpropoxy)carbonyl or $COOC(CH_3)_3$, in particular $COOCH_3$, $COOC_2H_5$ or $COOC(CH_3)_3$;

($C_1$–$C_4$-alkoxy)carbonyl-$C_1$–$C_4$-alkyl: $C_1$–$C_4$-alkyl which is substituted by ($C_1$–$C_4$-alkoxy)carbonyl as mentioned above, i.e. $CH_2COOCH_3$, $CH_2COOC_2H_5$, $CH_2CH_2COOCH_3$, $CH_2CH_2COOC_2H_5$, $CH(CH_3)COOCH_3$ or $CH(CH_3)COOC_2H_5$;

($C_1$–$C_4$-halogenalkoxy)carbonyl-$C_1$–$C_4$-alkyl: ($C_1$–$C_4$-alkoxy)carbonyl-$C_1$–$C_4$-alkyl as mentioned above whose alkoxy moiety is partially or fully substituted by fluorine, chlorine, bromine and/or iodine, i.e. $CH_2COOCH_2CF_3$ or $CH(CH_3)COOCH_2CF_3$;

($C_1$–$C_4$-alkylthio)carbonyl-$C_1$–$C_4$-alkyl: $C_1$–$C_4$-alkyl which is substituted by ($C_1$–$C_4$-alkylthio)carbonyl such as $COSCH_3$, $COSC_2H_5$, n-propylthiocarbonyl, 1-methylethylthiocarbonyl, n-butylthiocarbonyl, 1-methylpropylthiocarbonyl, 2-methylpropylthiocarbonyl or 1,1-dimethylethylthiocarbonyl, in particular $COSCH_3$ or $COSC_2H_5$, i.e. $CH_2COSCH_3$ or $CH_2COSC_2H_5$;

di($C_1$–$C_4$-alkyl)amino and the dialkylamino moiety of di($C_1$–$C_4$-alkyl)aminocarbonyl: for example $N(CH_3)_2$, $N(C_2H_5)_2$, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, in particular $N(CH_3)_2$ or $N(C_2H_5)_2$;

di($C_1$–$C_4$-alkyl)amino-$C_1$–$C_4$-alkyl: $C_1$–$C_4$-alkyl which is substituted by di($C_1$–$C_4$-alkyl)amino as mentioned above, i.e. $CH_2N(CH_3)_2$, $CH_2N(C_2H_5)_2$, N,N-dipropylaminomethyl, N,N-di(1-methylethyl)aminomethyl, N,N-dibutylaminomethyl, N,N-di(1-methylpropyl)aminomethyl, N,N-di(2-methylpropyl)aminomethyl, N,N-di(1,1-dimethylethyl)aminomethyl, N-ethyl-N-methylaminomethyl, N-methyl-N-propylaminomethyl, N-methyl-N-(1-methylethyl)aminomethyl, N-butyl-N-methylaminomethyl, N-methyl-N-(1-methylpropyl)aminomethyl, N-methyl-N-(2-methylpropyl)aminomethyl, N-(1,1-dimethylethyl)-N-methylaminomethyl, N-ethyl-N-propylaminomethyl, N-ethyl-N-(1-methylethyl)aminomethyl, N-butyl-N-ethylaminomethyl, N-ethyl-N-(1-methylpropyl)aminomethyl, N-ethyl-N-(2-methylpropyl)aminomethyl, N-ethyl-N-(1,1-dimethylethyl)aminomethyl, N-(1-methylethyl)-N-propylaminomethyl, N-butyl-N-propylaminomethyl, N-(1-methylpropyl)-N-propylaminomethyl, N-(2-methylpropyl)-N-propylaminomethyl, N-(1,1-dimethylethyl)-N-propylaminomethyl, N-butyl-N-(1-methylethyl)aminomethyl, N-(1-methylethyl)-N-(1-methylpropyl)aminomethyl, N-(1-methylethyl)-N-(2-methylpropyl)aminomethyl, N-(1,1-dimethylethyl)-N-(1-methylethyl)aminomethyl, N-butyl-N-(1-methylpropyl)aminomethyl, N-butyl-N-(2-methylpropyl)aminomethyl, N-butyl-N-(1,1-dimethylethyl)aminomethyl, N-(1-methylpropyl)-N-(2-methylpropyl)aminomethyl, N-(1,1-dimethylethyl)-N-(1-methylpropyl)aminomethyl, N-(1,1-dimethylethyl)-N-(2-methylpropyl)aminomethyl, N,N-dimethylaminoethyl, N,N-diethylaminoethyl, N,N-di(n-propyl)aminoethyl, N,N-di(1-methylethyl)aminoethyl, N,N-dibutylaminoethyl, N,N-di(1-methylpropyl)aminoethyl, N,N-di(2-methylpropyl)

aminoethyl, N,N-di(1,1-dimethylethyl)aminoethyl, N-ethyl-N-methylaminoethyl, N-methyl-N-propylaminoethyl, N-methyl-N-(1-methylethyl)aminoethyl, N-butyl-N-methylaminoethyl, N-methyl-N-(1-methylpropyl)aminoethyl, N-methyl-N-(2-methylpropyl)aminoethyl, N-(1,1-dimethylethyl)-N-methylaminoethyl, N-ethyl-N-propylaminoethyl, N-ethyl-N-(1-methyl-ethyl)aminoethyl, N-butyl-N-ethylaminoethyl, N-ethyl-N-(1-methylpropyl)aminoethyl, N-ethyl-N-(2-methylpropyl)aminoethyl, N-ethyl-N-( 1,1-dimethylethyl)aminoethyl, N-(1-methylethyl)-N-propylaminoethyl, N-butyl-N-propylaminoethyl, N-(1-methylpropyl)-N-propylaminoethyl, N-(2-methylpropyl)-N-propylaminoethyl, N-(1,1-dimethylethyl)-N-propylaminoethyl, N-butyl-N-(1-methylethyl)aminoethyl, N-(1-methylethyl)-N-(1-methylpropyl)aminoethyl, N-(1-methylethyl)-N-(2-methylpropyl)aminoethyl, N-(1,1-dimethylethyl)-N-(1-methylethyl)aminoethyl, N-butyl-N-(1-methylpropyl)aminoethyl, N-butyl-N-(2-methylpropyl)aminoethyl, N-butyl-N-(1,1-dimethylethyl)aminoethyl, N-(1-methylpropyl)-N-(2-methylpropyl)aminoethyl, N-(1,1-dimethylethyl)-N-(1-methylpropyl)aminoethyl or N-(1,1-dimethylethyl)-N-(2-methylpropyl)aminoethyl, in particular N,N-dimethylaminoethyl or N,N-diethylaminoethyl;

di($C_1$–$C_4$-alkyl)aminocarbonyl: a di($C_1$–$C_4$-alkyl)amino radical as mentioned above which is bonded via a carbonyl bridge, i.e. $CON(CH_3)_2$, $CON(C_2H_5)_2$, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl, or N-(1,1-dimethylethyl)-N-(2-methylpropyl)aminocarbonyl;

di($C_1$–$C_4$-alkyl)aminocarbonyl-$C_1$–$C_4$-alkyl: $C_1$–$C_4$-alkyl which is substituted by di($C_1$–$C_4$-alkyl)aminocarbonyl as mentioned above, i.e. $CH_2$—CON$(CH_3)_2$, $CH_2$—CON$(C_2H_5)_2$, N,N-dipropylamino-$COCH_2$-, N,N-di-(1-methylethyl)amino-$COCH_2$-, N,N-dibutylamino-$COCH_2$-, N,N-di-(1-methylpropyl)amino-$COCH_2$-, N,N-di(2-methylpropyl)amino-COCH $_2$-, N,N-di-(1,1-dimethylethyl)amino-$COCH_2$-, N-ethyl-N-methylamino-$COCH_2$-, N-methyl-N-propylamino-$COCH_2$-, N-methyl-N-(1-methylethyl)amino-$COCH_2$-, N-butyl-N-methylamino-$COCH_2$-, N-methyl-N-(1-methylpropyl)amino-$COCH_2$-, N-methyl-N-(2-methylpropyl)amino-$COCH_2$-, N-(1,1-dimethylethyl)-N-methylamino-$COCH_2$-, N-ethyl-N-propylamino-$COCH_2$-, N-ethyl-N-(1-methylethyl)amino-$COCH_2$-, N-butyl-N-ethylamino-$COCH_2$-, N-ethyl-N-(1-methylpropyl)amino-$COCH_2$-, N-ethyl-N-(2-methylpropyl)amino-$COCH_2$-, N-ethyl-N-(1,1-dimethylethyl)amino-$COCH_2$-, N-(1-methylethyl)-N-propylamino-$COCH_2$-, N-butyl-N-propylamino-$COCH_2$-, N-(1-methylpropyl)-N-propylamino-$COCH_2$-, N-(2-methylpropyl)-N-propylamino-$COCH_2$-, N-(1,1-dimethylethyl)-N-propylamino-$COCH_2$-, N-butyl-N-(1-methylethyl)amino-$COCH_2$-, N-(1-methylethyl)-N-(1-methylpropyl)amino-$COCH_2$-, N-(1-methylethyl)-N-(2-methylpropyl)amino-$COCH_2$-, N-(1,1-dimethylethyl)-N-(1-methylethyl)amino-$COCH_2$-, N-butyl-N-(1-methylpropyl)amino-$COCH_2$-, N-butyl-N-(2-methylpropyl)amino-$COCH_2$-, N-butyl-N-(1,1-dimethylethyl)amino-$COCH_2$-, N-(1-methylpropyl)-N-(2-methylpropyl)amino-$COCH_2$-, N-(1,1-dimethylethyl)-N-(1-methylpropyl)amino-$COCH_2$-, N-(1,1-dimethylethyl)-N-(2-methylpropyl)amino-$COCH_2$-, $C_2H_4$—CON$(CH_3)_2$, $C_2H_4$—CON$(C_2H_5)_2$, N,N-di(n-propyl)amino-$COC_2H_4$-, N,N-di-(1-methylethyl)amino-$COC_2H_4$-, N,N-dibutylamino-$COC_2H_4$-, N,N-di-(1-methylpropyl)amino-$COC_2H_4$-, N,N-di(2-methylpropyl)amino-$COC_2H_4$-, N,N-di(1,1-dimethylethyl)amino-$COC_2H_4$-, N-ethyl-N-methylamino-$COC_2H_4$-, N-methyl-N-propylamino-$COC_2H_4$-, N-methyl-N-(1-methylethyl)amino-$COC_2H_4$-, N-butyl-N-methylamino-$COC_2H_4$-, N-methyl-N-(1-methylpropyl)amino-$COC_2H_4$-, N-methyl-N-(2-methylpropyl)amino-$COC_2H_4$-, N-(1,1-dimethylethyl)-N-methylamino-$COC_2H_4$-, N-ethyl-N-propylamino-$COC_2H_4$-, N-ethyl-N-(1-methylethyl)amino-$COC_2H_4$-, N-butyl-N-ethylamino-$COC_2H_4$-, N-ethyl-N-(1-methylpropyl)amino-$COC_2H_4$-, N-ethyl-N-(2-methylpropyl)amino-$COC_2H_4$-, N-ethyl-N-(1,1-dimethylethyl)amino-$COC_2H_4$-, N-(1-methylethyl)-N-propylamino-$COC_2H_4$-, N-butyl-N-propylamino-$COC_2H_4$-, N-(1-methylpropyl)-N-propylamino-$COC_2H_4$-, N-(2-methylpropyl)-N-propylamino-$COC_2H_4$-, N-(1,1-dimethylethyl)-N-propylamino-$COC_2H_4$-, N-Butyl-N-(1-methylethyl)amino-$COC_2H_4$-, N-(1-methylethyl)-N-(1-methylpropyl)amino-$COC_2H_4$-, N-(1-methylethyl)-N-(2-methylpropyl)amino-$COC_2H_4$-, N-(1,1-dimethylethyl)-N-(1-methylethyl)amino-$COC_2H_4$-, N-butyl-N-(1-methylpropyl)amino-$COC_2H_4$-, N-butyl-N-(2-methylpropyl)amino-$COC_2H_4$-, N-butyl-N-(1,1-dimethylethyl)amino-$COC_2H_4$-, N-(1-methylpropyl)-N-(2-methylpropyl)amino-$COC_2H_4$-, N-(1,1-dimethylethyl)-N-(1-methylpropyl)amino-$COC_2H_4$- or N-(1,1-dimethylethyl)-N-(2-methylpropyl)amino-$COC_2H_5$-, in particular $CH_2$—CON$(CH_3)_2$, $CH_2$—CON$(C_2H_5)_2$, $CH(CH_3)$—CON$(CH_3)_2$ or $CH(CH_3)$CON$(C_2H_5)_2$;

$C_1$–$C_4$-alkyamino-$C_1$–$C_4$-alkyl: $C_1$–$C_4$-alkyl which is substituted by $C_1$–$C_4$-alkylamino, such as $H_3C$—NH—, $H_5C_2$—NH—, n-propyl-NH—, 1-methylethyl- NH—, n-butyl-NH—, 1-methylpropyl-NH—, $(H_3C)_2CH—CH—CH_2—NH—$ and 1,1-dimethylethyl—NH—, preferably $H_3C—NH—$ or $H_2C_2—NH—$, ie., for example $CH_2CH_2—NH—CH_3$, $CH_2CH_2—N(CH_3)_2$, $CH_2CH_2—NH—C_2H_5$ or $CH_2CH_2—N(C_2H_5)_2$;

($C_1$–$C_4$-alkylamino)carbonyl: $H_3C—NH—CO—$, $H_5C_2—NH—CO—$, n-propyl-NH—CO, 1-methylethyl-NH—CO—, n-butyl—NH—CO—, 1-methylpropyl-NH-CO, $—CONH—CH_2—(CH_3)_2$ or $—CONH—C(CH_3)_3$, in particular $—CONH—CH_3$ or $—CONH—C_2H_5$;

($C_1$–$C_4$-alkylamino)carbonyl-$C_1$–$C_4$-alkyl: $C_1$–$C_4$-alkyl which is substituted by ($C_1$–$C_4$-alkyamino)carbonyl as mentioned above, ie., for example, $CH_2—CONH—CH_3$, $CH_2—COHN—C_2H_5$, $CH(CH_3)—CONH—CH_3$ or $CH(CH_3)—CONH—C_2H_5$;

$C_3$–$C_6$-alkenyl: prop-1-en-1-yl, prop-2-en-1-yl, 1-methylethenyl, n-buten-1-yl, n-buten-2-yl, n-buten-3-yl, 1-methyl-prop-1-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 2-methylbut-2-en-1-yl, 3-methylbut-2-en-1-yl, 1-methylbut-3-en-1-yl, 1,1-dimethylprop-2-en-1-yl, 1,2-dimethylprop-1-en-1-yl, 1,2-dimethylprop-2-ene-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methyl-pent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethyl-but-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethyl-but-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,2,3-trimethylprop-2-en-1-yl, 1-ethyl-1-methylprop-2-en-1-yl, 1-ethyl-2-methylprop-1-en-1-yl or 1-ethyl-2-methylprop-2-en-1-yl, in particular allyl or 2-buten-1-yl;

$C_3$–$C_6$-haloalkenyl; $C_3$–$C_6$-alkenyl as mentioned above which is partially or fully substituted by fluorine, chlorine, bromine and/or iodine, ie., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl, 3-chloroallyl or 3,3-dichloroallyl;

cyano-$C_3$–$C_6$-alkenyl; for example 2-cyanoallyl, 3-cyanoallyl, 4-cyanobut-2-enyl, 4-cyanobut-3-enyl or 5-cyanopent-4-enyl, in particular 3-cyanoallyl or 4-cyanobut-2-enyl;

$C_3$–$C_6$-alkynyl: prop-1-yl, propargyl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl; n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yn, 4-methylpent-2-yn-4-yl or 4-methylpent-2-yn-5-yl, in particular propargyl;

$C_3$–$C_6$-haloalkyl: $C_3$–$C_6$-alkynyl as mentioned above which is partially or fully substituted by fluorine, chlorine, bromine and/or iodine, ie., for example, 1,1-difluoroprop-2-yn-1-yl, 4-fluorobut-2-yn-1-yl, 4-chlorobut-2-yn-1-yl, 1,1-difluorobut-2-yn-1-yl, 5-fluoropent-3-yn-1-yl or 6-fluoro-hex-4-yn-1-yl, in particular 4-fluorobut-2-yn-1-yl;

cyano-$C_3$–$C_6$-alkynl; for example 3-cyanopropargyl, 4-cyano-but-2-yn-1-yl, 5-cyanopent-3-yn-1-yl and 6-cyanohex-4-yn-1-yl;

$C_3$–$C_4$-alkenyloxy-$C_1$–$C_4$-alkyl: $C_1$–$C_4$-alkyl which is substituted by $C_3$–$C_4$-alkenyloxy, such as allyloxy, but 1-en-3-yloxy, but-1-en-4-yloxy, but-2-en-1-yloxy, 1-methylprop-2-enyloxy or 2-methylprop-2-enyloxy, ie., for example allyloxymethyl, 2-allyloxyethyl or but-1-en-4-yloxymethyl, in particular 2-allyloxyethyl;

$C_3$–$C_4$-alkynyloxy-$C_1$–$C_4$-alkyl which is substituted by $C_3$–$C_4$-alkynyloxy, such as propargyloxy, but-1-yn-3-yloxy, but-1-yn-4-yloxy, but-2-yn-1-yloxy, 1-methylprop-1-ynyloxy or 2-methylprop-2-ynloxy, preferably propargyloxy, ie., for example, propargyloxymethyl or 2-propargyloxyethy, in particular 2-propargyloxyethyl;

($C_3$–$C_4$-alkenyloxy)imino-$C_1$–$C_4$-alkyl; $C_1$–$C_4$-alkyl which is substituted by ($C_3$–$C_4$-alkenyloxy)imino, such as allyloxy, but-1-en-3-yloxyimino, but-1-en-4-yloxyimino, but-2-en-1-yloxyimino, 1-methylprop-2-enyloxyimino or 2-methylprop-2-enyloxyimino, ie., for example, allyloxyiminomethyl, 2-(allyloxyimino)ethyl or but-1-en-4-yloxyiminomethyl, in particular 2-(allyoxyimino)ethyl or 2-(2-buten-1-yloxyimino)ethyl;

$C_3$–$C_4$-alkenylthio-$C_1$–$C_4$-alkyl; $C_1$–$C_4$-alkyl which is substituted by $C_3$–$C_4$-alkenylthio, such as allyththio, but-1-en-3-yl-thio, but-1-en-4-ylthio, but-2-en-1-ylthio, 1-methylprop-2-enylthio or 2-methylprop-2-enylthio, ie., for example, allylthiomethyl, 2-allylthioethyl or but-1-en-4-ylthiomethyl, in particular 2-(allylthio)ethyl;

$C_3$–$C_4$-alkenylthio-$C_1$–$C_4$-alkyl; $C_1$–$C_4$-alkyl which is substituted by $C_3$–$C_4$-alkenylthio, such as propargylthio, but-1-yn-3-ylthio, but-1-yn-4-ylthio, but-2-yn-1-ylthio, 1-methylprop-2-ynylthio or 2-methylprop-2-ynylthio, preferably propargylthio, ie., for example, propargylthiomethyl or 2-propargylthioethyl, in particular 2-(propargylthio)ethyl;

$C_3$–$C_4$-alkenylthio-$C_1$–$C_4$-alkyl; $C_1$–$C_4$-alkyl which is substituted by $C_3$–$C_4$-alkenylthio, such as allysulfinyl, but-1-en-3-ylsulfinyl, but-1-en-4-ylsulfinyl, but-2-en-1-yl-sulfinyl, 1-methylprop-2-enylsulfinyl or 2-methylprop-2-enyl-sulfinyl, ie., for example, allylsulfinylmethyl, 2-allysulfinylethyl or but-1-en-4-ylsulfinylmethyl, in particular 2-(allylsulfinyl)ethyl;

$C_3$–$C_4$-alkenylthio-$C_1$–$C_4$-alkyl; $C_1$–$C_4$-alkyl which is substituted by $C_3$–$C_4$-alkenylthio, such as propargylsulfinyl, but-1-en-3-ylsulfinyfl, but-1-yn-4-ylsulfinyl, but-2-yn-1-yl-sulfinyl, 1-methylprop-2- ynylsulfinyl or 2-methylprop-2-ynyl-sulfinyl, preferably propargylsulfinyl, ie., for example, propargylsulfinylfmethyl or 2-proparglysulfinylethyl, in particular 2-(propargylsulfinyl)ethyl;

$C_3$–$C_4$-alkenylthio-$C_1$–$C_4$-alkyl; $C_1$–$C_4$-alkyl which is substituted by $C_3$–$C_4$-alkenylthio, such as allylsulfonyl, but-1-en-3-sulfonyl, but-1-en-4-ylsulfonyl, but-2-en-1-yl-sulfonyl, 1-methylprop-2-enylsulfonyl or 2-methylprop-2-enyl-sulfonyl, ie., for example, allylsulfonylmethyl, 2-allysulfonylethyl or but-1-en-4-ylsulfonylmethyl, in particular 2-(allysulfonyl)ethyl;

$C_3$–$C_4$-alkenylthio-$C_1$–$C_4$-alkyl; $C_1$–$C_4$-alkyl which is substituted by $C_3$–$C_4$-alkenylthio, such as propargylsulfonyl, but-1-yn-3-ylsulfonyl, but-1-yn-4-ylsulfony, but-2-yn-1-yl-sulfonyl, 1-methylprop-2-ynylsulfonyl or 2-methylprop-2-ynyl-sulfonyl, preferably propargylsulfonyl, ie., for example, propargylsulfonylmethyl or 2-propargylsulfonylethyl, in particular 2-(propargylsulfonyl)ethyl.

3- to 7-membered heterocycle is to be understood as meaning saturated, partially or fully unsaturated and also aromatic heterocycles having one to three hetero atoms selected from a group consisting of:

one to three nitrogen atoms, one or two oxygen atoms and one or two sulfur atoms.

Examples of saturated heterocycles which can contain a carbonyl or thiocarbonyl ring member are:

oxiranyl, thiiranyl, aziridin-1-yl, aziridin-2-yl, diaziridin-1-yl, diaziridin-3-yl, oxetan-2-yl, oxetan-3-yl, thietan-2-yl, thietan-3-yl, azetidin-1-yl, azetidin-2-yl, azetidin-3-yl, tetra-hydrofuran-2-yl, tetrahydrofuran-3-yl, tetrahydrothiophen-2-yl, tetrahydrothiophen-3-yl, pyrrolidin-1-yl, pyrrolidin-2-yl, pyrrolidin-3-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-oxazolidin-2-yl, 1,3-oxazolidin-3-yl, 1,3-oxazolidin-4-yl, 1,3-oxazolidin-5-yl, 1,2-oxazolidin-2-yl, 1,2-oxazolidin-3-yl, 1,2-oxazolidin-4-yl, 1,2-oxazolidin-5-yl, 1,3-dithiolan-2-yl, 1,3-dithiolan-4-yl, pyrrolidin-1-yl, pyrrolidin-2-yl, pyrrolidin-5-yl, tetrahydropyrazol-1-yl, tetrahydropyrazol-3-yl, tetrahydropyrazol-4-yl, tetrahydropyran-2-yl, tetrahydropyran-3-yl, tetrahydropyran-4-yl, tetrahydrothiopyran-2-yl, tetrahydrothiopyran-3-yl, tetrahydropyran-4-yl, piperidin-1-yl, piperidin-2-yl, piperidin-3-yl, piperidin-4-yl, 1,3-dioxan-2-yl, 1,3-dioxan-4-yl, 1,3-dioxan-5-yl, 1,4-dioxan-2-yl, 1,3-oxathioan-2-yl, 1,3-oxathian-4-yl, 1,3-oxathian-5-yl, 1,3-oxathian-6-yl, 1,4-oxathian-2-yl, 1,4-oxathian-3-yl, morpholin-2-yl, morpholin-3-yl, morpholin-4-yl, hexahydropyridazin-1-yl, hexahydropyridazin-3-yl, hexahydropyridazin-4-yl, hexahydropyrmidin-1-yl, hexahydropyrimidin-2-yl, hexahydropyrimidin-4-yl, hexahydropyrimidin-3-yl, hexahydropyridazin-4-yl, hexahydropyrimidin-1-yl, hexahydropyrimidin-2-yl, hexahydropyrimidin-4-yl, hexahydropyrimidin-5-yl, piperazin-1-yl, piperazin-2-yl, piperazin-3-yl, hexahydro-1,3,5-triazin-1-yl, hexahydro-1,3,5-triazin-2-yl, oxapan-2-yl, oxepan-3-yl, oxepan-4-yl, thiepan-2-yl, thiepan-3-yl, thiepan-4-yl, 1,3-dioxepan-2-yl, 1,3-dioxepan-4-yl, 1,3-dioxepan-5-yl, 1,3-dioxepan-6-yl, 1,3-dithiepan-2-yl, 1,3-dithiepan-2-yl, 1,3-dithiepan-2-yl, 1,3-dithiepan-2-yl, 1,4-dioxepan-2-yl, 1,4-dioxepen-7-yl, hexahydroazepin-1-yl, hexahydroazepin-2-yl, hexahydroazepin-3-yl, hexahydroazepin-4-yl, hexahydro-1,3-diazepin-4-yl, hexahydro-1,4-diazepin-1-yl and hexahydro-1,4-diazepin-2-yl Examples of unsaturated heterocycles which can contain a carbonyl or thiocarbonyl ring member are:

dihydrofuran-2-yl, 1,2-oxazolin-3-yl, 1,2-oxazolin-5-yl, 1,3-oxazolin-2-yl;

Preferred amongstthe heteroaromatics are the 5- and 6-membered structures, ie., for example, furyl, such as 2-furyl and 3-furyl, thienyl, such as 2-thienyl and 3-thienyl, pyrrolyl, such as 2-pyrrolyl and 3-pyrrolyl, isoxazolyl, such as 3-isoxazolyl, 4-isoxazolyl and 5-isoxazolyl, isothizolyl, such as 3-isothiazolyl, 4-isothiazolyl and 5-isothiazolyl, pyrazolyl, such as 3-pyrazolyl, 4-pyrazolyl and 5-pyrazolyl, oxazolyl, such as 2-thiazolyl, 4-thiazolyl and 5-thiazolyl, imidazolyl, such as 2-imidazolyl and 4-imidazolyl, oxadiazolyl, such as 1,2,4-oxadiazol-3-yl, 1,2,4-oxadiazol-5-yl and 1,3,4-oxadiazol-2-yl, thiadiazolyl, such as 1,2,4-thiadiazol-3-yl, 1,2,4-thiadiazol-5-yl and 1,3,4-thiadiazol-2-yl, triazoll, such as 1,2,4-triazol-1-yl, 1,2,4-triazol-3-yl and 1,2,4-triazol-4-yl, pyridinyl, such as 2-pyridinyl, 3-pyridinyl and 4-pyridinyl, pyridazinyl, such as 3-pyridazinyl, and 4-pyridazinyl, pyrimidinyl, such as 2-pyrimidinyl, 4-pyrimidinyl and 5-pyrimidinyl, and furthermore 2-pyrazinyl, 1,3,5-triazin-2-yl and 1,2,4-yl and 1,2,4-traizin-3-yl, in particular pyridyl, pyrimidyl, furanyl and thienyl.

All cycloalkyl, phenyl and heterocyclic rings are preferably unsubstituted or have a substituent attached to them.

Preferred with a view to the use of the substituted 3-phenylpyrazoles I as herbicides are those compounds I in which the variables have the following meanings, in each case alone or in combination:

$R^1$ is $C_1$–$C_4$-alkyl, in particular methyl:

$R^2$ is $C_1$–$C_4$-haloalkyl, $C_1$–$C_4$-haloalkoxy or $C_1$–$C_4$-alkylsulfonyl, in particular trifluoromethyl, difluoromethoxy or methylsulfonyl; difluoromethoxy is especially preferred;

$R^3$ is cyano or halogen, in particular chlorine, bromine or fluorine; chlorine is especially preferred;

$R^4$ is hydrogen, fluorine or chlorine, in particular fluorine or chlorine;

$R^5$ is cyano, halogen, or $C_1$–$C_4$-haloalkyl, in particular chlorine, bromine, or trifluoromethyl; chlorine is especially preferred;

$R^6$ is $C_1$–$C_6$-alkyl, $C_1$–$C_6$-haloalkyl, cyano-$C_1$–$C_4$-alkyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfonyl-$C_1$–$C_4$-alkyl, $C_3$–$C_6$-alkenyl, $C_3$–$C_6$-haloalkenyl, $C_3$–$C_6$-alkynyl, ($C_1$–$C_4$-alkyl)carbonyl, ($C_1$–$C_4$-haloalkyl) carbonyl, ($C_1$–$C_4$-alkoxy)carbonyl, di)$C_1$–$C_4$-alkyl)amino-carbonyl, ($C_1$–$C_4$-alkyl)carbonyl-$C_1$–$C_4$-alkyl, ($C_3$–$C_8$-cycloalkyl) carbonyl-$C_1$–$C_4$-alkyl, ($C_1$–$C_4$-alkoxy) imino-$C_1$–$C_4$-alkyl, hydroxycarbonyl-$C_1$–$C_4$-alkyl, ($C_1$–$C_4$-alkoxy)carbonyl-$C_1$–$C_4$-alkyl wich can have attached to it a ($C_1$–$C_4$-alkoxy)imino group, or di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl or phenyl-$C_1$–$C_4$-alkyl, in particular $C_1$–$C_6$-alkyl, $C_1$–$C_4$-alkoxy-$C_1$–$C_4$-alkyl, $C_3$–$C_6$-alkenyl, $C_3$–$C_6$-alkynyl, ($C_1$–$C_4$-alkyl)carbonyl, ($C_1$–$C_4$-alkoxy)carbonyl, di($C_1$–$C_4$-alkyl)aminocarbonyl, ($C_1$–$C_4$-alkyl)carbonyl-$C_1$–$C_4$-alkyl, ($C_3$–$C_8$-cycloalkyl)carbonyl-$C_1$–$C_4$-alkyl, ($C_1$–$C_4$-alkoxy)imino-$C_1$–$C_4$-alkyl, hydroxycarbonyl-$C_1$–$C_4$-alkyl, ($C_1$–$C_4$-alkoxy)carbonyl-$C_1$–$C_4$-alkyl which can have attached to it a ($C_1$–$C_4$-alkoxy)imino group, or di($C_1$–$C_4$-alkyl) aminocarbonyl-$C_1$–$C_4$-alkyl or phenyl-$C_1$–$C_4$-alkyl; especially preferred are $C_1$–$C_4$- alkyl, $C_1$–$C_4$-alkenyl, $C_1$–$C_6$-alkynyl, ($C_1$–$C_4$-alkyl)carbonyl, ($C_1$–$C_4$-alkoxy)carbonyl, di($C_1$–$C_4$-alkyl)aminocarbonyl, ($C_1$–$C_4$-alkoxy)carbonyl-$C_1$–$C_4$-alkyl or di($C_1$–$C_4$-alkyl)alminocarbonyl-$C_1$–$C_4$-alkyl;

$R^7$ is $C_1$–$C_4$-alkyl, $C_3$–$C_6$-alkenyl, $C_3$–$C_6$-alkynyl, ($C_1$–$C_4$-alkoxy)-carbonyl-$C_1$–$C_4$-alkyl, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl, phenyl or phenyl-$C_1$–$C_4$-alkyl, in particular $C_1$–$C_4$-alkyl, $C_3$–$C_6$-alkenyl, $C_3$–$C_6$-alkenyl, ($C_1$–$C_4$-alkoxy)carbonyl-$C_1$–$C_4$-alkyl or phenyl-$C_1$–$C_4$-alkyl.

X is a chemical bond, a 1,2-ethynediyl group or a group *—CH═C($R^8$)— which is bonded to the phenyl ring via the side characterized with an asterisk, where $R^8$ is hydrogen, cyano, chlorine, bromine or methyl, in particular chlorine; X is especially preferably a chemical bond; and Y is oxygen.

Very especially preferred are the compounds Ia which are listed in Table 1 below (=I where $R^1$=methyl, $R^2$=difluoromethoxy, $R^3$ and $R^5$=chlorine, X=chemical bond and Y=oxygen):

TABLE 1

I

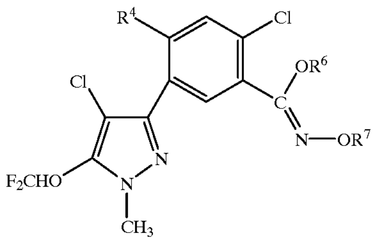

| No. | $R^4$ | $R^6$ | $R^7$ |
|---|---|---|---|
| Ia.1 | H | $CH_3$ | $CH_3$ |
| Ia.2 | F | $CH_3$ | $CH_3$ |
| Ia.3 | Cl | $CH_3$ | $CH_3$ |
| Ia.4 | H | $C_2H_5$ | $CH_3$ |
| Ia.5 | F | $C_2H_5$ | $CH_3$ |
| Ia.6 | Cl | $C_2H_5$ | $CH_3$ |
| Ia.7 | H | n-$C_3H_7$ | $CH_3$ |
| Ia.8 | F | n-$C_3H_7$ | $CH_3$ |
| Ia.9 | Cl | n-$C_3H_7$ | $CH_3$ |
| Ia.10 | H | $CH(CH_3)_2$ | $CH_3$ |
| Ia.11 | F | $CH(CH_3)_2$ | $CH_3$ |
| Ia.12 | Cl | $CH(CH_3)_2$ | $CH_3$ |
| Ia.13 | H | n-$C_4H_9$ | $CH_3$ |
| Ia.14 | F | n-$C_4H_9$ | $CH_3$ |
| Ia.15 | Cl | n-$C_4H_9$ | $CH_3$ |
| Ia.16 | H | s-$C_4H_9$ | $CH_3$ |
| Ia.17 | F | s-$C_4H_9$ | $CH_3$ |
| Ia.18 | Cl | s-$C_4H_9$ | $CH_3$ |
| Ia.19 | H | $CH_2$—$CH(CH_3)_2$ | $CH_3$ |
| Ia.20 | F | $CH_2$—$CH(CH_3)_2$ | $CH_3$ |
| Ia.21 | Cl | $CH_2$—$CH(CH_3)_2$ | $CH_3$ |
| Ia.22 | H | $C(CH_3)_3$ | $CH_3$ |
| Ia.23 | F | $C(CH_3)_3$ | $CH_3$ |
| Ia.24 | Cl | $C(CH_3)_3$ | $CH_3$ |
| Ia.25 | H | n-$C_5H_{11}$ | $CH_3$ |
| Ia.26 | F | n-$C_5H_{11}$ | $CH_3$ |
| Ia.27 | Cl | n-$C_5H_{11}$ | $CH_3$ |
| Ia.28 | H | n-$C_6H_{13}$ | $CH_3$ |
| Ia.29 | F | n-$C_6H_{13}$ | $CH_3$ |
| Ia.30 | Cl | n-$C_6H_{13}$ | $CH_3$ |
| Ia.31 | H | $CH_3$ | $C_2H_5$ |
| Ia.32 | F | $CH_3$ | $C_2H_5$ |
| Ia.33 | Cl | $CH_3$ | $C_2H_5$ |
| Ia.34 | H | $C_2H_5$ | $C_2H_5$ |
| Ia.35 | F | $C_2H_5$ | $C_2H_5$ |
| Ia.36 | Cl | $C_2H_5$ | $C_2H_5$ |
| Ia.37 | H | n-$C_3H_7$ | $C_2H_5$ |
| Ia.38 | F | n-$C_3H_7$ | $C_2H_5$ |
| Ia.39 | Cl | n-$C_3H_7$ | $C_2H_5$ |
| Ia.40 | H | $CH(CH_3)_2$ | $C_2H_5$ |
| Ia.41 | F | $CH(CH_3)_2$ | $C_2H_5$ |
| Ia.42 | Cl | $CH(CH_3)_2$ | $C_2H_5$ |
| Ia.43 | H | n-$C_4H_9$ | $C_2H_5$ |
| Ia.44 | F | n-$C_4H_9$ | $C_2H_5$ |
| Ia.45 | Cl | n-$C_4H_9$ | $C_2H_5$ |
| Ia.46 | H | s-$C_4H_9$ | $C_2H_5$ |
| Ia.47 | F | s-$C_4H_9$ | $C_2H_5$ |
| Ia.48 | Cl | s-$C_4H_9$ | $C_2H_5$ |

TABLE 1-continued

I

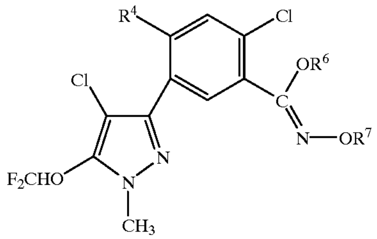

| No. | $R^4$ | $R^6$ | $R^7$ |
|---|---|---|---|
| Ia.49 | H | $CH_2$—$CH(CH_3)_2$ | $C_2H_5$ |
| Ia.50 | F | $CH_2$—$CH(CH_3)_2$ | $C_2H_5$ |
| Ia.51 | Cl | $CH_2$—$CH(CH_3)_2$ | $C_2H_5$ |
| Ia.52 | H | $C(CH_3)_3$ | $C_2H_5$ |
| Ia.53 | F | $C(CH_3)_3$ | $C_2H_5$ |
| Ia.54 | Cl | $C(CH_3)_3$ | $C_2H_5$ |
| Ia.55 | H | n-$C_5H_{11}$ | $C_2H_5$ |
| Ia.56 | F | n-$C_5H_{11}$ | $C_2H_5$ |
| Ia.57 | Cl | n-$C_5H_{11}$ | $C_2H_5$ |
| Ia.58 | H | n-$C_6H_{13}$ | $C_2H_5$ |
| Ia.59 | F | n-$C_6H_{13}$ | $C_2H_5$ |
| Ia.60 | Cl | n-$C_6H_{13}$ | $C_2H_5$ |
| Ia.61 | H | $CH_3$ | n-$C_3H_7$ |
| Ia.62 | F | $CH_3$ | n-$C_3H_7$ |
| Ia.63 | Cl | $CH_3$ | n-$C_3H_7$ |
| Ia.64 | H | $C_2H_5$ | n-$C_3H_7$ |
| Ia.65 | F | $C_2H_5$ | n-$C_3H_7$ |
| Ia.66 | Cl | $C_2H_5$ | n-$C_3H_7$ |
| Ia.67 | H | n-$C_3H_7$ | n-$C_3H_7$ |
| Ia.68 | F | n-$C_3H_7$ | n-$C_3H_7$ |
| Ia.69 | Cl | n-$C_3H_7$ | n-$C_3H_7$ |
| Ia.70 | H | $CH(CH_3)_2$ | n-$C_3H_7$ |
| Ia.71 | F | $CH(CH_3)_2$ | n-$C_3H_7$ |
| Ia.72 | Cl | $CH(CH_3)_2$ | n-$C_3H_7$ |
| Ia.73 | H | n-$C_4H_9$ | n-$C_3H_7$ |
| Ia.74 | F | n-$C_4H_9$ | n-$C_3H_7$ |
| Ia.75 | Cl | n-$C_4H_9$ | n-$C_3H_7$ |
| Ia.76 | H | s-$C_4H_9$ | n-$C_3H_7$ |
| Ia.77 | F | s-$C_4H_9$ | n-$C_3H_7$ |
| Ia.78 | Cl | s-$C_4H_9$ | n-$C_3H_7$ |
| Ia.79 | H | $CH_2$—$CH(CH_3)_2$ | n-$C_3H_7$ |
| Ia.80 | F | $CH_2$—$CH(CH_3)_2$ | n-$C_3H_7$ |
| Ia.81 | Cl | $CH_2$—$CH(CH_3)_2$ | n-$C_3H_7$ |
| Ia.82 | H | $C(CH_3)_3$ | n-$C_3H_7$ |
| Ia.83 | F | $C(CH_3)_3$ | n-$C_3H_7$ |
| Ia.84 | Cl | $C(CH_3)_3$ | n-$C_3H_7$ |
| Ia.85 | H | n-$C_5H_{11}$ | n-$C_3H_7$ |
| Ia.86 | F | n-$C_5H_{11}$ | n-$C_3H_7$ |
| Ia.87 | Cl | n-$C_5H_{11}$ | n-$C_3H_7$ |
| Ia.88 | H | n-$C_6H_{13}$ | n-$C_3H_7$ |
| Ia.89 | F | n-$C_6H_{13}$ | n-$C_3H_7$ |
| Ia.90 | Cl | n-$C_6H_{13}$ | n-$C_3H_7$ |
| Ia.91 | H | $CH_3$ | $CH(CH_3)_2$ |
| Ia.92 | F | $CH_3$ | $CH(CH_3)_2$ |
| Ia.93 | Cl | $CH_3$ | $CH(CH_3)_2$ |
| Ia.94 | H | $C_2H_5$ | $CH(CH_3)_2$ |
| Ia.95 | F | $C_2H_5$ | $CH(CH_3)_2$ |
| Ia.96 | Cl | $C_2H_5$ | $CH(CH_3)_2$ |
| Ia.97 | H | n-$C_3H_7$ | $CH(CH_3)_2$ |
| Ia.98 | F | n-$C_3H_7$ | $CH(CH_3)_2$ |
| Ia.99 | Cl | n-$C_3H_7$ | $CH(CH_3)_2$ |
| Ia.100 | H | $CH(CH_3)_2$ | $CH(CH_3)_2$ |
| Ia.101 | F | $CH(CH_3)_2$ | $CH(CH_3)_2$ |
| Ia.102 | Cl | $CH(CH_3)_2$ | $CH(CH_3)_2$ |
| Ia.103 | H | n-$C_4H_9$ | $CH(CH_3)_2$ |
| Ia.104 | F | n-$C_4H_9$ | $CH(CH_3)_2$ |
| Ia.105 | Cl | n-$C_4H_9$ | $CH(CH_3)_2$ |
| Ia.106 | H | s-$C_4H_9$ | $CH(CH_3)_2$ |
| Ia.107 | F | s-$C_4H_9$ | $CH(CH_3)_2$ |
| Ia.108 | Cl | s-$C_4H_9$ | $CH(CH_3)_2$ |
| Ia.109 | H | $CH_2$—$CH(CH_3)_2$ | $CH(CH_3)_2$ |
| Ia.110 | F | $CH_2$—$CH(CH_3)_2$ | $CH(CH_3)_2$ |
| Ia.111 | Cl | $CH_2$—$CH(CH_3)_2$ | $CH(CH_3)_2$ |

TABLE 1-continued

I

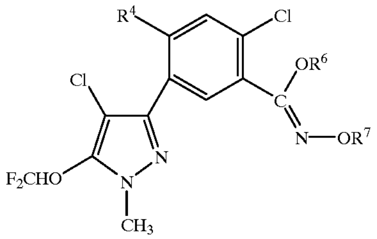

| No. | $R^4$ | $R^6$ | $R^7$ |
|---|---|---|---|
| Ia.112 | H | $C(CH_3)_3$ | $CH(CH_3)_2$ |
| Ia.113 | F | $C(CH_3)_3$ | $CH(CH_3)_2$ |
| Ia.114 | Cl | $C(CH_3)_3$ | $CH(CH_3)_2$ |
| Ia.115 | H | n-$C_5H_{11}$ | $CH(CH_3)_2$ |
| Ia.116 | F | n-$C_5H_{11}$ | $CH(CH_3)_2$ |
| Ia.117 | Cl | n-$C_5H_{11}$ | $CH(CH_3)_2$ |
| Ia.118 | H | n-$C_6H_{13}$ | $CH(CH_3)_2$ |
| Ia.119 | F | n-$C_6H_{13}$ | $CH(CH_3)_2$ |
| Ia.120 | Cl | n-$C_6H_{13}$ | $CH(CH_3)_2$ |
| Ia.121 | H | $CH_3$ | n-$C_4H_9$ |
| Ia.122 | F | $CH_3$ | n-$C_4H_9$ |
| Ia.123 | Cl | $CH_3$ | n-$C_4H_9$ |
| Ia.124 | H | $C_2H_5$ | n-$C_4H_9$ |
| Ia.125 | F | $C_2H_5$ | n-$C_4H_9$ |
| Ia.126 | Cl | $C_2H_5$ | n-$C_4H_9$ |
| Ia.127 | H | n-$C_3H_7$ | n-$C_4H_9$ |
| Ia.128 | F | n-$C_3H_7$ | n-$C_4H_9$ |
| Ia.129 | Cl | n-$C_3H_7$ | n-$C_4H_9$ |
| Ia.130 | H | $CH(CH_3)_2$ | n-$C_4H_9$ |
| Ia.131 | F | $CH(CH_3)_2$ | n-$C_4H_9$ |
| Ia.132 | Cl | $CH(CH_3)_2$ | n-$C_4H_9$ |
| Ia.133 | H | n-$C_4H_9$ | n-$C_4H_9$ |
| Ia.134 | F | n-$C_4H_9$ | n-$C_4H_9$ |
| Ia.135 | Cl | n-$C_4H_9$ | n-$C_4H_9$ |
| Ia.136 | H | s-$C_4H_9$ | n-$C_4H_9$ |
| Ia.137 | F | s-$C_4H_9$ | n-$C_4H_9$ |
| Ia.138 | Cl | s-$C_4H_9$ | n-$C_4H_9$ |
| Ia.139 | H | $CH_2—CH(CH_3)_2$ | n-$C_4H_9$ |
| Ia.140 | F | $CH_2—CH(CH_3)_2$ | n-$C_4H_9$ |
| Ia.141 | Cl | $CH_2—CH(CH_3)_2$ | n-$C_4H_9$ |
| Ia.142 | H | $C(CH_3)_3$ | n-$C_4H_9$ |
| Ia.143 | F | $C(CH_3)_3$ | n-$C_4H_9$ |
| Ia.144 | Cl | $C(CH_3)_3$ | n-$C_4H_9$ |
| Ia.145 | H | n-$C_5H_{11}$ | n-$C_4H_9$ |
| Ia.146 | F | n-$C_5H_{11}$ | n-$C_4H_9$ |
| Ia.147 | Cl | n-$C_5H_{11}$ | n-$C_4H_9$ |
| Ia.148 | H | n-$C_6H_{13}$ | n-$C_4H_9$ |
| Ia.149 | F | n-$C_6H_{13}$ | n-$C_4H_9$ |
| Ia.150 | Cl | n-$C_6H_{13}$ | n-$C_4H_9$ |
| Ia.151 | H | $CH_3$ | s-$C_4H_9$ |
| Ia.152 | F | $CH_3$ | s-$C_4H_9$ |
| Ia.153 | Cl | $CH_3$ | s-$C_4H_9$ |
| Ia.154 | H | $C_2H_5$ | s-$C_4H_9$ |
| Ia.155 | F | $C_2H_5$ | s-$C_4H_9$ |
| Ia.156 | Cl | $C_2H_5$ | s-$C_4H_9$ |
| Ia.157 | H | n-$C_3H_7$ | s-$C_4H_9$ |
| Ia.158 | F | n-$C_3H_7$ | s-$C_4H_9$ |
| Ia.159 | Cl | n-$C_3H_7$ | s-$C_4H_9$ |
| Ia.160 | H | $CH(CH_3)_2$ | s-$C_4H_9$ |
| Ia.161 | F | $CH(CH_3)_2$ | s-$C_4H_9$ |
| Ia.162 | Ci | $CH(CH_3)_2$ | s-$C_4H_9$ |
| Ia.163 | H | n-$C_4H_9$ | s-$C_4H_9$ |
| Ia.164 | F | n-$C_4H_9$ | s-$C_4H_9$ |
| Ia.165 | Cl | n-$C_4H_9$ | s-$C_4H_9$ |
| Ia.166 | H | s-$C_4H_9$ | s-$C_4H_9$ |
| Ia.167 | F | s-$C_4H_9$ | s-$C_4H_9$ |
| Ia.168 | Cl | s-$C_4H_9$ | s-$C_4H_9$ |
| Ia.169 | H | $CH_2—CH(CH_3)_2$ | s-$C_4H_9$ |
| Ia.170 | F | $CH_2—CH(CH_3)_2$ | s-$C_4H_9$ |
| Ia.171 | Cl | $CH_2—CH(CH_3)_2$ | s-$C_4H_9$ |
| Ia.172 | H | $C(CH_3)_3$ | s-$C_4H_9$ |
| Ia.173 | F | $C(CH_3)_3$ | s-$C_4H_9$ |
| la.174 | Cl | $C(CH_3)_3$ | s-$C_4H_9$ |

TABLE 1-continued

I

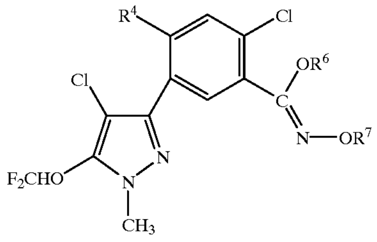

| No. | $R^4$ | $R^6$ | $R^7$ |
|---|---|---|---|
| Ia.175 | H | $n-C_5H_{11}$ | $s-C_4H_9$ |
| Ia.176 | F | $n-C_5H_{11}$ | $s-C_4H_9$ |
| Ia.177 | Cl | $n-C_5H_{11}$ | $s-C_4H_9$ |
| Ia.178 | H | $n-C_6H_{13}$ | $s-C_4H_9$ |
| Ia.179 | F | $n-C_6H_{13}$ | $s-C_4H_9$ |
| Ia.180 | Cl | $n-C_6H_{13}$ | $s-C_4H_9$ |
| Ia.181 | H | $CH_3$ | $CH_2—CH(CH_3)_2$ |
| Ia.182 | F | $CH_3$ | $CH_2—CH(CH_3)_2$ |
| Ia.183 | Cl | $CH_3$ | $CH_2—CH(CH_3)_2$ |
| Ia.184 | H | $C_2H_5$ | $CH_2—CH(CH_3)_2$ |
| Ia.185 | F | $C_2H_5$ | $CH_2—CH(CH_3)_2$ |
| Ia.186 | Cl | $C_2H_5$ | $CH_2—CH(CH_3)_2$ |
| Ia.187 | H | $n-C_3H_7$ | $CH_2—CH(CH_3)_2$ |
| Ia.188 | F | $n-C_3H_7$ | $CH_2—CH(CH_3)_2$ |
| Ia.189 | Cl | $n-C_3H_7$ | $CH_2—CH(CH_3)_2$ |
| Ia.190 | H | $CH(CH_3)_2$ | $CH_2—CH(CH_3)_2$ |
| Ia.191 | F | $CH(CH_3)_2$ | $CH_2—CH(CH_3)_2$ |
| Ia.192 | Cl | $CH(CH_3)_2$ | $CH_2—CH(CH_3)_2$ |
| Ia.193 | H | $n-C_4H_9$ | $CH_2—CH(CH_3)_2$ |
| Ia.194 | F | $n-C_4H_9$ | $CH_2—CH(CH_3)_2$ |
| Ia.195 | Cl | $n-C_4H_9$ | $CH_2—CH(CH_3)_2$ |
| Ia.196 | H | $s-C_4H_9$ | $CH_2—CH(CH_3)_2$ |
| Ia.197 | F | $s-C_4H_9$ | $CH_2—CH(CH_3)_2$ |
| Ia.198 | Cl | $s-C_4H_9$ | $CH_2—CH(CH_3)_2$ |
| Ia.199 | H | $CH_2—CH(CH_3)_2$ | $CH_2—CH(CH_3)_2$ |
| Ia.200 | F | $CH_2—CH(CH_3)_2$ | $CH_2—CH(CH_3)_2$ |
| Ia.201 | Cl | $CH_2—CH(CH_3)_2$ | $CH_2—CH(CH_3)_2$ |
| Ia.202 | H | $C(CH_3)_3$ | $CH_2—CH(CH_3)_2$ |
| Ia.203 | F | $C(CH_3)_3$ | $CH_2—CH(CH_3)_2$ |
| Ia.204 | Cl | $C(CH_3)_3$ | $CH_2—CH(CH_3)_2$ |
| Ia.205 | H | $n-C_5H_{11}$ | $CH_2—CH(CH_3)_2$ |
| Ia.206 | F | $n-C_5H_{11}$ | $CH_2—CH(CH_3)_2$ |
| Ia.207 | Cl | $n-C_5H_{11}$ | $CH_2—CH(CH_3)_2$ |
| Ia.208 | H | $n-C_6H_{13}$ | $CH_2—CH(CH_3)_2$ |
| Ia.209 | F | $n-C_6H_{13}$ | $CH_2—CH(CH_3)_2$ |
| Ia.210 | Cl | $n-C_6H_{13}$ | $CH_2—CH(CH_3)_2$ |
| Ia.211 | H | $CH_3$ | $C(CH_3)_3$ |
| Ia.212 | F | $CH_3$ | $C(CH_3)_3$ |
| Ia.213 | Cl | $CH_3$ | $C(CH_3)_3$ |
| Ia.214 | H | $C_2H_5$ | $C(CH_3)_3$ |
| Ia.215 | F | $C_2H_5$ | $C(CH_3)_3$ |
| Ia.216 | Cl | $C_2H_5$ | $C(CH_3)_3$ |
| Ia.217 | H | $n-C_3H_7$ | $C(CH_3)_3$ |
| Ia.218 | F | $n-C_3H_7$ | $C(CH_3)_3$ |
| Ia.219 | Cl | $n-C_3H_7$ | $C(CH_3)_3$ |
| Ia.220 | H | $CH(CH_3)_2$ | $C(CH_3)_3$ |
| Ia.221 | F | $CH(CH_3)_2$ | $C(CH_3)_3$ |
| Ia.222 | Cl | $CH(CH_3)_2$ | $C(CH_3)_3$ |
| Ia.223 | H | $n-C_4H_9$ | $C(CH_3)_3$ |
| Ia.224 | F | $n-C_4H_9$ | $C(CH_3)_3$ |
| Ia.225 | Cl | $n-C_4H_9$ | $C(CH_3)_3$ |
| Ia.226 | H | $s-C_4H_9$ | $C(CH_3)_3$ |
| Ia.227 | F | $s-C_4H_9$ | $C(CH_3)_3$ |
| Ia.228 | Cl | $s-C_4H_9$ | $C(CH_3)_3$ |
| Ia.229 | H | $CH_2—CH(CH_3)_2$ | $C(CH_3)_3$ |
| Ia.230 | F | $CH_2—CH(CH_3)_2$ | $C(CH_3)_3$ |
| Ia.231 | Cl | $CH_2—CH(CH_3)_2$ | $C(CH_3)_3$ |
| Ia.232 | H | $C(CH_3)_3$ | $C(CH_3)_3$ |
| Ia.233 | F | $C(CH_3)_3$ | $C(CH_3)_3$ |
| Ia.234 | Cl | $C(CH_3)_3$ | $C(CH_3)_3$ |
| Ia.235 | H | $n-C_5H_{11}$ | $C(CH_3)_3$ |
| Ia.236 | F | $n-C_5H_{11}$ | $C(CH_3)_3$ |
| Ia.237 | Cl | $n-C_5H_{11}$ | $C(CH_3)_3$ |

TABLE 1-continued

I

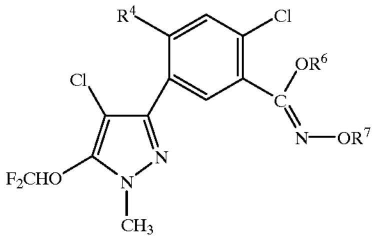

| No. | $R^4$ | $R^6$ | $R^7$ |
|---|---|---|---|
| Ia.238 | H | n-$C_6H_{13}$ | $C(CH_3)_3$ |
| Ia.239 | F | n-$C_6H_{13}$ | $C(CH_3)_3$ |
| Ia.240 | Cl | n-$C_6H_{13}$ | $C(CH_3)_3$ |
| Ia.241 | H | $CH_3$ | n-$C_5H_{11}$ |
| Ia.242 | F | $CH_3$ | n-$C_5H_{11}$ |
| Ia.243 | Cl | $CH_3$ | n-$C_5H_{11}$ |
| Ia.244 | H | $C_2H_5$ | n-$C_5H_{11}$ |
| Ia.245 | F | $C_2H_5$ | n-$C_5H_{11}$ |
| Ia.246 | Cl | $C_2H_5$ | n-$C_5H_{11}$ |
| Ia.247 | H | n-$C_3H_7$ | n-$C_5H_{11}$ |
| Ia.248 | F | n-$C_3H_7$ | n-$C_5H_{11}$ |
| Ia.249 | Cl | n-$C_3H_7$ | n-$C_5H_{11}$ |
| Ia.250 | H | $CH(CH_3)_2$ | n-$C_5H_{11}$ |
| Ia.251 | F | $CH(CH_3)_2$ | n-$C_5H_{11}$ |
| Ia.252 | Cl | $CH(CH_3)_2$ | n-$C_5H_{11}$ |
| Ia.253 | H | n-$C_4H_9$ | n-$C_5H_{11}$ |
| Ia.254 | F | n-$C_4H_9$ | n-$C_5H_{11}$ |
| Ia.255 | Cl | n-$C_4H_9$ | n-$C_5H_{11}$ |
| Ia.256 | H | s-$C_4H_9$ | n-$C_5H_{11}$ |
| Ia.257 | F | s-$C_4H_9$ | n-$C_5H_{11}$ |
| Ia.258 | Cl | s-$C_4H_9$ | n-$C_5H_{11}$ |
| Ia.259 | H | $CH_2$—$CH(CH_3)_2$ | n-$C_5H_{11}$ |
| Ia.260 | F | $CH_2$—$CH(CH_3)_2$ | n-$C_5H_{11}$ |
| Ia.261 | Cl | $CH_2$—$CH(CH_3)_2$ | n-$C_5H_{11}$ |
| Ia.262 | H | $C(CH_3)_3$ | n-$C_5H_{11}$ |
| Ia.263 | F | $C(CH_3)_3$ | n-$C_5H_{11}$ |
| Ia.264 | Cl | $C(CH_3)_3$ | n-$C_5H_{11}$ |
| Ia.265 | H | n-$C_5H_{11}$ | n-$C_5H_{11}$ |
| Ia.266 | F | n-$C_5H_{11}$ | n-$C_5H_{11}$ |
| Ia.267 | Cl | n-$C_5H_{11}$ | n-$C_5H_{11}$ |
| Ia.268 | H | n-$C_6H_{13}$ | n-$C_5H_{11}$ |
| Ia.269 | F | n-$C_6H_{13}$ | n-$C_5H_{11}$ |
| Ia.270 | Cl | n-$C_6H_{13}$ | n-$C_5H_{11}$ |
| Ia.271 | H | $CH_3$ | n-$C_6H_{13}$ |
| Ia.272 | F | $CH_3$ | n-$C_6H_{13}$ |
| Ia.273 | Cl | $CH_3$ | n-$C_6H_{13}$ |
| Ia.274 | H | $C_2H_5$ | n-$C_6H_{13}$ |
| Ia.275 | F | $C_2H_5$ | n-$C_6H_{13}$ |
| Ia.276 | Cl | $C_2H_5$ | n-$C_6H_{13}$ |
| Ia.277 | H | n-$C_3H_7$ | n-$C_6H_{13}$ |
| Ia.278 | F | n-$C_3H_7$ | n-$C_6H_{13}$ |
| Ia.279 | Cl | n-$C_3H_7$ | n-$C_6H_{13}$ |
| Ia.280 | H | $CH(CH_3)_2$ | n-$C_6H_{13}$ |
| Ia.281 | F | $CH(CH_3)_2$ | n-$C_6H_{13}$ |
| Ia.282 | Cl | $CH(CH_3)_2$ | n-$C_6H_{13}$ |
| Ia.283 | H | n-$C_4H_9$ | n-$C_6H_{13}$ |
| Ia.284 | F | n-$C_4H_9$ | n-$C_6H_{13}$ |
| Ia.285 | Cl | n-$C_4H_9$ | n-$C_6H_{13}$ |
| Ia.286 | H | s-$C_4H_9$ | n-$C_6H_{13}$ |
| Ia.287 | F | s-$C_4H_9$ | n-$C_6H_{13}$ |
| Ia.288 | Cl | s-$C_4H_9$ | n-$C_6H_{13}$ |
| Ia.289 | H | $CH_2$—$CH(CH_3)_2$ | n-$C_6H_{13}$ |
| Ia.290 | F | $CH_2$—$CH(CH_3)_2$ | n-$C_6H_{13}$ |
| Ia.291 | Cl | $CH_2$—$CH(CH_3)_2$ | n-$C_6H_{13}$ |
| Ia.292 | H | $C(CH_3)_3$ | n-$C_6H_{13}$ |
| Ia.293 | F | $C(CH_3)_3$ | n-$C_6H_{13}$ |
| Ia.294 | Cl | $C(CH_3)_3$ | n-$C_6H_{13}$ |
| Ia.295 | H | n-$C_5H_{11}$ | n-$C_6H_{13}$ |
| Ia.296 | F | n-$C_5H_{11}$ | n-$C_6H_{13}$ |
| Ia.297 | Cl | n-$C_5H_{11}$ | n-$C_6H_{13}$ |
| Ia.298 | H | n-$C_6H_{13}$ | n-$C_6H_{13}$ |
| Ia.299 | F | n-$C_6H_{13}$ | n-$C_6H_{13}$ |
| Ia.300 | Cl | n-$C_6H_{13}$ | n-$C_6H_{13}$ |

TABLE 1-continued

I

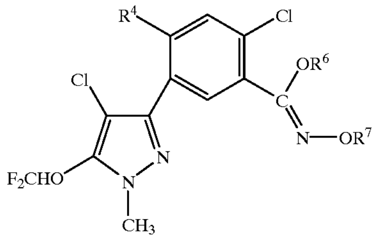

| No. | $R^4$ | $R^6$ | $R^7$ |
|---|---|---|---|
| Ia.301 | H | $CH_2—CH_2—Cl$ | $CH_3$ |
| Ia.302 | F | $CH_2—CH_2—Cl$ | $CH_3$ |
| Ia.303 | Cl | $CH_2—CH_2—Cl$ | $CH_3$ |
| Ia.304 | H | $CH_2—CH_2—Cl$ | $C_2H_5$ |
| Ia.305 | F | $CH_2—CH_2—Cl$ | $C_2H_5$ |
| Ia.306 | Cl | $CH_2—CH_2—Cl$ | $C_2H_5$ |
| Ia.307 | H | $CH_2—CH_2—Cl$ | n-$C_3H_7$ |
| Ia.308 | F | $CH_2—CH_2—Cl$ | n-$C_3H_7$ |
| Ia.309 | Cl | $CH_2—CH_2—Cl$ | n-$C_3H_7$ |
| Ia.310 | H | $CH_2—CH_2—Cl$ | n-$C_4H_9$ |
| Ia.311 | F | $CH_2—CH_2—Cl$ | n-$C_4H_9$ |
| Ia.312 | Cl | $CH_2—CH_2—Cl$ | n-$C_4H_9$ |
| Ia.313 | H | $CH_2—CH_2—Cl$ | $CH_2—CH═CH_2$ |
| Ia.314 | F | $CH_2—CH_2—Cl$ | $CH_2—CH═CH_2$ |
| Ia.315 | Cl | $CH_2—CH_2—Cl$ | $CH_2—CH═CH_2$ |
| Ia.316 | H | $CH_2—CH_2—Cl$ | $CH_2—C≡CH$ |
| Ia.317 | F | $CH_2—CH_2—Cl$ | $CH_2—C≡CH$ |
| Ia.318 | Cl | $CH_2—CH_2—Cl$ | $CH_2—C≡CH$ |
| Ia.319 | H | $CH_2—CH_2—Cl$ | $CH_2—CO—OCH_3$ |
| Ia.320 | F | $CH_2—CH_2—Cl$ | $CH_2—CO—OCH_3$ |
| Ia.321 | Cl | $CH_2—CH_2—Cl$ | $CH_2—CO—OCH_3$ |
| Ia.322 | H | $CH_2—CH_2—Cl$ | $CH_2$-phenyl |
| Ia.323 | F | $CH_2—CH_2—Cl$ | $CH_2$-phenyl |
| Ia.324 | Cl | $CH_2—CH_2—Cl$ | $CH_2$-phenyl |
| Ia.325 | H | $CH_2—CF_3$ | $CH_3$ |
| Ia.326 | F | $CH_2—CF_3$ | $CH_3$ |
| Ia.327 | Cl | $CH_2—CF_3$ | $CH_3$ |
| Ia.328 | H | $CH_2—CF_3$ | $C_2H_5$ |
| Ia.329 | F | $CH_2—CF_3$ | $C_2H_5$ |
| Ia.330 | Cl | $CH_2—CF_3$ | $C_2H_5$ |
| Ia.331 | H | $CH_2—CF_3$ | n-$C_3H_7$ |
| Ia.332 | F | $CH_2—CF_3$ | n-$C_3H_7$ |
| Ia.333 | Cl | $CH_2—CF_3$ | n-$C_3H_7$ |
| Ia.334 | H | $CH_2—CF_3$ | n-$C_4H_9$ |
| Ia.335 | F | $CH_2—CF_3$ | n-$C_4H_9$ |
| Ia.336 | Cl | $CH_2—CF_3$ | n-$C_4H_9$ |
| Ia.337 | H | $CH_2—CF_3$ | $CH_2—CH═CH_2$ |
| Ia.338 | F | $CH_2—CF_3$ | $CH_2—CH═CH_2$ |
| Ia.339 | Cl | $CH_2—CF_3$ | $CH_2—CH═CH_2$ |
| Ia.340 | H | $CH_2—CF_3$ | $CH_2—C≡CH$ |
| Ia.341 | F | $CH_2—CF_3$ | $CH_2—C≡CH$ |
| Ia.342 | Cl | $CH_2—CF_3$ | $CH_2—C≡CH$ |
| Ia.343 | H | $CH_2—CF_3$ | $CH_2—CO—OCH_3$ |
| Ia.344 | F | $CH_2—CF_3$ | $CH_2—CO—OCH_3$ |
| Ia.345 | Cl | $CH_2—CF_3$ | $CH_2—CO—OCH_3$ |
| Ia.346 | H | $CH_2—CF_3$ | $CH_2$-phenyl |
| Ia.347 | F | $CH_2—CF_3$ | $CH_2$-phenyl |
| Ia.348 | Cl | $CH_2—CF_3$ | $CH_2$-phenyl |
| Ia.349 | H | $CH_2—CH_2—OH$ | $CH_3$ |
| Ia.350 | F | $CH_2—CH_2—OH$ | $CH_3$ |
| Ia.351 | Cl | $CH_2—CH_2—OH$ | $CH_3$ |
| Ia.352 | H | $CH_2—CH_2—OH$ | $C_2H_5$ |
| Ia.353 | F | $CH_2—CH_2—OH$ | $C_2H_5$ |
| Ia.354 | Cl | $CH_2—CH_2—OH$ | $C_2H_5$ |
| Ia.355 | H | $CH_2—CH_2—OH$ | n-$C_3H_7$ |
| Ia.356 | F | $CH_2—CH_2—OH$ | n-$C_3H_7$ |
| Ia.357 | Cl | $CH_2—CH_2—OH$ | n-$C_3H_7$ |
| Ia.358 | H | $CH_2—CH_2—OH$ | n-$C_4H_9$ |
| Ia.359 | F | $CH_2—CH_2—OH$ | n-$C_4H_9$ |
| Ia.360 | Cl | $CH_2—CH_2—OH$ | n-$C_4H_9$ |
| Ia.361 | H | $CH_2—CH_2—OH$ | $CH_2—CH═CH_2$ |
| Ia.362 | F | $CH_2—CH_2—OH$ | $CH_2—CH═CH_2$ |
| Ia.363 | Cl | $CH_2—CH_2—OH$ | $CH_2—CH═CH_2$ |

TABLE 1-continued

I

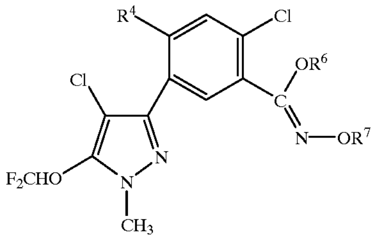

| No. | $R^4$ | $R^6$ | $R^7$ |
|---|---|---|---|
| Ia.364 | H | $CH_2$—$CH_2$—OH | $CH_2$—C≡CH |
| Ia.365 | F | $CH_2$—$CH_2$—OH | $CH_2$—C≡CH |
| Ia.366 | Cl | $CH_2$—$CH_2$—OH | $CH_2$—C≡CH |
| Ia.367 | H | $CH_2$—$CH_2$—OH | $CH_2$—CO—$OCH_3$ |
| Ia.368 | F | $CH_2$—$CH_2$—OH | $CH_2$—CO—$OCH_3$ |
| Ia.369 | Cl | $CH_2$—$CH_2$—OH | $CH_2$—CO—$OCH_3$ |
| Ia.370 | H | $CH_2$—$CH_2$—OH | $CH_2$-phenyl |
| Ia.371 | F | $CH_2$—$CH_2$—OH | $CH_2$-phenyl |
| Ia.372 | Cl | $CH_2$—$CH_2$—OH | $CH_2$-phenyl |
| Ia.373 | H | $CH_2$—$CH(CH_3)$—OH | $CH_3$ |
| Ia.374 | F | $CH_2$—$CH(CH_3)$—OH | $CH_3$ |
| Ia.375 | Cl | $CH_2$—$CH(CH_3)$—OH | $CH_3$ |
| Ia.376 | H | $CH_2$—$CH(CH_3)$—OH | $C_2H_5$ |
| Ia.377 | F | $CH_2$—$CH(CH_3)$—OH | $C_2H_5$ |
| Ia.378 | Ci | $CH_2$—$CH(CH_3)$—OH | $C_2H_5$ |
| Ia.379 | H | $CH_2$—$CH(CH_3)$—OH | n-$C_3H_7$ |
| Ia.380 | F | $CH_2$—$CH(CH_3)$—OH | n-$C_3H_7$ |
| Ia.381 | Cl | $CH_2$—$CH(CH_3)$—OH | n-$C_3H_7$ |
| Ia.382 | H | $CH_2$—$CH(CH_3)$—OH | n-$C_4H_9$ |
| Ia.383 | F | $CH_2$—$CH(CH_3)$—OH | n-$C_4H_9$ |
| Ia.384 | Cl | $CH_2$—$CH(CH_3)$—OH | n-$C_4H_9$ |
| Ia.385 | H | $CH_2$—$CH(CH_3)$—OH | $CH_2$—CH═$CH_2$ |
| Ia.386 | F | $CH_2$—$CH(CH_3)$—OH | $CH_2$—CH═$CH_2$ |
| Ia.387 | Cl | $CH_2$—$CH(CH_3)$—OH | $CH_2$—CH═$CH_2$ |
| Ia.388 | H | $CH_2$—$CH(CH_3)$—OH | $CH_2$—C≡CH |
| Ia.389 | F | $CH_2$—$CH(CH_3)$—OH | $CH_2$—C≡CH |
| Ia.390 | Cl | $CH_2$—$CH(CH_3)$—OH | $CH_2$—C≡CH |
| Ia.391 | H | $CH_2$—$CH(CH_3)$—OH | $CH_2$—CO—$OCH_3$ |
| Ia.392 | F | $CH_2$—$CH(CH_3)$—OH | $CH_2$—CO—$OCH_3$ |
| Ia.393 | Cl | $CH_2$—$CH(CH_3)$—OH | $CH_2$—CO—$OCH_3$ |
| Ia.394 | H | $CH_2$—$CH(CH_3)$—OH | $CH_2$-phenyl |
| Ia.395 | F | $CH_2$—$CH(CH_3)$—OH | $CH_2$-phenyl |
| Ia.396 | Cl | $CH_2$—$CH(CH_3)$—OH | $CH_2$-phenyl |
| Ia.397 | H | $CH_2$—$CH_2$—N | $CH_3$ |
| Ia.398 | F | $CH_2$—$CH_2$—N | $CH_3$ |
| Ia.399 | Cl | $CH_2$—$CH_2$—N | $CH_3$ |
| Ia.400 | H | $CH_2$—$CH_2$—N | $C_2H_5$ |
| Ia.401 | F | $CH_2$—$CH_2$—N | $C_2H_5$ |
| Ia.402 | Cl | $CH_2$—$CH_2$—N | $C_2H_5$ |
| Ia.403 | H | $CH_2$—$CH_2$—N | n-$C_3H_7$ |
| Ia.404 | F | $CH_2$—$CH_2$—N | n-$C_3H_7$ |
| Ia.405 | Cl | $CH_2$—$CH_2$—N | n-$C_3H_7$ |
| Ia.406 | H | $CH_2$—$CH_2$—N | n-$C_4H_9$ |
| Ia.407 | F | $CH_2$—$CH_2$—N | n-$C_4H_9$ |
| Ia.408 | Cl | $CH_2$—$CH_2$—N | n-$C_4H_9$ |
| Ia.409 | H | $CH_2$—$CH_2$—N | $CH_2$—CH═$CH_2$ |
| Ia.410 | F | $CH_2$—$CH_2$—N | $CH_2$—CH═$CH_2$ |
| Ia.411 | Cl | $CH_2$—$CH_2$—CN | $CH_2$—CH═$CH_2$ |
| Ia.412 | H | $CH_2$—$CH_2$—CN | $CH_2$—C≡CH |
| Ia.413 | F | $CH_2$—$CH_2$—CN | $CH_2$—C≡CH |
| Ia.414 | Cl | $CH_2$—$CH_2$—CN | $CH_2$—C≡CH |
| Ia.415 | H | $CH_2$—$CH_2$—CN | $CH_2$—CO—$OCH_3$ |
| Ia.416 | F | $CH_2$—$CH_2$—CN | $CH_2$—CO—$OCH_3$ |
| Ia.417 | Cl | $CH_2$—$CH_2$—CN | $CH_2$—CO—$OCH_3$ |
| Ia.418 | H | $CH_2$—$CH_2$—CN | $CH_2$-phenyl |
| Ia.419 | F | $CH_2$—$CH_2$—CN | $CH_2$-phenyl |
| Ia.420 | Cl | $CH_2$—$CH_2$—CN | $CH_2$-phenyl |
| Ia.421 | H | $CH_2$—$OCH_3$ | $CH_3$ |
| Ia.422 | F | $CH_2$—$OCH_3$ | $CH_3$ |
| Ia.423 | Cl | $CH_2$—$OCH_3$ | $CH_3$ |
| Ia.424 | H | $CH_2$—$OCH_3$ | $C_2H_5$ |
| Ia.425 | F | $CH_2$—$OCH_3$ | $C_2H_5$ |
| Ia.426 | Cl | $CH_2$—$OCH_3$ | $C_2H_5$ |

TABLE 1-continued

I

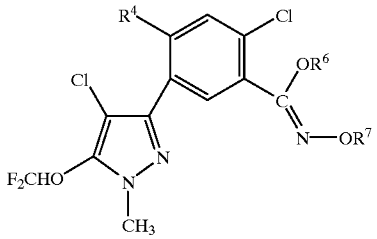

| No. | $R^4$ | $R^6$ | $R^7$ |
|---|---|---|---|
| Ia.427 | H | $CH_2$—$OCH_3$ | n-$C_3H_7$ |
| Ia.428 | F | $CH_2$—$OCH_3$ | n-$C_3H_7$ |
| Ia.429 | Cl | $CH_2$—$OCH_3$ | n-$C_3H_7$ |
| Ia.430 | H | $CH_2$—$OCH_3$ | n-$C_4H_9$ |
| Ia.431 | F | $CH_2$—$OCH_3$ | n-$C_4H_9$ |
| Ia.432 | Cl | $CH_2$—$OCH_3$ | n-$C_4H_9$ |
| Ia.433 | H | $CH_2$—$OCH_3$ | $CH_2$—CH=$CH_2$ |
| Ia.434 | F | $CH_2$—$OCH_3$ | $CH_2$—CH=$CH_2$ |
| Ia.435 | Cl | $CH_2$—$OCH_3$ | $CH_2$—CH=$CH_2$ |
| Ia.436 | H | $CH_2$—$OCH_3$ | $CH_2$—C≡CH |
| Ia.437 | F | $CH_2$—$OCH_3$ | $CH_2$—C≡CH |
| Ia.438 | Cl | $CH_2$—$OCH_3$ | $CH_2$—C≡CH |
| Ia.439 | H | $CH_2$—$OCH_3$ | $CH_2$—CO—$OCH_3$ |
| Ia.440 | F | $CH_2$—$OCH_3$ | $CH_2$—CO—$OCH_3$ |
| Ia.441 | Cl | $CH_2$—$OCH_3$ | $CH_2$—CO—$OCH_3$ |
| Ia.442 | H | $CH_2$—$OCH_3$ | $CH_2$-phenyl |
| Ia.443 | F | $CH_2$—$OCH_3$ | $CH_2$-phenyl |
| Ia.444 | Cl | $CH_2$—$OCH_3$ | $CH_2$-phenyl |
| Ia.445 | H | $CH_2$—$CH_2$—$OCH_3$ | $CH_3$ |
| Ia.446 | F | $CH_2$—$CH_2$—$OCH_3$ | $CH_3$ |
| Ia.447 | Cl | $CH_2$—$CH_2$—$OCH_3$ | $CH_3$ |
| Ia.448 | H | $CH_2$—$CH_2$—$OCH_3$ | $C_2H_5$ |
| Ia.449 | F | $CH_2$—$CH_2$—$OCH_3$ | $C_2H_5$ |
| Ia.450 | Cl | $CH_2$—$CH_2$—$OCH_3$ | $C_2H_5$ |
| Ia.451 | H | $CH_2$—$CH_2$—$OCH_3$ | n-$C_3H_7$ |
| Ia.452 | F | $CH_2$—$CH_2$—$OCH_3$ | n-$C_3H_7$ |
| Ia.453 | Cl | $CH_2$—$CH_2$—$OCH_3$ | n-$C_3H_7$ |
| Ia.454 | H | $CH_2$—$CH_2$—$OCH_3$ | n-$C_4H_9$ |
| Ia.455 | F | $CH_2$—$CH_2$—$OCH_3$ | n-$C_4H_9$ |
| Ia.456 | Cl | $CH_2$—$CH_2$—$OCH_3$ | n-$C_4H_9$ |
| Ia.457 | H | $CH_2$—$CH_2$—$OCH_3$ | $CH_2$—CH=$CH_2$ |
| Ia.458 | F | $CH_2$—$CH_2$—$OCH_3$ | $CH_2$—CH=$CH_2$ |
| Ia.459 | Cl | $CH_2$—$CH_2$—$OCH_3$ | $CH_2$—CH=$CH_2$ |
| Ia.460 | H | $CH_2$—$CH_2$—$OCH_3$ | $CH_2$—C≡CH |
| Ia.461 | F | $CH_2$—$CH_2$—$OCH_3$ | $CH_2$—C≡CH |
| Ia.462 | Cl | $CH_2$—$CH_2$—$OCH_3$ | $CH_2$—C≡CH |
| Ia.463 | H | $CH_2$—$CH_2$—$OCH_3$ | $CH_2$—CO—$OCH_3$ |
| Ia.464 | F | $CH_2$—$CH_2$—$OCH_3$ | $CH_2$—CO—$OCH_3$ |
| Ia.465 | Cl | $CH_2$—$CH_2$—$OCH_3$ | $CH_2$—CO—$OCH_3$ |
| Ia.466 | H | $CH_2$—$CH_2$—$OCH_3$ | $CH_2$-phenyl |
| Ia.467 | F | $CH_2$—$CH_2$—$OCH_3$ | $CH_2$-phenyl |
| Ia.468 | Cl | $CH_2$—$CH_2$—$OCH_3$ | $CH_2$-phenyl |
| la.469 | H | $CH_2$—$CH_2$—$OCH_2$—CH=$CH_2$ | $CH_3$ |
| Ia.470 | F | $CH_2$—$CH_2$—$OCH_2$—CH=$CH_2$ | $CH_3$ |
| Ia.471 | Cl | $CH_2$—$CH_2$—$OCH_2$—CH=$CH_2$ | $CH_3$ |
| Ia.472 | H | $CH_2$—$CH_2$—$OCH_2$—CH=$CH_2$ | $C_2H_5$ |
| Ia.473 | F | $CH_2$—$CH_2$—$OCH_2$—CH=$CH_2$ | $C_2H_5$ |
| Ia.474 | Cl | $CH_2$—$CH_2$—$OCH_2$—CH=$CH_2$ | $C_2H_5$ |
| Ia.475 | H | $CH_2$—$CH_2$—$OCH_2$—CH=$CH_2$ | n-$C_3H_7$ |
| Ia.476 | F | $CH_2$—$CH_2$—$OCH_2$—CH=$CH_2$ | n-$C_3H_7$ |
| Ia.477 | Cl | $CH_2$—$CH_2$—$OCH_2$—CH=$CH_2$ | n-$C_3H_7$ |
| Ia.478 | H | $CH_2$—$CH_2$—$OCH_2$—CH=$CH_2$ | n-$C_4H_9$ |
| Ia.479 | F | $CH_2$—$CH_2$—$OCH_2$—CH=$CH_2$ | n-$C_4H_9$ |
| Ia.480 | Cl | $CH_2$—$CH_2$—$OCH_2$—CH=$CH_2$ | n-$C_4H_9$ |
| Ia.481 | H | $CH_2$—$CH_2$—$OCH_2$—CH=$CH_2$ | $CH_2$—CH=$CH_2$ |
| la.482 | F | $CH_2$—$CH_2$—$OCH_2$—CH=$CH_2$ | $CH_2$—CH=$CH_2$ |
| Ia.483 | Cl | $CH_2$—$CH_2$—$OCH_2$—CH=$CH_2$ | $CH_2$—CH=$CH_2$ |
| Ia.484 | H | $CH_2$—$CH_2$—$OCH_2$—CH=$CH_2$ | $CH_2$—C≡CH |
| Ia.485 | F | $CH_2$—$CH_2$—$OCH_2$—CH=$CH_2$ | $CH_2$—C≡CH |
| Ia.486 | Cl | $CH_2$—$CH_2$—$OCH_2$—CH=$CH_2$ | $CH_2$—C≡CH |
| Ia.487 | H | $CH_2$—$CH_2$—$OCH_2$—CH=$CH_2$ | $CH_2$—CO—$OCH_3$ |
| Ia.488 | F | $CH_2$—$CH_2$—$OCH_2$—CH=$CH_2$ | $CH_2$—CO—$OCH_3$ |
| Ia.489 | Cl | $CH_2$—$CH_2$—$OCH_2$—CH=$CH_2$ | $CH_2$—CO—$OCH_3$ |

TABLE 1-continued

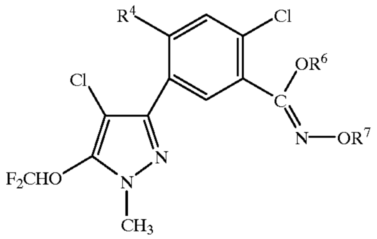

I

| No. | $R^4$ | $R^6$ | $R^7$ |
|---|---|---|---|
| Ia.490 | H | $CH_2{-}CH_2{-}OCH_2{-}CH{=}CH_2$ | $CH_2$-phenyl |
| Ia.491 | F | $CH_2{-}CH_2{-}OCH_2{-}CH{=}CH_2$ | $CH_2$-phenyl |
| Ia.492 | Cl | $CH_2{-}CH_2{-}OCH_2{-}CH{=}CH_2$ | $CH_2$-phenyl |
| Ia.493 | H | $CH_2{-}CH_2{-}$O-cyclopentyl | $CH_3$ |
| Ia.494 | F | $CH_2{-}CH_2{-}$O-cyclopentyl | $CH_3$ |
| Ia.495 | Cl | $CH_2{-}CH_2{-}$O-cyclopentyl | $CH_3$ |
| Ia.496 | H | $CH_2{-}CH_2{-}$O-cyclopentyl | $C_2H_5$ |
| Ia.497 | F | $CH_2{-}CH_2{-}$O-cyclopentyl | $C_2H_5$ |
| Ia.498 | Cl | $CH_2{-}CH_2{-}$O-cyclopentyl | $C_2H_5$ |
| Ia.499 | H | $CH_2{-}CH_2{-}$O-cyclopentyl | n-$C_3H_7$ |
| Ia.500 | F | $CH_2{-}CH_2{-}$O-cyclopentyl | n-$C_3H_7$ |
| Ia.501 | Cl | $CH_2{-}CH_2{-}$O-cyclopentyl | n-$C_3H_7$ |
| Ia.502 | H | $CH_2{-}CH_2{-}$O-cyclopentyl | n-$C_4H_9$ |
| Ia.503 | F | $CH_2{-}CH_2{-}$O-cyclopentyl | n-$C_4H_9$ |
| Ia.504 | Cl | $CH_2{-}CH_2{-}$O-cyclopentyl | n-$C_4H_9$ |
| Ia.505 | H | $CH_2{-}CH_2{-}$O-cyclopentyl | $CH_2{-}CH{=}CH_2$ |
| Ia.506 | F | $CH_2{-}CH_2{-}$O-cyclopentyl | $CH_2{-}CH{=}CH_2$ |
| Ia.507 | Cl | $CH_2{-}CH_2{-}$O-cyclopentyl | $CH_2{-}CH{=}CH_2$ |
| Ia.508 | H | $CH_2{-}CH_2{-}$O-cyclopentyl | $CH_2{-}C{\equiv}CH$ |
| Ia.509 | F | $CH_2{-}CH_2{-}$O-cyclopentyl | $CH_2{-}C{\equiv}CH$ |
| Ia.510 | Cl | $CH_2{-}CH_2{-}$O-cyclopentyl | $CH_2{-}C{\equiv}CH$ |
| Ia.511 | H | $CH_2{-}CH_2{-}$O-cyclopentyl | $CH_2{-}CO{-}OCH_3$ |
| Ia.512 | F | $CH_2{-}CH_2{-}$O-cyclopentyl | $CH_2{-}CO{-}OCH_3$ |
| Ia.513 | Cl | $CH_2{-}CH_2{-}$O-cyclopentyl | $CH_2{-}CO{-}OCH_3$ |
| Ia.514 | H | $CH_2{-}CH_2{-}$O-cyclopentyl | $CH_2$-phenyl |
| Ia.515 | F | $CH_2{-}CH_2{-}$O-cyclopentyl | $CH_2$-phenyl |
| Ia.516 | Cl | $CH_2{-}CH_2{-}$O-cyclopentyl | $CH_2$-phenyl |
| Ia.517 | H | $CH_2{-}CH_2{-}N(CH_3)_2$ | $CH_3$ |
| Ia.518 | F | $CH_2{-}CH_2{-}N(CH_3)_2$ | $CH_3$ |
| Ia.519 | Cl | $CH_2{-}CH_2{-}N(CH_3)_2$ | $CH_3$ |
| Ia.520 | H | $CH_2{-}CH_2{-}N(CH_3)_2$ | $C_2H_5$ |
| Ia.521 | F | $CH_2{-}CH_2{-}N(CH_3)_2$ | $C_2H_5$ |
| Ia.522 | Cl | $CH_2{-}CH_2{-}N(CH_3)_2$ | $C_2H_5$ |
| Ia.523 | H | $CH_2{-}CH_2{-}N(CH_3)_2$ | n-$C_3H_7$ |
| Ia.524 | F | $CH_2{-}CH_2{-}N(CH_3)_2$ | n-$C_3H_7$ |
| Ia.525 | Cl | $CH_2{-}CH_2{-}N(CH_3)_2$ | n-$C_3H_7$ |
| Ia.526 | H | $CH_2{-}CH_2{-}N(CH_3)_2$ | n-$C_4H_9$ |
| Ia.527 | F | $CH_2{-}CH_2{-}N(CH_3)_2$ | n-$C_4H_9$ |
| Ia.528 | Cl | $CH_2{-}CH_2{-}N(CH_3)_2$ | n-$C_4H_9$ |
| Ia.529 | H | $CH_2{-}CH_2{-}N(CH_3)_2$ | $CH_2{-}CH{=}CH_2$ |
| Ia.530 | F | $CH_2{-}CH_2{-}N(CH_3)_2$ | $CH_2{-}CH{=}CH_2$ |
| Ia.531 | Cl | $CH_2{-}CH_2{-}N(CH_3)_2$ | $CH_2{-}CH{=}CH_2$ |
| Ia.532 | H | $CH_2{-}CH_2{-}N(CH_3)_2$ | $CH_2{-}C{\equiv}CH$ |
| Ia.533 | F | $CH_2{-}CH_2{-}N(CH_3)_2$ | $CH_2{-}C{\equiv}CH$ |
| Ia.534 | Cl | $CH_2{-}CH_2{-}N(CH_3)_2$ | $CH_2{-}C{\equiv}CH$ |
| Ia.535 | H | $CH_2{-}CH_2{-}N(CH_3)_2$ | $CH_2{-}CO{-}OCH_3$ |
| Ia.536 | F | $CH_2{-}CH_2{-}N(CH_3)_2$ | $CH_2{-}CO{-}OCH_3$ |
| Ia.537 | Cl | $CH_2{-}CH_2{-}N(CH_3)_2$ | $CH_2{-}CO{-}OCH_3$ |
| Ia.538 | H | $CH_2{-}CH_2{-}N(CH_3)_2$ | $CH_2$-phenyl |
| Ia.539 | F | $CH_2{-}CH_2{-}N(CH_3)_2$ | $CH_2$-phenyl |
| Ia.540 | Cl | $CH_2{-}CH_2{-}N(CH_3)_2$ | $CH_2$-phenyl |
| Ia.541 | H | $CH_2{-}CH_2{-}CH_3$ | $CH_3$ |
| Ia.542 | F | $CH_2{-}CH_2{-}CH_3$ | $CH_3$ |
| Ia.543 | Cl | $CH_2{-}CH_2{-}CH_3$ | $CH_3$ |
| Ia.544 | H | $CH_2{-}CH_2{-}SCH_3$ | $C_2H_5$ |
| Ia.545 | F | $CH_2{-}CH_2{-}SCH_3$ | $C_2H_5$ |
| Ia.546 | Cl | $CH_2{-}CH_2{-}SCH_3$ | $C_2H_5$ |
| Ia.547 | H | $CH_2{-}CH_2{-}SCH_3$ | n-$C_3H_7$ |
| Ia.548 | F | $CH_2{-}CH_2{-}SCH_3$ | n-$C_3H_7$ |
| Ia.549 | Cl | $CH_2{-}CH_2{-}SCH_3$ | n-$C_3H_7$ |
| Ia.550 | H | $CH_2{-}CH_2{-}SCH_3$ | n-$C_4H_9$ |
| Ia.551 | F | $CH_2{-}CH_2{-}SCH_3$ | n-$C_4H_9$ |
| Ia.552 | Cl | $CH_2{-}CH_2{-}SCH_3$ | n-$C_4H_9$ |

TABLE 1-continued

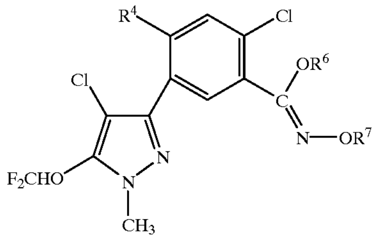

I

| No. | $R^4$ | $R^6$ | $R^7$ |
|---|---|---|---|
| Ia.553 | H | $CH_2$—$CH_2$—$SCH_3$ | $CH_2$—CH═$CH_2$ |
| Ia.554 | F | $CH_2$—$CH_2$—$SCH_3$ | $CH_2$—CH═$CH_2$ |
| Ia.555 | Cl | $CH_2$—$CH_2$—$SCH_3$ | $CH_2$—CH═$CH_2$ |
| Ia.556 | H | $CH_2$—$CH_2$—$SCH_3$ | $CH_2$—C≡CH |
| Ia.557 | F | $CH_2$—$CH_2$—$SCH_3$ | $CH_2$—C≡CH |
| Ia.558 | Cl | $CH_2$—$CH_2$—$SCH_3$ | $CH_2$—C≡CH |
| Ia.559 | H | $CH_2$—$CH_2$—$SCH_3$ | $CH_2$—CO—$OCH_3$ |
| Ia.560 | F | $CH_2$—$CH_2$—$SCH_3$ | $CH_2$—CO—$OCH_3$ |
| Ia.561 | Cl | $CH_2$—$CH_2$—$SCH_3$ | $CH_2$—CO—$OCH_3$ |
| Ia.562 | H | $CH_2$—$CH_2$—$SCH_3$ | $CH_2$-phenyl |
| Ia.563 | F | $CH_2$—$CH_2$—$SCH_3$ | $CH_2$-phenyl |
| Ia.564 | Cl | $CH_2$—$CH_2$—$SCH_3$ | $CH_2$-phenyl |
| Ia.565 | H | $CH_2$—$CH_2$—$SO_2$—$CH_3$ | $CH_3$ |
| Ia.566 | F | $CH_2$—$CH_2$—$SO_2$—$CH_3$ | $CH_3$ |
| Ia.567 | Cl | $CH_2$—$CH_2$—$SO_2$—$CH_3$ | $CH_3$ |
| Ia.568 | H | $CH_2$—$CH_2$—$SO_2$—$CH_3$ | $C_2H_5$ |
| Ia.569 | F | $CH_2$—$CH_2$—$SO_2$—$CH_3$ | $C_2H_5$ |
| Ia.570 | Cl | $CH_2$—$CH_2$—$SO_2$—$CH_3$ | $C_2H_5$ |
| Ia.571 | H | $CH_2$—$CH_2$—$SO_2$—$CH_3$ | n-$C_3H_7$ |
| Ia.572 | F | $CH_2$—$CH_2$—$SO_2$—$CH_3$ | n-$C_3H_7$ |
| Ia.573 | Cl | $CH_2$—$CH_2$—$SO_2$—$CH_3$ | n-$C_3H_7$ |
| Ia.574 | H | $CH_2$—$CH_2$—$SO_2$—$CH_3$ | n-$C_4H_9$ |
| Ia.575 | F | $CH_2$—$CH_2$—$SO_2$—$CH_3$ | n-$C_4H_9$ |
| Ia.576 | Cl | $CH_2$—$CH_2$—$SO_2$—$CH_3$ | n-$C_4H_9$ |
| Ia.577 | H | $CH_2$—$CH_2$—$SO_2$—$CH_3$ | $CH_2$—CH═$CH_2$ |
| Ia.578 | F | $CH_2$—$CH_2$—$SO_2$—$CH_3$ | $CH_2$—CH═$CH_2$ |
| Ia.579 | Cl | $CH_2$—$CH_2$—$SO_2$—$CH_3$ | $CH_2$—CH═$CH_2$ |
| Ia.580 | H | $CH_2$—$CH_2$—$SO_2$—$CH_3$ | $CH_2$—C≡CH |
| Ia.581 | F | $CH_2$—$CH_2$—$SO_2$—$CH_3$ | $CH_2$—C≡CH |
| Ia.582 | Cl | $CH_2$—$CH_2$—$SO_2$—$CH_3$ | $CH_2$—C≡CH |
| la.583 | H | $CH_2$—$CH_2$—$SO_2$—$CH_3$ | $CH_2$—CO—$OCH_3$ |
| Ia.584 | F | $CH_2$—$CH_2$—$SO_2$—$CH_3$ | $CH_2$—CO—$OCH_3$ |
| Ia.585 | Cl | $CH_2$—$CH_2$—$SO_2$—$CH_3$ | $CH_2$—CO—$OCH_3$ |
| Ia.586 | H | $CH_2$—$CH_2$—$SO_2$—$CH_3$ | $CH_2$-phenyl |
| Ia.587 | F | $CH_2$—$CH_2$—$SO_2$—$CH_3$ | $CH_2$-phenyl |
| Ia.588 | Cl | $CH_2$—$CH_2$—$SO_2$—$CH_3$ | $CH_2$-phenyl |
| Ia.589 | H | $CH_2$—CH═$CH_2$ | $CH_3$ |
| Ia.590 | F | $CH_2$—CH═$CH_2$ | $CH_3$ |
| Ia.591 | Cl | $CH_2$—CH═$CH_2$ | $CH_3$ |
| Ia.592 | H | $CH_2$—CH═$CH_2$ | $C_2H_5$ |
| Ia.593 | F | $CH_2$—CH═$CH_2$ | $C_2H_5$ |
| Ia.594 | Cl | $CH_2$—CH═$CH_2$ | $C_2H_5$ |
| Ia.595 | H | $CH_2$—CH═$CH_2$ | n-$C_3H_7$ |
| Ia.596 | F | $CH_2$—CH═$CH_2$ | n-$C_3H_7$ |
| Ia.597 | Cl | $CH_2$—CH═$CH_2$ | n-$C_3H_7$ |
| Ia.598 | H | $CH_2$—CH═$CH_2$ | n-$C_4H_9$ |
| Ia.599 | F | $CH_2$—CH═$CH_2$ | n-$C_4H_9$ |
| Ia.600 | Cl | $CH_2$—CH═$CH_2$ | n-$C_4H_9$ |
| Ia.601 | H | $CH_2$—CH═$CH_2$ | $CH_2$—CH═$CH_2$ |
| Ia.602 | F | $CH_2$—CH═$CH_2$ | $CH_2$—CH═$CH_2$ |
| Ia.603 | Cl | $CH_2$—CH═$CH_2$ | $CH_2$—CH═$CH_2$ |
| Ia.604 | H | $CH_2$—CH═$CH_2$ | $CH_2$—C≡CH |
| Ia.605 | F | $CH_2$—CH═$CH_2$ | $CH_2$—C≡CH |
| Ia.606 | Cl | $CH_2$—CH═$CH_2$ | $CH_2$—C≡CH |
| Ia.607 | H | $CH_2$—CH═$CH_2$ | $CH_2$—CO—$OCH_3$ |
| Ia.608 | F | $CH_2$—CH═$CH_2$ | $CH_2$—CO—$OCH_3$ |
| Ia.609 | Cl | $CH_2$—CH═$CH_2$ | $CH_2$—CO—$OCH_3$ |
| Ia.610 | H | $CH_2$—CH═$CH_2$ | $CH_2$-phenyl |
| Ia.611 | F | $CH_2$—CH═$CH_2$ | $CH_2$-phenyl |
| Ia.612 | Cl | $CH_2$—CH═$CH_2$ | $CH_2$-phenyl |
| Ia.613 | H | $CH_2$—CH═CH—$CH_3$ | $CH_3$ |
| Ia.614 | F | $CH_2$—CH═CH—$CH_3$ | $CH_3$ |
| Ia.615 | Cl | $CH_2$—CH═CH—$CH_3$ | $CH_3$ |

TABLE 1-continued

I

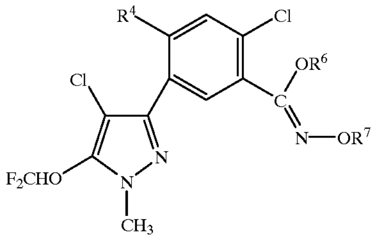

| No. | $R^4$ | $R^6$ | $R^7$ |
|---|---|---|---|
| Ia.616 | H | $CH_2$—CH═CH—$CH_3$ | $C_2H_5$ |
| Ia.617 | F | $CH_2$—CH═CH—$CH_3$ | $C_2H_5$ |
| Ia.618 | Cl | $CH_2$—CH═CH—$CH_3$ | $C_2H_5$ |
| Ia.619 | H | $CH_2$—CH═CH—$CH_3$ | n-$C_3H_7$ |
| Ia.620 | F | $CH_2$—CH═CH—$CH_3$ | n-$C_3H_7$ |
| Ia.621 | Cl | $CH_2$—CH═CH—$CH_3$ | n-$C_3H_7$ |
| Ia.622 | H | $CH_2$—CH═CH—$CH_3$ | n-$C_4H_9$ |
| Ia.623 | F | $CH_2$—CH═CH—$CH_3$ | n-$C_4H_9$ |
| Ia.624 | Cl | $CH_2$—CH═CH—$CH_3$ | n-$C_4H_9$ |
| Ia.625 | H | $CH_2$—CH═CH—$CH_3$ | $CH_2$—CH═$CH_2$ |
| Ia.626 | F | $CH_2$—CH═CH—$CH_3$ | $CH_2$—CH═$CH_2$ |
| Ia.627 | Cl | $CH_2$—CH═CH—$CH_3$ | $CH_2$—CH═$CH_2$ |
| Ia.628 | H | $CH_2$—CH═CH—$CH_3$ | $CH_2$—C≡CH |
| Ia.629 | F | $CH_2$—CH═CH—$CH_3$ | $CH_2$—C≡CH |
| Ia.631 | F | $CH_2$—CH═CH—$CH_3$ | $CH_2$—CO—$OCH_3$ |
| Ia.632 | F | $CH_2$—CH═CH—$CH_3$ | $CH_2$—CO—$OCH_3$ |
| Ia.633 | Cl | $CH_2$—CH═CH—$CH_3$ | $CH_2$—CO—$OCH_3$ |
| Ia.634 | H | $CH_2$—CH═CH—$CH_3$ | $CH_2$—phenyl |
| Ia.635 | F | $CH_2$—CH═CH—$CH_3$ | $CH_2$—phenyl |
| Ia.636 | Cl | $CH_2$—CH═CH—$CH_3$ | $CH_2$—phenyl |
| Ia.637 | H | $CH_2$—CH═CH—Cl | $CH_3$ |
| Ia.638 | F | $CH_2$—CH═CH—Cl | $CH_3$ |
| Ia.639 | Cl | $CH_2$—CH═CH—Cl | $CH_3$ |
| Ia.640 | H | $CH_2$—CH═CH—Cl | $C_2H_5$ |
| Ia.641 | F | $CH_2$—CH═CH—Cl | $C_2H_5$ |
| Ia.642 | Cl | $CH_2$—CH═CH—Cl | $C_2H_5$ |
| Ia.643 | H | $CH_2$—CH═CH—Cl | n-$C_3H_7$ |
| Ia.644 | F | $CH_2$—CH═CH—Cl | n-$C_3H_7$ |
| Ia.645 | Cl | $CH_2$—CH═CH—Cl | n-$C_3H_7$ |
| Ia.646 | H | $CH_2$—CH═CH—Cl | n-$C_4H_9$ |
| Ia.647 | F | $CH_2$—CH═CH—Cl | n-$C_4H_9$ |
| Ia.648 | Cl | $CH_2$—CH═CH—Cl | n-$C_4H_9$ |
| Ia.649 | H | $CH_2$—CH═CH—Cl | $CH_2$—CH═$CH_2$ |
| Ia.650 | F | $CH_2$—CH═CH—Cl | $CH_2$—CH═$CH_2$ |
| Ia.651 | Cl | $CH_2$—CH═CH—Cl | $CH_2$—CH═$CH_2$ |
| Ia.652 | H | $CH_2$—CH═CH—Cl | $CH_2$—C≡CH |
| Ia.653 | F | $CH_2$—CH═CH—Cl | $CH_2$—C≡CH |
| Ia.654 | Cl | $CH_2$—CH═CH—Cl | $CH_2$—C≡CH |
| Ia.655 | H | $CH_2$—CH═CH—Cl | $CH_2$—CO—$OCH_3$ |
| Ia.656 | F | $CH_2$—CH═CH—Cl | $CH_2$—CO—$OCH_3$ |
| Ia.657 | Cl | $CH_2$—CH═CH—Cl | $CH_2$—CO—$OCH_3$ |
| Ia.658 | H | $CH_2$—CH═CH—Cl | $CH_2$-phenyl |
| Ia.659 | F | $CH_2$—CH═CH—Cl | $CH_2$-phenyl |
| Ia.660 | Cl | $CH_2$—CH═CH—Cl | $CH_2$-phenyl |
| Ia.661 | H | $CH_2$—C≡CH | $CH_3$ |
| Ia.662 | F | $CH_2$—C≡CH | $CH_3$ |
| Ia.663 | Cl | $CH_2$—C≡CH | $CH_3$ |
| Ia.664 | H | $CH_2$—C≡CH | $C_2H_5$ |
| Ia.665 | F | $CH_2$—C≡CH | $C_2H_5$ |
| Ia.666 | Cl | $CH_2$—C≡CH | $C_2H_5$ |
| Ia.667 | H | $CH_2$—C≡CH | n-$C_3H_7$ |
| Ia.668 | F | $CH_2$—C≡CH | n-$C_3H_7$ |
| Ia.669 | Cl | $CH_2$—C≡CH | n-$C_3H_7$ |
| Ia.670 | H | $CH_2$—C≡CH | n-$C_4H_9$ |
| Ia.671 | F | $CH_2$—C≡CH | n-$C_4H_9$ |
| Ia.672 | Cl | $CH_2$—C≡CH | n-$C_4H_9$ |
| Ia.673 | H | $CH_2$—C≡CH | $CH_2$—CH═$CH_2$ |
| Ia.674 | F | $CH_2$—C≡CH | $CH_2$—CH═$CH_2$ |
| Ia.675 | Cl | $CH_2$—C≡CH | $CH_2$—CH═$CH_2$ |
| Ia.676 | H | $CH_2$—C≡CH | $CH_2$—C≡CH |
| Ia.677 | F | $CH_2$—C≡CH | $CH_2$—C≡CH |
| Ia.678 | Cl | $CH_2$—C≡CH | $CH_2$—C≡CH |
| Ia.679 | H | $CH_2$—C≡CH | $CH_2$—CO—$OCH_3$ |

TABLE 1-continued

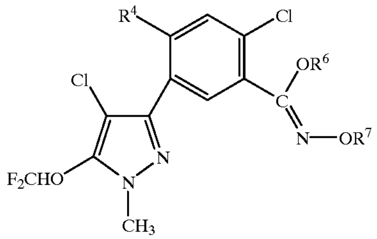

I

| No. | $R^4$ | $R^6$ | $R^7$ |
|---|---|---|---|
| Ia.680 | F | $CH_2$—C≡CH | $CH_2$—CO—$OCH_3$ |
| Ia.681 | Cl | $CH_2$—C≡CH | $CH_2$—CO—$OCH_3$ |
| Ia.682 | H | $CH_2$—C≡CH | $CH_2$-phenyl |
| Ia.683 | F | $CH_2$—C≡CH | $CH_2$-phenyl |
| Ia.684 | Cl | $CH_2$—C≡CH | $CH_2$-phenyl |
| Ia.685 | H | CO—$CH_3$ | $CH_3$ |
| Ia.686 | F | CO—$CH_3$ | $CH_3$ |
| Ia.687 | Cl | CO—$CH_3$ | $CH_3$ |
| Ia.688 | H | CO—$CH_3$ | $C_2H_5$ |
| Ia.689 | F | CO—$CH_3$ | $C_2H_5$ |
| Ia.690 | Cl | CO—$CH_3$ | $C_2H_5$ |
| Ia.691 | H | CO—$CH_3$ | n-$C_3H_7$ |
| Ia.692 | F | CO—$CH_3$ | n-$C_3H_7$ |
| Ia.693 | Cl | CO—$CH_3$ | n-$C_3H_7$ |
| Ia.694 | H | CO—$CH_3$ | n-$C_4H_9$ |
| Ia.695 | F | CO—$CH_3$ | n-$C_4H_9$ |
| Ia.696 | Cl | CO—$CH_3$ | n-$C_4H_9$ |
| Ia.697 | H | CO—$CH_3$ | $CH_2$—CH═$CH_2$ |
| Ia.698 | F | CO—$CH_3$ | $CH_2$—CH═$CH_2$ |
| Ia.699 | Cl | CO—$CH_3$ | $CH_2$—CH═$CH_2$ |
| Ia.700 | H | CO—$CH_3$ | $CH_2$—C≡CH |
| Ia.701 | F | CO—$CH_3$ | $CH_2$—C≡CH |
| Ia.702 | Cl | CO—$CH_3$ | $CH_2$—C≡CH |
| Ia.703 | H | CO—$CH_3$ | $CH_2$—CO—$OCH_3$ |
| Ia.704 | F | CO—$CH_3$ | $CH_2$—CO—$OCH_3$ |
| Ia.705 | Cl | CO—$CH_3$ | $CH_2$—CO—$OCH_3$ |
| Ia.706 | H | CO—$CH_3$ | $CH_2$-phenyl |
| Ia.707 | F | CO—$CH_3$ | $CH_2$-phenyl |
| Ia.708 | Cl | CO—$CH_3$ | $CH_2$-phenyl |
| Ia.709 | H | CO—$C_2H_5$ | $CH_3$ |
| Ia.710 | F | CO—$C_2H_5$ | $CH_3$ |
| Ia.711 | Cl | CO—$C_2H_5$ | $CH_3$ |
| Ia.712 | H | CO—$C_2H_5$ | $C_2H_5$ |
| Ia.713 | F | CO—$C_2H_5$ | $C_2H_5$ |
| Ia.714 | Cl | CO—$C_2H_5$ | $C_2H_5$ |
| Ia.715 | H | CO—$C_2H_5$ | n-$C_3H_7$ |
| Ia.716 | F | CO—$C_2H_5$ | n-$C_3H_7$ |
| Ia.717 | Cl | CO—$C_2H_5$ | n-$C_3H_7$ |
| Ia.718 | H | CO—$C_2H_5$ | n-$C_4H_9$ |
| Ia.719 | F | CO—$C_2H_5$ | n-$C_4H_9$ |
| Ia.720 | Cl | CO—$C_2H_5$ | n-$C_4H_9$ |
| Ia.721 | H | CO—$C_2H_5$ | $CH_2$—CH═$CH_2$ |
| Ia.722 | F | CO—$C_2H_5$ | $CH_2$—CH═$CH_2$ |
| Ia.723 | Cl | CO—$C_2H_5$ | $CH_2$—CH═$CH_2$ |
| Ia.724 | H | CO—$C_2H_5$ | $CH_2$—C≡CH |
| Ia.725 | F | CO—$C_2H_5$ | $CH_2$—C≡CH |
| Ia.726 | Cl | CO—$C_2H_5$ | $CH_2$—C≡CH |
| Ia.727 | H | CO—$C_2H_5$ | $CH_2$—CO—$OCH_3$ |
| Ia.728 | F | CO—$C_2H_5$ | $CH_2$—CO—$OCH_3$ |
| Ia.729 | Cl | CO—$C_2H_5$ | $CH_2$—CO—$OCH_3$ |
| Ia.730 | H | CO—$C_2H_5$ | $CH_2$-phenyl |
| Ia.731 | F | CO—$C_2H_5$ | $CH_2$-phenyl |
| Ia.732 | Cl | CO—$C_2H_5$ | $CH_2$-phenyl |
| Ia.733 | H | CO—$CH_2Cl$ | $CH_3$ |
| Ia.734 | F | CO—$CH_2Cl$ | $CH_3$ |
| Ia.735 | Cl | CO—$CH_2Cl$ | $CH_3$ |
| Ia.736 | H | CO—$CH_2Cl$ | $C_2H_5$ |
| Ia.737 | F | CO—$CH_2Cl$ | $C_2H_5$ |
| Ia.738 | Cl | CO—$CH_2Cl$ | $C_2H_5$ |
| Ia.739 | H | CO—$CH_2Cl$ | n-$C_3H_7$ |
| Ia.740 | F | CO—$CH_2Cl$ | n-$C_3H_7$ |
| Ia.741 | Cl | CO—$CH_2Cl$ | n-$C_3H_7$ |
| Ia.742 | H | CO—$CH_2Cl$ | n-$C_4H_9$ |

TABLE 1-continued

I

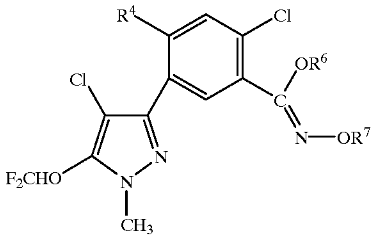

| No. | $R^4$ | $R^6$ | $R^7$ |
|---|---|---|---|
| Ia.743 | F | CO—$CH_2Cl$ | n-$C_4H_9$ |
| Ia.744 | Cl | CO—$CH_2Cl$ | n-$C_4H_9$ |
| Ia.745 | H | CO—$CH_2Cl$ | $CH_2$—CH═$CH_2$ |
| Ia.746 | F | CO—$CH_2Cl$ | $CH_2$—CH═$CH_2$ |
| Ia.747 | Cl | CO—$CH_2Cl$ | $CH_2$—CH═$CH_2$ |
| Ia.748 | H | CO—$CH_2Cl$ | $CH_2$—C≡CH |
| Ia.749 | F | CO—$CH_2Cl$ | $CH_2$—C≡CH |
| Ia.750 | Cl | CO—$CH_2Cl$ | $CH_2$—C≡CH |
| Ia.751 | H | CO—$CH_2Cl$ | $CH_2$—CO—$OCH_3$ |
| Ia.752 | F | CO—$CH_2Cl$ | $CH_2$—CO—$OCH_3$ |
| Ia.753 | Cl | CO—$CH_2Cl$ | $CH_2$—CO—$OCH_3$ |
| Ia.754 | H | CO—$CH_2Cl$ | $CH_2$-phenyl |
| Ia.755 | F | CO—$CH_2Cl$ | $CH_2$-phenyl |
| Ia.756 | Cl | CO—$CH_2Cl$ | $CH_2$-phenyl |
| Ia.757 | H | CO—$CF_3$ | $CH_3$ |
| Ia.758 | F | CO—$CF_3$ | $CH_3$ |
| Ia.759 | Cl | CO—$CF_3$ | $CH_3$ |
| Ia.760 | H | CO—$CF_3$ | $C_2H_5$ |
| Ia.761 | F | CO—$CF_3$ | $C_2H_5$ |
| Ia.762 | Cl | CO—$CF_3$ | $C_2H_5$ |
| Ia.763 | H | CO—$CF_3$ | n-$C_3H_7$ |
| Ia.764 | F | CO—$CF_3$ | n-$C_3H_7$ |
| Ia.765 | Cl | CO—$CF_3$ | n-$C_3H_7$ |
| Ia.766 | H | CO—$CF_3$ | n-$C_4H_9$ |
| Ia.767 | F | CO—$CF_3$ | n-$C_4H_9$ |
| Ia.768 | Cl | CO—$CF_3$ | n-$C_4H_9$ |
| Ia.769 | H | CO—$CF_3$ | $CH_2$—CH═$CH_2$ |
| Ia.770 | F | CO—$CF_3$ | $CH_2$—CH═$CH_2$ |
| Ia.771 | Cl | CO—$CF_3$ | $CH_2$—CH═$CH_2$ |
| Ia.772 | H | CO—$CF_3$ | $CH_2$—C≡CH |
| Ia.773 | F | CO—$CF_3$ | $CH_2$—C≡CH |
| Ia.774 | Cl | CO—$CF_3$ | $CH_2$—C≡CH |
| Ia.775 | H | CO—$CF_3$ | $CH_2$—CO—$OCH_3$ |
| Ia.776 | F | CO—$CF_3$ | $CH_2$—CO—$OCH_3$ |
| Ia.777 | Cl | CO—$CF_3$ | $CH_2$—CO—$OCH_3$ |
| Ia.778 | H | CO—$CF_3$ | $CH_2$-phenyl |
| Ia.779 | F | CO—$CF_3$ | $CH_2$-phenyl |
| Ia.780 | Cl | CO—$CF_3$ | $CH_2$-phenyl |
| Ia.781 | H | CO—$OCH_3$ | $CH_3$ |
| Ia.782 | F | CO—$OCH_3$ | $CH_3$ |
| Ia.783 | Cl | CO—$OCH_3$ | $CH_3$ |
| Ia.784 | H | CO—$OCH_3$ | $C_2H_5$ |
| Ia.785 | F | CO—$OCH_3$ | $C_2H_5$ |
| Ia.786 | Cl | CO—$OCH_3$ | $C_2H_5$ |
| la.787 | H | CO—$OCH_3$ | n-$C_3H_7$ |
| Ia.788 | F | CO—$OCH_3$ | n-$C_3H_7$ |
| Ia.789 | Cl | CO—$OCH_3$ | n-$C_3H_7$ |
| Ia.790 | H | CO—$OCH_3$ | n-$C_4H_9$ |
| Ia.791 | F | CO—$OCH_3$ | n-$C_4H_9$ |
| Ia.792 | Cl | CO—$OCH_3$ | n-$C_4H_9$ |
| Ia.793 | H | CO—$OCH_3$ | $CH_2$—CH═$CH_2$ |
| Ia.794 | F | CO—$OCH_3$ | $CH_2$—CH═$CH_2$ |
| Ia.795 | Cl | CO—$OCH_3$ | $CH_2$—CH═$CH_2$ |
| Ia.796 | H | CO—$OCH_3$ | $CH_2$—C≡CH |
| Ia.797 | F | CO—$OCH_3$ | $CH_2$—C≡CH |
| Ia.798 | Cl | CO—$OCH_3$ | $CH_2$—C≡CH |
| Ia.799 | H | CO—$OCH_3$ | $CH_2$—CO—$OCH_3$ |
| Ia.800 | F | CO—$OCH_3$ | $CH_2$—CO—$OCH_3$ |
| Ia.801 | Cl | CO—$OCH_3$ | $CH_2$—CO—$OCH_3$ |
| Ia.802 | H | CO—$OCH_3$ | $CH_2$-phenyl |
| Ia.803 | F | CO—$OCH_3$ | $CH_2$-phenyl |
| Ia.804 | Cl | CO—$OCH_3$ | $CH_2$-phenyl |
| Ia.805 | H | CO—$OC_2H_5$ | $CH_3$ |

TABLE 1-continued

I

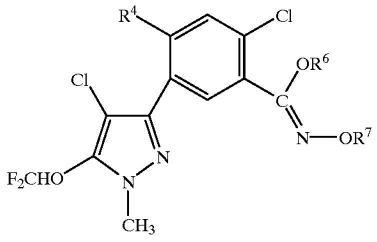

| No. | $R^4$ | $R^6$ | $R^7$ |
|---|---|---|---|
| Ia.806 | F | CO—$OC_2H_5$ | $CH_3$ |
| Ia.807 | Cl | CO—$OC_2H_5$ | $CH_3$ |
| Ia.808 | H | CO—$OC_2H_5$ | $C_2H_5$ |
| Ia.809 | F | CO—$OC_2H_5$ | $C_2H_5$ |
| Ia.810 | Cl | CO—$OC_2H_5$ | $C_2H_5$ |
| Ia.811 | H | CO—$OC_2H_5$ | n-$C_3H_7$ |
| Ia.812 | F | CO—$OC_2H_5$ | n-$C_3H_7$ |
| Ia.813 | Cl | CO—$OC_2H_5$ | n-$C_3H_7$ |
| Ia.814 | H | CO—$OC_2H_5$ | n-$C_4H_9$ |
| Ia.815 | F | CO—$OC_2H_5$ | n-$C_4H_9$ |
| Ia.816 | Cl | CO—$OC_2H_5$ | n-$C_4H_9$ |
| Ia.817 | H | CO—$OC_2H_5$ | $CH_2$—CH═$CH_2$ |
| Ia.818 | F | CO—$OC_2H_5$ | $CH_2$—CH═$CH_2$ |
| Ia.819 | Cl | CO—$OC_2H_5$ | $CH_2$—CH═$CH_2$ |
| Ia.820 | H | CO—$OC_2H_5$ | $CH_2$—C≡CH |
| Ia.821 | F | CO—$OC_2H_5$ | $CH_2$—C≡CH |
| Ia.822 | Cl | CO—$OC_2H_5$ | $CH_2$—C≡CH |
| Ia.823 | H | CO—$OC_2H_5$ | $CH_2$—CO—$OCH_3$ |
| Ia.824 | F | CO—$OC_2H_5$ | $CH_2$—CO—$OCH_3$ |
| Ia.825 | Cl | CO—$OC_2H_5$ | $CH_2$—CO—$OCH_3$ |
| Ia.826 | H | CO—$OC_2H_5$ | $CH_2$-phenyl |
| Ia.827 | F | CO—$OC_2H_5$ | $CH_2$-phenyl |
| Ia.828 | Cl | CO—$OC_2H_5$ | $CH_2$-phenyl |
| Ia.829 | H | CO—$N(CH_3)_2$ | $CH_3$ |
| Ia.830 | F | CO—$N(CH_3)_2$ | $CH_3$ |
| Ia.831 | Cl | CO—$N(CH_3)_2$ | $CH_3$ |
| Ia.832 | H | CO—$N(CH_3)_2$ | $C_2H_5$ |
| Ia.833 | F | CO—$N(CH_3)_2$ | $C_2H_5$ |
| Ia.834 | Cl | CO—$N(CH_3)_2$ | $C_2H_5$ |
| Ia.835 | H | CO—$N(CH_3)_2$ | n-$C_3H_7$ |
| Ia.836 | F | CO—$N(CH_3)_2$ | n-$C_3H_7$ |
| Ia.837 | Cl | CO—$N(CH_3)_2$ | n-$C_3H_7$ |
| Ia.838 | H | CO—$N(CH_3)_2$ | n-$C_4H_9$ |
| Ia.839 | F | CO—$N(CH_3)_2$ | n-$C_4H_9$ |
| Ia.840 | Cl | CO—$N(CH_3)_2$ | n-$C_4H_9$ |
| Ia.841 | H | CO—$N(CH_3)_2$ | $CH_2$—CH═$CH_2$ |
| Ia.842 | F | CO—$N(CH_3)_2$ | $CH_2$—CH═$CH_2$ |
| Ia.843 | Cl | CO—$N(CH_3)_2$ | $CH_2$—CH═$CH_2$ |
| Ia.844 | H | CO—$N(CH_3)_2$ | $CH_2$—C≡CH |
| Ia.845 | F | CO—$N(CH_3)_2$ | $CH_2$—C≡CH |
| Ia.846 | Cl | CO—$N(CH_3)_2$ | $CH_2$—C≡CH |
| Ia.847 | H | CO—$N(CH_3)_2$ | $CH_2$—CO—$OCH_3$ |
| Ia.848 | F | CO—$N(CH_3)_2$ | $CH_2$—CO—$OCH_3$ |
| Ia.849 | Cl | CO—$N(CH_3)_2$ | $CH_2$—CO—$OCH_3$ |
| Ia.850 | H | CO—$N(CH_3)_2$ | $CH_2$-phenyl |
| Ia.851 | F | CO—$N(CH_3)_2$ | $CH_2$-phenyl |
| Ia.852 | Cl | CO—$N(CH_3)_2$ | $CH_2$-phenyl |
| Ia.853 | H | CO—$N(C_2H_5)_2$ | $CH_3$ |
| Ia.854 | F | CO—$N(C_2H_5)_2$ | $CH_3$ |
| Ia.855 | Cl | CO—$N(C_2H_5)_2$ | $CH_3$ |
| Ia.856 | H | CO—$N(C_2H_5)_2$ | $C_2H_5$ |
| Ia.857 | F | CO—$N(C_2H_5)_2$ | $C_2H_5$ |
| Ia.858 | Cl | CO—$N(C_2H_5)_2$ | $C_2H_5$ |
| Ia.859 | H | CO—$N(C_2H_5)_2$ | n-$C_3H_7$ |
| Ia.860 | F | CO—$N(C_2H_5)_2$ | n-$C_3H_7$ |
| Ia.861 | Cl | CO—$N(C_2H_5)_2$ | n-$C_3H_7$ |
| Ia.862 | H | CO—$N(C_2H_5)_2$ | n-$C_4H_9$ |
| Ia.863 | F | CO—$N(C_2H_5)_2$ | n-$C_4H_9$ |
| Ia.864 | Cl | CO—$N(C_2H_5)_2$ | n-$C_4H_9$ |
| Ia.865 | H | CO—$N(C_2H_5)_2$ | $CH_2$—CH═$CH_2$ |
| Ia.866 | F | CO—$N(C_2H_5)_2$ | $CH_2$—CH═$CH_2$ |
| Ia.867 | Cl | CO—$N(C_2H_5)_2$ | $CH_2$—CH═$CH_2$ |
| Ia.868 | H | CO—$N(C_2H_5)_2$ | $CH_2$—C≡CH |

TABLE 1-continued

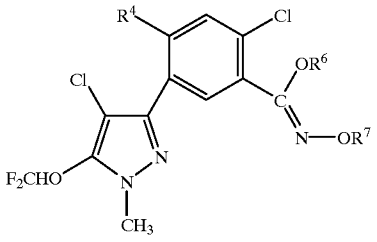

I

| No. | $R^4$ | $R^6$ | $R^7$ |
|---|---|---|---|
| Ia.869 | F | $CO—N(C_2H_5)_2$ | $CH_2—C≡CH$ |
| Ia.870 | Cl | $CO—N(C_2H_5)_2$ | $CH_2—C≡CH$ |
| Ia.871 | H | $CO—N(C_2H_5)_2$ | $CH_2—CO—OCH_3$ |
| Ia.872 | F | $CO—N(C_2H_5)_2$ | $CH_2—CO—OCH_3$ |
| Ia.873 | Cl | $CO—N(C_2H_5)_2$ | $CH_2—CO—OCH_3$ |
| Ia.874 | H | $CO—N(C_2H_5)_2$ | $CH_2$-phenyl |
| Ia.875 | F | $CO—N(C_2H_5)_2$ | $CH_2$-phenyl |
| Ia.876 | Cl | $CO—N(C_2H_5)_2$ | $CH_2$-phenyl |
| Ia.877 | H | $SO_2—CH_3$ | $CH_3$ |
| Ia.878 | F | $SO_2—CH_3$ | $CH_3$ |
| Ia.879 | Cl | $SO_2—CH_3$ | $CH_3$ |
| Ia.880 | H | $SO_2—CH_3$ | $C_2H_5$ |
| Ia.881 | F | $SO_2—CH_3$ | $C_2H_5$ |
| Ia.882 | Cl | $SO_2—CH_3$ | $C_2H_5$ |
| Ia.883 | H | $SO_2—CH_3$ | n-$C_3H_7$ |
| Ia.884 | F | $SO_2—CH_3$ | n-$C_3H_7$ |
| Ia.885 | Cl | $SO_2—CH_3$ | n-$C_3H_7$ |
| Ia.886 | H | $SO_2—CH_3$ | n-$C_4H_9$ |
| Ia.887 | F | $SO_2—CH_3$ | n-$C_4H_9$ |
| Ia.888 | Cl | $SO_2—CH_3$ | n-$C_4H_9$ |
| Ia.889 | H | $SO_2—CH_3$ | $CH_2—CH{=}CH_2$ |
| Ia.890 | F | $SO_2—CH_3$ | $CH_2—CH{=}CH_2$ |
| Ia.891 | Cl | $SO_2—CH_3$ | $CH_2—CH{=}CH_2$ |
| Ia.892 | H | $SO_2—CH_3$ | $CH_2—C≡CH$ |
| Ia.893 | F | $SO_2—CH_3$ | $CH_2—C≡CH$ |
| Ia.894 | Cl | $SO_2—CH_3$ | $CH_2—C≡CH$ |
| Ia.895 | H | $SO_2—CH_3$ | $CH_2—CO—OCH_3$ |
| Ia.896 | F | $SO_2—CH_3$ | $CH_2—CO—OCH_3$ |
| Ia.897 | Cl | $SO_2—CH_3$ | $CH_2—CO—OCH_3$ |
| Ia.898 | H | $SO_2—CH_3$ | $CH_2$-phenyl |
| Ia.899 | F | $SO_2—CH_3$ | $CH_2$-phenyl |
| Ia.900 | Cl | $SO_2—CH_3$ | $CH_2$-phenyl |
| Ia.901 | H | $CH_2—CO—CH_3$ | $CH_3$ |
| Ia.902 | p | $CH_2—CO—CH_3$ | $CH_3$ |
| Ia.903 | Cl | $CH_2—CO—CH_3$ | $CH_3$ |
| Ia.904 | H | $CH_2—CO—CH_3$ | $C_2H_5$ |
| Ia.905 | F | $CH_2—CO—CH_3$ | $C_2H_5$ |
| Ia.906 | Cl | $CH_2—CO—CH_3$ | $C_2H_5$ |
| Ia.907 | H | $CH_2—CO—CH_3$ | n-$C_3H_7$ |
| Ia.908 | F | $CH_2—CO—CH_3$ | n-$C_3H_7$ |
| Ia.909 | Cl | $CH_2—CO—CH_3$ | n-$C_3H_7$ |
| Ia.910 | H | $CH_2—CO—CH_3$ | n-$C_4H_9$ |
| Ia.911 | F | $CH_2—CO—CH_3$ | n-$C_4H_9$ |
| Ia.912 | Cl | $CH_2—CO—CH_3$ | n-$C_4H_9$ |
| Ia.913 | H | $CH_2—CO—CH_3$ | $CH_2—CH{=}CH_2$ |
| Ia.914 | F | $CH_2—CO—CH_3$ | $CH_2—CH{=}CH_2$ |
| Ia.915 | Cl | $CH_2—CO—CH_3$ | $CH_2—CH{=}CH_2$ |
| Ia.916 | H | $CH_2—CO—CH_3$ | $CH_2—C≡CH$ |
| Ia.917 | F | $CH_2—CO—CH_3$ | $CH_2—C≡CH$ |
| Ia.918 | Cl | $CH_2—CO—CH_3$ | $CH_2—C≡CH$ |
| Ia.919 | H | $CH_2—CO—CH_3$ | $CH_2—CO—OCH_3$ |
| Ia.920 | F | $CH_2—CO—CH_3$ | $CH_2—CO—OCH_3$ |
| Ia.921 | Cl | $CH_2—CO—CH_3$ | $CH_2—CO—OCH_3$ |
| Ia.922 | H | $CH_2—CO—CH_3$ | $CH_2$-phenyl |
| Ia.923 | F | $CH_2—CO—CH_3$ | $CH_2$-phenyl |
| Ia.924 | Cl | $CH_2—CO—CH_3$ | $CH_2$-phenyl |
| Ia.925 | H | $CH_2—CO—C_2H_5$ | $CH_3$ |
| Ia.926 | F | $CH_2—CO—C_2H_5$ | $CH_3$ |
| Ia.927 | Cl | $CH_2—CO—C_2H_5$ | $CH_3$ |
| Ia.928 | H | $CH_2—CO—C_2H_5$ | $C_2H_5$ |
| Ia.929 | F | $CH_2—CO—C_2H_5$ | $C_2H_5$ |
| Ia.930 | Cl | $CH_2—CO—C_2H_5$ | $C_2H_5$ |
| Ia.931 | H | $CH_2—CO—C_2H_5$ | n-$C_3H_7$ |

TABLE 1-continued

I

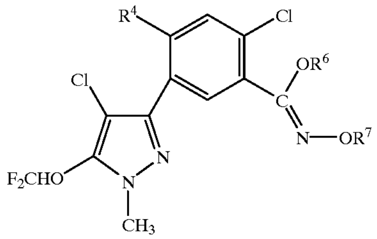

| No. | $R^4$ | $R^6$ | $R^7$ |
|---|---|---|---|
| Ia.932 | F | $CH_2$—CO—$C_2H_5$ | n-$C_3H_7$ |
| Ia.933 | Cl | $CH_2$—CO—$C_2H_5$ | n-$C_3H_7$ |
| Ia.934 | H | $CH_2$—CO—$C_2H_5$ | n-$C_4H_9$ |
| Ia.935 | F | $CH_2$—CO—$C_2H_5$ | n-$C_4H_9$ |
| Ia.936 | Cl | $CH_2$—CO—$C_2H_5$ | n-$C_4H_9$ |
| Ia.937 | H | $CH_2$—CO—$C_2H_5$ | $CH_2$—CH═$CH_2$ |
| Ia.938 | F | $CH_2$—CO—$C_2H_5$ | $CH_2$—CH═$CH_2$ |
| Ia.939 | Cl | $CH_2$—CO—$C_2H_5$ | $CH_2$—CH═$CH_2$ |
| Ia.940 | H | $CH_2$—CO—$C_2H_5$ | $CH_2$—C≡CH |
| Ia.941 | F | $CH_2$—CO—$C_2H_5$ | $CH_2$—C≡CH |
| Ia.942 | Cl | $CH_2$—CO—$C_2H_5$ | $CH_2$—C≡CH |
| Ia.943 | H | $CH_2$—CO—$C_2H_5$ | $CH_2$—CO—$OCH_3$ |
| Ia.944 | F | $CH_2$—CO—$C_2H_5$ | $CH_2$—CO—$OCH_3$ |
| Ia.945 | Cl | $CH_2$—CO—$C_2H_5$ | $CH_2$—CO—$OCH_3$ |
| Ia.946 | H | $CH_2$—CO—$C_2H_5$ | $CH_2$-phenyl |
| Ia.947 | F | $CH_2$—CO—$C_2H_5$ | $CH_2$-phenyl |
| Ia.948 | Cl | $CH_2$—CO—$C_2H_5$ | $CH_2$-phenyl |
| Ia.949 | H | $CH_2$—CO—$CH_2Cl$ | $CH_3$ |
| Ia.950 | F | $CH_2$—CO—$CH_2Cl$ | $CH_3$ |
| Ia.951 | Cl | $CH_2$—CO—$CH_2Cl$ | $CH_3$ |
| Ia.952 | H | $CH_2$—CO—$CH_2Cl$ | $C_2H_5$ |
| Ia.953 | F | $CH_2$—CO—$CH_2Cl$ | $C_2H_5$ |
| Ia.954 | Cl | $CH_2$—CO—$CH_2Cl$ | $C_2H_5$ |
| Ia.955 | H | $CH_2$—CO—$CH_2Cl$ | n-$C_3H_7$ |
| Ia.956 | F | $CH_2$—CO—$CH_2Cl$ | n-$C_3H_7$ |
| Ia.957 | Cl | $CH_2$—CO—$CH_2Cl$ | n-$C_3H_7$ |
| Ia.958 | H | $CH_2$—CO—$CH_2Cl$ | n-$C_4H_9$ |
| Ia.959 | F | $CH_2$—CO—$CH_2Cl$ | n-$C_4H_9$ |
| Ia.960 | Cl | $CH_2$—CO—$CH_2Cl$ | n-$C_4H_9$ |
| Ia.961 | H | $CH_2$—CO—$CH_2Cl$ | $CH_2$—CH═$CH_2$ |
| Ia.962 | F | $CH_2$—CO—$CH_2Cl$ | $CH_2$—CH═$CH_2$ |
| Ia.963 | Cl | $CH_2$—CO—$CH_2Cl$ | $CH_2$—CH═$CH_2$ |
| la.964 | H | $CH_2$—CO—$CH_2Cl$ | $CH_2$—C≡CH |
| Ia.965 | F | $CH_2$—CO—$CH_2Cl$ | $CH_2$—C≡CH |
| Ia.966 | Cl | $CH_2$—CO—$CH_2Cl$ | $CH_2$—C≡CH |
| Ia.967 | H | $CH_2$—CO—$CH_2Cl$ | $CH_2$—CO—$OCH_3$ |
| Ia.968 | F | $CH_2$—CO—$CH_2Cl$ | $CH_2$—CO—$OCH_3$ |
| Ia.969 | Cl | $CH_2$—CO—$CH_2Cl$ | $CH_2$—CO—$OCH_3$ |
| Ia.970 | H | $CH_2$—CO—$CH_2Cl$ | $CH_2$-phenyl |
| Ia.971 | F | $CH_2$—CO—$CH_2Cl$ | $CH_2$-phenyl |
| Ia.972 | Cl | $CH_2$—CO—$CH_2Cl$ | $CH_2$-phenyl |
| Ia.973 | H | $CH_2$—CO—$CF_3$ | $CH_3$ |
| Ia.974 | F | $CH_2$—CO—$CF_3$ | $CH_3$ |
| Ia.975 | Cl | $CH_2$—CO—$CF_3$ | $CH_3$ |
| Ia.976 | H | $CH_2$—CO—$CF_3$ | $C_2H_5$ |
| Ia.977 | F | $CH_2$—CO—$CF_3$ | $C_2H_5$ |
| Ia.978 | Cl | $CH_2$—CO—$CF_3$ | $C_2H_5$ |
| Ia.979 | H | $CH_2$—CO—$CF_3$ | n-$C_3H_7$ |
| Ia.980 | F | $CH_2$—CO—$CF_3$ | n-$C_3H_7$ |
| Ia.981 | Cl | $CH_2$—CO—$CF_3$ | n-$C_3H_7$ |
| Ia.982 | H | $CH_2$—CO—$CF_3$ | n-$C_4H_9$ |
| Ia.983 | F | $CH_2$—CO—$CF_3$ | n-$C_4H_9$ |
| Ia.984 | Cl | $CH_2$—CO—$CF_3$ | n-$C_4H_9$ |
| Ia.985 | H | $CH_2$—CO—$CF_3$ | $CH_2$—CH═$CH_2$ |
| Ia.986 | F | $CH_2$—CO—$CF_3$ | $CH_2$—CH═$CH_2$ |
| Ia.987 | Cl | $CH_2$—CO—$CF_3$ | $CH_2$—CH═$CH_2$ |
| Ia.988 | H | $CH_2$—CO—$CF_3$ | $CH_2$—C≡CH |
| Ia.989 | F | $CH_2$—CO—$CF_3$ | $CH_2$—C≡CH |
| Ia.990 | Cl | $CH_2$—CO—$CF_3$ | $CH_2$—C≡CH |
| Ia.991 | H | $CH_2$—CO—$CF_3$ | $CH_2$—CO—$OCH_3$ |
| Ia.992 | F | $CH_2$—CO—$CF_3$ | $CH_2$—CO—$OCH_3$ |
| Ia.993 | Cl | $CH_2$—CO—$CF_3$ | $CH_2$—CO—$OCH_3$ |
| Ia.994 | H | $CH_2$—CO—$CF_3$ | $CH_2$-phenyl |

TABLE 1-continued

I

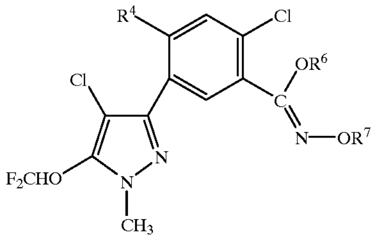

| No. | $R^4$ | $R^6$ | $R^7$ |
|---|---|---|---|
| Ia.995 | F | $CH_2$—CO—$CF_3$ | $CH_2$-phenyl |
| Ia.996 | Cl | $CH_2$—CO—$CF_3$ | $CH_2$-phenyl |
| Ia.997 | H | $CH_2$—CO-cyclopropyl | $CH_3$ |
| Ia.998 | F | $CH_2$—CO-cyclopropyl | $CH_3$ |
| Ia.999 | Cl | $CH_2$—CO-cyclopropyl | $CH_3$ |
| Ia.1000 | H | $CH_2$—CO-cyclopropyl | $C_2H_5$ |
| Ia.1001 | F | $CH_2$—CO-cyclopropyl | $C_2H_5$ |
| Ia.1002 | Cl | $CH_2$—CO-cyclopropyl | $C_2H_5$ |
| Ia.1003 | H | $CH_2$—CO-cyclopropyl | n-$C_3H_7$ |
| Ia.1004 | F | $CH_2$—CO-cyclopropyl | n-$C_3H_7$ |
| Ia.1005 | Cl | $CH_2$—CO-cyclopropyl | n-$C_3H_7$ |
| Ia.1006 | H | $CH_2$—CO-cyclopropyl | n-$C_4H_9$ |
| Ia.1007 | F | $CH_2$—CO-cyclopropyl | n-$C_4H_9$ |
| Ia.1008 | Cl | $CH_2$—CO-cyclopropyl | n-$C_4H_9$ |
| Ia.1009 | H | $CH_2$—CO-cyclopropyl | $CH_2$—CH═$CH_2$ |
| Ia.1010 | F | $CH_2$—CO-cyclopropyl | $CH_2$—CH═$CH_2$ |
| Ia.1011 | Cl | $CH_2$—CO-cyclopropyl | $CH_2$—CH═$CH_2$ |
| Ia.1012 | H | $CH_2$—CO-cyclopropyl | $CH_2$—C≡CH |
| Ia.1013 | F | $CH_2$—CO-cyclopropyl | $CH_2$—C≡CH |
| Ia.1014 | Cl | $CH_2$—CO-cyclopropyl | $CH_2$—C≡CH |
| Ia.1015 | H | $CH_2$—CO-cyclopropyl | $CH_2$—CO—$OCH_3$ |
| Ia.1016 | F | $CH_2$—CO-cyclopropyl | $CH_2$—CO—$OCH_3$ |
| Ia.1017 | Cl | $CH_2$—CO-cyclopropyl | $CH_2$—CO—$OCH_3$ |
| Ia.1018 | H | $CH_2$—CO-cyclopropyl | $CH_2$-phenyl |
| Ia.1019 | F | $CH_2$—CO-cyclopropyl | $CH_2$-phenyl |
| Ia.1020 | Cl | $CH_2$—CO-cyclopropyl | $CH_2$-phenyl |
| Ia.1021 | H | $CH_2$—CO-cyclobutyl | $CH_3$ |
| Ia.1022 | F | $CH_2$—CO-cyclobutyl | $CH_3$ |
| Ia.1023 | Cl | $CH_2$—CO-cyclobutyl | $CH_3$ |
| Ia.1024 | H | $CH_2$—CO-cyclobutyl | $C_2H_5$ |
| Ia.1025 | F | $CH_2$—CO-cyclobutyl | $C_2H_5$ |
| Ia.1026 | Cl | $CH_2$—CO-cyclobutyl | $C_2H_5$ |
| Ia.1027 | H | $CH_2$—CO-cyclobutyl | n-$C_3H_7$ |
| Ia.1028 | F | $CH_2$—CO-cyclobutyl | n-$C_3H_7$ |
| Ia.1029 | Cl | $CH_2$—CO-cyclobutyl | n-$C_3H_7$ |
| Ia.1030 | H | $CH_2$—CO-cyclobutyl | n-$C_4H_9$ |
| Ia.1031 | F | $CH_2$—CO-cyclobutyl | n-$C_4H_9$ |
| Ia.1032 | Cl | $CH_2$—CO-cyclobutyl | n-$C_4H_9$ |
| Ia.1033 | H | $CH_2$—CO-cyclobutyl | $CH_2$—CH═$CH_2$ |
| Ia.1034 | F | $CH_2$—CO-cyclobutyl | $CH_2$—CH═$CH_2$ |
| Ia.1035 | Cl | $CH_2$—CO-cyclobutyl | $CH_2$—CH═$CH_2$ |
| Ia.1036 | H | $CH_2$—CO-cyclobutyl | $CH_2$—C≡CH |
| Ia.1037 | F | $CH_2$—CO-cyclobutyl | $CH_2$—C≡CH |
| Ia.1038 | Cl | $CH_2$—CO-cyclobutyl | $CH_2$—C≡CH |
| Ia.1039 | H | $CH_2$—CO-cyclobutyl | $CH_2$—CO—$OCH_3$ |
| Ia.1040 | F | $CH_2$—CO-cyclobutyl | $CH_2$—CO—$OCH_3$ |
| Ia.1041 | Cl | $CH_2$—CO-cyclobutyl | $CH_2$—CO—$OCH_3$ |
| Ia.1042 | H | $CH_2$—CO-cyclobutyl | $CH_2$-phenyl |
| Ia.1043 | F | $CH_2$—CO-cyclobutyl | $CH_2$-phenyl |
| Ia.1044 | Cl | $CH_2$—CO-cyclobutyl | $CH_2$-phenyl |
| Ia.1045 | H | $CH_2$—CO-cyclopentyl | $CH_3$ |
| Ia.1046 | F | $CH_2$—CO-cyclopentyl | $CH_3$ |
| Ia.1047 | Cl | $CH_2$—CO-cyclopentyl | $CH_3$ |
| Ia.1048 | H | $CH_2$—CO-cyclopentyl | $C_2H_5$ |
| Ia.1049 | F | $CH_2$—CO-cyclopentyl | $C_2H_5$ |
| Ia.2099 | Cl | $CH_2$—CO-cyclopentyl | $C_2H_5$ |
| Ia.2100 | H | $CH_2$—CO-cyclopentyl | n-$C_3H_7$ |
| Ia.2101 | F | $CH_2$—CO-cyclopentyl | n-$C_3H_7$ |
| Ia.2102 | Cl | $CH_2$—CO-cyclopentyl | n-$C_3H_7$ |
| Ia.2103 | H | $CH_2$—CO-cyclopentyl | n-$C_4H_9$ |
| Ia.2104 | F | $CH_2$—CO-cyclopentyl | n-$C_4H_9$ |
| Ia.2105 | Cl | $CH_2$—CO-cyclopentyl | n-$C_4H_9$ |
| Ia.2106 | H | $CH_2$—CO-cyclopentyl | $CH_2$—CH═$CH_2$ |

TABLE 1-continued

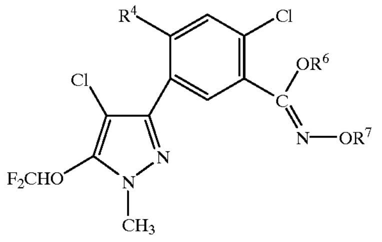

I

| No. | $R^4$ | $R^6$ | $R^7$ |
|---|---|---|---|
| Ia.2107 | F | $CH_2$—CO-cyclopentyl | $CH_2$—CH=$CH_2$ |
| Ia.2108 | Cl | $CH_2$—CO-cyclopentyl | $CH_2$—CH=$CH_2$ |
| Ia.2109 | H | $CH_2$—CO-cyclopentyl | $CH_2$—C≡CH |
| Ia.2110 | F | $CH_2$—CO-cyclopentyl | $CH_2$—C≡CH |
| Ia.2111 | Cl | $CH_2$—CO-cyclopentyl | $CH_2$—C≡CH |
| Ia.2112 | H | $CH_2$—CO-cyclopentyl | $CH_2$—CO—$OCH_3$ |
| Ia.2113 | F | $CH_2$—CO-cyclopentyl | $CH_2$—CO—$OCH_3$ |
| Ia.2114 | Cl | $CH_2$—CO-cyclopentyl | $CH_2$—CO—$OCH_3$ |
| Ia.2115 | H | $CH_2$—CO-cyclopentyl | $CH_2$-phenyl |
| Ia.2116 | F | $CH_2$—CO-cyclopentyl | $CH_2$-phenyl |
| Ia.2117 | Cl | $CH_2$—CO-cyclopentyl | $CH_2$-phenyl |
| Ia.2118 | H | $CH_2$—CO-cyclohexyl | $CH_3$ |
| Ia.2119 | F | $CH_2$—CO-cyclohexyl | $CH_3$ |
| Ia.2120 | Cl | $CH_2$—CO-cyclohexyl | $CH_3$ |
| Ia.2121 | H | $CH_2$—CO-cyclohexyl | $C_2H_5$ |
| Ia.2122 | F | $CH_2$—CO-cyclohexyl | $C_2H_5$ |
| Ia.2123 | Cl | $CH_2$—CO-cyclohexyl | $C_2H_5$ |
| Ia.2124 | H | $CH_2$—CO-cyclohexyl | n-$C_3H_7$ |
| Ia.2125 | F | $CH_2$—CO-cyclohexyl | n-$C_3H_7$ |
| Ia.2126 | Cl | $CH_2$—CO-cyclohexyl | n-$C_3H_7$ |
| Ia.2127 | H | $CH_2$—CO-cyclohexyl | n-$C_4H_9$ |
| Ia.2128 | F | $CH_2$—CO-cyclohexyl | n-$C_4H_9$ |
| Ia.2129 | Cl | $CH_2$—CO-cyclohexyl | n-$C_4H_9$ |
| Ia.2130 | H | $CH_2$—CO-cyclohexyl | $CH_2$—CH=$CH_2$ |
| Ia.2131 | F | $CH_2$—CO-cyclohexyl | $CH_2$—CH=$CH_2$ |
| Ia.2132 | Cl | $CH_2$—CO-cyclohexyl | $CH_2$—CH=$CH_2$ |
| Ia.2133 | H | $CH_2$—CO-cyclohexyl | $CH_2$—C≡CH |
| Ia.2134 | F | $CH_2$—CO-cyclohexyl | $CH_2$—C≡CH |
| Ia.2135 | Cl | $CH_2$—CO-cyclohexyl | $CH_2$—C≡CH |
| Ia.2136 | H | $CH_2$—CO-cyclohexyl | $CH_2$—CO—$OCH_3$ |
| Ia.2137 | F | $CH_2$—CO-cyclohexyl | $CH_2$—CO—$OCH_3$ |
| Ia.2138 | Cl | $CH_2$—CO-cyclohexyl | $CH_2$—CO—$OCH_3$ |
| Ia.2139 | H | $CH_2$—CO-cyclohexyl | $CH_2$-phenyl |
| Ia.2140 | F | $CH_2$—CO-cyclohexyl | $CH_2$-phenyl |
| Ia.2141 | Cl | $CH_2$—CO-cyclohexyl | $CH_2$-phenyl |
| Ia.2142 | H | $CH_2$—CH=N—$OCH_3$ | $CH_3$ |
| Ia.2143 | F | $CH_2$—CH=N—$OCH_3$ | $CH_3$ |
| Ia.2144 | Cl | $CH_2$—CH=N—$OCH_3$ | $CH_3$ |
| Ia.2145 | H | $CH_2$—CH=N—$OCH_3$ | $C_2H_5$ |
| Ia.2146 | F | $CH_2$—CH=N—$OCH_3$ | $C_2H_5$ |
| Ia.2147 | Cl | $CH_2$—CH=N—$OCH_3$ | $C_2H_5$ |
| Ia.2148 | H | $CH_2$—CH=N—$OCH_3$ | n-$C_3H_7$ |
| Ia.2149 | F | $CH_2$—CH=N—$OCH_3$ | n-$C_3H_7$ |
| Ia.2150 | Cl | $CH_2$—CH=N—$OCH_3$ | n-$C_3H_7$ |
| Ia.2151 | H | $CH_2$—CH=N—$OCH_3$ | n-$C_4H_9$ |
| Ia.2152 | F | $CH_2$—CH=N—$OCH_3$ | n-$C_4H_9$ |
| Ia.2153 | Cl | $CH_2$—CH=N—$OCH_3$ | n-$C_4H_9$ |
| Ia.2154 | H | $CH_2$—CH=N—$OCH_3$ | $CH_2$—CH=$CH_2$ |
| Ia.2155 | F | $CH_2$—CH=N—$OCH_3$ | $CH_2$—CH=$CH_2$ |
| Ia.2156 | Cl | $CH_2$—CH=N—$OCH_3$ | $CH_2$—CH=$CH_2$ |
| Ia.2157 | H | $CH_2$—CH=N—$OCH_3$ | $CH_2$—C≡CH |
| Ia.2158 | F | $CH_2$—CH=N—$OCH_3$ | $CH_2$—C≡CH |
| Ia.2159 | Cl | $CH_2$—CH=N—$OCH_3$ | $CH_2$—C≡CH |
| Ia.2160 | H | $CH_2$—CH=N—$OCH_3$ | $CH_2$—CO—$OCH_3$ |
| Ia.2161 | F | $CH_2$—CH=N—$OCH_3$ | $CH_2$—CO—$OCH_3$ |
| Ia.2162 | Cl | $CH_2$—CH=N—$OCH_3$ | $CH_2$—CO—$OCH_3$ |
| Ia.2163 | H | $CH_2$—CH=N—$OCH_3$ | $CH_2$-phenyl |
| Ia.2164 | F | $CH_2$—CH=N—$OCH_3$ | $CH_2$-phenyl |
| Ia.2165 | Cl | $CH_2$—CH=N—$OCH_3$ | $CH_2$-phenyl |
| Ia.2166 | H | $CH_2$—CH=N—$OC_2H_5$ | $CH_3$ |
| Ia.2167 | F | $CH_2$—CH=N—$OC_2H_5$ | $CH_3$ |
| Ia.2168 | Cl | $CH_2$—CH=N—$OC_2H_5$ | $CH_3$ |
| Ia.2169 | H | $CH_2$—CH=N—$OC_2H_5$ | $C_2H_5$ |

TABLE 1-continued

I

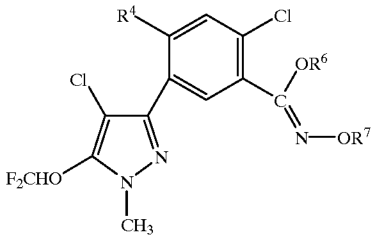

| No. | $R^4$ | $R^6$ | $R^7$ |
|---|---|---|---|
| Ia.2170 | F | $CH_2$—CH═N—$OC_2H_5$ | $C_2H_5$ |
| Ia.2171 | Cl | $CH_2$—CH═N—$OC_2H_5$ | $C_2H_5$ |
| Ia.2172 | H | $CH_2$—CH═N—$OC_2H_5$ | n-$C_3H_7$ |
| Ia.2173 | F | $CH_2$—CH═N—$OC_2H_5$ | n-$C_3H_7$ |
| Ia.2174 | Cl | $CH_2$—CH═N—$OC_2H_5$ | n-$C_3H_7$ |
| Ia.2175 | H | $CH_2$—CH═N—$OC_2H_5$ | n-$C_4H_9$ |
| Ia.2176 | F | $CH_2$—CH═N—$OC_2H_5$ | n-$C_4H_9$ |
| Ia.2177 | Cl | $CH_2$—CH═N—$OC_2H_5$ | n-$C_4H_9$ |
| Ia.2178 | H | $CH_2$—CH═N—$OC_2H_5$ | $CH_2$—CH═$CH_2$ |
| Ia.2179 | F | $CH_2$—CH═N—$OC_2H_5$ | $CH_2$—CH═$CH_2$ |
| Ia.2180 | Cl | $CH_2$—CH═N—$OC_2H_5$ | $CH_2$—CH═$CH_2$ |
| Ia.2181 | H | $CH_2$—CH═N—$OC_2H_5$ | $CH_2$—C≡CH |
| Ia.2182 | F | $CH_2$—CH═N—$OC_2H_5$ | $CH_2$—C≡CH |
| Ia.2183 | Cl | $CH_2$—CH═N—$OC_2H_5$ | $CH_2$—C≡CH |
| Ia.2184 | H | $CH_2$—CH═N—$OC_2H_5$ | $CH_2$—CO—$OCH_3$ |
| Ia.2185 | F | $CH_2$—CH═N—$OC_2H_5$ | $CH_2$—CO—$OCH_3$ |
| Ia.2186 | Cl | $CH_2$—CH═N—$OC_2H_5$ | $CH_2$—CO—$OCH_3$ |
| Ia.2187 | H | $CH_2$—CH═N—$OC_2H_5$ | $CH_2$-phenyl |
| Ia.2188 | F | $CH_2$—CH═N—$OC_2H_5$ | $CH_2$-phenyl |
| Ia.2189 | Cl | $CH_2$—CH═N—$OC_2H_5$ | $CH_2$-phenyl |
| Ia.2190 | H | $CH_2$—CH═N—O(n-$C_3H_7$) | $CH_3$ |
| Ia.2191 | F | $CH_2$—CH═N—O(n-$C_3H_7$) | $CH_3$ |
| Ia.2192 | Cl | $CH_2$—CH═N—O(n-$C_3H_7$) | $CH_3$ |
| Ia.2193 | H | $CH_2$—CH═N—O(n-$C_3H_7$) | $C_2H_5$ |
| Ia.2194 | F | $CH_2$—CH═N—O(n-$C_3H_7$) | $C_2H_5$ |
| Ia.2195 | Cl | $CH_2$—CH═N—O(n-$C_3H_7$) | $C_2H_5$ |
| Ia.2196 | H | $CH_2$—CH═N—O(n-$C_3H_7$) | n-$C_3H_7$ |
| Ia.2197 | F | $CH_2$—CH═N—O(n-$C_3H_7$) | n-$C_3H_7$ |
| Ia.2198 | Cl | $CH_2$—CH═N—O(n-$C_3H_7$) | n-$C_3H_7$ |
| Ia.2199 | H | $CH_2$—CH═N—O(n-$C_3H_7$) | n-$C_4H_9$ |
| Ia.2200 | F | $CH_2$—CH═N—O(n-$C_3H_7$) | n-$C_4H_9$ |
| Ia.2201 | Cl | $CH_2$—CH═N—O(n-$C_3H_7$) | n-$C_4H_9$ |
| Ia.2202 | H | $CH_2$—CH═N—O(n-$C_3H_7$) | $CH_2$—CH═$CH_2$ |
| Ia.2203 | F | $CH_2$—CH═N—O(n-$C_3H_7$) | $CH_2$—CH═$CH_2$ |
| Ia.2204 | Cl | $CH_2$—CH═N—O(n-$C_3H_7$) | $CH_2$—CH═$CH_2$ |
| Ia.2205 | H | $CH_2$—CH═N—O(n-$C_3H_7$) | $CH_2$—C≡CH |
| Ia.2206 | F | $CH_2$—CH═N—O(n-$C_3H_7$) | $CH_2$—C≡CH |
| Ia.2207 | Cl | $CH_2$—CH═N—O(n-$C_3H_7$) | $CH_2$—C≡CH |
| Ia.2208 | H | $CH_2$—CH═N—O(n-$C_3H_7$) | $CH_2$—CO—$OCH_3$ |
| Ia.2209 | F | $CH_2$—CH═N—O(n-$C_3H_7$) | $CH_2$—CO—$OCH_3$ |
| Ia.2210 | Cl | $CH_2$—CH═N—O(n-$C_3H_7$) | $CH_2$—CO—$OCH_3$ |
| Ia.2211 | H | $CH_2$—CH═N—O(n-$C_3H_7$) | $CH_2$-phenyl |
| Ia.2212 | F | $CH_2$—CH═N—O(n-$C_3H_7$) | $CH_2$-phenyl |
| Ia.2213 | Cl | $CH_2$—CH═N—O(n-$C_3H_7$) | $CH_2$-phenyl |
| Ia.2214 | H | $CH_2$—CH═N—O(n-$C_4H_9$) | $CH_3$ |
| Ia.2215 | F | $CH_2$—CH═N—O(n-$C_4H_9$) | $CH_3$ |
| Ia.2216 | Cl | $CH_2$—CH═N—O(n-$C_4H_9$) | $CH_3$ |
| Ia.2217 | H | $CH_2$—CH═N—O(n-$C_4H_9$) | $C_2H_5$ |
| Ia.2218 | F | $CH_2$—CH═N—O(n-$C_4H_9$) | $C_2H_5$ |
| Ia.2219 | Cl | $CH_2$—CH═N—O(n-$C_4H_9$) | $C_2H_5$ |
| Ia.2220 | H | $CH_2$—CH═N—O(n-$C_4H_9$) | n-$C_3H_7$ |
| Ia.2221 | F | $CH_2$—CH═N—O(n-$C_4H_9$) | n-$C_3H_7$ |
| Ia.2222 | Cl | $CH_2$—CH═N—O(n-$C_4H_9$) | n-$C_3H_7$ |
| Ia.2223 | H | $CH_2$—CH═N—O(n-$C_4H_9$) | n-$C_4H_9$ |
| Ia.2224 | F | $CH_2$—CH═N—O(n-$C_4H_9$) | n-$C_4H_9$ |
| Ia.2225 | Cl | $CH_2$—CH═N—O(n-$C_4H_9$) | n-$C_4H_9$ |
| Ia.2226 | H | $CH_2$—CH═N—O(n-$C_4H_9$) | $CH_2$—CH═$CH_2$ |
| Ia.2227 | F | $CH_2$—CH═N—O(n-$C_4H_9$) | $CH_2$—CH═$CH_2$ |
| Ia.2228 | Cl | $CH_2$—CH═N—O(n-$C_4H_9$) | $CH_2$—CH═$CH_2$ |
| Ia.2229 | H | $CH_2$—CH═N—O(n-$C_4H_9$) | $CH_2$—C≡CH |
| Ia.2230 | F | $CH_2$—CH═N—O(n-$C_4H_9$) | $CH_2$—C≡CH |
| Ia.2231 | Cl | $CH_2$—CH═N—O(n-$C_4H_9$) | $CH_2$—C≡CH |
| Ia.2232 | H | $CH_2$—CH═N—O(n-$C_4H_9$) | $CH_2$—CO—$OCH_3$ |

TABLE 1-continued

I

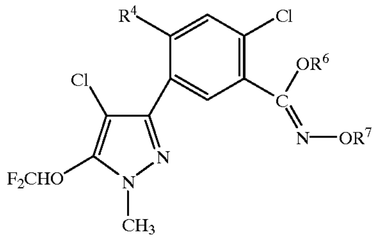

| No. | $R^4$ | $R^6$ | $R^7$ |
|---|---|---|---|
| Ia.2233 | F | $CH_2$—CH═N—O(n-$C_4H_9$) | $CH_2$—CO—$OCH_3$ |
| Ia.2234 | Cl | $CH_2$—CH═N—O(n-$C_4H_9$) | $CH_2$—CO—$OCH_3$ |
| Ia.2235 | H | $CH_2$—CH═N—O(n-$C_4H_9$) | $CH_2$-phenyl |
| Ia.2236 | F | $CH_2$—CH═N—O(n-$C_4H_9$) | $CH_2$-phenyl |
| Ia.2237 | Cl | $CH_2$—CH═N—O(n-$C_4H_9$) | $CH_2$-phenyl |
| Ia.2238 | H | $CH_2$—CH═N—$OCH_2$—CH═$CH_2$ | $CH_3$ |
| Ia.2239 | F | $CH_2$—CH═N—$OCH_2$—CH═$CH_2$ | $CH_3$ |
| Ia.2240 | Cl | $CH_2$—CH═N—$OCH_2$—CH═$CH_2$ | $CH_3$ |
| Ia.2241 | H | $CH_2$—CH═N—$OCH_2$—CH═$CH_2$ | $C_2H_5$ |
| Ia.2242 | F | $CH_2$—CH═N—$OCH_2$—CH═$CH_2$ | $C_2H_5$ |
| Ia.2243 | Cl | $CH_2$—CH═N—$OCH_2$—CH═$CH_2$ | $C_2H_5$ |
| Ia.2244 | H | $CH_2$—CH═N—$OCH_2$—CH═$CH_2$ | n-$C_3H_7$ |
| Ia.2245 | F | $CH_2$—CH═N—$OCH_2$—CH═$CH_2$ | n-$C_3H_7$ |
| Ia.2246 | Cl | $CH_2$—CH═N—$OCH_2$—CH═$CH_2$ | n-$C_3H_7$ |
| Ia.2247 | H | $CH_2$—CH═N—$OCH_2$—CH═$CH_2$ | n-$C_4H_9$ |
| Ia.2248 | F | $CH_2$—CH═N—$OCH_2$—CH═$CH_2$ | n-$C_4H_9$ |
| Ia.2249 | Cl | $CH_2$—CH═N—$OCH_2$—CH═$CH_2$ | n-$C_4H_9$ |
| Ia.2250 | H | $CH_2$—CH═N—$OCH_2$—CH═$CH_2$ | $CH_2$—CH═$CH_2$ |
| Ia.2251 | F | $CH_2$—CH═N—$OCH_2$—CH═$CH_2$ | $CH_2$—CH═$CH_2$ |
| Ia.2252 | Cl | $CH_2$—CH═N—$OCH_2$—CH═$CH_2$ | $CH_2$—CH═$CH_2$ |
| Ia.2253 | H | $CH_2$—CH═N—$OCH_2$—CH═$CH_2$ | $CH_2$—C≡CH |
| Ia.2254 | F | $CH_2$—CH═N—$OCH_2$—CH═$CH_2$ | $CH_2$—C≡CH |
| Ia.2255 | Cl | $CH_2$—CH═N—$OCH_2$—CH═$CH_2$ | $CH_2$—C≡CH |
| Ia.2256 | H | $CH_2$—CH═N—$OCH_2$—CH═$CH_2$ | $CH_2$—CO—$OCH_3$ |
| Ia.2257 | F | $CH_2$—CH═N—$OCH_2$—CH═$CH_2$ | $CH_2$—CO—$OCH_3$ |
| Ia.2258 | Cl | $CH_2$—CH═N—$OCH_2$—CH═$CH_2$ | $CH_2$—CO—$OCH_3$ |
| Ia.2259 | H | $CH_2$—CH═N—$OCH_2$—CH═$CH_2$ | $CH_2$-phenyl |
| la.2260 | F | $CH_2$—CH═N—$OCH_2$—CH═$CH_2$ | $CH_2$-phenyl |
| Ia.2261 | Cl | $CH_2$—CH═N—$OCH_2$—CH═$CH_2$ | $CH_2$-phenyl |
| Ia.2262 | H | $CH_2$—C(═N—$OCH_3$)—CO—$OCH_3$ | $CH_3$ |
| Ia.2263 | F | $CH_2$—C(═N—$OCH_3$)—CO—$OCH_3$ | $CH_3$ |
| Ia.2264 | Cl | $CH_2$—C(═N—$OCH_3$)—CO—$OCH_3$ | $CH_3$ |
| Ia.2265 | H | $CH_2$—C(═N—$OCH_3$)—CO—$OCH_3$ | $C_2H_5$ |
| Ia.2266 | F | $CH_2$—C(═N—$OCH_3$)—CO—$OCH_3$ | $C_2H_5$ |
| Ia.2267 | Cl | $CH_2$—C(═N—$OCH_3$)—CO—$OCH_3$ | $C_2H_5$ |
| Ia.2268 | H | $CH_2$—C(═N—$OCH_3$)—CO—$OCH_3$ | n-$C_3H_7$ |
| Ia.2269 | F | $CH_2$—C(═N—$OCH_3$)—CO—$OCH_3$ | n-$C_3H_7$ |
| Ia.2270 | Cl | $CH_2$—C(═N—$OCH_3$)—CO—$OCH_3$ | n-$C_3H_7$ |
| Ia.2271 | H | $CH_2$—C(═N—$OCH_3$)—CO—$OCH_3$ | n-$C_4H_9$ |
| Ia.2272 | F | $CH_2$—C(═N—$OCH_3$)—CO—$OCH_3$ | n-$C_4H_9$ |
| Ia.2273 | Cl | $CH_2$—C(═N—$OCH_3$)—CO—$OCH_3$ | n-$C_4H_9$ |
| Ia.2274 | H | $CH_2$—C(═N—$OCH_3$)—CO—$OCH_3$ | $CH_2$—CH═$CH_2$ |
| Ia.2275 | F | $CH_2$—C(═N—$OCH_3$)—CO—$OCH_3$ | $CH_2$—CH═$CH_2$ |
| Ia.2276 | Cl | $CH_2$—C(═N—$OCH_3$)—CO—$OCH_3$ | $CH_2$—CH═$CH_2$ |
| Ia.2277 | H | $CH_2$—C(═N—$OCH_3$)—CO—$OCH_3$ | $CH_2$—C≡CH |
| Ia.2278 | F | $CH_2$—C(═N—$OCH_3$)—CO—$OCH_3$ | $CH_2$—C≡CH |
| Ia.2279 | Cl | $CH_2$—C(═N—$OCH_3$)—CO—$OCH_3$ | $CH_2$—C≡CH |
| Ia.2280 | H | $CH_2$—C(═N—$OCH_3$)—CO—$OCH_3$ | $CH_2$—CO—$OCH_3$ |
| Ia.2281 | F | $CH_2$—C(═N—$OCH_3$)—CO—$OCH_3$ | $CH_2$—CO—$OCH_3$ |
| Ia.2282 | Cl | $CH_2$—C(═N—$OCH_3$)—CO—$OCH_3$ | $CH_2$—CO—$OCH_3$ |
| Ia.2283 | H | $CH_2$—C(═N—$OCH_3$)—CO—$OCH_3$ | $CH_2$-phenyl |
| Ia.2284 | F | $CH_2$—C(═N—$OCH_3$)—CO—$OCH_3$ | $CH_2$-phenyl |
| Ia.2285 | Cl | $CH_2$—C(═N—$OCH_3$)—CO—$OCH_3$ | $CH_2$-phenyl |
| Ia.2286 | H | $CH_2$—COOH | $CH_3$ |
| Ia.2287 | F | $CH_2$—COOH | $CH_3$ |
| Ia.2288 | Cl | $CH_2$—COOH | $CH_3$ |
| Ia.2289 | H | $CH_2$—COOH | $C_2H_5$ |
| Ia.2290 | F | $CH_2$—COOH | $C_2H_5$ |
| Ia.2291 | Cl | $CH_2$—COOH | $C_2H_5$ |
| Ia.2292 | H | $CH_2$—COOH | n-$C_3H_7$ |
| Ia.2293 | F | $CH_2$—COOH | n-$C_3H_7$ |
| Ia.2294 | Cl | $CH_2$—COOH | n-$C_3H_7$ |
| Ia.2295 | H | $CH_2$—COOH | n-$C_4H_9$ |

TABLE 1-continued

I

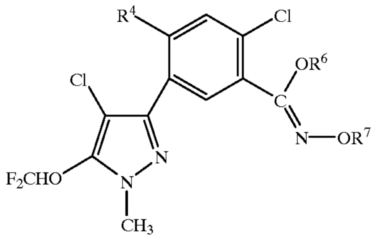

| No. | $R^4$ | $R^6$ | $R^7$ |
|---|---|---|---|
| Ia.2296 | F | $CH_2$—COOH | n-$C_4H_9$ |
| la.2297 | Cl | $CH_2$—COOH | n-$C_4H_9$ |
| Ia.2298 | H | $CH_2$—COOH | $CH_2$—CH=$CH_2$ |
| Ia.2299 | F | $CH_2$—COOH | $CH_2$—CH=$CH_2$ |
| Ia.2300 | Cl | $CH_2$—COOH | $CH_2$—CH=$CH_2$ |
| Ia.2301 | H | $CH_2$—COOH | $CH_2$—C≡CH |
| la.2302 | F | $CH_2$—COOH | $CH_2$—C≡CH |
| Ia.2303 | Cl | $CH_2$—COOH | $CH_2$—C≡CH |
| Ia.2304 | H | $CH_2$—COOH | $CH_2$—CO—$OCH_3$ |
| Ia.2305 | F | $CH_2$—COOH | $CH_2$—CO—$OCH_3$ |
| Ia.2306 | Cl | $CH_2$—COOH | $CH_2$—CO—$OCH_3$ |
| Ia.2307 | H | $CH_2$—COOH | $CH_2$-phenyl |
| Ia.2308 | F | $CH_2$—COOH | $CH_2$-phenyl |
| la.2309 | Cl | $CH_2$—COOH | $CH_2$-phenyl |
| Ia.2310 | H | $CH(CH_3)$—COOH | $CH_3$ |
| Ia.2311 | F | $CH(CH_3)$—COOH | $CH_3$ |
| Ia.2312 | Cl | $CH(CH_3)$—COOH | $CH_3$ |
| Ia.2313 | H | $CH(CH_3)$—COOH | $C_2H_5$ |
| Ia.2314 | F | $CH(CH_3)$—COOH | $C_2H_5$ |
| Ia.2315 | Cl | $CH(CH_3)$—COOH | $C_2H_5$ |
| Ia.2316 | H | $CH(CH_3)$—COOH | n-$C_3H_7$ |
| Ia.2317 | F | $CH(CH_3)$—COOH | n-$C_3H_7$ |
| Ia.2318 | Cl | $CH(CH_3)$—COOH | n-$C_3H_7$ |
| Ia.2319 | H | $CH(CH_3)$—COOH | n-$C_4H_9$ |
| Ia.2320 | F | $CH(CH_3)$—COOH | n-$C_4H_9$ |
| Ia.2321 | Cl | $CH(CH_3)$—COOH | n-$C_4H_9$ |
| Ia.2322 | H | $CH(CH_3)$—COOH | $CH_2$—CH=$CH_2$ |
| Ia.2323 | F | $CH(CH_3)$—COOH | $CH_2$—CH=$CH_2$ |
| Ia.2324 | Cl | $CH(CH_3)$—COOH | $CH_2$—CH=$CH_2$ |
| Ia.2325 | H | $CH(CH_3)$—COOH | $CH_2$—C≡CH |
| Ia.2326 | F | $CH(CH_3)$—COOH | $CH_2$—C≡CH |
| Ia.2327 | Cl | $CH(CH_3)$—COOH | $CH_2$—C≡CH |
| Ia.2328 | H | $CH(CH_3)$—COOH | $CH_2$—CO—$OCH_3$ |
| Ia.2329 | F | $CH(CH_3)$—COOH | $CH_2$—CO—$OCH_3$ |
| Ia.2330 | Cl | $CH(CH_3)$—COOH | $CH_2$—CO—$OCH_3$ |
| Ia.2331 | H | $CH(CH_3)$—COOH | $CH_2$-phenyl |
| Ia.2332 | F | $CH(CH_3)$—COOH | $CH_2$-phenyl |
| Ia.2333 | Cl | $CH(CH_3)$—COOH | $CH_2$-phenyl |
| Ia.2334 | H | $CH(C_2H_5)$—COOH | $CH_3$ |
| Ia.2335 | F | $CH(C_2H_5)$—COOH | $CH_3$ |
| Ia.2336 | Cl | $CH(C_2H_5)$—COOH | $CH_3$ |
| Ia.2337 | H | $CH(C_2H_5)$—COOH | $C_2H_5$ |
| Ia.2338 | F | $CH(C_2H_5)$—COOH | $C_2H_5$ |
| Ia.2339 | Cl | $CH(C_2H_5)$—COOH | $C_2H_5$ |
| Ia.2340 | H | $CH(C_2H_5)$—COOH | n-$C_3H_7$ |
| Ia.2341 | F | $CH(C_2H_5)$—COOH | n-$C_3H_7$ |
| Ia.2342 | Cl | $CH(C_2H_5)$—COOH | n-$C_3H_7$ |
| Ia 2343 | H | $CH(C_2H_5)$—COOH | n-$C_4H_9$ |
| Ia.2344 | F | $CH(C_2H_5)$—COOH | n-$C_4H_9$ |
| Ia.2345 | Cl | $CH(C_2H_5)$—COOH | n-$C_4H_9$ |
| Ia.2346 | H | $CH(C_2H_5)$—COOH | $CH_2$—CH=$CH_2$ |
| Ia.2347 | F | $CH(C_2H_5)$—COOH | $CH_2$—CH=$CH_2$ |
| Ia.2348 | Cl | $CH(C_2H_5)$—COOH | $CH_2$—CH=$CH_2$ |
| Ia.2349 | H | $CH(C_2H_5)$—COOH | $CH_2$—C≡CH |
| Ia.2350 | F | $CH(C_2H_5)$—COOH | $CH_2$—C≡CH |
| Ia.2351 | Cl | $CH(C_2H_5)$—COOH | $CH_2$—C≡CH |
| Ia.2352 | H | $CH(C_2H_5)$—COOH | $CH_2$—CO—$OCH_3$ |
| Ia.2353 | F | $CH(C_2H_5)$—COOH | $CH_2$—CO—$OCH_3$ |
| Ia.2354 | Cl | $CH(C_2H_5)$—COOH | $CH_2$—CO—$OCH_3$ |
| Ia.2355 | H | $CH(C_2H_5)$—COOH | $CH_2$-phenyl |
| Ia.2356 | F | $CH(C_2H_5)$—COOH | $CH_2$-phenyl |
| Ia.2357 | Cl | $CH(C_2H_5)$—COOH | $CH_2$-phenyl |
| Ia.2358 | H | $CH_2$—CO—$OCH_3$ | $CH_3$ |

TABLE 1-continued

I

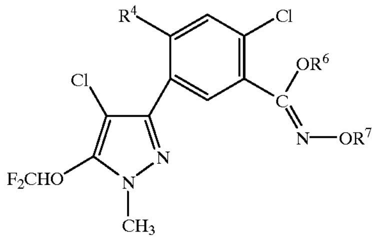

| No. | $R^4$ | $R^6$ | $R^7$ |
|---|---|---|---|
| Ia.2359 | F | $CH_2$—CO—$OCH_3$ | $CH_3$ |
| Ia.2360 | Cl | $CH_2$—CO—$OCH_3$ | $CH_3$ |
| Ia.2361 | H | $CH_2$—CO—$OCH_3$ | $C_2H_5$ |
| Ia.2362 | F | $CH_2$—CO—$OCH_3$ | $C_2H_5$ |
| Ia.2363 | Cl | $CH_2$—CO—$OCH_3$ | $C_2H_5$ |
| Ia.2364 | H | $CH_2$—CO—$OCH_3$ | n-$C_3H_7$ |
| Ia.2365 | F | $CH_2$—CO—$OCH_3$ | n-$C_3H_7$ |
| Ia.2366 | Cl | $CH_2$—CO—$OCH_3$ | n-$C_3H_7$ |
| Ia.2367 | H | $CH_2$—CO—$OCH_3$ | n-$C_4H_9$ |
| Ia.2368 | F | $CH_2$—CO—$OCH_3$ | n-$C_4H_9$ |
| Ia.2369 | Cl | $CH_2$—CO—$OCH_3$ | n-$C_4H_9$ |
| Ia.2370 | H | $CH_2$—CO—$OCH_3$ | $CH_2$—CH═$CH_2$ |
| Ia.2371 | F | $CH_2$—CO—$OCH_3$ | $CH_2$—CH═$CH_2$ |
| Ia.2372 | Cl | $CH_2$—CO—$OCH_3$ | $CH_2$—CH═$CH_2$ |
| Ia.2373 | H | $CH_2$—CO—$OCH_3$ | $CH_2$—C≡CH |
| Ia.2374 | F | $CH_2$—CO—$OCH_3$ | $CH_2$—C≡CH |
| Ia.2375 | Cl | $CH_2$—CO—$OCH_3$ | $CH_2$—C≡CH |
| Ia.2376 | H | $CH_2$—CO—$OCH_3$ | $CH_2$—CO—$OCH_3$ |
| Ia.2377 | F | $CH_2$—CO—$OCH_3$ | $CH_2$—CO—$OCH_3$ |
| Ia.2378 | Cl | $CH_2$—CO—$OCH_3$ | $CH_2$—CO—$OCH_3$ |
| Ia.2379 | H | $CH_2$—CO—$OCH_3$ | $CH_2$-phenyl |
| Ia.2380 | F | $CH_2$—CO—$OCH_3$ | $CH_2$-phenyl |
| Ia.2381 | Cl | $CH_2$—CO—$OCH_3$ | $CH_2$-phenyl |
| Ia.2382 | H | $CH(CH_3)$—CO—$OCH_3$ | $CH_3$ |
| Ia.2383 | F | $CH(CH_3)$—CO—$OCH_3$ | $CH_3$ |
| Ia.2384 | Cl | $CH(CH_3)$—CO—$OCH_3$ | $CH_3$ |
| Ia.2385 | H | $CH(CH_3)$—CO—$OCH_3$ | $C_2H_5$ |
| Ia.2386 | F | $CH(CH_3)$—CO—$OCH_3$ | $C_2H_5$ |
| Ia.2387 | Cl | $CH(CH_3)$—CO—$OCH_3$ | $C_2H_5$ |
| Ia.2388 | H | $CH(CH_3)$—CO—$OCH_3$ | n-$C_3H_7$ |
| Ia.2389 | F | $CH(CH_3)$—CO—$OCH_3$ | n-$C_3H_7$ |
| Ia.2390 | Cl | $CH(CH_3)$—CO—$OCH_3$ | n-$C_3H_7$ |
| Ia.2391 | H | $CH(CH_3)$—CO—$OCH_3$ | n-$C_4H_9$ |
| Ia.2392 | F | $CH(CH_3)$—CO—$OCH_3$ | n-$C_4H_9$ |
| Ia.2393 | Cl | $CH(CH_3)$—CO—$OCH_3$ | n-$C_4H_9$ |
| Ia.2394 | H | $CH(CH_3)$—CO—$OCH_3$ | $CH_2$—CH═$CH_2$ |
| Ia.2395 | F | $CH(CH_3)$—CO—$OCH_3$ | $CH_2$—CH═$CH_2$ |
| Ia.2396 | Cl | $CH(CH_3)$—CO—$OCH_3$ | $CH_2$—CH═$CH_2$ |
| Ia.2397 | H | $CH(CH_3)$—CO—$OCH_3$ | $CH_2$—C≡CH |
| Ia.2398 | F | $CH(CH_3)$—CO—$OCH_3$ | $CH_2$—C≡CH |
| Ia.2399 | Cl | $CH(CH_3)$—CO—$OCH_3$ | $CH_2$—C≡CH |
| Ia.2400 | H | $CH(CH_3)$—CO—$OCH_3$ | $CH_2$—CO—$OCH_3$ |
| Ia.2401 | F | $CH(CH_3)$—CO—$OCH_3$ | $CH_2$—CO—$OCH_3$ |
| Ia.2402 | Cl | $CH(CH_3)$—CO—$OCH_3$ | $CH_2$—CO—$OCH_3$ |
| Ia.2403 | H | $CH(CH_3)$—CO—$OCH_3$ | $CH_2$-phenyl |
| Ia.2404 | F | $CH(CH_3)$—CO—$OCH_3$ | $CH_2$-phenyl |
| Ia.2405 | Cl | $CH(CH_3)$—CO—$OCH_3$ | $CH_2$-phenyl |
| Ia.2406 | H | $CH(C_2H_5)$—CO—$OCH_3$ | $CH_3$ |
| Ia.2407 | F | $CH(C_2H_5)$—CO—$OCH_3$ | $CH_3$ |
| Ia.2408 | Cl | $CH(C_2H_5)$—CO—$OCH_3$ | $CH_3$ |
| Ia.2409 | H | $CH(C_2H_5)$—CO—$OCH_3$ | $C_2H_5$ |
| Ia.2410 | F | $CH(C_2H_5)$—CO—$OCH_3$ | $C_2H_5$ |
| Ia.2411 | Cl | $CH(C_2H_5)$—CO—$OCH_3$ | $C_2H_5$ |
| Ia.2412 | H | $CH(C_2H_5)$—CO—$OCH_3$ | n-$C_3H_7$ |
| Ia.2413 | F | $CH(C_2H_5)$—CO—$OCH_3$ | n-$C_3H_7$ |
| Ia.2414 | Cl | $CH(C_2H_5)$—CO—$OCH_3$ | n-$C_3H_7$ |
| Ia.2415 | H | $CH(C_2H_5)$—CO—$OCH_3$ | n-$C_4H_9$ |
| Ia.2416 | F | $CH(C_2H_5)$—CO—$OCH_3$ | n-$C_4H_9$ |
| Ia.2417 | Cl | $CH(C_2H_5)$—CO—$OCH_3$ | n-$C_4H_9$ |
| Ia.2418 | H | $CH(C_2H_5)$—CO—$OCH_3$ | $CH_2$—CH═$CH_2$ |
| Ia.2419 | F | $CH(C_2H_5)$—CO—$OCH_3$ | $CH_2$—CH═$CH_2$ |
| Ia.2420 | Cl | $CH(C_2H_5)$—CO—$OCH_3$ | $CH_2$—CH═$CH_2$ |
| Ia.2421 | H | $CH(C_2H_5)$—CO—$OCH_3$ | $CH_2$—C≡CH |

TABLE 1-continued

I

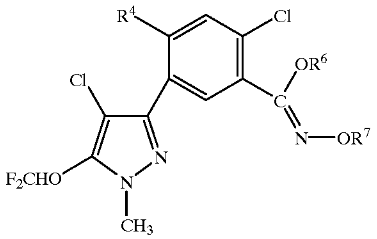

| No. | $R^4$ | $R^6$ | $R^7$ |
|---|---|---|---|
| Ia.2422 | F | $CH(C_2H_5)$—CO—$OCH_3$ | $CH_2$—C≡CH |
| Ia.2423 | Cl | $CH(C_2H_5)$—CO—$OCH_3$ | $CH_2$—C≡CH |
| Ia.2424 | H | $CH(C_2H_5)$—CO—$OCH_3$ | $CH_2$—CO—$OCH_3$ |
| Ia.2425 | F | $CH(C_2H_5)$—CO—$OCH_3$ | $CH_2$—CO—$OCH_3$ |
| Ia.2426 | Cl | $CH(C_2H_5)$—CO—$OCH_3$ | $CH_2$—CO—$OCH_3$ |
| Ia.2427 | H | $CH(C_2H_5)$—CO—$OCH_3$ | $CH_2$-phenyl |
| Ia.2428 | F | $CH(C_2H_5)$—CO—$OCH_3$ | $CH_2$-phenyl |
| Ia.2429 | Cl | $CH(C_2H_5)$—CO—$OCH_3$ | $CH_2$-phenyl |
| Ia.2430 | H | $CH_2$—CO—$OC_2H_5$ | $CH_3$ |
| Ia.2431 | F | $CH_2$—CO—$OC_2H_5$ | $CH_3$ |
| Ia.2432 | Cl | $CH_2$—CO—$OC_2H_5$ | $CH_3$ |
| Ia.2433 | H | $CH_2$—CO—$OC_2H_5$ | $C_2H_5$ |
| Ia.2434 | F | $CH_2$—CO—$OC_2H_5$ | $C_2H_5$ |
| Ia.2435 | Cl | $CH_2$—CO—$OC_2H_5$ | $C_2H_5$ |
| Ia.2436 | H | $CH_2$—CO—$OC_2H_5$ | n-$C_3H_7$ |
| Ia.2437 | F | $CH_2$—CO—$OC_2H_5$ | n-$C_3H_7$ |
| Ia.2438 | Cl | $CH_2$—CO—$OC_2H_5$ | n-$C_3H_7$ |
| Ia.2439 | H | $CH_2$—CO—$OC_2H_5$ | n-$C_4H_9$ |
| Ia.2440 | F | $CH_2$—CO—$OC_2H_5$ | n-$C_4H_9$ |
| Ia.2441 | Cl | $CH_2$—CO—$OC_2H_5$ | n-$C_4H_9$ |
| Ia.2442 | H | $CH_2$—CO—$OC_2H_5$ | $CH_2$—CH=$CH_2$ |
| Ia.2443 | F | $CH_2$—CO—$OC_2H_5$ | $CH_2$—CH=$CH_2$ |
| Ia.2444 | Cl | $CH_2$—CO—$OC_2H_5$ | $CH_2$—CH=$CH_2$ |
| Ia.2445 | H | $CH_2$—CO—$OC_2H_5$ | $CH_2$—C≡CH |
| Ia.2446 | F | $CH_2$—CO—$OC_2H_5$ | $CH_2$—C≡CH |
| Ia.2447 | Cl | $CH_2$—CO—$OC_2H_5$ | $CH_2$—C≡CH |
| Ia.2448 | H | $CH_2$—CO—$OC_2H_5$ | $CH_2$—CO—$OCH_3$ |
| Ia.2449 | F | $CH_2$—CO—$OC_2H_5$ | $CH_2$—CO—$OCH_3$ |
| Ia.2450 | Cl | $CH_2$—CO—$OC_2H_5$ | $CH_2$—CO—$OCH_3$ |
| Ia.2451 | H | $CH_2$—CO—$OC_2H_5$ | $CH_2$-phenyl |
| Ia.2452 | F | $CH_2$—CO—$OC_2H_5$ | $CH_2$-phenyl |
| Ia.2453 | Cl | $CH_2$—CO—$OC_2H_5$ | $CH_2$-phenyl |
| Ia.2454 | H | $CH(CH_3)$—CO—$OC_2H_5$ | $CH_3$ |
| Ia.2455 | F | $CH(CH_3)$—CO—$OC_2H_5$ | $CH_3$ |
| Ia.2456 | Cl | $CH(CH_3)$—CO—$OC_2H_5$ | $CH_3$ |
| Ia.2457 | H | $CH(CH_3)$—CO—$OC_2H_5$ | $C_2H_5$ |
| Ia.2458 | F | $CH(CH_3)$—CO—$OC_2H_5$ | $C_2H_5$ |
| Ia.2459 | Cl | $CH(CH_3)$—CO—$OC_2H_5$ | $C_2H_5$ |
| Ia.2460 | H | $CH(CH_3)$—CO—$OC_2H_5$ | n-$C_3H_7$ |
| Ia.2461 | F | $CH(CH_3)$—CO—$OC_2H_5$ | n-$C_3H_7$ |
| Ia.2462 | Cl | $CH(CH_3)$—CO—$OC_2H_5$ | n-$C_3H_7$ |
| Ia.2463 | H | $CH(CH_3)$—CO—$OC_2H_5$ | n-$C_4H_9$ |
| Ia.2464 | F | $CH(CH_3)$—CO—$OC_2H_5$ | n-$C_4H_9$ |
| Ia.2465 | Cl | $CH(CH_3)$—CO—$OC_2H_5$ | n-$C_4H_9$ |
| Ia.2466 | H | $CH(CH_3)$—CO—$OC_2H_5$ | $CH_2$—CH=$CH_2$ |
| Ia.2467 | F | $CH(CH_3)$—CO—$OC_2H_5$ | $CH_2$—CH=$CH_2$ |
| Ia.2468 | Cl | $CH(CH_3)$—CO—$OC_2H_5$ | $CH_2$—CH=$CH_2$ |
| Ia.2469 | H | $CH(CH_3)$—CO—$OC_2H_5$ | $CH_2$—C≡CH |
| Ia.2470 | F | $CH(CH_3)$—CO—$OC_2H_5$ | $CH_2$—C≡CH |
| Ia.2471 | Cl | $CH(CH_3)$—CO—$OC_2H_5$ | $CH_2$—C≡CH |
| Ia.2472 | H | $CH(CH_3)$—CO—$OC_2H_5$ | $CH_2$—CO—$OCH_3$ |
| Ia.2473 | F | $CH(CH_3)$—CO—$OC_2H_5$ | $CH_2$—CO—$OCH_3$ |
| Ia.2474 | Cl | $CH(CH_3)$—CO—$OC_2H_5$ | $CH_2$—CO—$OCH_3$ |
| Ia.2475 | H | $CH(CH_3)$—CO—$OC_2H_5$ | $CH_2$-phenyl |
| Ia.2476 | F | $CH(CH_3)$—CO—$OC_2H_5$ | $CH_2$-phenyl |
| Ia.2477 | Cl | $CH(CH_3)$—CO—$OC_2H_5$ | $CH_2$-phenyl |
| Ia.2478 | H | $CH(C_2H_5)$—CO—$OC_2H_5$ | $CH_3$ |
| Ia.2479 | F | $CH(C_2H_5)$—CO—$OC_2H_5$ | $CH_3$ |
| Ia.2480 | Cl | $CH(C_2H_5)$—CO—$OC_2H_5$ | $CH_3$ |
| Ia.2481 | H | $CH(C_2H_5)$—CO—$OC_2H_5$ | $C_2H_5$ |
| Ia.2482 | F | $CH(C_2H_5)$—CO—$OC_2H_5$ | $C_2H_5$ |
| Ia.2483 | Cl | $CH(C_2H_5)$—CO—$OC_2H_5$ | $C_2H_5$ |
| Ia.2484 | H | $CH(C_2H_5)$—CO—$OC_2H_5$ | n-$C_3H_7$ |

TABLE 1-continued

I

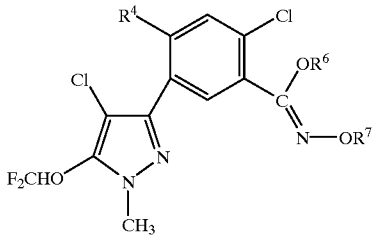

| No. | $R^4$ | $R^6$ | $R^7$ |
|---|---|---|---|
| Ia.2485 | F | $CH(C_2H_5)$—CO—$OC_2H_5$ | n-$C_3H_7$ |
| Ia.2486 | Cl | $CH(C_2H_5)$—CO—$OC_2H_5$ | n-$C_3H_7$ |
| Ia.2487 | H | $CH(C_2H_5)$—CO—$OC_2H_5$ | n-$C_4H_9$ |
| Ia.2488 | F | $CH(C_2H_5)$—CO—$OC_2H_5$ | n-$C_4H_9$ |
| Ia.2489 | Cl | $CH(C_2H_5)$—CO—$OC_2H_5$ | n-$C_4H_9$ |
| Ia.2490 | H | $CH(C_2H_5)$—CO—$OC_2H_5$ | $CH_2$—CH═$CH_2$ |
| Ia.2491 | F | $CH(C_2H_5)$—CO—$OC_2H_5$ | $CH_2$—CH═$CH_2$ |
| Ia.2492 | Cl | $CH(C_2H_5)$—CO—$OC_2H_5$ | $CH_2$—CH═$CH_2$ |
| Ia.2493 | H | $CH(C_2H_5)$—CO—$OC_2H_5$ | $CH_2$—C≡CH |
| Ia.2494 | F | $CH(C_2H_5)$—CO—$OC_2H_5$ | $CH_2$—C≡CH |
| Ia.2495 | Cl | $CH(C_2H_5)$—CO—$OC_2H_5$ | $CH_2$—C≡CH |
| Ia.2496 | H | $CH(C_2H_5)$—CO—$OC_2H_5$ | $CH_2$—CO—$OCH_3$ |
| Ia.2497 | F | $CH(C_2H_5)$—CO—$OC_2H_5$ | $CH_2$—CO—$OCH_3$ |
| Ia.2498 | Cl | $CH(C_2H_5)$—CO—$OC_2H_5$ | $CH_2$—CO—$OCH_3$ |
| Ia.2499 | H | $CH(C_2H_5)$—CO—$OC_2H_5$ | $CH_2$-phenyl |
| Ia.2500 | F | $CH(C_2H_5)$—CO—$OC_2H_5$ | $CH_2$-phenyl |
| Ia.2501 | Cl | $CH(C_2H_5)$—CO—$OC_2H_5$ | $CH_2$-phenyl |
| Ia.2502 | H | $CH_2$—CO—$OC(CH_3)_3$ | $CH_3$ |
| Ia.2503 | F | $CH_2$—CO—$OC(CH_3)_3$ | $CH_3$ |
| Ia.2504 | Cl | $CH_2$—CO—$OC(CH_3)_3$ | $CH_3$ |
| Ia.2505 | H | $CH_2$—CO—$OC(CH_3)_3$ | $C_2H_5$ |
| Ia.2506 | F | $CH_2$—CO—$OC(CH_3)_3$ | $C_2H_5$ |
| Ia.2507 | Cl | $CH_2$—CO—$OC(CH_3)_3$ | $C_2H_5$ |
| Ia.2508 | H | $CH_2$—CO—$OC(CH_3)_3$ | n-$C_3H_7$ |
| Ia.2509 | F | $CH_2$—CO—$OC(CH_3)_3$ | n-$C_3H_7$ |
| Ia.2510 | Cl | $CH_2$—CO—$OC(CH_3)_3$ | n-$C_3H_7$ |
| Ia.2511 | H | $CH_2$—CO—$OC(CH_3)_3$ | n-$C_4H_9$ |
| Ia.2512 | F | $CH_2$—CO—$OC(CH_3)_3$ | n-$C_4H_9$ |
| Ia.2513 | Cl | $CH_2$—CO—$OC(CH_3)_3$ | n-$C_4H_9$ |
| Ia.2514 | H | $CH_2$—CO—$OC(CH_3)_3$ | $CH_2$—CH═$CH_2$ |
| Ia.2515 | F | $CH_2$—CO—$OC(CH_3)_3$ | $CH_2$—CH═$CH_2$ |
| Ia.2516 | Cl | $CH_2$—CO—$OC(CH_3)_3$ | $CH_2$—CH═$CH_2$ |
| Ia.2517 | H | $CH_2$—CO—$OC(CH_3)_3$ | $CH_2$—C≡CH |
| Ia.2518 | F | $CH_2$—CO—$OC(CH_3)_3$ | $CH_2$—C≡CH |
| Ia.2519 | Cl | $CH_2$—CO—$OC(CH_3)_3$ | $CH_2$—C≡CH |
| Ia.2520 | H | $CH_2$—CO—$OC(CH_3)_3$ | $CH_2$—CO—$OCH_3$ |
| Ia.2521 | F | $CH_2$—CO—$OC(CH_3)_3$ | $CH_2$—CO—$OCH_3$ |
| Ia.2522 | Cl | $CH_2$—CO—$OC(CH_3)_3$ | $CH_2$—CO—$OCH_3$ |
| Ia.2523 | H | $CH_2$—CO—$OC(CH_3)_3$ | $CH_2$-phenyl |
| Ia.2524 | F | $CH_2$—CO—$OC(CH_3)_3$ | $CH_2$-phenyl |
| Ia.2525 | Cl | $CH_2$—CO—$OC(CH_3)_3$ | $CH_2$-phenyl |
| Ia.2526 | H | $CH(CH_3)$—CO—$OC(CH_3)_3$ | $CH_3$ |
| Ia.2527 | F | $CH(CH_3)$—CO—$OC(CH_3)_3$ | $CH_3$ |
| Ia.2528 | Cl | $CH(CH_3)$—CO—$OC(CH_3)_3$ | $CH_3$ |
| Ia.2529 | H | $CH(CH_3)$—CO—$OC(CH_3)_3$ | $C_2H_5$ |
| Ia.2530 | F | $CH(CH_3)$—CO—$OC(CH_3)_3$ | $C_2H_5$ |
| Ia.2531 | Cl | $CH(CH_3)$—CO—$OC(CH_3)_3$ | $C_2H_5$ |
| Ia.2532 | H | $CH(CH_3)$—CO—$OC(CH_3)_3$ | n-$C_3H_7$ |
| Ia.2533 | F | $CH(CH_3)$—CO—$OC(CH_3)_3$ | n-$C_3H_7$ |
| Ia.2534 | Cl | $CH(CH_3)$—CO—$OC(CH_3)_3$ | n-$C_3H_7$ |
| Ia.2535 | H | $CH(CH_3)$—CO—$OC(CH_3)_3$ | n-$C_4H_9$ |
| Ia.2536 | F | $CH(CH_3)$—CO—$OC(CH_3)_3$ | n-$C_4H_9$ |
| Ia.2537 | Cl | $CH(CH_3)$—CO—$OC(CH_3)_3$ | n-$C_4H_9$ |
| Ia.2538 | H | $CH(CH_3)$—CO—$OC(CH_3)_3$ | $CH_2$—CH═$CH_2$ |
| Ia.2539 | F | $CH(CH_3)$—CO—$OC(CH_3)_3$ | $CH_2$—CH═$CH_2$ |
| Ia.2540 | Cl | $CH(CH_3)$—CO—$OC(CH_3)_3$ | $CH_2$—CH═$CH_2$ |
| Ia.2541 | H | $CH(CH_3)$—CO—$OC(CH_3)_3$ | $CH_2$—C≡CH |
| Ia.2542 | F | $CH(CH_3)$—CO—$OC(CH_3)_3$ | $CH_2$—C≡CH |
| Ia.2543 | Cl | $CH(CH_3)$—CO—$OC(CH_3)_3$ | $CH_2$—C≡CH |
| Ia.2544 | H | $CH(CH_3)$—CO—$OC(CH_3)_3$ | $CH_2$—CO—$OCH_3$ |
| Ia.2545 | F | $CH(CH_3)$—CO—$OC(CH_3)_3$ | $CH_2$—CO—$OCH_3$ |
| Ia.2546 | Cl | $CH(CH_3)$—CO—$OC(CH_3)_3$ | $CH_2$—CO—$OCH_3$ |
| Ia.2547 | H | $CH(CH_3)$—CO—$OC(CH_3)_3$ | $CH_2$-phenyl |

TABLE 1-continued

I

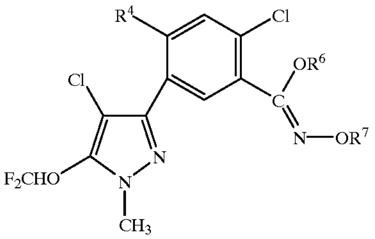

| No. | $R^4$ | $R^6$ | $R^7$ |
|---|---|---|---|
| Ia.2548 | F | $CH(CH_3)—CO—OC(CH_3)_3$ | $CH_2$-phenyl |
| Ia.2549 | Cl | $CH(CH_3)—CO—OC(CH_3)_3$ | $CH_2$-phenyl |
| Ia.2550 | H | $CH(C_2H_5)—CO—OC(CH_3)_3$ | $CH_3$ |
| Ia.2551 | F | $CH(C_2H_5)—CO—OC(CH_3)_3$ | $CH_3$ |
| Ia.2552 | Cl | $CH(C_2H_5)—CO—OC(CH_3)_3$ | $CH_3$ |
| Ia.2553 | H | $CH(C_2H_5)—CO—OC(CH_3)_3$ | $C_2H_5$ |
| Ia.2554 | F | $CH(C_2H_5)—CO—OC(CH_3)_3$ | $C_2H_5$ |
| Ia.2555 | Cl | $CH(C_2H_5)—CO—OC(CH_3)_3$ | $C_2H_5$ |
| Ia.2556 | H | $CH(C_2H_5)—CO—OC(CH_3)_3$ | n-$C_3H_7$ |
| Ia.2557 | F | $CH(C_2H_5)—CO—OC(CH_3)_3$ | n-$C_3H_7$ |
| Ia.2558 | Cl | $CH(C_2H_5)—CO—OC(CH_3)_3$ | n-$C_3H_7$ |
| Ia.2559 | H | $CH(C_2H_5)—CO—OC(CH_3)_3$ | n-$C_4H_9$ |
| Ia.2560 | F | $CH(C_2H_5)—CO—OC(CH_3)_3$ | n-$C_4H_9$ |
| Ia.2561 | Cl | $CH(C_2H_5)—CO—OC(CH_3)_3$ | n-$C_4H_9$ |
| Ia.2562 | H | $CH(C_2H_5)—CO—OC(CH_3)_3$ | $CH_2—CH{=}CH_2$ |
| Ia.2563 | F | $CH(C_2H_5)—CO—OC(CH_3)_3$ | $CH_2—CH{=}CH_2$ |
| Ia.2564 | Cl | $CH(C_2H_5)—CO—OC(CH_3)_3$ | $CH_2—CH{=}CH_2$ |
| Ia.2565 | H | $CH(C_2H_5)—CO—OC(CH_3)_3$ | $CH_2—C{\equiv}CH$ |
| Ia.2566 | F | $CH(C_2H_5)—CO—OC(CH_3)_3$ | $CH_2—C{\equiv}CH$ |
| Ia.2567 | Cl | $CH(C_2H_5)—CO—OC(CH_3)_3$ | $CH_2—C{\equiv}CH$ |
| Ia.2568 | H | $CH(C_2H_5)—CO—OC(CH_3)_3$ | $CH_2—CO—OCH_3$ |
| Ia.2569 | F | $CH(C_2H_5)—CO—OC(CH_3)_3$ | $CH_2—CO—OCH_3$ |
| Ia.2570 | Cl | $CH(C_2H_5)—CO—OC(CH_3)_3$ | $CH_2—CO—OCH_3$ |
| Ia.2571 | H | $CH(C_2H_5)—CO—OC(CH_3)_3$ | $CH_2$-phenyl |
| Ia.2572 | F | $CH(C_2H_5)—CO—OC(CH_3)_3$ | $CH_2$-phenyl |
| Ia.2573 | Cl | $CH(C_2H_5)—CO—OC(CH_3)_3$ | $CH_2$-phenyl |
| Ia.2574 | H | $CH_2—CO—SCH_3$ | $CH_3$ |
| Ia.2575 | F | $CH_2—CO—SCH_3$ | $CH_3$ |
| Ia.2576 | Cl | $CH_2—CO—SCH_3$ | $CH_3$ |
| Ia.2577 | H | $CH_2—CO—SCH_3$ | $C_2H_5$ |
| Ia.2578 | F | $CH_2—CO—SCH_3$ | $C_2H_5$ |
| Ia.2579 | Cl | $CH_2—CO—SCH_3$ | $C_2H_5$ |
| Ia.2580 | H | $CH_2—CO—SCH_3$ | n-$C_3H_7$ |
| Ia.2581 | F | $CH_2—CO—SCH_3$ | n-$C_3H_7$ |
| Ia.2582 | Cl | $CH_2—CO—SCH_3$ | n-$C_3H_7$ |
| Ia.2583 | H | $CH_2—CO—SCH_3$ | n-$C_4H_9$ |
| Ia.2584 | F | $CH_2—CO—SCH_3$ | n-$C_4H_9$ |
| Ia.2585 | Cl | $CH_2—CO—SCH_3$ | n-$C_4H_9$ |
| Ia.2586 | H | $CH_2—CO—SCH_3$ | $CH_2—CH{=}CH_2$ |
| Ia.2587 | F | $CH_2—CO—SCH_3$ | $CH_2—CH{=}CH_2$ |
| Ia.2588 | Cl | $CH_2—CO—SCH_3$ | $CH_2—CH{=}CH_2$ |
| Ia.2589 | H | $CH_2—CO—SCH_3$ | $CH_2—C{\equiv}CH$ |
| Ia.2590 | F | $CH_2—CO—SCH_3$ | $CH_2—C{\equiv}CH$ |
| Ia.2591 | Cl | $CH_2—CO—SCH_3$ | $CH_2—C{\equiv}CH$ |
| Ia.2592 | H | $CH_2—CO—SCH_3$ | $CH_2—CO—OCH_3$ |
| Ia.2593 | F | $CH_2—CO—SCH_3$ | $CH_2—CO—OCH_3$ |
| Ia.2594 | Cl | $CH_2—CO—SCH_3$ | $CH_2—CO—OCH_3$ |
| Ia.2595 | H | $CH_2—CO—SCH_3$ | $CH_2$-phenyl |
| Ia.2596 | F | $CH_2—CO—SCH_3$ | $CH_2$-phenyl |
| Ia.2597 | Cl | $CH_2—CO—SCH_3$ | $CH_2$-phenyl |
| Ia.2598 | H | $CH_2—CO—NH_2$ | $CH_3$ |
| Ia.2599 | F | $CH_2—CO—NH_2$ | $CH_3$ |
| Ia.2600 | Cl | $CH_2—CO—NH_2$ | $CH_3$ |
| Ia.2601 | H | $CH_2—CO—NH_2$ | $C_2H_5$ |
| Ia.2602 | F | $CH_2—CO—NH_2$ | $C_2H_5$ |
| Ia.2603 | Cl | $CH_2—CO—NH_2$ | $C_2H_5$ |
| Ia.2604 | H | $CH_2—CO—NH_2$ | n-$C_3H_7$ |
| Ia.2605 | F | $CH_2—CO—NH_2$ | n-$C_3H_7$ |
| Ia.2606 | Cl | $CH_2—CO—NH_2$ | n-$C_3H_7$ |
| Ia.2607 | H | $CH_2—CO—NH_2$ | n-$C_4H_9$ |
| Ia.2608 | F | $CH_2—CO—NH_2$ | n-$C_4H_9$ |
| Ia.2609 | Cl | $CH_2—CO—NH_2$ | n-$C_4H_9$ |
| Ia.2610 | H | $CH_2—CO—NH_2$ | $CH_2—CH{=}CH_2$ |

TABLE 1-continued

I

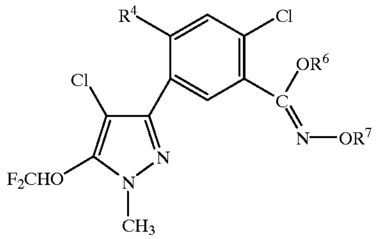

| No. | $R^4$ | $R^6$ | $R^7$ |
|---|---|---|---|
| Ia.2611 | F | $CH_2$—CO—$NH_2$ | $CH_2$—CH=$CH_2$ |
| Ia.2612 | Cl | $CH_2$—CO—$NH_2$ | $CH_2$—CH=$CH_2$ |
| Ia.2613 | H | $CH_2$—CO—$NH_2$ | $CH_2$—C≡CH |
| Ia.2614 | F | $CH_2$—CO—$NH_2$ | $CH_2$—C≡CH |
| Ia.2615 | Cl | $CH_2$—CO—$NH_2$ | $CH_2$—C≡CH |
| Ia.2616 | H | $CH_2$—CO—$NH_2$ | $CH_2$—CO—$OCH_3$ |
| Ia.2617 | F | $CH_2$—CO—$NH_2$ | $CH_2$—CO—$OCH_3$ |
| Ia.2618 | Cl | $CH_2$—CO—$NH_2$ | $CH_2$—CO—$OCH_3$ |
| Ia.2619 | H | $CH_2$—CO—$NH_2$ | $CH_2$-phenyl |
| Ia.2620 | F | $CH_2$—CO—$NH_2$ | $CH_2$-phenyl |
| Ia.2621 | Cl | $CH_2$—CO—$NH_2$ | $CH_2$-phenyl |
| Ia.2622 | H | $CH(CH_3)$—CO—$NH_2$ | $CH_3$ |
| Ia.2623 | F | $CH(CH_3)$—CO—$NH_2$ | $CH_3$ |
| Ia.2624 | Cl | $CH(CH_3)$—CO—$NH_2$ | $CH_3$ |
| Ia.2625 | H | $CH(CH_3)$—CO—$NH_2$ | $C_2H_5$ |
| Ia.2626 | F | $CH(CH_3)$—CO—$NH_2$ | $C_2H_5$ |
| Ia.2627 | Cl | $CH(CH_3)$—CO—$NH_2$ | $C_2H_5$ |
| Ia.2628 | H | $CH(CH_3)$—CO—$NH_2$ | n-$C_3H_7$ |
| Ia.2629 | F | $CH(CH_3)$—CO—$NH_2$ | n-$C_3H_7$ |
| Ia.2630 | Cl | $CH(CH_3)$—CO—$NH_2$ | n-$C_3H_7$ |
| Ia.2631 | H | $CH(CH_3)$—CO—$NH_2$ | n-$C_4H_9$ |
| Ia.2632 | F | $CH(CH_3)$—CO—$NH_2$ | n-$C_4H_9$ |
| Ia.2633 | Cl | $CH(CH_3)$—CO—$NH_2$ | n-$C_4H_9$ |
| Ia.2634 | H | $CH(CH_3)$—CO—$NH_2$ | $CH_2$—CH=$CH_2$ |
| Ia.2635 | F | $CH(CH_3)$—CO—$NH_2$ | $CH_2$—CH=$CH_2$ |
| Ia.2636 | Cl | $CH(CH_3)$—CO—$NH_2$ | $CH_2$—CH=$CH_2$ |
| Ia.2637 | H | $CH(CH_3)$—CO—$NH_2$ | $CH_2$—C≡CH |
| Ia.2638 | F | $CH(CH_3)$—CO—$NH_2$ | $CH_2$—C≡CH |
| Ia.2639 | Cl | $CH(CH_3)$—CO—$NH_2$ | $CH_2$—C≡CH |
| Ia.2640 | H | $CH(CH_3)$—CO—$NH_2$ | $CH_2$—CO—$OCH_3$ |
| Ia.2641 | F | $CH(CH_3)$—CO—$NH_2$ | $CH_2$—CO—$OCH_3$ |
| Ia.2642 | Cl | $CH(CH_3)$—CO—$NH_2$ | $CH_2$—CO—$OCH_3$ |
| Ia.2643 | H | $CH(CH_3)$—CO—$NH_2$ | $CH_2$-phenyl |
| Ia.2644 | F | $CH(CH_3)$—CO—$NH_2$ | $CH_2$-phenyl |
| Ia.2645 | Cl | $CH(CH_3)$—CO—$NH_2$ | $CH_2$-phenyl |
| Ia.2646 | H | $CH(C_2H_5)$—CO—$NH_2$ | $CH_3$ |
| Ia.2647 | F | $CH(C_2H_5)$—CO—$NH_2$ | $CH_3$ |
| Ia.2648 | Cl | $CH(C_2H_5)$—CO—$NH_2$ | $CH_3$ |
| Ia.2649 | H | $CH(C_2H_5)$—CO—$NH_2$ | $C_2H_5$ |
| Ia.2650 | F | $CH(C_2H_5)$—CO—$NH_2$ | $C_2H_5$ |
| Ia.2651 | Cl | $CH(C_2H_5)$—CO—$NH_2$ | $C_2H_5$ |
| Ia.2652 | H | $CH(C_2H_5)$—CO—$NH_2$ | n-$C_3H_7$ |
| Ia.2653 | F | $CH(C_2H_5)$—CO—$NH_2$ | n-$C_3H_7$ |
| Ia.2654 | Cl | $CH(C_2H_5)$—CO—$NH_2$ | n-$C_3H_7$ |
| Ia.2655 | H | $CH(C_2H_5)$—CO—$NH_2$ | n-$C_4H_9$ |
| Ia.2656 | F | $CH(C_2H_5)$—CO—$NH_2$ | n-$C_4H_9$ |
| Ia.2657 | Cl | $CH(C_2H_5)$—CO—$NH_2$ | n-$C_4H_9$ |
| Ia.2658 | H | $CH(C_2H_5)$—CO—$NH_2$ | $CH_2$—CH=$CH_2$ |
| Ia.2659 | F | $CH(C_2H_5)$—CO—$NH_2$ | $CH_2$—CH=$CH_2$ |
| Ia.2660 | Cl | $CH(C_2H_5)$—CO—$NH_2$ | $CH_2$—CH=$CH_2$ |
| Ia.2661 | H | $CH(C_2H_5)$—CO—$NH_2$ | $CH_2$—C≡CH |
| Ia.2662 | F | $CH(C_2H_5)$—CO—$NH_2$ | $CH_2$—C≡CH |
| Ia.2663 | Cl | $CH(C_2H_5)$—CO—$NH_2$ | $CH_2$—C≡CH |
| Ia.2664 | H | $CH(C_2H_5)$—CO—$NH_2$ | $CH_2$—CO—$OCH_3$ |
| Ia.2665 | F | $CH(C_2H_5)$—CO—$NH_2$ | $CH_2$—CO—$OCH_3$ |
| Ia.2666 | Cl | $CH(C_2H_5)$—CO—$NH_2$ | $CH_2$—CO—$OCH_3$ |
| Ia.2667 | H | $CH(C_2H_5)$—CO—$NH_2$ | $CH_2$-phenyl |
| Ia.2668 | F | $CH(C_2H_5)$—CO—$NH_2$ | $CH_2$-phenyl |
| Ia.2669 | Cl | $CH(C_2H_5)$—CO—$NH_2$ | $CH_2$-phenyl |
| Ia.2670 | H | $CH_2$—CO—NH—$CH_3$ | $CH_3$ |
| Ia.2671 | F | $CH_2$—CO—NH—$CH_3$ | $CH_3$ |
| Ia.2672 | Cl | $CH_2$—CO—NH—$CH_3$ | $CH_3$ |
| Ia.2673 | H | $CH_2$—CO—NH—$CH_3$ | $C_2H_5$ |

TABLE 1-continued

I

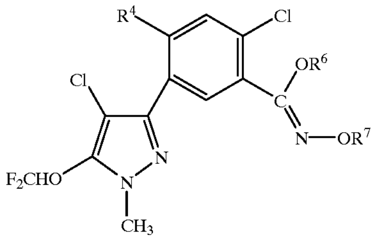

| No. | $R^4$ | $R^6$ | $R^7$ |
|---|---|---|---|
| Ia.2674 | F | $CH_2$—CO—NH—$CH_3$ | $C_2H_5$ |
| Ia.2675 | Cl | $CH_2$—CO—NH—$CH_3$ | $C_2H_5$ |
| Ia.2676 | H | $CH_2$—CO—NH—$CH_3$ | n-$C_3H_7$ |
| Ia.2677 | F | $CH_2$—CO—NH—$CH_3$ | n-$C_3H_7$ |
| Ia.2678 | Cl | $CH_2$—CO—NH—$CH_3$ | n-$C_3H_7$ |
| Ia.2679 | H | $CH_2$—CO—NH—$CH_3$ | n-$C_4H_9$ |
| Ia.2680 | F | $CH_2$—CO—NH—$CH_3$ | n-$C_4H_9$ |
| Ia.2681 | Cl | $CH_2$—CO—NH—$CH_3$ | n-$C_4H_9$ |
| Ia.2682 | H | $CH_2$—CO—NH—$CH_3$ | $CH_2$—CH=$CH_2$ |
| Ia.2683 | F | $CH_2$—CO—NH—$CH_3$ | $CH_2$—CH=$CH_2$ |
| Ia.2684 | Cl | $CH_2$—CO—NH—$CH_3$ | $CH_2$—CH=$CH_2$ |
| Ia.2685 | H | $CH_2$—CO—NH—$CH_3$ | $CH_2$—C≡CH |
| Ia.2686 | F | $CH_2$—CO—NH—$CH_3$ | $CH_2$—C≡CH |
| Ia.2687 | Cl | $CH_2$—CO—NH—$CH_3$ | $CH_2$—C≡CH |
| Ia.2688 | H | $CH_2$—CO—NH—$CH_3$ | $CH_2$—CO—$OCH_3$ |
| Ia.2689 | F | $CH_2$—CO—NH—$CH_3$ | $CH_2$—CO—$OCH_3$ |
| Ia.2690 | Cl | $CH_2$—CO—NH—$CH_3$ | $CH_2$—CO—$OCH_3$ |
| Ia.2691 | H | $CH_2$—CO—NH—$CH_3$ | $CH_2$-phenyl |
| Ia.2692 | F | $CH_2$—CO—NH—$CH_3$ | $CH_2$-phenyl |
| Ia.2693 | Cl | $CH_2$—CO—NH—$CH_3$ | $CH_2$-phenyl |
| Ia.2694 | H | $CH(CH_3)$—CO—NH—$CH_3$ | $CH_3$ |
| Ia.2695 | F | $CH(CH_3)$—CO—NH—$CH_3$ | $CH_3$ |
| Ia.2696 | Cl | $CH(CH_3)$—CO—NH—$CH_3$ | $CH_3$ |
| Ia.2697 | H | $CH(CH_3)$—CO—NH—$CH_3$ | $C_2H_5$ |
| Ia.2698 | F | $CH(CH_3)$—CO—NH—$CH_3$ | $C_2H_5$ |
| Ia.2699 | Cl | $CH(CH_3)$—CO—NH—$CH_3$ | $C_2H_5$ |
| Ia.2700 | H | $CH(CH_3)$—CO—NH—$CH_3$ | n-$C_3H_7$ |
| Ia.2701 | F | $CH(CH_3)$—CO—NH—$CH_3$ | n-$C_3H_7$ |
| Ia.2702 | Cl | $CH(CH_3)$—CO—NH—$CH_3$ | n-$C_3H_7$ |
| Ia.2703 | H | $CH(CH_3)$—CO—NH—$CH_3$ | n-$C_4H_9$ |
| Ia.2704 | F | $CH(CH_3)$—CO—NH—$CH_3$ | n-$C_4H_9$ |
| Ia.2705 | Cl | $CH(CH_3)$—CO—NH—$CH_3$ | n-$C_4H_9$ |
| Ia.2706 | H | $CH(CH_3)$—CO—NH—$CH_3$ | $CH_2$—CH=$CH_2$ |
| Ia.2707 | F | $CH(CH_3)$—CO—NH—$CH_3$ | $CH_2$—CH=$CH_2$ |
| Ia.2708 | Cl | $CH(CH_3)$—CO—NH—$CH_3$ | $CH_2$—CH=$CH_2$ |
| Ia.2709 | H | $CH(CH_3)$—CO—NH—$CH_3$ | $CH_2$—C≡CH |
| Ia.2710 | F | $CH(CH_3)$—CO—NH—$CH_3$ | $CH_2$—C≡CH |
| Ia.2711 | Cl | $CH(CH_3)$—CO—NH—$CH_3$ | $CH_2$—C≡CH |
| Ia.2712 | H | $CH(CH_3)$—CO—NH—$CH_3$ | $CH_2$—CO—$OCH_3$ |
| Ia.2713 | F | $CH(CH_3)$—CO—NH—$CH_3$ | $CH_2$—CO—$OCH_3$ |
| Ia.2714 | Cl | $CH(CH_3)$—CO—NH—$CH_3$ | $CH_2$—CO—$OCH_3$ |
| Ia.2715 | H | $CH(CH_3)$—CO—NH—$CH_3$ | $CH_2$-phenyl |
| Ia.2716 | F | $CH(CH_3)$—CO—NH—$CH_3$ | $CH_2$-phenyl |
| Ia.2717 | Cl | $CH(CH_3)$—CO—NH—$CH_3$ | $CH_2$-phenyl |
| Ia.2718 | H | $CH(C_2H_5)$—CO—NH—$CH_3$ | $CH_3$ |
| Ia.2719 | F | $CH(C_2H_5)$—CO—NH—$CH_3$ | $CH_3$ |
| Ia.2720 | Cl | $CH(C_2H_5)$—CO—NH—$CH_3$ | $CH_3$ |
| Ia.2721 | H | $CH(C_2H_5)$—CO—NH—$CH_3$ | $C_2H_5$ |
| Ia.2722 | F | $CH(C_2H_5)$—CO—NH—$CH_3$ | $C_2H_5$ |
| Ia.2723 | Cl | $CH(C_2H_5)$—CO—NH—$CH_3$ | $C_2H_5$ |
| Ia.2724 | H | $CH(C_2H_5)$—CO—NH—$CH_3$ | n-$C_3H_7$ |
| Ia.2725 | F | $CH(C_2H_5)$—CO—NH—$CH_3$ | n-$C_3H_7$ |
| Ia.2726 | Cl | $CH(C_2H_5)$—CO—NH—$CH_3$ | n-$C_3H_7$ |
| Ia.2727 | H | $CH(C_2H_5)$—CO—NH—$CH_3$ | n-$C_4H_9$ |
| Ia.2728 | F | $CH(C_2H_5)$—CO—NH—$CH_3$ | n-$C_4H_9$ |
| Ia.2729 | Cl | $CH(C_2H_5)$—CO—NH—$CH_3$ | n-$C_4H_9$ |
| Ia.2730 | H | $CH(C_2H_5)$—CO—NH—$CH_3$ | $CH_2$—CH=$CH_2$ |
| Ia.2731 | F | $CH(C_2H_5)$—CO—NH—$CH_3$ | $CH_2$—CH=$CH_2$ |
| Ia.2732 | Cl | $CH(C_2H_5)$—CO—NH—$CH_3$ | $CH_2$—CH=$CH_2$ |
| Ia.2733 | H | $CH(C_2H_5)$—CO—NH—$CH_3$ | $CH_2$—C≡CH |
| Ia.2734 | F | $CH(C_2H_5)$—CO—NH—$CH_3$ | $CH_2$—C≡CH |
| Ia.2735 | Cl | $CH(C_2H_5)$—CO—NH—$CH_3$ | $CH_2$—C≡CH |
| Ia.2736 | H | $CH(C_2H_5)$—CO—NH—$CH_3$ | $CH_2$—CO—$OCH_3$ |

TABLE 1-continued

I

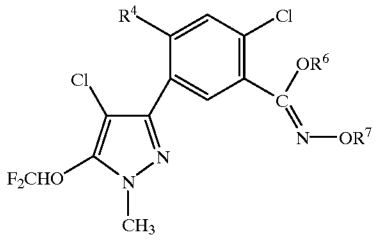

| No. | $R^4$ | $R^6$ | $R^7$ |
|---|---|---|---|
| Ia.2737 | F | $CH(C_2H_5)$—CO—NH—$CH_3$ | $CH_2$—CO—$OCH_3$ |
| Ia.2738 | Cl | $CH(C_2H_5)$—CO—NH—$CH_3$ | $CH_2$—CO—$OCH_3$ |
| Ia.2739 | H | $CH(C_2H_5)$—CO—NH—$CH_3$ | $CH_2$-phenyl |
| Ia.2740 | F | $CH(C_2H_5)$—CO—NH—$CH_3$ | $CH_2$-phenyl |
| Ia.2741 | Cl | $CH(C_2H_5)$—CO—NH—$CH_3$ | $CH_2$-phenyl |
| Ia.2742 | H | $CH_2$—CO—$N(CH_3)_2$ | $CH_3$ |
| Ia.2743 | F | $CH_2$—CO—$N(CH_3)_2$ | $CH_3$ |
| Ia.2744 | Cl | $CH_2$—CO—$N(CH_3)_2$ | $CH_3$ |
| Ia.2745 | H | $CH_2$—CO—$N(CH_3)_2$ | $C_2H_5$ |
| Ia.2746 | F | $CH_2$—CO—$N(CH_3)_2$ | $C_2H_5$ |
| Ia.2747 | Cl | $CH_2$—CO—$N(CH_3)_2$ | $C_2H_5$ |
| Ia.2748 | H | $CH_2$—CO—$N(CH_3)_2$ | n-$C_3H_7$ |
| Ia.2749 | F | $CH_2$—CO—$N(CH_3)_2$ | n-$C_3H_7$ |
| Ia.2750 | Cl | $CH_2$—CO—$N(CH_3)_2$ | n-$C_3H_7$ |
| Ia.2751 | H | $CH_2$—CO—$N(CH_3)_2$ | n-$C_4H_9$ |
| Ia.2752 | F | $CH_2$—CO—$N(CH_3)_2$ | n-$C_4H_9$ |
| Ia.2753 | Cl | $CH_2$—CO—$N(CH_3)_2$ | n-$C_4H_9$ |
| Ia.2754 | H | $CH_2$—CO—$N(CH_3)_2$ | $CH_2$—CH═$CH_2$ |
| Ia.2755 | F | $CH_2$—CO—$N(CH_3)_2$ | $CH_2$—CH═$CH_2$ |
| Ia.2756 | Cl | $CH_2$—CO—$N(CH_3)_2$ | $CH_2$—CH═$CH_2$ |
| Ia.2757 | H | $CH_2$—CO—$N(CH_3)_2$ | $CH_2$—C≡CH |
| Ia.2758 | F | $CH_2$—CO—$N(CH_3)_2$ | $CH_2$—C≡CH |
| Ia.2759 | Cl | $CH_2$—CO—$N(CH_3)_2$ | $CH_2$—C≡CH |
| Ia.2760 | H | $CH_2$—CO—$N(CH_3)_2$ | $CH_2$—CO—$OCH_3$ |
| Ia.2761 | F | $CH_2$—CO—$N(CH_3)_2$ | $CH_2$—CO—$OCH_3$ |
| Ia.2762 | Cl | $CH_2$—CO—$N(CH_3)_2$ | $CH_2$—CO—$OCH_3$ |
| Ia.2763 | H | $CH_2$—CO—$N(CH_3)_2$ | $CH_2$-phenyl |
| Ia.2764 | F | $CH_2$—CO—$N(CH_3)_2$ | $CH_2$-phenyl |
| Ia.2765 | Cl | $CH_2$—CO—$N(CH_3)_2$ | $CH_2$-phenyl |
| Ia.2766 | H | $CH(CH_3)$—CO—$N(CH_3)_2$ | $CH_3$ |
| Ia.2767 | F | $CH(CH_3)$—CO—$N(CH_3)_2$ | $CH_3$ |
| Ia.2768 | Cl | $CH(CH_3)$—CO—$N(CH_3)_2$ | $CH_3$ |
| Ia.2769 | H | $CH(CH_3)$—CO—$N(CH_3)_2$ | $C_2H_5$ |
| Ia.2770 | F | $CH(CH_3)$—CO—$N(CH_3)_2$ | $C_2H_5$ |
| Ia.2771 | Cl | $CH(CH_3)$—CO—$N(CH_3)_2$ | $C_2H_5$ |
| Ia.2772 | H | $CH(CH_3)$—CO—$N(CH_3)_2$ | n-$C_3H_7$ |
| Ia.2773 | F | $CH(CH_3)$—CO—$N(CH_3)_2$ | n-$C_3H_7$ |
| Ia.2774 | Cl | $CH(CH_3)$—CO—$N(CH_3)_2$ | n-$C_3H_7$ |
| Ia.2775 | H | $CH(CH_3)$—CO—$N(CH_3)_2$ | n-$C_4H_9$ |
| Ia.2776 | F | $CH(CH_3)$—CO—$N(CH_3)_2$ | n-$C_4H_9$ |
| Ia.2777 | Cl | $CH(CH_3)$—CO—$N(CH_3)_2$ | n-$C_4H_9$ |
| Ia.2778 | H | $CH(CH_3)$—CO—$N(CH_3)_2$ | $CH_2$—CH═$CH_2$ |
| Ia.2779 | F | $CH(CH_3)$—CO—$N(CH_3)_2$ | $CH_2$—CH═$CH_2$ |
| Ia.2780 | Cl | $CH(CH_3)$—CO—$N(CH_3)_2$ | $CH_2$—CH═$CH_2$ |
| Ia.2781 | H | $CH(CH_3)$—CO—$N(CH_3)_2$ | $CH_2$—C≡CH |
| Ia.2782 | F | $CH(CH_3)$—CO—$N(CH_3)_2$ | $CH_2$—C≡CH |
| Ia.2783 | Cl | $CH(CH_3)$—CO—$N(CH_3)_2$ | $CH_2$—C≡CH |
| Ia.2784 | H | $CH(CH_3)$—CO—$N(CH_3)_2$ | $CH_2$—CO—$OCH_3$ |
| Ia.2785 | F | $CH(CH_3)$—CO—$N(CH_3)_2$ | $CH_2$—CO—$OCH_3$ |
| Ia.2786 | Cl | $CH(CH_3)$—CO—$N(CH_3)_2$ | $CH_2$—CO—$OCH_3$ |
| Ia.2787 | H | $CH(CH_3)$—CO—$N(CH_3)_2$ | $CH_2$-phenyl |
| Ia.2788 | F | $CH(CH_3)$—CO—$N(CH_3)_2$ | $CH_2$-phenyl |
| Ia.2789 | Cl | $CH(CH_3)$—CO—$N(CH_3)_2$ | $CH_2$-phenyl |
| Ia.2790 | H | $CH(C_2H_5)$—CO—$N(CH_3)_2$ | $CH_3$ |
| Ia.2791 | F | $CH(C_2H_5)$—CO—$N(CH_3)_2$ | $CH_3$ |
| Ia.2792 | Cl | $CH(C_2H_5)$—CO—$N(CH_3)_2$ | $CH_3$ |
| Ia.2793 | H | $CH(C_2H_5)$—CO—$N(CH_3)_2$ | $C_2H_5$ |
| Ia.2794 | F | $CH(C_2H_5)$—CO—$N(CH_3)_2$ | $C_2H_5$ |
| Ia.2795 | Cl | $CH(C_2H_5)$—CO—$N(CH_3)_2$ | $C_2H_5$ |
| Ia.2796 | H | $CH(C_2H_5)$—CO—$N(CH_3)_2$ | n-$C_3H_7$ |
| Ia.2797 | F | $CH(C_2H_5)$—CO—$N(CH_3)_2$ | n-$C_3H_7$ |
| Ia.2798 | Cl | $CH(C_2H_5)$—CO—$N(CH_3)_2$ | n-$C_3H_7$ |
| Ia.2799 | H | $CH(C_2H_5)$—CO—$N(CH_3)_2$ | n-$C_4H_9$ |

TABLE 1-continued

I

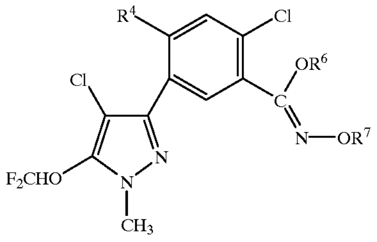

| No. | $R^4$ | $R^6$ | $R^7$ |
|---|---|---|---|
| Ia.2800 | F | $CH(C_2H_5)—CO—N(CH_3)_2$ | $n-C_4H_9$ |
| Ia.2801 | Cl | $CH(C_2H_5)—CO—N(CH_3)_2$ | $n-C_4H_9$ |
| Ia.2802 | H | $CH(C_2H_5)—CO—N(CH_3)_2$ | $CH_2—CH═CH_2$ |
| Ia.2803 | F | $CH(C_2H_5)—CO—N(CH_3)_2$ | $CH_2—CH═CH_2$ |
| Ia.2804 | Cl | $CH(C_2H_5)—CO—N(CH_3)_2$ | $CH_2—CH═CH_2$ |
| Ia.2805 | H | $CH(C_2H_5)—CO—N(CH_3)_2$ | $CH_2—C≡CH$ |
| Ia.2806 | F | $CH(C_2H_5)—CO—N(CH_3)_2$ | $CH_2—C≡CH$ |
| Ia.2807 | Cl | $CH(C_2H_5)—CO—N(CH_3)_2$ | $CH_2—C≡CH$ |
| Ia.2808 | H | $CH(C_2H_5)—CO—N(CH_3)_2$ | $CH_2—CO—OCH_3$ |
| Ia.2809 | F | $CH(C_2H_5)—CO—N(CH_3)_2$ | $CH_2—CO—OCH_3$ |
| Ia.2810 | Cl | $CH(C_2H_5)—CO—N(CH_3)_2$ | $CH_2—CO—OCH_3$ |
| Ia.2811 | H | $CH(C_2H_5)—CO—N(CH_3)_2$ | $CH_2$-phenyl |
| Ia.2812 | F | $CH(C_2H_5)—CO—N(CH_3)_2$ | $CH_2$-phenyl |
| Ia.2813 | Cl | $CH(C_2H_5)—CO—N(CH_3)_2$ | $CH_2$-phenyl |
| Ia.2814 | H | cyclopentyl | $CH_3$ |
| Ia.2815 | F | cyclopentyl | $CH_3$ |
| Ia.2816 | Cl | cyclopentyl | $CH_3$ |
| Ia.2817 | H | cyclopentyl | $C_2H_5$ |
| Ia.2818 | F | cyclopentyl | $C_2H_5$ |
| Ia.2819 | Cl | cyclopentyl | $C_2H_5$ |
| Ia.2820 | H | cyclopentyl | $n-C_3H_7$ |
| Ia.2821 | F | cyclopentyl | $n-C_3H_7$ |
| Ia.2822 | Cl | cyclopentyl | $n-C_3H_7$ |
| Ia.2823 | H | cyclopentyl | $n-C_4H_9$ |
| Ia.2824 | F | cyclopentyl | $n-C_4H_9$ |
| Ia.2825 | Cl | cyclopentyl | $n-C_4H_9$ |
| Ia.2826 | H | cyclopentyl | $CH_2—CH═CH_2$ |
| Ia.2827 | F | cyclopentyl | $CH_2—CH═CH_2$ |
| Ia.2828 | Cl | cyclopentyl | $CH_2—CH═CH_2$ |
| Ia.2829 | H | cyclopentyl | $CH_2—C≡CH$ |
| Ia.2830 | F | cyclopentyl | $CH_2—C≡CH$ |
| Ia.2831 | Cl | cyclopentyl | $CH_2—C≡CH$ |
| Ia.2832 | H | cyclopentyl | $CH_2—CO—OCH_3$ |
| Ia.2833 | F | cyclopentyl | $CH_2—CO—OCH_3$ |
| Ia.2834 | Cl | cyclopentyl | $CH_2—CO—OCH_3$ |
| Ia.2835 | H | cyclopentyl | $CH_2$-phenyl |
| Ia.2836 | F | cyclopentyl | $CH_2$-phenyl |
| Ia.2837 | Cl | cyclopentyl | $CH_2$-phenyl |
| Ia.2838 | H | cyclohexyl | $CH_3$ |
| Ia.2839 | F | cyclohexyl | $CH_3$ |
| Ia.2840 | Cl | cyclohexyl | $CH_3$ |
| Ia.2841 | H | cyclohexyl | $C_2H_5$ |
| Ia.2842 | F | cyclohexyl | $C_2H_5$ |
| Ia.2843 | Cl | cyclohexyl | $C_2H_5$ |
| Ia.2844 | H | cyclohexyl | $n-C_3H_7$ |
| Ia.2845 | F | cyclohexyl | $n-C_3H_7$ |
| Ia.2846 | Cl | cyclohexyl | $n-C_3H_7$ |
| Ia.2847 | H | cyclohexyl | $n-C_4H_9$ |
| Ia.2848 | F | cyclohexyl | $n-C_4H_9$ |
| Ia.2849 | Cl | cyclohexyl | $n-C_4H_9$ |
| Ia.2850 | H | cyclohexyl | $CH_2—CH═CH_2$ |
| Ia.2851 | F | cyclohexyl | $CH_2—CH═CH_2$ |
| Ia.2852 | Cl | cyclohexyl | $CH_2—CH═CH_2$ |
| Ia.2853 | H | cyclohexyl | $CH_2—C≡CH$ |
| Ia.2854 | F | cyclohexyl | $CH_2—C≡CH$ |
| Ia.2855 | Cl | cyclohexyl | $CH_2—C≡CH$ |
| Ia.2856 | H | cyclohexyl | $CH_2—CO—OCH_3$ |
| Ia.2857 | F | cyclohexyl | $CH_2—CO—OCH_3$ |
| Ia.2858 | Cl | cyclohexyl | $CH_2—CO—OCH_3$ |
| Ia.2859 | H | cyclohexyl | $CH_2$-phenyl |
| Ia.2860 | F | cyclohexyl | $CH_2$-phenyl |
| Ia.2861 | Cl | cyclohexyl | $CH_2$-phenyl |
| Ia.2862 | H | $CH_2$-cyclopentyl | $CH_3$ |

TABLE 1-continued

I

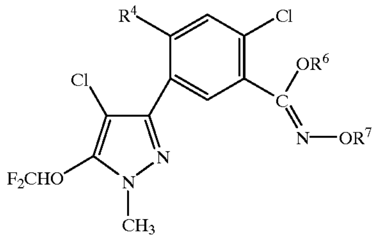

| No. | $R^4$ | $R^6$ | $R^7$ |
|---|---|---|---|
| Ia.2863 | F | $CH_2$-cyclopentyl | $CH_3$ |
| Ia.2864 | Cl | $CH_2$-cyclopentyl | $CH_3$ |
| Ia.2865 | H | $CH_2$-cyclopentyl | $C_2H_5$ |
| Ia.2866 | F | $CH_2$-cyclopentyl | $C_2H_5$ |
| Ia.2867 | Cl | $CH_2$-cyclopentyl | $C_2H_5$ |
| Ia.2868 | H | $CH_2$-cyclopentyl | n-$C_3H_7$ |
| Ia.2869 | F | $CH_2$-cyclopentyl | n-$C_3H_7$ |
| Ia.2870 | Cl | $CH_2$-cyclopentyl | n-$C_3H_7$ |
| Ia.2871 | H | $CH_2$-cyclopentyl | n-$C_4H_9$ |
| Ia.2872 | F | $CH_2$-cyclopentyl | n-$C_4H_9$ |
| Ia.2873 | Cl | $CH_2$-cyclopentyl | n-$C_4H_9$ |
| Ia.2874 | H | $CH_2$-cyclopentyl | $CH_2$—CH═$CH_2$ |
| Ia.2875 | F | $CH_2$-cyclopentyl | $CH_2$—CH═$CH_2$ |
| Ia.2876 | Cl | $CH_2$-cyclopentyl | $CH_2$—CH═$CH_2$ |
| Ia.2877 | H | $CH_2$-cyclopentyl | $CH_2$—C≡CH |
| Ia.2878 | F | $CH_2$-cyclopentyl | $CH_2$—C≡CH |
| Ia.2879 | Cl | $CH_2$-cyclopentyl | $CH_2$—C≡CH |
| Ia.2880 | H | $CH_2$-cyclopentyl | $CH_2$—CO—$OCH_3$ |
| Ia.2881 | F | $CH_2$-cyclopentyl | $CH_2$—CO—$OCH_3$ |
| Ia.2882 | Cl | $CH_2$-cyclopentyl | $CH_2$—CO—$OCH_3$ |
| Ia.2883 | H | $CH_2$-cyclopentyl | $CH_2$-phenyl |
| Ia.2884 | F | $CH_2$-cyclopentyl | $CH_2$-phenyl |
| Ia.2885 | Cl | $CH_2$-cyclopentyl | $CH_2$-phenyl |
| Ia.2886 | H | $CH_2$-cyclohexyl | $CH_3$ |
| Ia.2887 | F | $CH_2$-cyclohexyl | $CH_3$ |
| Ia.2888 | Cl | $CH_2$-cyclohexyl | $CH_3$ |
| Ia.2889 | H | $CH_2$-cyclohexyl | $C_2H_5$ |
| Ia.2890 | F | $CH_2$-cyclohexyl | $C_2H_5$ |
| Ia.2891 | Cl | $CH_2$-cyclohexyl | $C_2H_5$ |
| Ia.2892 | H | $CH_2$-cyclohexyl | n-$C_3H_7$ |
| Ia.2893 | F | $CH_2$-cyclohexyl | n-$C_3H_7$ |
| Ia.2894 | Cl | $CH_2$-cyclohexyl | n-$C_3H_7$ |
| Ia.2895 | H | $CH_2$-cyclohexyl | n-$C_4H_9$ |
| Ia.2896 | F | $CH_2$-cyclohexyl | n-$C_4H_9$ |
| Ia.2897 | Cl | $CH_2$-cyclohexyl | n-$C_4H_9$ |
| Ia.2898 | H | $CH_2$-cyclohexyl | $CH_2$—CH═$CH_2$ |
| Ia.2899 | F | $CH_2$-cyclohexyl | $CH_2$—CH═$CH_2$ |
| Ia.2900 | Cl | $CH_2$-cyclohexyl | $CH_2$—CH═$CH_2$ |
| Ia.2901 | H | $CH_2$-cyclohexyl | $CH_2$—C≡CH |
| Ia.2902 | F | $CH_2$-cyclohexyl | $CH_2$—C≡CH |
| Ia.2903 | Cl | $CH_2$-cyclohexyl | $CH_2$—C≡CH |
| Ia.2904 | H | $CH_2$-cyclohexyl | $CH_2$—CO—$OCH_3$ |
| Ia.2905 | F | $CH_2$-cyclohexyl | $CH_2$—CO—$OCH_3$ |
| Ia.2906 | Cl | $CH_2$-cyclohexyl | $CH_2$—CO—$OCH_3$ |
| Ia.2907 | H | $CH_2$-cyclohexyl | $CH_2$-phenyl |
| Ia.2908 | F | $CH_2$-cyclohexyl | $CH_2$-phenyl |
| Ia.2909 | Cl | $CH_2$-cyclohexyl | $CH_2$-phenyl |
| Ia.2910 | H | $CH_2$-phenyl | $CH_3$ |
| Ia.2911 | F | $CH_2$-phenyl | $CH_3$ |
| Ia.2912 | Cl | $CH_2$-phenyl | $CH_3$ |
| Ia.2913 | H | $CH_2$-phenyl | $C_2H_5$ |
| Ia.2914 | F | $CH_2$-phenyl | $C_2H_5$ |
| Ia.2915 | Cl | $CH_2$-phenyl | $C_2H_5$ |
| Ia.2916 | H | $CH_2$-phenyl | n-$C_3H_7$ |
| Ia.2917 | F | $CH_2$-phenyl | n-$C_3H_7$ |
| Ia.2918 | Cl | $CH_2$-phenyl | n-$C_3H_7$ |
| Ia.2919 | H | $CH_2$-phenyl | n-$C_4H_9$ |
| Ia.2920 | F | $CH_2$-phenyl | n-$C_4H_9$ |
| Ia.2921 | Cl | $CH_2$-phenyl | n-$C_4H_9$ |
| Ia.2922 | H | $CH_2$-phenyl | $CH_2$—CH═$CH_2$ |
| Ia.2923 | F | $CH_2$-phenyl | $CH_2$—CH═$CH_2$ |
| Ia.2924 | Cl | $CH_2$-phenyl | $CH_2$—CH═$CH_2$ |
| Ia.2925 | H | $CH_2$-phenyl | $CH_2$—C≡CH |

TABLE 1-continued

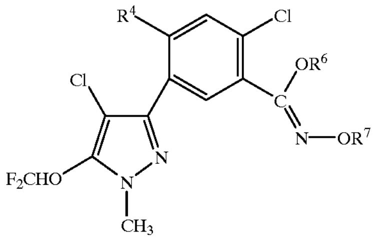

I

| No. | $R^4$ | $R^6$ | $R^7$ |
|---|---|---|---|
| Ia.2926 | F | $CH_2$-phenyl | $CH_2—C{\equiv}CH$ |
| Ia.2927 | Cl | $CH_2$-phenyl | $CH_2—C{\equiv}CH$ |
| Ia.2928 | H | $CH_2$-phenyl | $CH_2—CO—OCH_3$ |
| Ia.2929 | F | $CH_2$-phenyl | $CH_2—CO—OCH_3$ |
| Ia.2930 | Cl | $CH_2$-phenyl | $CH_2—CO—OCH_3$ |
| Ia.2931 | H | $CH_2$-phenyl | $CH_2$-phenyl |
| Ia.2932 | F | $CH_2$-phenyl | $CH_2$-phenyl |
| Ia.2933 | Cl | $CH_2$-phenyl | $CH_2$-phenyl |
| Ia.2934 | H | $CH_2$-(oxiran-2-yl) | $CH_3$ |
| Ia.2935 | F | $CH_2$-(oxiran-2-yl) | $CH_3$ |
| Ia.2936 | Cl | $CH_2$-(oxiran-2-yl) | $CH_3$ |
| Ia.2937 | H | $CH_2$-(oxiran-2-yl) | $C_2H_5$ |
| Ia.2938 | F | $CH_2$-(oxiran-2-yl) | $C_2H_5$ |
| Ia.2939 | Cl | $CH_2$-(oxiran-2-yl) | $C_2H_5$ |
| Ia.2940 | H | $CH_2$-(oxiran-2-yl) | n-$C_3H_7$ |
| Ia.2941 | F | $CH_2$-(oxiran-2-yl) | n-$C_3H_7$ |
| Ia.2942 | Cl | $CH_2$-(oxiran-2-yl) | n-$C_3H_7$ |
| Ia.2943 | H | $CH_2$-(oxiran-2-yl) | n-$C_4H_9$ |
| Ia.2944 | F | $CH_2$-(oxiran-2-yl) | n-$C_4H_9$ |
| Ia.2945 | Cl | $CH_2$-(oxiran-2-yl) | n-$C_4H_9$ |
| Ia.2946 | H | $CH_2$-(oxiran-2-yl) | $CH_2—CH{=}CH_2$ |
| Ia.2947 | F | $CH_2$-(oxiran-2-yl) | $CH_2—CH{=}CH_2$ |
| Ia.2948 | Cl | $CH_2$-(oxiran-2-yl) | $CH_2—CH{=}CH_2$ |
| Ia.2949 | H | $CH_2$-(oxiran-2-yl) | $CH_2—C{\equiv}CH$ |
| Ia.2950 | F | $CH_2$-(oxiran-2-yl) | $CH_2—C{\equiv}CH$ |
| Ia.2951 | Cl | $CH_2$-(oxiran-2-yl) | $CH_2—C{\equiv}CH$ |
| Ia.2952 | H | $CH_2$-(oxiran-2-yl) | $CH_2—CO—OCH_3$ |
| Ia.2953 | F | $CH_2$-(oxiran-2-yl) | $CH_2—CO—OCH_3$ |
| Ia.2954 | Cl | $CH_2$-(oxiran-2-yl) | $CH_2—CO—OCH_3$ |
| Ia.2955 | H | $CH_2$-(oxiran-2-yl) | $CH_2$-phenyl |
| Ia.2956 | F | $CH_2$-(oxiran-2-yl) | $CH_2$-phenyl |
| Ia.2957 | Cl | $CH_2$-(oxiran-2-yl) | $CH_2$-phenyl |
| Ia.2958 | H | $CH_2$-(oxetan-3-yl) | $CH_3$ |
| Ia.2959 | F | $CH_2$-(oxetan-3-yl) | $CH_3$ |
| Ia.2960 | Cl | $CH_2$-(oxetan-3-yl) | $CH_3$ |
| Ia.2961 | H | $CH_2$-(oxetan-3-yl) | $C_2H_5$ |
| Ia.2962 | F | $CH_2$-(oxetan-3-yl) | $C_2H_5$ |
| Ia.2963 | Cl | $CH_2$-(oxetan-3-yl) | $C_2H_5$ |
| Ia.2964 | H | $CH_2$-(oxetan-3-yl) | n-$C_3H_7$ |
| Ia.2965 | F | $CH_2$-(oxetan-3-yl) | n-$C_3H_7$ |
| Ia.2966 | Cl | $CH_2$-(oxetan-3-yl) | n-$C_3H_7$ |
| Ia.2967 | H | $CH_2$-(oxetan-3-yl) | n-$C_4H_9$ |
| Ia.2968 | F | $CH_2$-(oxetan-3-yl) | n-$C_4H_9$ |
| Ia.2969 | Cl | $CH_2$-(oxetan-3-yl) | n-$C_4H_9$ |
| Ia.2970 | H | $CH_2$-(oxetan-3-yl) | $CH_2—CH{=}CH_2$ |
| Ia.2971 | F | $CH_2$-(oxetan-3-yl) | $CH_2—CH{=}CH_2$ |
| Ia.2972 | Cl | $CH_2$-(oxetan-3-yl) | $CH_2—CH{=}CH_2$ |
| Ia.2973 | H | $CH_2$-(oxetan-3-yl) | $CH_2—C{\equiv}CH$ |
| Ia.2974 | F | $CH_2$-(oxetan-3-yl) | $CH_2—C{\equiv}CH$ |
| Ia.2975 | Cl | $CH_2$-(oxetan-3-yl) | $CH_2—C{\equiv}CH$ |
| Ia.2976 | H | $CH_2$-(oxetan-3-yl) | $CH_2—CO—OCH_3$ |
| Ia.2977 | F | $CH_2$-(oxetan-3-yl) | $CH_2—CO—OCH_3$ |
| Ia.2978 | Cl | $CH_2$-(oxetan-3-yl) | $CH_2—CO—OCH_3$ |
| Ia.2979 | H | $CH_2$-(oxetan-3-yl) | $CH_2$-phenyl |
| Ia.2980 | F | $CH_2$-(oxetan-3-yl) | $CH_2$-phenyl |
| Ia.2981 | Cl | $CH_2$-(oxetan-3-yl) | $CH_2$-phenyl |
| Ia.2982 | H | $CH_2—CH_2$-(pyrrolidin-1-yl) | $CH_3$ |
| Ia.2983 | F | $CH_2—CH_2$-(pyrrolidin-1-yl) | $CH_3$ |
| Ia.2984 | Cl | $CH_2—CH_2$-(pyrrolidin-1-yl) | $CH_3$ |
| Ia.2985 | H | $CH_2—CH_2$-(pyrrolidin-1-yl) | $C_2H_5$ |
| Ia.2986 | F | $CH_2—CH_2$-(pyrrolidin-1-yl) | $C_2H_5$ |
| Ia.2987 | Cl | $CH_2—CH_2$-(pyrrolidin-1-yl) | $C_2H_5$ |
| Ia.2988 | H | $CH_2—CH_2$-(pyrrolidin-1-yl) | n-$C_3H_7$ |

TABLE 1-continued

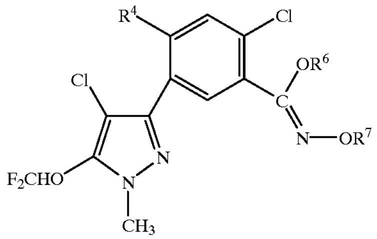

I

| No. | $R^4$ | $R^6$ | $R^7$ |
|---|---|---|---|
| Ia.2989 | F | $CH_2$—$CH_2$-(pyrrolidin-1-yl) | n-$C_3H_7$ |
| Ia.2990 | Cl | $CH_2$—$CH_2$-(pyrrolidin-1-yl) | n-$C_3H_7$ |
| Ia.2991 | H | $CH_2$—$CH_2$-(pyrrolidin-1-yl) | n-$C_4H_9$ |
| Ia.2992 | F | $CH_2$—$CH_2$-(pyrrolidin-1-yl) | n-$C_4H_9$ |
| Ia.2993 | Cl | $CH_2$—$CH_2$-(pyrrolidin-1-yl) | n-$C_4H_9$ |
| Ia.2994 | H | $CH_2$—$CH_2$-(pyrrolidin-1-yl) | $CH_2$—CH═$CH_2$ |
| Ia.2995 | F | $CH_2$—$CH_2$-(pyrrolidin-1-yl) | $CH_2$—CH═$CH_2$ |
| Ia.2996 | Cl | $CH_2$—$CH_2$-(pyrrolidin-1-yl) | $CH_2$—CH═$CH_2$ |
| Ia.2997 | H | $CH_2$—$CH_2$-(pyrrolidin-1-yl) | $CH_2$—C≡CH |
| Ia.2998 | F | $CH_2$—$CH_2$-(pyrrolidin-1-yl) | $CH_2$—C≡CH |
| Ia.2999 | Cl | $CH_2$—$CH_2$-(pyrrolidin-1-yl) | $CH_2$—C≡CH |
| Ia.3000 | H | $CH_2$—$CH_2$-(pyrrolidin-1-yl) | $CH_2$—CO—$OCH_3$ |
| Ia.3001 | F | $CH_2$—$CH_2$-(pyrrolidin-1-yl) | $CH_2$—CO—$OCH_3$ |
| Ia.3002 | Cl | $CH_2$—$CH_2$-(pyrrolidin-1-yl) | $CH_2$—CO—$OCH_3$ |
| Ia.3003 | H | $CH_2$—$CH_2$-(pyrrolidin-1-yl) | $CH_2$-phenyl |
| Ia.3004 | F | $CH_2$—$CH_2$-(pyrrolidin-1-yl) | $CH_2$-phenyl |
| Ia.3005 | Cl | $CH_2$—$CH_2$-(pyrrolidin-1-yl) | $CH_2$-phenyl |
| Ia.3006 | H | $CH_2$-(pyridin-2-yl) | $CH_3$ |
| Ia.3007 | F | $CH_2$-(pyridin-2-yl) | $CH_3$ |
| Ia.3008 | Cl | $CH_2$-(pyridin-2-yl) | $CH_3$ |
| Ia.3009 | H | $CH_2$-(pyridin-2-yl) | $C_2H_5$ |
| Ia.3010 | F | $CH_2$-(pyridin-2-yl) | $C_2H_5$ |
| Ia.3011 | Cl | $CH_2$-(pyridin-2-yl) | $C_2H_5$ |
| Ia.3012 | H | $CH_2$-(pyridin-2-yl) | n-$C_3H_7$ |
| Ia.3013 | F | $CH_2$-(pyridin-2-yl) | n-$C_3H_7$ |
| Ia.3014 | Cl | $CH_2$-(pyridin-2-yl) | n-$C_3H_7$ |
| Ia.3015 | H | $CH_2$-(pyridin-2-yl) | n-$C_4H_9$ |
| Ia.3016 | F | $CH_2$-(pyridin-2-yl) | n-$C_4H_9$ |
| Ia.3017 | Cl | $CH_2$-(pyridin-2-yl) | n-$C_4H_9$ |
| Ia.3018 | H | $CH_2$-(pyridin-2-yl) | $CH_2$—CH═$CH_2$ |
| Ia.3019 | F | $CH_2$-(pyridin-2-yl) | $CH_2$—CH═$CH_2$ |
| Ia.3020 | Cl | $CH_2$-(pyridin-2-yl) | $CH_2$—CH═$CH_2$ |
| Ia.3021 | H | $CH_2$-(pyridin-2-yl) | $CH_2$—C≡CH |
| Ia.3022 | F | $CH_2$-(pyridin-2-yl) | $CH_2$—C≡CH |
| Ia.3023 | Cl | $CH_2$-(pyridin-2-yl) | $CH_2$—C≡CH |
| Ia.3024 | H | $CH_2$-(pyridin-2-yl) | $CH_2$—CO—$OCH_3$ |
| Ia.3025 | F | $CH_2$-(pyridin-2-yl) | $CH_2$—CO—$OCH_3$ |
| Ia.3026 | Cl | $CH_2$-(pyridin-2-yl) | $CH_2$—CO—$OCH_3$ |
| Ia.3027 | H | $CH_2$-(pyridin-2-yl) | $CH_2$-phenyl |
| Ia.3028 | F | $CH_2$-(pyridin-2-yl) | $CH_2$-phenyl |
| Ia.3029 | Cl | $CH_2$-(pyridin-2-yl) | $CH_2$-phenyl |
| Ia.3030 | H | $CH_3$ | $CH_2$—$CH_2$—Cl |
| Ia.3031 | F | $CH_3$ | $CH_2$—$CH_2$—Cl |
| Ia.3032 | Cl | $CH_3$ | $CH_2$—$CH_2$—Cl |
| Ia.3033 | H | $C_2H_5$ | $CH_2$—$CH_2$—Cl |
| Ia.3034 | F | $C_2H_5$ | $CH_2$—$CH_2$—Cl |
| Ia.3035 | Cl | $C_2H_5$ | $CH_2$—$CH_2$—Cl |
| Ia.3036 | H | n-$C_3H_7$ | $CH_2$—$CH_2$—Cl |
| Ia.3037 | F | n-$C_3H_7$ | $CH_2$—$CH_2$—Cl |
| Ia.3038 | Cl | n-$C_3H_7$ | $CH_2$—$CH_2$—Cl |
| Ia.3039 | H | n-$C_4H_9$ | $CH_2$—$CH_2$—Cl |
| Ia.3040 | F | n-$C_4H_9$ | $CH_2$—$CH_2$—Cl |
| Ia.3041 | Cl | n-$C_4H_9$ | $CH_2$—$CH_2$—Cl |
| Ia.3042 | H | $CH_2$—CH═$CH_2$ | $CH_2$—$CH_2$—Cl |
| Ia.3043 | F | $CH_2$—CH═$CH_2$ | $CH_2$—$CH_2$—Cl |
| Ia.3044 | Cl | $CH_2$—CH═$CH_2$ | $CH_2$—$CH_2$—Cl |
| Ia.3045 | H | $CH_2$—C≡CH | $CH_2$—$CH_2$—Cl |
| Ia.3046 | F | $CH_2$—C≡CH | $CH_2$—$CH_2$—Cl |
| Ia.3047 | Cl | $CH_2$—C≡CH | $CH_2$—$CH_2$—Cl |
| Ia.3048 | H | $CH_2$—CO—$OCH_3$ | $CH_2$—$CH_2$—Cl |
| Ia.3049 | F | $CH_2$—CO—$OCH_3$ | $CH_2$—$CH_2$—Cl |
| Ia.3050 | Cl | $CH_2$—CO—$OCH_3$ | $CH_2$—$CH_2$—Cl |
| Ia.3051 | H | $CH_2$-phenyl | $CH_2$—$CH_2$—Cl |

TABLE 1-continued

I

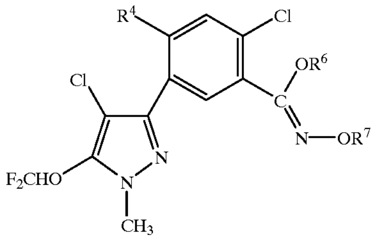

| No. | $R^4$ | $R^6$ | $R^7$ |
|---|---|---|---|
| Ia.3052 | F | $CH_2$-phenyl | $CH_2—CH_2—Cl$ |
| Ia.3053 | Cl | $CH_2$-phenyl | $CH_2—CH_2—Cl$ |
| Ia.3054 | H | $CH_3$ | $CH_2—CF_3$ |
| Ia.3055 | F | $CH_3$ | $CH_2—CF_3$ |
| Ia 3056 | Cl | $CH_3$ | $CH_2—CF_3$ |
| Ia.3057 | H | $C_2H_5$ | $CH_2—CF_3$ |
| Ia.3058 | F | $C_2H_5$ | $CH_2—CF_3$ |
| Ia.3059 | Cl | $C_2H_5$ | $CH_2—CF_3$ |
| Ia.3060 | H | n-$C_3H_7$ | $CH_2—CF_3$ |
| Ia.3061 | F | n-$C_3H_7$ | $CH_2—CF_3$ |
| Ia.3062 | Cl | n-$C_3H_7$ | $CH_2—CF_3$ |
| Ia.3063 | H | n-$C_4H_9$ | $CH_2—CF_3$ |
| Ia.3064 | F | n-$C_4H_9$ | $CH_2—CF_3$ |
| Ia.3065 | Cl | n-$C_4H_9$ | $CH_2—CF_3$ |
| Ia.3066 | H | $CH_2—CH═CH_2$ | $CH_2—CF_3$ |
| Ia.3067 | F | $CH_2—CH═CH_2$ | $CH_2—CF_3$ |
| Ia.3068 | Cl | $CH_2—CH═CH_2$ | $CH_2—CF_3$ |
| Ia.3069 | H | $CH_2—C≡CH$ | $CH_2—CF_3$ |
| Ia.3070 | F | $CH_2—C≡CH$ | $CH_2—CF_3$ |
| Ia.3071 | Cl | $CH_2—C≡CH$ | $CH_2—CF_3$ |
| Ia.3072 | H | $CH_2—CO—OCH_3$ | $CH_2—CF_3$ |
| Ia.3073 | F | $CH_2—CO—OCH_3$ | $CH_2—CF_3$ |
| Ia.3074 | Cl | $CH_2—CO—OCH_3$ | $CH_2—CF_3$ |
| Ia.3075 | H | $CH_2$-phenyl | $CH_2—CF_3$ |
| Ia.3076 | F | $CH_2$-phenyl | $CH_2—CF_3$ |
| Ia.3077 | Cl | $CH_2$-phenyl | $CH_2—CF_3$ |
| Ia.3078 | H | $CH_3$ | $CH_2—CH_2—OH$ |
| Ia.3079 | F | $CH_3$ | $CH_2—CH_2—OH$ |
| Ia.3080 | Cl | $CH_3$ | $CH_2—CH_2—OH$ |
| Ia.3081 | H | $C_2H_5$ | $CH_2—CH_2—OH$ |
| Ia.3082 | F | $C_2H_5$ | $CH_2—CH_2—OH$ |
| Ia.3083 | Cl | $C_2H_5$ | $CH_2—CH_2—OH$ |
| Ia.3084 | H | n-$C_3H_7$ | $CH_2—CH_2—OH$ |
| Ia.3085 | F | n-$C_3H_7$ | $CH_2—CH_2—OH$ |
| Ia.3086 | Cl | n-$C_3H_7$ | $CH_2—CH_2—OH$ |
| Ia.3087 | H | n-$C_4H_9$ | $CH_2—CH_2—OH$ |
| Ia.3088 | F | n-$C_4H_9$ | $CH_2—CH_2—OH$ |
| Ia.3089 | Cl | n-$C_4H_9$ | $CH_2—CH_2—OH$ |
| Ia.3090 | H | $CH_2—CH═CH_2$ | $CH_2—CH_2—OH$ |
| Ia.3091 | F | $CH_2—CH═CH_2$ | $CH_2—CH_2—OH$ |
| Ia.3092 | Cl | $CH_2—CH═CH_2$ | $CH_2—CH_2—OH$ |
| Ia.3093 | H | $CH_2—C≡CH$ | $CH_2—CH_2—OH$ |
| Ia.3094 | F | $CH_2—C≡CH$ | $CH_2—CH_2—OH$ |
| Ia.3095 | Cl | $CH_2—C≡CH$ | $CH_2—CH_2—OH$ |
| Ia.3096 | H | $CH_2—CO—OCH_3$ | $CH_2—CH_2—OH$ |
| Ia.3097 | F | $CH_2—CO—OCH_3$ | $CH_2—CH_2—OH$ |
| Ia.3098 | Cl | $CH_2—CO—OCH_3$ | $CH_2—CH_2—OH$ |
| Ia.3099 | H | $CH_2$-phenyl | $CH_2—CH_2—OH$ |
| Ia.3100 | F | $CH_2$-phenyl | $CH_2—CH_2—OH$ |
| Ia.3101 | Cl | $CH_2$-phenyl | $CH_2—CH_2—OH$ |
| Ia.3102 | H | $CH_3$ | $CH_2—CH(CH_3)—OH$ |
| Ia.3103 | F | $CH_3$ | $CH_2—CH(CH_3)—OH$ |
| Ia.3104 | Cl | $CH_3$ | $CH_2—CH(CH_3)—OH$ |
| Ia.3105 | H | $C_2H_5$ | $CH_2—CH(CH_3)—OH$ |
| Ia.3106 | F | $C_2H_5$ | $CH_2—CH(CH_3)—OH$ |
| Ia.3107 | Cl | $C_2H_5$ | $CH_2—CH(CH_3)—OH$ |
| Ia.3108 | H | n-$C_3H_7$ | $CH_2—CH(CH_3)—OH$ |
| Ia.3109 | F | n-$C_3H_7$ | $CH_2—CH(CH_3)—OH$ |
| Ia.3110 | Cl | n-$C_3H_7$ | $CH_2—CH(CH_3)—OH$ |
| Ia.3111 | H | n-$C_4H_9$ | $CH_2—CH(CH_3)—OH$ |
| Ia.3112 | F | n-$C_4H_9$ | $CH_2—CH(CH_3)—OH$ |
| Ia.3113 | Cl | n-$C_4H_9$ | $CH_2—CH(CH_3)—OH$ |
| Ia.3114 | H | $CH_2—CH═CH_2$ | $CH_2—CH(CH_3)—OH$ |

TABLE 1-continued

I

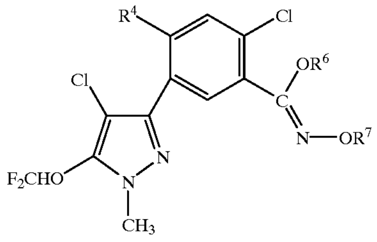

| No. | $R^4$ | $R^6$ | $R^7$ |
|---|---|---|---|
| Ia.3115 | F | $CH_2$—CH═$CH_2$ | $CH_2$—CH($CH_3$)—OH |
| Ia.3116 | Cl | $CH_2$—CH═$CH_2$ | $CH_2$—CH($CH_3$)—OH |
| Ia.3117 | H | $CH_2$—C≡CH | $CH_2$—CH($CH_3$)—OH |
| Ia.3118 | F | $CH_2$—C≡CH | $CH_2$—CH($CH_3$)—OH |
| Ia.3119 | Cl | $CH_2$—C≡CH | $CH_2$—CH($CH_3$)—OH |
| Ia.3120 | H | $CH_2$—CO—$OCH_3$ | $CH_2$—CH($CH_3$)—OH |
| Ia.3121 | F | $CH_2$—CO—$OCH_3$ | $CH_2$—CH($CH_3$)—OH |
| Ia.3122 | Cl | $CH_2$—CO—$OCH_3$ | $CH_2$—CH($CH_3$)—OH |
| Ia.3123 | H | $CH_2$-phenyl | $CH_2$—CH($CH_3$)—OH |
| Ia.3124 | F | $CH_2$-phenyl | $CH_2$—CH($CH_3$)—OH |
| Ia.3125 | Cl | $CH_2$-phenyl | $CH_2$—CH($CH_3$)—OH |
| Ia.3126 | H | $CH_3$ | $CH_2$—$CH_2$—CN |
| Ia.3127 | F | $CH_3$ | $CH_2$—$CH_2$—CN |
| Ia.3128 | Cl | $CH_3$ | $CH_2$—$CH_2$—CN |
| Ia.3129 | H | $C_2H_5$ | $CH_2$—$CH_2$—CN |
| Ia.3130 | F | $C_2H_5$ | $CH_2$—$CH_2$—CN |
| Ia.3131 | Cl | $C_2H_5$ | $CH_2$—$CH_2$—CN |
| Ia.3132 | H | n-$C_3H_7$ | $CH_2$—$CH_2$—CN |
| Ia.3133 | F | n-$C_3H_7$ | $CH_2$—$CH_2$—CN |
| Ia.3134 | Cl | n-$C_3H_7$ | $CH_2$—$CH_2$—CN |
| Ia.3135 | H | n-$C_4H_9$ | $CH_2$—$CH_2$—CN |
| Ia.3136 | F | n-$C_4H_9$ | $CH_2$—$CH_2$—CN |
| Ia.3137 | Cl | n-$C_4H_9$ | $CH_2$—$CH_2$—CN |
| Ia.3138 | H | $CH_2$—CH═$CH_2$ | $CH_2$—$CH_2$—CN |
| Ia.3139 | F | $CH_2$—CH═$CH_2$ | $CH_2$—$CH_2$—CN |
| Ia.3140 | Cl | $CH_2$—CH═$CH_2$ | $CH_2$—$CH_2$—CN |
| Ia.3141 | H | $CH_2$—C≡CH | $CH_2$—$CH_2$—CN |
| Ia.3142 | F | $CH_2$—C≡CH | $CH_2$—$CH_2$—CN |
| Ia.3143 | Cl | $CH_2$—C≡CH | $CH_2$—$CH_2$—CN |
| Ia.3144 | H | $CH_2$—CO—$OCH_3$ | $CH_2$—$CH_2$—CN |
| Ia.3145 | F | $CH_2$—CO—$OCH_3$ | $CH_2$—$CH_2$—CN |
| Ia.3146 | Cl | $CH_2$—CO—$OCH_3$ | $CH_2$—$CH_2$—CN |
| Ia.3147 | H | $CH_2$-phenyl | $CH_2$—$CH_2$—CN |
| Ia.3148 | F | $CH_2$-phenyl | $CH_2$—$CH_2$—CN |
| Ia.3149 | Cl | $CH_2$-phenyl | $CH_2$—$CH_2$—CN |
| Ia.3150 | H | $CH_3$ | $CH_2$—$OCH_3$ |
| Ia.3151 | F | $CH_3$ | $CH_2$—$OCH_3$ |
| Ia.3152 | Cl | $CH_3$ | $CH_2$—$OCH_3$ |
| Ia.3153 | H | $C_2H_5$ | $CH_2$—$OCH_3$ |
| Ia.3154 | F | $C_2H_5$ | $CH_2$—$OCH_3$ |
| Ia.3155 | Cl | $C_2H_5$ | $CH_2$—$OCH_3$ |
| Ia.3156 | H | n-$C_3H_7$ | $CH_2$—$OCH_3$ |
| Ia.3157 | F | n-$C_3H_7$ | $CH_2$—$OCH_3$ |
| Ia.3158 | Cl | n-$C_3H_7$ | $CH_2$—$OCH_3$ |
| Ia.4219 | H | n-$C_4H_9$ | $CH_2$—$OCH_3$ |
| Ia.4220 | F | n-$C_4H_9$ | $CH_2$—$OCH_3$ |
| Ia.4221 | Cl | n-$C_4H_9$ | $CH_2$—$OCH_3$ |
| Ia.4222 | H | $CH_2$—CH═$CH_2$ | $CH_2$—$OCH_3$ |
| Ia.4223 | F | $CH_2$—CH═$CH_2$ | $CH_2$—$OCH_3$ |
| Ia.4224 | Cl | $CH_2$—CH═$CH_2$ | $CH_2$—$OCH_3$ |
| Ia.4225 | H | $CH_2$—C≡CH | $CH_2$—$OCH_3$ |
| Ia.4226 | F | $CH_2$—C≡CH | $CH_2$—$OCH_3$ |
| Ia.4227 | Cl | $CH_2$—C≡CH | $CH_2$—$OCH_3$ |
| Ia.4228 | H | $CH_2$—CO—$OCH_3$ | $CH_2$—$OCH_3$ |
| Ia.4229 | F | $CH_2$—CO—$OCH_3$ | $CH_2$—$OCH_3$ |
| Ia.4230 | Cl | $CH_2$—CO—$OCH_3$ | $CH_2$—$OCH_3$ |
| Ia.4231 | H | $CH_2$-phenyl | $CH_2$—$OCH_3$ |
| Ia.4232 | F | $CH_2$-phenyl | $CH_2$—$OCH_3$ |
| Ia.4233 | Cl | $CH_2$-phenyl | $CH_2$—$OCH_3$ |
| Ia.4234 | H | $CH_3$ | $CH_2$—$CH_2$—$OCH_3$ |
| Ia.4235 | F | $CH_3$ | $CH_2$—$CH_2$—$OCH_3$ |
| Ia.4236 | Cl | $CH_3$ | $CH_2$—$CH_2$—$OCH_3$ |
| Ia.4237 | H | $C_2H_5$ | $CH_2$—$CH_2$—$OCH_3$ |

TABLE 1-continued

I

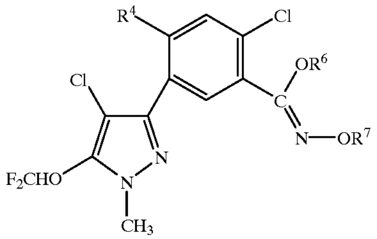

| No. | $R^4$ | $R^6$ | $R^7$ |
|---|---|---|---|
| Ia.4238 | F | $C_2H_5$ | $CH_2$—$CH_2$—$OCH_3$ |
| Ia.4239 | Cl | $C_2H_5$ | $CH_2$—$CH_2$—$OCH_3$ |
| Ia.4240 | H | n-$C_3H_7$ | $CH_2$—$CH_2$—$OCH_3$ |
| Ia.4241 | F | n-$C_3H_7$ | $CH_2$—$CH_2$—$OCH_3$ |
| Ia.4242 | Cl | n-$C_3H_7$ | $CH_2$—$CH_2$—$OCH_3$ |
| Ia.4243 | H | n-$C_4H_9$ | $CH_2$—$CH_2$—$OCH_3$ |
| Ia.4244 | F | n-$C_4H_9$ | $CH_2$—$CH_2$—$OCH_3$ |
| Ia.4245 | Cl | n-$C_4H_9$ | $CH_2$—$CH_2$—$OCH_3$ |
| Ia.4246 | H | $CH_2$—CH═$CH_2$ | $CH_2$—$CH_2$—$OCH_3$ |
| Ia.4247 | F | $CH_2$—CH═$CH_2$ | $CH_2$—$CH_2$—$OCH_3$ |
| Ia.4248 | Cl | $CH_2$—CH═$CH_2$ | $CH_2$—$CH_2$—$OCH_3$ |
| Ia.4249 | H | $CH_2$—C≡CH | $CH_2$—$CH_2$—$OCH_3$ |
| Ia.4250 | F | $CH_2$—C≡CH | $CH_2$—$CH_2$—$OCH_3$ |
| Ia.4251 | Cl | $CH_2$—C≡CH | $CH_2$—$CH_2$—$OCH_3$ |
| Ia.4252 | H | $CH_2$—CO—$OCH_3$ | $CH_2$—$CH_2$—$OCH_3$ |
| Ia.4253 | F | $CH_2$—CO—$OCH_3$ | $CH_2$—$CH_2$—$OCH_3$ |
| Ia.4254 | Cl | $CH_2$—CO—$OCH_3$ | $CH_2$—$CH_2$—$OCH_3$ |
| Ia.4255 | H | $CH_2$-phenyl | $CH_2$—$CH_2$—$OCH_3$ |
| Ia.4256 | F | $CH_2$-phenyl | $CH_2$—$CH_2$—$OCH_3$ |
| Ia.4257 | Cl | $CH_2$-phenyl | $CH_2$—$CH_2$—$OCH_3$ |
| Ia.4258 | H | $CH_3$ | $CH_2$—$CH_2$—$OCH_2$—CH═$CH_2$ |
| Ia.4259 | F | $CH_3$ | $CH_2$—$CH_2$—$OCH_2$—CH═$CH_2$ |
| Ia.4260 | Cl | $CH_3$ | $CH_2$—$CH_2$—$OCH_2$—CH═$CH_2$ |
| Ia.4261 | H | $C_2H_5$ | $CH_2$—$CH_2$—$OCH_2$—CH═$CH_2$ |
| Ia.4262 | F | $C_2H_5$ | $CH_2$—$CH_2$—$OCH_2$—CH═$CH_2$ |
| Ia.4263 | Cl | $C_2H_5$ | $CH_2$—$CH_2$—$OCH_2$—CH═$CH_2$ |
| Ia.4264 | H | n-$C_3H_7$ | $CH_2$—$CH_2$—$OCH_2$—CH═$CH_2$ |
| Ia.4265 | F | n-$C_3H_7$ | $CH_2$—$CH_2$—$OCH_2$—CH═$CH_2$ |
| Ia.4266 | Cl | n-$C_3H_7$ | $CH_2$—$CH_2$—$OCH_2$—CH═$CH_2$ |
| Ia.4267 | H | n-$C_4H_9$ | $CH_2$—$CH_2$—$OCH_2$—CH═$CH_2$ |
| Ia.4268 | F | n-$C_4H_9$ | $CH_2$—$CH_2$—$OCH_2$—CH═$CH_2$ |
| Ia.4269 | Cl | n-$C_4H_9$ | $CH_2$—$CH_2$—$OCH_2$—CH═$CH_2$ |
| Ia.4270 | H | $CH_2$—CH═$CH_2$ | $CH_2$—$CH_2$—$OCH_2$—CH═$CH_2$ |
| Ia.4271 | F | $CH_2$—CH═$CH_2$ | $CH_2$—$CH_2$—$OCH_2$—CH═$CH_2$ |
| Ia.4272 | Cl | $CH_2$—CH═$CH_2$ | $CH_2$—$CH_2$—$OCH_2$—CH═$CH_2$ |
| Ia.4273 | H | $CH_2$—C≡CH | $CH_2$—$CH_2$—$OCH_2$—CH═$CH_2$ |
| Ia.4274 | F | $CH_2$—C≡CH | $CH_2$—$CH_2$—$OCH_2$—CH═$CH_2$ |
| Ia.4275 | Cl | $CH_2$—C≡CH | $CH_2$—$CH_2$—$OCH_2$—CH═$CH_2$ |
| Ia.4276 | H | $CH_2$—CO—$OCH_3$ | $CH_2$—$CH_2$—$OCH_2$—CH═$CH_2$ |
| Ia.4277 | F | $CH_2$—CO—$OCH_3$ | $CH_2$—$CH_2$—$OCH_2$—CH═$CH_2$ |
| Ia.4278 | Cl | $CH_2$—CO—$OCH_3$ | $CH_2$—$CH_2$—$OCH_2$—CH═$CH_2$ |
| Ia.4279 | H | $CH_2$-phenyl | $CH_2$—$CH_2$—$OCH_2$—CH═$CH_2$ |
| Ia.4280 | F | $CH_2$-phenyl | $CH_2$—$CH_2$—$OCH_2$—CH═$CH_2$ |
| Ia.4281 | Cl | $CH_2$-phenyl | $CH_2$—$CH_2$—$OCH_2$—CH═$CH_2$ |
| Ia.4282 | H | $CH_3$ | $CH_2$—$CH_2$—O-cyclopentyl |
| Ia.4283 | F | $CH_3$ | $CH_2$—$CH_2$—O-cyclopentyl |
| Ia.4284 | Cl | $CH_3$ | $CH_2$—$CH_2$—O-cyclopentyl |
| Ia.4285 | H | $C_2H_5$ | $CH_2$—$CH_2$—O-cyclopentyl |
| Ia.4286 | F | $C_2H_5$ | $CH_2$—$CH_2$—O-cyclopentyl |
| Ia.4287 | Cl | $C_2H_5$ | $CH_2$—$CH_2$—O-cyclopentyl |
| Ia.4288 | H | n-$C_3H_7$ | $CH_2$—$CH_2$—O-cyclopentyl |
| Ia.4289 | F | n-$C_3H_7$ | $CH_2$—$CH_2$—O-cyclopentyl |
| Ia.4290 | Cl | n-$C_3H_7$ | $CH_2$—$CH_2$—O-cyclopentyl |
| Ia.4291 | H | n-$C_4H_9$ | $CH_2$—$CH_2$—O-cyclopentyl |
| Ia.4292 | F | n-$C_4H_9$ | $CH_2$—$CH_2$—O-cyclopentyl |
| Ia.4293 | Cl | n-$C_4H_9$ | $CH_2$—$CH_2$—O-cyclopentyl |
| Ia.4294 | H | $CH_2$—CH═$CH_2$ | $CH_2$—$CH_2$—O-cyclopentyl |
| Ia.4295 | F | $CH_2$—CH═$CH_2$ | $CH_2$—$CH_2$—O-cyclopentyl |
| Ia.4296 | Cl | $CH_2$—CH═$CH_2$ | $CH_2$—$CH_2$—O-cyclopentyl |
| Ia.4297 | H | $CH_2$—C≡CH | $CH_2$—$CH_2$—O-cyclopentyl |
| Ia.4298 | F | $CH_2$—C≡CH | $CH_2$—$CH_2$—O-cyclopentyl |
| Ia.4299 | Cl | $CH_2$—C≡CH | $CH_2$—$CH_2$—O-cyclopentyl |
| Ia.4300 | H | $CH_2$—CO—$OCH_3$ | $CH_2$—$CH_2$—O-cyclopentyl |

TABLE 1-continued

I

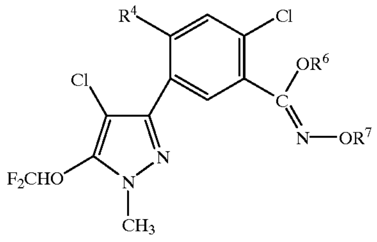

| No. | $R^4$ | $R^6$ | $R^7$ |
|---|---|---|---|
| Ia.4301 | F | $CH_2$—CO—$OCH_3$ | $CH_2$—$CH_2$—O-cyclopentyl |
| Ia.4302 | Cl | $CH_2$—CO—$OCH_3$ | $CH_2$—$CH_2$—O-cyclopentyl |
| Ia.4303 | H | $CH_2$-phenyl | $CH_2$—$CH_2$—O-cyclopentyl |
| Ia.4304 | F | $CH_2$-phenyl | $CH_2$—$CH_2$—O-cyclopentyl |
| Ia.4305 | Cl | $CH_2$-phenyl | $CH_2$—$CH_2$—O-cyclopentyl |
| Ia.4306 | H | $CH_3$ | $CH_2$—$CH_2$—$N(CH_3)_2$ |
| Ia.4307 | F | $CH_3$ | $CH_2$—$CH_2$—$N(CH_3)_2$ |
| Ia.4308 | Cl | $CH_3$ | $CH_2$—$CH_2$—$N(CH_3)_2$ |
| Ia.4309 | H | $C_2H_5$ | $CH_2$—$CH_2$—$N(CH_3)_2$ |
| Ia.4310 | F | $C_2H_5$ | $CH_2$—$CH_2$—$N(CH_3)_2$ |
| Ia.4311 | Cl | $C_2H_5$ | $CH_2$—$CH_2$—$N(CH_3)_2$ |
| Ia.4312 | H | n-$C_3H_7$ | $CH_2$—$CH_2$—$N(CH_3)_2$ |
| Ia.4313 | F | n-$C_3H_7$ | $CH_2$—$CH_2$—$N(CH_3)_2$ |
| Ia.4314 | Cl | n-$C_3H_7$ | $CH_2$—$CH_2$—$N(CH_3)_2$ |
| Ia.4315 | H | n-$C_4H_9$ | $CH_2$—$CH_2$—$N(CH_3)_2$ |
| Ia.4316 | F | n-$C_4H_9$ | $CH_2$—$CH_2$—$N(CH_3)_2$ |
| Ia.4317 | Cl | n-$C_4H_9$ | $CH_2$—$CH_2$—$N(CH_3)_2$ |
| Ia.4318 | H | $CH_2$—CH═$CH_2$ | $CH_2$—$CH_2$—$N(CH_3)_2$ |
| Ia.4319 | F | $CH_2$—CH═$CH_2$ | $CH_2$—$CH_2$—$N(CH_3)_2$ |
| Ia.4320 | Cl | $CH_2$—CH═$CH_2$ | $CH_2$—$CH_2$—$N(CH_3)_2$ |
| Ia.4321 | H | $CH_2$—C≡CH | $CH_2$—$CH_2$—$N(CH_3)_2$ |
| Ia.4322 | F | $CH_2$—C≡CH | $CH_2$—$CH_2$—$N(CH_3)_2$ |
| Ia.4323 | Cl | $CH_2$—C≡CH | $CH_2$—$CH_2$—$N(CH_3)_2$ |
| Ia.4324 | H | $CH_2$—CO—$OCH_3$ | $CH_2$—$CH_2$—$N(CH_3)_2$ |
| Ia.4325 | F | $CH_2$—CO—$OCH_3$ | $CH_2$—$CH_2$—$N(CH_3)_2$ |
| Ia.4326 | Cl | $CH_2$—CO—$OCH_3$ | $CH_2$—$CH_2$—$N(CH_3)_2$ |
| Ia.4327 | H | $CH_2$-phenyl | $CH_2$—$CH_2$—$N(CH_3)_2$ |
| Ia.4328 | F | $CH_2$-phenyl | $CH_2$—$CH_2$—$N(CH_3)_2$ |
| Ia.4329 | Cl | $CH_2$-phenyl | $CH_2$—$CH_2$—$N(CH_3)_2$ |
| Ia.4330 | H | $CH_3$ | $CH_2$—$CH_2$—$SCH_3$ |
| Ia.4331 | F | $CH_3$ | $CH_2$—$CH_2$—$SCH_3$ |
| Ia.4332 | Cl | $CH_3$ | $CH_2$—$CH_2$—$SCH_3$ |
| Ia.4333 | H | $C_2H_5$ | $CH_2$—$CH_2$—$SCH_3$ |
| Ia.4334 | F | $C_2H_5$ | $CH_2$—$CH_2$—$SCH_3$ |
| Ia.4335 | Cl | $C_2H_5$ | $CH_2$—$CH_2$—$SCH_3$ |
| Ia.4336 | H | n-$C_3H_7$ | $CH_2$—$CH_2$—$SCH_3$ |
| Ia.4337 | F | n-$C_3H_7$ | $CH_2$—$CH_2$—$SCH_3$ |
| Ia.4338 | Cl | n-$C_3H_7$ | $CH_2$—$CH_2$—$SCH_3$ |
| Ia.4339 | H | n-$C_4H_9$ | $CH_2$—$CH_2$—$SCH_3$ |
| Ia.4340 | F | n-$C_4H_9$ | $CH_2$—$CH_2$—$SCH_3$ |
| Ia.4341 | Cl | n-$C_4H_9$ | $CH_2$—$CH_2$—$SCH_3$ |
| Ia.4342 | H | $CH_2$—CH═$CH_2$ | $CH_2$—$CH_2$—$SCH_3$ |
| Ia.4343 | F | $CH_2$—CH═$CH_2$ | $CH_2$—$CH_2$—$SCH_3$ |
| Ia.4344 | Cl | $CH_2$—CH═$CH_2$ | $CH_2$—$CH_2$—$SCH_3$ |
| Ia.4345 | H | $CH_2$—C≡CH | $CH_2$—$CH_2$—$SCH_3$ |
| Ia.4346 | F | $CH_2$—C≡CH | $CH_2$—$CH_2$—$SCH_3$ |
| Ia.4347 | Cl | $CH_2$—C≡CH | $CH_2$—$CH_2$—$SCH_3$ |
| Ia.4348 | H | $CH_2$—CO—$OCH_3$ | $CH_2$—$CH_2$—$SCH_3$ |
| Ia.4349 | F | $CH_2$—CO—$OCH_3$ | $CH_2$—$CH_2$—$SCH_3$ |
| Ia.4350 | Cl | $CH_2$—CO—$OCH_3$ | $CH_2$—$CH_2$—$SCH_3$ |
| Ia.4351 | H | $CH_2$-phenyl | $CH_2$—$CH_2$—$SCH_3$ |
| Ia.4352 | F | $CH_2$-phenyl | $CH_2$—$CH_2$—$SCH_3$ |
| Ia.4353 | Cl | $CH_2$-phenyl | $CH_2$—$CH_2$—$SCH_3$ |
| Ia.4354 | H | $CH_3$ | $CH_2$—$CH_2$—$SO_2$—$CH_3$ |
| Ia.4355 | F | $CH_3$ | $CH_2$—$CH_2$—$SO_2$—$CH_3$ |
| Ia.4356 | Cl | $CH_3$ | $CH_2$—$CH_2$—$SO_2$—$CH_3$ |
| Ia.4357 | H | $C_2H_5$ | $CH_2$—$CH_2$—$SO_2$—$CH_3$ |
| Ia.4358 | F | $C_2H_5$ | $CH_2$—$CH_2$—$SO_2$—$CH_3$ |
| Ia.4359 | Cl | $C_2H_5$ | $CH_2$—$CH_2$—$SO_2$—$CH_3$ |
| Ia.4360 | H | n-$C_3H_7$ | $CH_2$—$CH_2$—$SO_2$—$CH_3$ |
| Ia.4361 | F | n-$C_3H_7$ | $CH_2$—$CH_2$—$SO_2$—$CH_3$ |
| Ia.4362 | Cl | n-$C_3H_7$ | $CH_2$—$CH_2$—$SO_2$—$CH_3$ |
| Ia.4363 | H | n-$C_4H_9$ | $CH_2$—$CH_2$—$SO_2$—$CH_3$ |

TABLE 1-continued

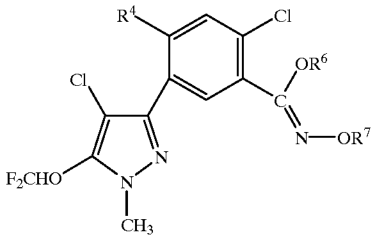

I

| No. | $R^4$ | $R^6$ | $R^7$ |
|---|---|---|---|
| Ia.4364 | F | n-$C_4H_9$ | $CH_2$—$CH_2$—$SO_2$—$CH_3$ |
| Ia.4365 | Cl | n-$C_4H_9$ | $CH_2$—$CH_2$—$SO_2$—$CH_3$ |
| Ia.4366 | H | $CH_2$—CH=$CH_2$ | $CH_2$—$CH_2$—$SO_2$—$CH_3$ |
| Ia.4367 | F | $CH_2$—CH=$CH_2$ | $CH_2$—$CH_2$—$SO_2$—$CH_3$ |
| Ia.4368 | Cl | $CH_2$—CH=$CH_2$ | $CH_2$—$CH_2$—$SO_2$—$CH_3$ |
| Ia.4369 | H | $CH_2$—C≡CH | $CH_2$—$CH_2$—$SO_2$—$CH_3$ |
| Ia.4370 | F | $CH_2$—C≡CH | $CH_2$—$CH_2$—$SO_2$—$CH_3$ |
| Ia.4371 | Cl | $CH_2$—C≡CH | $CH_2$—$CH_2$—$SO_2$—$CH_3$ |
| Ia.4372 | H | $CH_2$—CO—$OCH_3$ | $CH_2$—$CH_2$—$SO_2$—$CH_3$ |
| Ia.4373 | F | $CH_2$—CO—$OCH_3$ | $CH_2$—$CH_2$—$SO_2$—$CH_3$ |
| Ia.4374 | Cl | $CH_2$—CO—$OCH_3$ | $CH_2$—$CH_2$—$SO_2$—$CH_3$ |
| Ia.4375 | H | $CH_2$-phenyl | $CH_2$—$CH_2$—$SO_2$—$CH_3$ |
| Ia.4376 | F | $CH_2$-phenyl | $CH_2$—$CH_2$—$SO_2$—$CH_3$ |
| Ia.4377 | Cl | $CH_2$-phenyl | $CH_2$—$CH_2$—$SO_2$—$CH_3$ |
| Ia.4378 | H | $CH_3$ | $CH_2$—CH=$CH_2$ |
| Ia.4379 | F | $CH_3$ | $CH_2$—CH=$CH_2$ |
| Ia.4380 | Cl | $CH_3$ | $CH_2$—CH=$CH_2$ |
| Ia.4381 | H | $C_2H_5$ | $CH_2$—CH=$CH_2$ |
| Ia.4382 | F | $C_2H_5$ | $CH_2$—CH=$CH_2$ |
| Ia.4383 | Cl | $C_2H_5$ | $CH_2$—CH=$CH_2$ |
| Ia.4384 | H | n-$C_3H_7$ | $CH_2$—CH=$CH_2$ |
| Ia.4385 | F | n-$C_3H_7$ | $CH_2$—CH=$CH_2$ |
| Ia.4386 | Cl | n-$C_3H_7$ | $CH_2$—CH=$CH_2$ |
| Ia.4387 | H | n-$C_4H_9$ | $CH_2$—CH=$CH_2$ |
| Ia.4388 | F | n-$C_4H_9$ | $CH_2$—CH=$CH_2$ |
| Ia.4389 | Cl | n-$C_4H_9$ | $CH_2$—CH=$CH_2$ |
| Ia.4390 | H | $CH_3$ | $CH_2$—CH=CH—$CH_3$ |
| Ia.4391 | F | $CH_3$ | $CH_2$—CH=CH—$CH_3$ |
| Ia.4392 | Cl | $CH_3$ | $CH_2$—CH=CH—$CH_3$ |
| Ia.4393 | H | $C_2H_5$ | $CH_2$—CH=CH—$CH_3$ |
| Ia.4394 | F | $C_2H_5$ | $CH_2$—CH=CH—$CH_3$ |
| Ia.4395 | Cl | $C_2H_5$ | $CH_2$—CH=CH—$CH_3$ |
| Ia.4396 | H | n-$C_3H_7$ | $CH_2$—CH=CH—$CH_3$ |
| Ia.4397 | F | n-$C_3H_7$ | $CH_2$—CH=CH—$CH_3$ |
| Ia.4398 | Cl | n-$C_3H_7$ | $CH_2$—CH=CH—$CH_3$ |
| Ia.4399 | H | n-$C_4H_9$ | $CH_2$—CH=CH—$CH_3$ |
| Ia.4400 | F | n-$C_4H_9$ | $CH_2$—CH=CH—$CH_3$ |
| Ia.4401 | Cl | n-$C_4H_9$ | $CH_2$—CH=CH—$CH_3$ |
| Ia.4402 | H | $CH_2$—CH=$CH_2$ | $CH_2$—CH=CH—$CH_3$ |
| Ia.4403 | F | $CH_2$—CH=$CH_2$ | $CH_2$—CH=CH—$CH_3$ |
| Ia.4404 | Cl | $CH_2$—CH=$CH_2$ | $CH_2$—CH=CH—$CH_3$ |
| Ia.4405 | H | $CH_2$—C≡CH | $CH_2$—CH=CH—$CH_3$ |
| Ia.4406 | F | $CH_2$—C≡CH | $CH_2$—CH=CH—$CH_3$ |
| Ia.4407 | Cl | $CH_2$—C≡CH | $CH_2$—CH=CH—$CH_3$ |
| Ia.4408 | H | $CH_2$—CO—$OCH_3$ | $CH_2$—CH=CH—$CH_3$ |
| Ia.4409 | F | $CH_2$—CO—$OCH_3$ | $CH_2$—CH=CH—$CH_3$ |
| Ia.4410 | Cl | $CH_2$—CO—$OCH_3$ | $CH_2$—CH=CH—$CH_3$ |
| Ia.4411 | H | $CH_2$-phenyl | $CH_2$—CH=CH—$CH_3$ |
| Ia.4412 | F | $CH_2$-phenyl | $CH_2$—CH=CH—$CH_3$ |
| Ia.4413 | Cl | $CH_2$-phenyl | $CH_2$—CH=CH—$CH_3$ |
| Ia.4414 | H | $CH_3$ | $CH_2$—CH=CH—Cl |
| Ia.4415 | F | $CH_3$ | $CH_2$—CH=CH—Cl |
| Ia.4416 | Cl | $CH_3$ | $CH_2$—CH=CH—Cl |
| Ia.4417 | H | $C_2H_5$ | $CH_2$—CH=CH—Cl |
| Ia.4418 | F | $C_2H_5$ | $CH_2$—CH=CH—Cl |
| Ia.4419 | Cl | $C_2H_5$ | $CH_2$—CH=CH—Cl |
| Ia.4420 | H | n-$C_3H_7$ | $CH_2$—CH=CH—Cl |
| Ia.4421 | F | n-$C_3H_7$ | $CH_2$—CH=CH—Cl |
| Ia.4422 | Cl | n-$C_3H_7$ | $CH_2$—CH=CH—Cl |
| Ia.4423 | H | n-$C_4H_9$ | $CH_2$—CH=CH—Cl |
| Ia.4424 | F | n-$C_4H_9$ | $CH_2$—CH=CH—Cl |
| Ia.4425 | Cl | n-$C_4H_9$ | $CH_2$—CH=CH—Cl |
| Ia.4426 | H | $CH_2$—CH=$CH_2$ | $CH_2$—CH=CH—Cl |

TABLE 1-continued

I

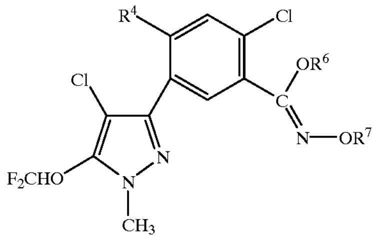

| No. | $R^4$ | $R^6$ | $R^7$ |
|---|---|---|---|
| Ia.4427 | F | $CH_2$—CH═$CH_2$ | $CH_2$—CH═CH—Cl |
| Ia.4428 | Cl | $CH_2$—CH═$CH_2$ | $CH_2$—CH═CH—Cl |
| Ia.4429 | H | $CH_2$—C≡CH | $CH_2$—CH═CH—Cl |
| Ia.4430 | F | $CH_2$—C≡CH | $CH_2$—CH═CH—Cl |
| Ia.4431 | Cl | $CH_2$—C≡CH | $CH_2$—CH═CH—Cl |
| Ia.4432 | H | $CH_2$—CO—$OCH_3$ | $CH_2$—CH═CH—Cl |
| Ia.4433 | F | $CH_2$—CO—$OCH_3$ | $CH_2$—CH═CH—Cl |
| Ia.4434 | Cl | $CH_2$—CO—$OCH_3$ | $CH_2$—CH═CH—Cl |
| Ia.4435 | H | $CH_2$-phenyl | $CH_2$—CH═CH—Cl |
| Ia.4436 | F | $CH_2$-phenyl | $CH_2$—CH═CH—Cl |
| Ia.4437 | Cl | $CH_2$-phenyl | $CH_2$—CH═CH—Cl |
| Ia.4438 | H | $CH_3$ | $CH_2$—C≡CH |
| Ia.4439 | F | $CH_3$ | $CH_2$—C≡CH |
| Ia.4440 | Cl | $CH_3$ | $CH_2$—C≡CH |
| Ia.4441 | H | $C_2H_5$ | $CH_2$—C≡CH |
| Ia.4442 | F | $C_2H_5$ | $CH_2$—C≡CH |
| Ia.4443 | Cl | $C_2H_5$ | $CH_2$—C≡CH |
| Ia.4444 | H | n-$C_3H_7$ | $CH_2$—C≡CH |
| Ia.4445 | F | n-$C_3H_7$ | $CH_2$—C≡CH |
| Ia.4446 | Cl | n-$C_3H_7$ | $CH_2$—C≡CH |
| Ia.4447 | H | n-$C_4H_9$ | $CH_2$—C≡CH |
| Ia.4448 | F | n-$C_4H_9$ | $CH_2$—C≡CH |
| Ia.4449 | Cl | n-$C_4H_9$ | $CH_2$—C≡CH |
| Ia.4450 | H | $CH_3$ | $CH_2$—CH═N—$OCH_3$ |
| Ia.4451 | F | $CH_3$ | $CH_2$—CH═N—$OCH_3$ |
| Ia.4452 | Cl | $CH_3$ | $CH_2$—CH═N—$OCH_3$ |
| Ia.4453 | H | $C_2H_5$ | $CH_2$—CH═N—$OCH_3$ |
| Ia.4454 | F | $C_2H_5$ | $CH_2$—CH═N—$OCH_3$ |
| Ia.4455 | Cl | $C_2H_5$ | $CH_2$—CH═N—$OCH_3$ |
| Ia.4456 | H | n-$C_3H_7$ | $CH_2$—CH═N—$OCH_3$ |
| Ia.4457 | F | n-$C_3H_7$ | $CH_2$—CH═N—$OCH_3$ |
| Ia.4458 | Cl | n-$C_3H_7$ | $CH_2$—CH═N—$OCH_3$ |
| Ia.4459 | H | n-$C_4H_9$ | $CH_2$—CH═N—$OCH_3$ |
| Ia.4460 | F | n-$C_4H_9$ | $CH_2$—CH═N—$OCH_3$ |
| Ia.4461 | Cl | n-$C_4H_9$ | $CH_2$—CH═N—$OCH_3$ |
| Ia.4462 | H | $CH_2$—CH═$CH_2$ | $CH_2$—CH═N—$OCH_3$ |
| Ia.4463 | F | $CH_2$—CH═$CH_2$ | $CH_2$—CH═N—$OCH_3$ |
| Ia.4464 | Cl | $CH_2$—CH═$CH_2$ | $CH_2$—CH═N—$OCH_3$ |
| Ia.4465 | H | $CH_2$—C≡CH | $CH_2$—CH═N—$OCH_3$ |
| Ia.4466 | F | $CH_2$—C≡CH | $CH_2$—CH═N—$OCH_3$ |
| Ia.4467 | Cl | $CH_2$—C≡CH | $CH_2$—CH═N—$OCH_3$ |
| Ia.4468 | H | $CH_2$—CO—$OCH_3$ | $CH_2$—CH═N—$OCH_3$ |
| Ia.4469 | F | $CH_2$—CO—$OCH_3$ | $CH_2$—CH═N—$OCH_3$ |
| Ia.4470 | Cl | $CH_2$—CO—$OCH_3$ | $CH_2$—CH═N—$OCH_3$ |
| Ia.4471 | H | $CH_2$-phenyl | $CH_2$—CH═N—$OCH_3$ |
| Ia.4472 | F | $CH_2$-phenyl | $CH_2$—CH═N—$OCH_3$ |
| Ia.4473 | Cl | $CH_2$-phenyl | $CH_2$—CH═N—$OCH_3$ |
| Ia.4474 | H | $CH_3$ | $CH_2$—CH═N—$OC_2H_5$ |
| Ia.4475 | F | $CH_3$ | $CH_2$—CH═N—$OC_2H_5$ |
| Ia.4476 | Cl | $CH_3$ | $CH_2$—CH═N—$OC_2H_5$ |
| Ia.4477 | H | $C_2H_5$ | $CH_2$—CH═N—$OC_2H_5$ |
| Ia.4478 | F | $C_2H_5$ | $CH_2$—CH═N—$OC_2H_5$ |
| Ia.4479 | Cl | $C_2H_5$ | $CH_2$—CH═N—$OC_2H_5$ |
| Ia.4480 | H | n-$C_3H_7$ | $CH_2$—CH═N—$OC_2H_5$ |
| Ia.4481 | F | n-$C_3H_7$ | $CH_2$—CH═N—$OC_2H_5$ |
| Ia.4482 | Cl | n-$C_3H_7$ | $CH_2$—CH═N—$OC_2H_5$ |
| Ia.4483 | H | n-$C_4H_9$ | $CH_2$—CH═N—$OC_2H_5$ |
| Ia.4484 | F | n-$C_4H_9$ | $CH_2$—CH═N—$OC_2H_5$ |
| Ia.4485 | Cl | n-$C_4H_9$ | $CH_2$—CH═N—$OC_2H_5$ |
| Ia.4486 | H | $CH_2$—CH═$CH_2$ | $CH_2$—CH═N—$OC_2H_5$ |
| Ia.4487 | F | $CH_2$—CH═$CH_2$ | $CH_2$—CH═N—$OC_2H_5$ |
| Ia.4488 | Cl | $CH_2$—CH═$CH_2$ | $CH_2$—CH═N—$OC_2H_5$ |
| Ia.4489 | H | $CH_2$—C≡CH | $CH_2$—CH═N—$OC_2H_5$ |

TABLE 1-continued

I

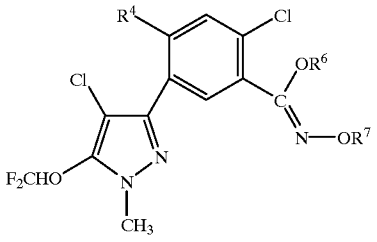

| No. | $R^4$ | $R^6$ | $R^7$ |
|---|---|---|---|
| Ia.4490 | F | $CH_2$—C≡CH | $CH_2$—CH=N—$OC_2H_5$ |
| Ia.4491 | Cl | $CH_2$—C≡CH | $CH_2$—CH=N—$OC_2H_5$ |
| Ia.4492 | H | $CH_2$—CO—$OCH_3$ | $CH_2$—CH=N—$OC_2H_5$ |
| Ia.4493 | F | $CH_2$—CO—$OCH_3$ | $CH_2$—CH=N—$OC_2H_5$ |
| Ia.4494 | Cl | $CH_2$—CO—$OCH_3$ | $CH_2$—CH=N—$OC_2H_5$ |
| Ia.4495 | H | $CH_2$-phenyl | $CH_2$—CH=N—$OC_2H_5$ |
| Ia.4496 | F | $CH_2$-phenyl | $CH_2$—CH=N—$OC_2H_5$ |
| Ia.4497 | Cl | $CH_2$-phenyl | $CH_2$—CH=N—$OC_2H_5$ |
| Ia.4498 | H | $CH_3$ | $CH_2$—CH=N—O(n-$C_3H_7$) |
| Ia.4499 | F | $CH_3$ | $CH_2$—CH=N—O(n-$C_3H_7$) |
| Ia.4500 | Cl | $CH_3$ | $CH_2$—CH=N—O(n-$C_3H_7$) |
| Ia.4501 | H | $C_2H_5$ | $CH_2$—CH=N—O(n-$C_3H_7$) |
| Ia.4502 | F | $C_2H_5$ | $CH_2$—CH=N—O(n-$C_3H_7$) |
| Ia.4503 | Cl | $C_2H_5$ | $CH_2$—CH=N—O(n-$C_3H_7$) |
| Ia.4504 | H | n-$C_3H_7$ | $CH_2$—CH=N—O(n-$C_3H_7$) |
| Ia.4505 | F | n-$C_3H_7$ | $CH_2$—CH=N—O(n-$C_3H_7$) |
| Ia.4506 | Cl | n-$C_3H_7$ | $CH_2$—CH=N—O(n-$C_3H_7$) |
| Ia.4507 | H | n-$C_4H_9$ | $CH_2$—CH=N—O(n-$C_3H_7$) |
| Ia.4508 | F | n-$C_4H_9$ | $CH_2$—CH=N—O(n-$C_3H_7$) |
| Ia.4509 | Cl | n-$C_4H_9$ | $CH_2$—CH=N—O(n-$C_3H_7$) |
| Ia.4510 | H | $CH_2$—CH=$CH_2$ | $CH_2$—CH=N—O(n-$C_3H_7$) |
| Ia.4511 | F | $CH_2$—CH=$CH_2$ | $CH_2$—CH=N—O(n-$C_3H_7$) |
| Ia.4512 | Cl | $CH_2$—CH=$CH_2$ | $CH_2$—CH=N—O(n-$C_3H_7$) |
| Ia.4513 | H | $CH_2$—C≡CH | $CH_2$—CH=N—O(n-$C_3H_7$) |
| Ia.4514 | F | $CH_2$—C≡CH | $CH_2$—CH=N—O(n-$C_3H_7$) |
| Ia.4515 | Cl | $CH_2$—C≡CH | $CH_2$—CH=N—O(n-$C_3H_7$) |
| Ia.4516 | H | $CH_2$—CO—$OCH_3$ | $CH_2$—CH=N—O(n-$C_3H_7$) |
| Ia.4517 | F | $CH_2$—CO—$OCH_3$ | $CH_2$—CH=N—O(n-$C_3H_7$) |
| Ia.4518 | Cl | $CH_2$—CO—$OCH_3$ | $CH_2$—CH=N—O(n-$C_3H_7$) |
| Ia.4519 | H | $CH_2$-phenyl | $CH_2$—CH=N—O(n-$C_3H_7$) |
| Ia.4520 | F | $CH_2$-phenyl | $CH_2$—CH=N—O(n-$C_3H_7$) |
| Ia.4521 | Cl | $CH_2$-phenyl | $CH_2$—CH=N—O(n-$C_3H_7$) |
| Ia.4522 | H | $CH_3$ | $CH_2$—CH=N—O(n-$C_4H_9$) |
| Ia.4523 | F | $CH_3$ | $CH_2$—CH=N—O(n-$C_4H_9$) |
| Ia.4524 | Cl | $CH_3$ | $CH_2$—CH=N—O(n-$C_4H_9$) |
| Ia.4525 | H | $C_2H_5$ | $CH_2$—CH=N—O(n-$C_4H_9$) |
| Ia.4526 | F | $C_2H_5$ | $CH_2$—CH=N—O(n-$C_4H_9$) |
| Ia.4527 | Cl | $C_2H_5$ | $CH_2$—CH=N—O(n-$C_4H_9$) |
| Ia.4528 | H | n-$C_3H_7$ | $CH_2$—CH=N—O(n-$C_4H_9$) |
| Ia.4529 | F | n-$C_3H_7$ | $CH_2$—CH=N—O(n-$C_4H_9$) |
| Ia.4530 | Cl | n-$C_3H_7$ | $CH_2$—CH=N—O(n-$C_4H_9$) |
| Ia.4531 | H | n-$C_4H_9$ | $CH_2$—CH=N—O(n-$C_4H_9$) |
| Ia.4532 | F | n-$C_4H_9$ | $CH_2$—CH=N—O(n-$C_4H_9$) |
| Ia.4533 | Cl | n-$C_4H_9$ | $CH_2$—CH=N—O(n-$C_4H_9$) |
| Ia.4534 | H | $CH_2$—CH=$CH_2$ | $CH_2$—CH=N—O(n-$C_4H_9$) |
| Ia.4535 | F | $CH_2$—CH=$CH_2$ | $CH_2$—CH=N—O(n-$C_4H_9$) |
| Ia.4536 | Cl | $CH_2$—CH=$CH_2$ | $CH_2$—CH=N—O(n-$C_4H_9$) |
| Ia.4537 | H | $CH_2$—C≡CH | $CH_2$—CH=N—O(n-$C_4H_9$) |
| Ia.4538 | F | $CH_2$—C≡CH | $CH_2$—CH=N—O(n-$C_4H_9$) |
| Ia.4539 | Cl | $CH_2$—C≡CH | $CH_2$—CH=N—O(n-$C_4H_9$) |
| Ia.4540 | H | $CH_2$—CO—$OCH_3$ | $CH_2$—CH=N—O(n-$C_4H_9$) |
| Ia.4541 | F | $CH_2$—CO—$OCH_3$ | $CH_2$—CH=N—O(n-$C_4H_9$) |
| Ia.4542 | Cl | $CH_2$—CO—$OCH_3$ | $CH_2$—CH=N—O(n-$C_4H_9$) |
| Ia.4543 | H | $CH_2$-phenyl | $CH_2$—CH=N—O(n-$C_4H_9$) |
| Ia.4544 | F | $CH_2$-phenyl | $CH_2$—CH=N—O(n-$C_4H_9$) |
| Ia.4545 | Cl | $CH_2$-phenyl | $CH_2$—CH=N—O(n-$C_4H_9$) |
| Ia.4546 | H | $CH_3$ | $CH_2$—CH=N—$OCH_2$—CH=$CH_2$ |
| Ia.4547 | F | $CH_3$ | $CH_2$—CH=N—$OCH_2$—CH=$CH_2$ |
| Ia.4548 | Cl | $CH_3$ | $CH_2$—CH=N—$OCH_2$—CH=$CH_2$ |
| Ia.4549 | H | $C_2H_5$ | $CH_2$—CH=N—$OCH_2$—CH=$CH_2$ |
| Ia.4550 | F | $C_2H_5$ | $CH_2$—CH=N—$OCH_2$—CH=$CH_2$ |
| Ia.4551 | Cl | $C_2H_5$ | $CH_2$—CH=N—$OCH_2$—CH=$CH_2$ |
| Ia.4552 | H | n-$C_3H_7$ | $CH_2$—CH=N—$OCH_2$—CH=$CH_2$ |

TABLE 1-continued

I

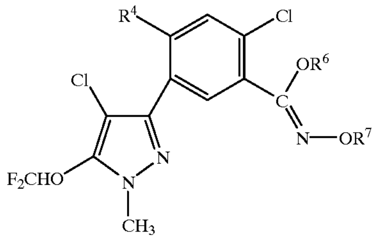

| No. | $R^4$ | $R^6$ | $R^7$ |
|---|---|---|---|
| Ia.4553 | F | n-$C_3H_7$ | $CH_2$—CH═N—$OCH_2$—CH═$CH_2$ |
| Ia.4554 | Cl | n-$C_3H_7$ | $CH_2$—CH═N—$OCH_2$—CH═$CH_2$ |
| Ia.4555 | H | n-$C_4H_9$ | $CH_2$—CH═N—$OCH_2$—CH═$CH_2$ |
| Ia.4556 | F | n-$C_4H_9$ | $CH_2$—CH═N—$OCH_2$—CH═$CH_2$ |
| Ia.4557 | Cl | n-$C_4H_9$ | $CH_2$—CH═N—$OCH_2$—CH═$CH_2$ |
| Ia.4558 | H | $CH_2$—CH═$CH_2$ | $CH_2$—CH═N—$OCH_2$—CH═$CH_2$ |
| Ia.4559 | F | $CH_2$—CH═$CH_2$ | $CH_2$—CH═N—$OCH_2$—CH═$CH_2$ |
| Ia.4560 | Cl | $CH_2$—CH═$CH_2$ | $CH_2$—CH═N—$OCH_2$—CH═$CH_2$ |
| Ia.4561 | H | $CH_2$—C≡CH | $CH_2$—CH═N—$OCH_2$—CH═$CH_2$ |
| Ia.4562 | F | $CH_2$—C≡CH | $CH_2$—CH═N—$OCH_2$—CH═$CH_2$ |
| Ia.4563 | Cl | $CH_2$—C≡CH | $CH_2$—CH═N—$OCH_2$—CH═$CH_2$ |
| Ia.4564 | H | $CH_2$—CO—$OCH_3$ | $CH_2$—CH═N—$OCH_2$—CH═$CH_2$ |
| Ia.4565 | F | $CH_2$—CO—$OCH_3$ | $CH_2$—CH═N—$OCH_2$—CH═$CH_2$ |
| Ia.4566 | Cl | $CH_2$—CO—$OCH_3$ | $CH_2$—CH═N—$OCH_2$—CH═$CH_2$ |
| Ia.4567 | H | $CH_2$-phenyl | $CH_2$—CH═N—$OCH_2$—CH═$CH_2$ |
| Ia.4568 | F | $CH_2$-phenyl | $CH_2$—CH═N—$OCH_2$—CH═$CH_2$ |
| Ia.4569 | Cl | $CH_2$-phenyl | $CH_2$—CH═N—$OCH_2$—CH═$CH_2$ |
| Ia.4570 | H | $CH_3$ | $CH_2$—COOH |
| Ia.4571 | F | $CH_3$ | $CH_2$—COOH |
| Ia.4572 | Cl | $CH_3$ | $CH_2$—COOH |
| Ia.4573 | H | $C_2H_5$ | $CH_2$—COOH |
| Ia.4574 | F | $C_2H_5$ | $CH_2$—COOH |
| Ia.4575 | Cl | $C_2H_5$ | $CH_2$—COOH |
| Ia.4576 | H | n-$C_3H_7$ | $CH_2$—COOH |
| Ia.4577 | F | n-$C_3H_7$ | $CH_2$—COOH |
| Ia.4578 | Cl | n-$C_3H_7$ | $CH_2$—COOH |
| Ia.4579 | H | n-$C_4H_9$ | $CH_2$—COOH |
| Ia.4580 | F | n-$C_4H_9$ | $CH_2$—COOH |
| Ia.4581 | Cl | n-$C_4H_9$ | $CH_2$—COOH |
| Ia.4582 | H | $CH_2$—CH═$CH_2$ | $CH_2$—COOH |
| Ia.4583 | F | $CH_2$—CH═$CH_2$ | $CH_2$—COOH |
| Ia.4584 | Cl | $CH_2$—CH═$CH_2$ | $CH_2$—COOH |
| Ia.4585 | H | $CH_2$—C≡CH | $CH_2$—COOH |
| Ia.4586 | F | $CH_2$—C≡CH | $CH_2$—COOH |
| Ia.4587 | Cl | $CH_2$—C≡CH | $CH_2$—COOH |
| Ia.4588 | H | $CH_2$—CO—$OCH_3$ | $CH_2$—COOH |
| Ia.4589 | F | $CH_2$—CO—$OCH_3$ | $CH_2$—COOH |
| Ia.4590 | Cl | $CH_2$—CO—$OCH_3$ | $CH_2$—COOH |
| Ia.4591 | H | $CH_2$-phenyl | $CH_2$—COOH |
| Ia.4592 | F | $CH_2$-phenyl | $CH_2$—COOH |
| Ia.4593 | Cl | $CH_2$-phenyl | $CH_2$—COOH |
| Ia.4594 | H | $CH_3$ | $CH(CH_3)$—COOH |
| Ia.4595 | F | $CH_3$ | $CH(CH_3)$—COOH |
| Ia.4596 | Cl | $CH_3$ | $CH(CH_3)$—COOH |
| Ia.4597 | H | $C_2H_5$ | $CH(CH_3)$—COOH |
| Ia.4598 | F | $C_2H_5$ | $CH(CH_3)$—COOH |
| Ia.4599 | Cl | $C_2H_5$ | $CH(CH_3)$—COOH |
| Ia.4600 | H | n-$C_3H_7$ | $CH(CH_3)$—COOH |
| Ia.4601 | F | n-$C_3H_7$ | $CH(CH_3)$—COOH |
| Ia.4602 | Cl | n-$C_3H_7$ | $CH(CH_3)$—COOH |
| Ia.4603 | H | n-$C_4H_9$ | $CH(CH_3)$—COOH |
| Ia.4604 | F | n-$C_4H_9$ | $CH(CH_3)$—COOH |
| Ia.4605 | Cl | n-$C_4H_9$ | $CH(CH_3)$—COOH |
| Ia.4606 | H | $CH_2$—CH═$CH_2$ | $CH(CH_3)$—COOH |
| Ia.4607 | F | $CH_2$—CH═$CH_2$ | $CH(CH_3)$—COOH |
| Ia.4608 | Cl | $CH_2$—CH═$CH_2$ | $CH(CH_3)$—COOH |
| Ia.4609 | H | $CH_2$—C≡CH | $CH(CH_3)$—COOH |
| Ia.4610 | F | $CH_2$—C≡CH | $CH(CH_3)$—COOH |
| Ia.4611 | Cl | $CH_2$—C≡CH | $CH(CH_3)$—COOH |
| Ia.4612 | H | $CH_2$—CO—$OCH_3$ | $CH(CH_3)$—COOH |
| Ia.4613 | F | $CH_2$—CO—$OCH_3$ | $CH(CH_3)$—COOH |
| Ia.4614 | Cl | $CH_2$—CO—$OCH_3$ | $CH(CH_3)$—COOH |
| Ia.4615 | H | $CH_2$-phenyl | $CH(CH_3)$—COOH |

TABLE 1-continued

I

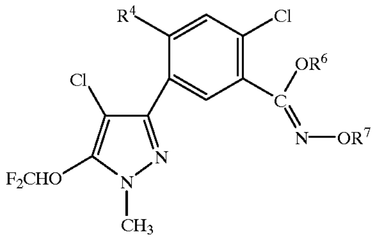

| No. | $R^4$ | $R^6$ | $R^7$ |
|---|---|---|---|
| Ia.4616 | F | $CH_2$-phenyl | $CH(CH_3)$—COOH |
| Ia.4617 | Cl | $CH_2$-phenyl | $CH(CH_3)$—COOH |
| Ia.4618 | H | $CH_3$ | $CH(C_2H_5)$—COOH |
| Ia.4619 | F | $CH_3$ | $CH(C_2H_5)$—COOH |
| Ia.4620 | Cl | $CH_3$ | $CH(C_2H_5)$—COOH |
| Ia.4621 | H | $C_2H_5$ | $CH(C_2H_5)$—COOH |
| Ia.4622 | F | $C_2H_5$ | $CH(C_2H_5)$—COOH |
| Ia.4623 | Cl | $C_2H_5$ | $CH(C_2H_5)$—COOH |
| Ia.4624 | H | n-$C_3H_7$ | $CH(C_2H_5)$—COOH |
| Ia.4625 | F | n-$C_3H_7$ | $CH(C_2H_5)$—COOH |
| Ia.4626 | Cl | n-$C_3H_7$ | $CH(C_2H_5)$—COOH |
| Ia.4627 | H | n-$C_4H_9$ | $CH(C_2H_5)$—COOH |
| Ia.4628 | F | n-$C_4H_9$ | $CH(C_2H_5)$—COOH |
| Ia.4629 | Cl | n-$C_4H_9$ | $CH(C_2H_5)$—COOH |
| Ia.4630 | H | $CH_2$—CH═$CH_2$ | $CH(C_2H_5)$—COOH |
| Ia.4631 | F | $CH_2$—CH═$CH_2$ | $CH(C_2H_5)$—COOH |
| Ia.4632 | Cl | $CH_2$—CH═$CH_2$ | $CH(C_2H_5)$—COOH |
| Ia.4633 | H | $CH_2$—C≡CH | $CH(C_2H_5)$—COOH |
| Ia.4634 | F | $CH_2$—C≡CH | $CH(C_2H_5)$—COOH |
| Ia.4635 | Cl | $CH_2$—C≡CH | $CH(C_2H_5)$—COOH |
| Ia.4636 | H | $CH_2$—CO—$OCH_3$ | $CH(C_2H_5)$—COOH |
| Ia.4637 | F | $CH_2$—CO—$OCH_3$ | $CH(C_2H_5)$—COOH |
| Ia.4638 | Cl | $CH_2$—CO—$OCH_3$ | $CH(C_2H_5)$—COOH |
| Ia.4639 | H | $CH_2$-phenyl | $CH(C_2H_5)$—COOH |
| Ia.4640 | F | $CH_2$-phenyl | $CH(C_2H_5)$—COOH |
| Ia.4641 | Cl | $CH_2$-phenyl | $CH(C_2H_5)$—COOH |
| Ia.4642 | H | $CH_3$ | $CH_2$—CO—$OCH_3$ |
| Ia.4643 | F | $CH_3$ | $CH_2$—CO—$OCH_3$ |
| Ia.4644 | Cl | $CH_3$ | $CH_2$—CO—$OCH_3$ |
| Ia.4645 | H | $C_2H_5$ | $CH_2$—CO—$OCH_3$ |
| Ia.4646 | F | $C_2H_5$ | $CH_2$—CO—$OCH_3$ |
| Ia.4647 | Cl | $C_2H_5$ | $CH_2$—CO—$OCH_3$ |
| Ia.4648 | H | n-$C_3H_7$ | $CH_2$—CO—$OCH_3$ |
| Ia.4649 | F | n-$C_3H_7$ | $CH_2$—CO—$OCH_3$ |
| Ia.4650 | Cl | n-$C_3H_7$ | $CH_2$—CO—$OCH_3$ |
| Ia.4651 | H | n-$C_4H_9$ | $CH_2$—CO—$OCH_3$ |
| Ia.4652 | F | n-$C_4H_9$ | $CH_2$—CO—$OCH_3$ |
| Ia.4653 | Cl | n-$C_4H_9$ | $CH_2$—CO—$OCH_3$ |
| Ia.4654 | H | $CH_3$ | $CH(CH_3)$—CO—$OCH_3$ |
| Ia.4655 | F | $CH_3$ | $CH(CH_3)$—CO—$OCH_3$ |
| Ia.4656 | Cl | $CH_3$ | $CH(CH_3)$—CO—$OCH_3$ |
| Ia.4657 | H | $C_2H_5$ | $CH(CH_3)$—CO—$OCH_3$ |
| Ia.4658 | F | $C_2H_5$ | $CH(CH_3)$—CO—$OCH_3$ |
| Ia.4659 | Cl | $C_2H_5$ | $CH(CH_3)$—CO—$OCH_3$ |
| Ia.4660 | H | n-$C_3H_7$ | $CH(CH_3)$—CO—$OCH_3$ |
| Ia.4661 | F | n-$C_3H_7$ | $CH(CH_3)$—CO—$OCH_3$ |
| Ia.4662 | Cl | n-$C_3H_7$ | $CH(CH_3)$—CO—$OCH_3$ |
| Ia.4663 | H | n-$C_4H_9$ | $CH(CH_3)$—CO—$OCH_3$ |
| Ia.4664 | F | n-$C_4H_9$ | $CH(CH_3)$—CO—$OCH_3$ |
| Ia.4665 | Cl | n-$C_4H_9$ | $CH(CH_3)$—CO—$OCH_3$ |
| Ia.4666 | H | $CH_2$—CH═$CH_2$ | $CH(CH_3)$—CO—$OCH_3$ |
| Ia.4667 | F | $CH_2$—CH═$CH_2$ | $CH(CH_3)$—CO—$OCH_3$ |
| Ia.4668 | Cl | $CH_2$—CH═$CH_2$ | $CH(CH_3)$—CO—$OCH_3$ |
| Ia.4669 | H | $CH_2$—C≡CH | $CH(CH_3)$—CO—$OCH_3$ |
| Ia.4670 | F | $CH_2$—C≡CH | $CH(CH_3)$—CO—$OCH_3$ |
| Ia.4671 | Cl | $CH_2$—C≡CH | $CH(CH_3)$—CO—$OCH_3$ |
| Ia.4672 | H | $CH_2$—CO—$OCH_3$ | $CH(CH_3)$—CO—$OCH_3$ |
| Ia.4673 | F | $CH_2$—CO—$OCH_3$ | $CH(CH_3)$—CO—$OCH_3$ |
| Ia.4674 | Cl | $CH_2$—CO—$OCH_3$ | $CH(CH_3)$—CO—$OCH_3$ |
| Ia.4675 | H | $CH_2$-phenyl | $CH(CH_3)$—CO—$OCH_3$ |
| Ia.4676 | F | $CH_2$-phenyl | $CH(CH_3)$—CO—$OCH_3$ |
| Ia.4677 | Cl | $CH_2$-phenyl | $CH(CH_3)$—CO—$OCH_3$ |
| Ia.4678 | H | $CH_3$ | $CH(C_2H_5)$—CO—$OCH_3$ |

TABLE 1-continued

I

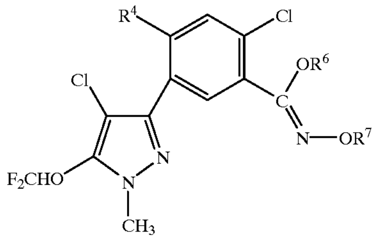

| No. | $R^4$ | $R^6$ | $R^7$ |
|---|---|---|---|
| Ia.4679 | F | $CH_3$ | $CH(C_2H_5)—CO—OCH_3$ |
| Ia.4680 | Cl | $CH_3$ | $CH(C_2H_5)—CO—OCH_3$ |
| Ia.4681 | H | $C_2H_5$ | $CH(C_2H_5)—CO—OCH_3$ |
| Ia.4682 | F | $C_2H_5$ | $CH(C_2H_5)—CO—OCH_3$ |
| Ia.4683 | Cl | $C_2H_5$ | $CH(C_2H_5)—CO—OCH_3$ |
| Ia.4684 | H | n-$C_3H_7$ | $CH(C_2H_5)—CO—OCH_3$ |
| Ia.4685 | F | n-$C_3H_7$ | $CH(C_2H_5)—CO—OCH_3$ |
| Ia.4686 | Cl | n-$C_3H_7$ | $CH(C_2H_5)—CO—OCH_3$ |
| Ia.4687 | H | n-$C_4H_9$ | $CH(C_2H_5)—CO—OCH_3$ |
| Ia.4688 | F | n-$C_4H_9$ | $CH(C_2H_5)—CO—OCH_3$ |
| Ia.4689 | Cl | n-$C_4H_9$ | $CH(C_2H_5)—CO—OCH_3$ |
| Ia.4690 | H | $CH_2—CH=CH_2$ | $CH(C_2H_5)—CO—OCH_3$ |
| Ia.4691 | F | $CH_2—CH=CH_2$ | $CH(C_2H_5)—CO—OCH_3$ |
| Ia.4692 | Cl | $CH_2—CH=CH_2$ | $CH(C_2H_5)—CO—OCH_3$ |
| Ia.4693 | H | $CH_2—C≡CH$ | $CH(C_2H_5)—CO—OCH_3$ |
| Ia.4694 | F | $CH_2—C≡CH$ | $CH(C_2H_5)—CO—OCH_3$ |
| Ia.4695 | Cl | $CH_2—C≡CH$ | $CH(C_2H_5)—CO—OCH_3$ |
| Ia.4696 | H | $CH_2—CO—OCH_3$ | $CH(C_2H_5)—CO—OCH_3$ |
| Ia.4697 | F | $CH_2—CO—OCH_3$ | $CH(C_2H_5)—CO—OCH_3$ |
| Ia.4698 | Cl | $CH_2—CO—OCH_3$ | $CH(C_2H_5)—CO—OCH_3$ |
| Ia.4699 | H | $CH_2$-phenyl | $CH(C_2H_5)—CO—OCH_3$ |
| Ia.4700 | F | $CH_2$-phenyl | $CH(C_2H_5)—CO—OCH_3$ |
| Ia.4701 | Cl | $CH_2$-phenyl | $CH(C_2H_5)—CO—OCH_3$ |
| Ia.4702 | H | $CH_3$ | $CH_2—CO—OC_2H_5$ |
| Ia.4703 | F | $CH_3$ | $CH_2—CO—OC_2H_5$ |
| Ia.4704 | Cl | $CH_3$ | $CH_2—CO—OC_2H_5$ |
| Ia.4705 | H | $C_2H_5$ | $CH_2—CO—OC_2H_5$ |
| Ia.4706 | F | $C_2H_5$ | $CH_2—CO—OC_2H_5$ |
| Ia.4707 | Cl | $C_2H_5$ | $CH_2—CO—OC_2H_5$ |
| Ia.4708 | H | n-$C_3H_7$ | $CH_2—CO—OC_2H_5$ |
| Ia.4709 | F | n-$C_3H_7$ | $CH_2—CO—OC_2H_5$ |
| Ia.4710 | Cl | n-$C_3H_7$ | $CH_2—CO—OC_2H_5$ |
| Ia.4711 | H | n-$C_4H_9$ | $CH_2—CO—OC_2H_5$ |
| Ia.4712 | F | n-$C_4H_9$ | $CH_2—CO—OC_2H_5$ |
| Ia.4713 | Cl | n-$C_4H_9$ | $CH_2—CO—OC_2H_5$ |
| Ia.4714 | H | $CH_2—CH=CH_2$ | $CH_2—CO—OC_2H_5$ |
| Ia.4715 | F | $CH_2—CH=CH_2$ | $CH_2—CO—OC_2H_5$ |
| Ia.4716 | Cl | $CH_2—CH=CH_2$ | $CH_2—CO—OC_2H_5$ |
| Ia.4717 | H | $CH_2—C≡CH$ | $CH_2—CO—OC_2H_5$ |
| Ia.4718 | F | $CH_2—C≡CH$ | $CH_2—CO—OC_2H_5$ |
| Ia.4719 | Cl | $CH_2—C≡CH$ | $CH_2—CO—OC_2H_5$ |
| Ia.4720 | H | $CH_2—CO—OCH_3$ | $CH_2—CO—OC_2H_5$ |
| Ia.4721 | F | $CH_2—CO—OCH_3$ | $CH_2—CO—OC_2H_5$ |
| Ia.4722 | Cl | $CH_2—CO—OCH_3$ | $CH_2—CO—OC_2H_5$ |
| Ia.4723 | H | $CH_2$-phenyl | $CH_2—CO—OC_2H_5$ |
| Ia.4724 | F | $CH_2$-phenyl | $CH_2—CO—OC_2H_5$ |
| Ia.4725 | Cl | $CH_2$-phenyl | $CH_2—CO—OC_2H_5$ |
| Ia.4726 | H | $CH_3$ | $CH(CH_3)—CO—OC_2H_5$ |
| Ia.4727 | F | $CH_3$ | $CH(CH_3)—CO—OC_2H_5$ |
| Ia.4728 | Cl | $CH_3$ | $CH(CH_3)—CO—OC_2H_5$ |
| Ia.4729 | H | $C_2H_5$ | $CH(CH_3)—CO—OC_2H_5$ |
| Ia.4730 | F | $C_2H_5$ | $CH(CH_3)—CO—OC_2H_5$ |
| Ia.4731 | Cl | $C_2H_5$ | $CH(CH_3)—CO—OC_2H_5$ |
| Ia.4732 | H | n-$C_3H_7$ | $CH(CH_3)—CO—OC_2H_5$ |
| Ia.4733 | F | n-$C_3H_7$ | $CH(CH_3)—CO—OC_2H_5$ |
| Ia.4734 | Cl | n-$C_3H_7$ | $CH(CH_3)—CO—OC_2H_5$ |
| Ia.4735 | H | n-$C_4H_9$ | $CH(CH_3)—CO—OC_2H_5$ |
| Ia.4736 | F | n-$C_4H_9$ | $CH(CH_3)—CO—OC_2H_5$ |
| Ia.4737 | Cl | n-$C_4H_9$ | $CH(CH_3)—CO—OC_2H_5$ |
| Ia.4738 | H | $CH_2—CH=CH_2$ | $CH(CH_3)—CO—OC_2H_5$ |
| Ia.4739 | F | $CH_2—CH=CH_2$ | $CH(CH_3)—CO—OC_2H_5$ |
| Ia.4740 | Cl | $CH_2—CH=CH_2$ | $CH(CH_3)—CO—OC_2H_5$ |
| Ia.4741 | H | $CH_2—C≡CH$ | $CH(CH_3)—CO—OC_2H_5$ |

TABLE 1-continued

I

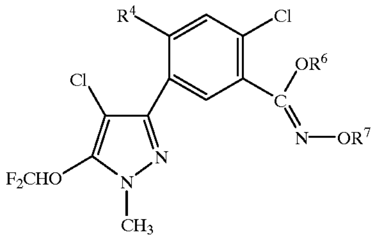

| No. | $R^4$ | $R^6$ | $R^7$ |
|---|---|---|---|
| Ia.4742 | F | $CH_2—C≡CH$ | $CH(CH_3)—CO—OC_2H_5$ |
| Ia.4743 | Cl | $CH_2—C≡CH$ | $CH(CH_3)—CO—OC_2H_5$ |
| Ia.4744 | H | $CH_2—CO—OCH_3$ | $CH(CH_3)—CO—OC_2H_5$ |
| Ia.4745 | F | $CH_2—CO—OCH_3$ | $CH(CH_3)—CO—OC_2H_5$ |
| Ia.4746 | Cl | $CH_2—CO—OCH_3$ | $CH(CH_3)—CO—OC_2H_5$ |
| Ia.4747 | H | $CH_2$-phenyl | $CH(CH_3)—CO—OC_2H_5$ |
| Ia.4748 | F | $CH_2$-phenyl | $CH(CH_3)—CO—OC_2H_5$ |
| Ia.4749 | Cl | $CH_2$-phenyl | $CH(CH_3)—CO—OC_2H_5$ |
| Ia.4750 | H | $CH_3$ | $CH(C_2H_5)—CO—OC_2H_5$ |
| Ia.4751 | F | $CH_3$ | $CH(C_2H_5)—CO—OC_2H_5$ |
| Ia.4752 | Cl | $CH_3$ | $CH(C_2H_5)—CO—OC_2H_5$ |
| Ia.4753 | H | $C_2H_5$ | $CH(C_2H_5)—CO—OC_2H_5$ |
| Ia.4754 | F | $C_2H_5$ | $CH(C_2H_5)—CO—OC_2H_5$ |
| Ia.4755 | Cl | $C_2H_5$ | $CH(C_2H_5)—CO—OC_2H_5$ |
| Ia.4756 | H | n-$C_3H_7$ | $CH(C_2H_5)—CO—OC_2H_5$ |
| Ia.4757 | F | n-$C_3H_7$ | $CH(C_2H_5)—CO—OC_2H_5$ |
| Ia.4758 | Cl | n-$C_3H_7$ | $CH(C_2H_5)—CO—OC_2H_5$ |
| Ia.4759 | H | n-$C_4H_9$ | $CH(C_2H_5)—CO—OC_2H_5$ |
| Ia.4760 | F | n-$C_4H_9$ | $CH(C_2H_5)—CO—OC_2H_5$ |
| Ia.4761 | Cl | n-$C_4H_9$ | $CH(C_2H_5)—CO—OC_2H_5$ |
| Ia.4762 | H | $CH_2—CH{=}CH_2$ | $CH(C_2H_5)—CO—OC_2H_5$ |
| Ia.4763 | F | $CH_2—CH{=}CH_2$ | $CH(C_2H_5)—CO—OC_2H_5$ |
| Ia.4764 | Cl | $CH_2—CH{=}CH_2$ | $CH(C_2H_5)—CO—OC_2H_5$ |
| Ia.4765 | H | $CH_2—C≡CH$ | $CH(C_2H_5)—CO—OC_2H_5$ |
| Ia.4766 | F | $CH_2—C≡CH$ | $CH(C_2H_5)—CO—OC_2H_5$ |
| Ia.4767 | Cl | $CH_2—C≡CH$ | $CH(C_2H_5)—CO—OC_2H_5$ |
| Ia.4768 | H | $CH_2—CO—OCH_3$ | $CH(C_2H_5)—CO—OC_2H_5$ |
| Ia.4769 | F | $CH_2—CO—OCH_3$ | $CH(C_2H_5)—CO—OC_2H_5$ |
| Ia.4770 | Cl | $CH_2—CO—OCH_3$ | $CH(C_2H_5)—CO—OC_2H_5$ |
| Ia.4771 | H | $CH_2$-phenyl | $CH(C_2H_5)—CO—OC_2H_5$ |
| Ia.4772 | F | $CH_2$-phenyl | $CH(C_2H_5)—CO—OC_2H_5$ |
| Ia.4773 | Cl | $CH_2$-phenyl | $CH(C_2H_5)—CO—OC_2H_5$ |
| Ia.4774 | H | $CH_3$ | $CH_2—CO—OC(CH_3)_3$ |
| Ia.4775 | F | $CH_3$ | $CH_2—CO—OC(CH_3)_3$ |
| Ia.4776 | Cl | $CH_3$ | $CH_2—CO—OC(CH_3)_3$ |
| Ia.4777 | H | $C_2H_5$ | $CH_2—CO—OC(CH_3)_3$ |
| Ia.4778 | F | $C_2H_5$ | $CH_2—CO—OC(CH_3)_3$ |
| Ia.4779 | Cl | $C_2H_5$ | $CH_2—CO—OC(CH_3)_3$ |
| Ia.4780 | H | n-$C_3H_7$ | $CH_2—CO—OC(CH_3)_3$ |
| Ia.4781 | F | n-$C_3H_7$ | $CH_2—CO—OC(CH_3)_3$ |
| Ia.4782 | Cl | n-$C_3H_7$ | $CH_2—CO—OC(CH_3)_3$ |
| Ia.4783 | H | n-$C_4H_9$ | $CH_2—CO—OC(CH_3)_3$ |
| Ia.4784 | F | n-$C_4H_9$ | $CH_2—CO—OC(CH_3)_3$ |
| Ia.4785 | Cl | n-$C_4H_9$ | $CH_2—CO—OC(CH_3)_3$ |
| Ia.4786 | H | $CH_2—CH{=}CH_2$ | $CH_2—CO—OC(CH_3)_3$ |
| Ia.4787 | F | $CH_2—CH{=}CH_2$ | $CH_2—CO—OC(CH_3)_3$ |
| Ia.4788 | Cl | $CH_2—CH{=}CH_2$ | $CH_2—CO—OC(CH_3)_3$ |
| Ia.4789 | H | $CH_2—C≡CH$ | $CH_2—CO—OC(CH_3)_3$ |
| Ia.4790 | F | $CH_2—C≡CH$ | $CH_2—CO—OC(CH_3)_3$ |
| Ia.4791 | Cl | $CH_2—C≡CH$ | $CH_2—CO—OC(CH_3)_3$ |
| Ia.4792 | H | $CH_2—CO—OCH_3$ | $CH_2—CO—OC(CH_3)_3$ |
| Ia.4793 | F | $CH_2—CO—OCH_3$ | $CH_2—CO—OC(CH_3)_3$ |
| Ia.4794 | Cl | $CH_2—CO—OCH_3$ | $CH_2—CO—OC(CH_3)_3$ |
| Ia.4795 | H | $CH_2$-phenyl | $CH_2—CO—OC(CH_3)_3$ |
| Ia.4796 | F | $CH_2$-phenyl | $CH_2—CO—OC(CH_3)_3$ |
| Ia.4797 | Cl | $CH_2$-phenyl | $CH_2—CO—OC(CH_3)_3$ |
| Ia.4798 | H | $CH_3$ | $CH(CH_3)—CO—OC(CH_3)_3$ |
| Ia.4799 | F | $CH_3$ | $CH(CH_3)—CO—OC(CH_3)_3$ |
| Ia.4800 | Cl | $CH_3$ | $CH(CH_3)—CO—OC(CH_3)_3$ |
| Ia.4801 | H | $C_2H_5$ | $CH(CH_3)—CO—OC(CH_3)_3$ |
| Ia.4802 | F | $C_2H_5$ | $CH(CH_3)—CO—OC(CH_3)_3$ |
| Ia.4803 | Cl | $C_2H_5$ | $CH(CH_3)—CO—OC(CH_3)_3$ |
| Ia.4804 | H | n-$C_3H_7$ | $CH(CH_3)—CO—OC(CH_3)_3$ |

TABLE 1-continued

I

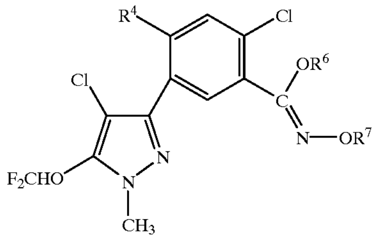

| No. | $R^4$ | $R^6$ | $R^7$ |
|---|---|---|---|
| Ia.4805 | F | n-$C_3H_7$ | $CH(CH_3)$—CO—$OC(CH_3)_3$ |
| Ia.4806 | Cl | n-$C_3H_7$ | $CH(CH_3)$—CO—$OC(CH_3)_3$ |
| Ia.4807 | H | n-$C_4H_9$ | $CH(CH_3)$—CO—$OC(CH_3)_3$ |
| Ia.4808 | F | n-$C_4H_9$ | $CH(CH_3)$—CO—$OC(CH_3)_3$ |
| Ia.4809 | Cl | n-$C_4H_9$ | $CH(CH_3)$—CO—$OC(CH_3)_3$ |
| Ia.4810 | H | $CH_2$—CH═$CH_2$ | $CH(CH_3)$—CO—$OC(CH_3)_3$ |
| Ia.4811 | F | $CH_2$—CH═$CH_2$ | $CH(CH_3)$—CO—$OC(CH_3)_3$ |
| Ia.4812 | Cl | $CH_2$—CH═$CH_2$ | $CH(CH_3)$—CO—$OC(CH_3)_3$ |
| Ia.4813 | H | $CH_2$—C≡CH | $CH(CH_3)$—CO—$OC(CH_3)_3$ |
| Ia.4814 | F | $CH_2$—C≡CH | $CH(CH_3)$—CO—$OC(CH_3)_3$ |
| Ia.4815 | Cl | $CH_2$—C≡CH | $CH(CH_3)$—CO—$OC(CH_3)_3$ |
| Ia.4816 | H | $CH_2$—CO—$OCH_3$ | $CH(CH_3)$—CO—$OC(CH_3)_3$ |
| Ia.4817 | F | $CH_2$—CO—$OCH_3$ | $CH(CH_3)$—CO—$OC(CH_3)_3$ |
| Ia.4818 | Cl | $CH_2$—CO—$OCH_3$ | $CH(CH_3)$—CO—$OC(CH_3)_3$ |
| Ia.4819 | H | $CH_2$-phenyl | $CH(CH_3)$—CO—$OC(CH_3)_3$ |
| Ia.4820 | F | $CH_2$-phenyl | $CH(CH_3)$—CO—$OC(CH_3)_3$ |
| Ia.4821 | Cl | $CH_2$-phenyl | $CH(CH_3)$—CO—$OC(CH_3)_3$ |
| Ia.4822 | H | $CH_3$ | $CH(C_2H_5)$—CO—$OC(CH_3)_3$ |
| Ia.4823 | F | $CH_3$ | $CH(C_2H_5)$—CO—$OC(CH_3)_3$ |
| Ia.4824 | Cl | $CH_3$ | $CH(C_2H_5)$—CO—$OC(CH_3)_3$ |
| Ia.4825 | H | $C_2H_5$ | $CH(C_2H_5)$—CO—$OC(CH_3)_3$ |
| Ia.4826 | F | $C_2H_5$ | $CH(C_2H_5)$—CO—$OC(CH_3)_3$ |
| Ia.4827 | Cl | $C_2H_5$ | $CH(C_2H_5)$—CO—$OC(CH_3)_3$ |
| Ia.4828 | H | n-$C_3H_7$ | $CH(C_2H_5)$—CO—$OC(CH_3)_3$ |
| Ia.4829 | F | n-$C_3H_7$ | $CH(C_2H_5)$—CO—$OC(CH_3)_3$ |
| Ia.4830 | Cl | n-$C_3H_7$ | $CH(C_2H_5)$—CO—$OC(CH_3)_3$ |
| Ia.4831 | H | n-$C_4H_9$ | $CH(C_2H_5)$—CO—$OC(CH_3)_3$ |
| Ia.4832 | F | n-$C_4H_9$ | $CH(C_2H_5)$—CO—$OC(CH_3)_3$ |
| Ia.4833 | Cl | n-$C_4H_9$ | $CH(C_2H_5)$—CO—$OC(CH_3)_3$ |
| Ia.4834 | H | $CH_2$—CH═$CH_2$ | $CH(C_2H_5)$—CO—$OC(CH_3)_3$ |
| Ia.4835 | F | $CH_2$—CH═$CH_2$ | $CH(C_2H_5)$—CO—$OC(CH_3)_3$ |
| Ia.4836 | Cl | $CH_2$—CH═$CH_2$ | $CH(C_2H_5)$—CO—$OC(CH_3)_3$ |
| Ia.4837 | H | $CH_2$—C≡CH | $CH(C_2H_5)$—CO—$OC(CH_3)_3$ |
| Ia.4838 | F | $CH_2$—C≡CH | $CH(C_2H_5)$—CO—$OC(CH_3)_3$ |
| Ia.4839 | Cl | $CH_2$—C≡CH | $CH(C_2H_5)$—CO—$OC(CH_3)_3$ |
| Ia.4840 | H | $CH_2$—CO—$OCH_3$ | $CH(C_2H_5)$—CO—$OC(CH_3)_3$ |
| Ia.4841 | F | $CH_2$—CO—$OCH_3$ | $CH(C_2H_5)$—CO—$OC(CH_3)_3$ |
| Ia.4842 | Cl | $CH_2$—CO—$OCH_3$ | $CH(C_2H_5)$—CO—$OC(CH_3)_3$ |
| Ia.4843 | H | $CH_2$-phenyl | $CH(C_2H_5)$—CO—$OC(CH_3)_3$ |
| Ia.4844 | F | $CH_2$-phenyl | $CH(C_2H_5)$—CO—$OC(CH_3)_3$ |
| Ia.4845 | Cl | $CH_2$-phenyl | $CH(C_2H_5)$—CO—$OC(CH_3)_3$ |
| Ia.4846 | H | $CH_3$ | $CH_2$—CO—$SCH_3$ |
| Ia.4847 | F | $CH_3$ | $CH_2$—CO—$SCH_3$ |
| Ia.4848 | Cl | $CH_3$ | $CH_2$—CO—$SCH_3$ |
| Ia.4849 | H | $C_2H_5$ | $CH_2$—CO—$SCH_3$ |
| Ia.4850 | F | $C_2H_5$ | $CH_2$—CO—$SCH_3$ |
| Ia.4851 | Cl | $C_2H_5$ | $CH_2$—CO—$SCH_3$ |
| Ia.4852 | H | n-$C_3H_7$ | $CH_2$—CO—$SCH_3$ |
| Ia.4853 | F | n-$C_3H_7$ | $CH_2$—CO—$SCH_3$ |
| Ia.4854 | Cl | n-$C_3H_7$ | $CH_2$—CO—$SCH_3$ |
| Ia.4855 | H | n-$C_4H_9$ | $CH_2$—CO—$SCH_3$ |
| Ia.4856 | F | n-$C_4H_9$ | $CH_2$—CO—$SCH_3$ |
| Ia.4857 | Cl | n-$C_4H_9$ | $CH_2$—CO—$SCH_3$ |
| Ia.4858 | H | $CH_2$—CH═$CH_2$ | $CH_2$—CO—$SCH_3$ |
| Ia.4859 | F | $CH_2$—CH═$CH_2$ | $CH_2$—CO—$SCH_3$ |
| Ia.4860 | Cl | $CH_2$—CH═$CH_2$ | $CH_2$—CO—$SCH_3$ |
| Ia.4861 | H | $CH_2$—C≡CH | $CH_2$—CO—$SCH_3$ |
| Ia.4862 | F | $CH_2$—C≡CH | $CH_2$—CO—$SCH_3$ |
| Ia.4863 | Cl | $CH_2$—C≡CH | $CH_2$—CO—$SCH_3$ |
| Ia.4864 | H | $CH_2$—CO—$OCH_3$ | $CH_2$—CO—$SCH_3$ |
| Ia.4865 | F | $CH_2$—CO—$OCH_3$ | $CH_2$—CO—$SCH_3$ |
| Ia.4866 | Cl | $CH_2$—CO—$OCH_3$ | $CH_2$—CO—$SCH_3$ |
| Ia.4867 | H | $CH_2$-phenyl | $CH_2$—CO—$SCH_3$ |

TABLE 1-continued

I

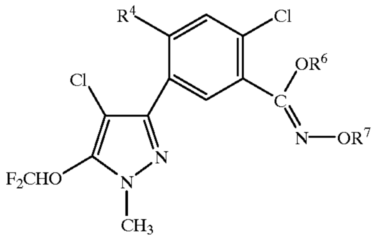

| No. | $R^4$ | $R^6$ | $R^7$ |
|---|---|---|---|
| Ia.4868 | F | $CH_2$-phenyl | $CH_2$—CO—$SCH_3$ |
| Ia.4869 | Cl | $CH_2$-phenyl | $CH_2$—CO—$SCH_3$ |
| Ia.4870 | H | $CH_3$ | $CH_2$—CO—$N(CH_3)_2$ |
| Ia.4871 | F | $CH_3$ | $CH_2$—CO—$N(CH_3)_2$ |
| Ia.4872 | Cl | $CH_3$ | $CH_2$—CO—$N(CH_3)_2$ |
| Ia.4873 | H | $C_2H_5$ | $CH_2$—CO—$N(CH_3)_2$ |
| Ia.4874 | F | $C_2H_5$ | $CH_2$—CO—$N(CH_3)_2$ |
| Ia.4875 | Cl | $C_2H_5$ | $CH_2$—CO—$N(CH_3)_2$ |
| Ia.4876 | H | n-$C_3H_7$ | $CH_2$—CO—$N(CH_3)_2$ |
| Ia.4877 | F | n-$C_3H_7$ | $CH_2$—CO—$N(CH_3)_2$ |
| Ia.4878 | Cl | n-$C_3H_7$ | $CH_2$—CO—$N(CH_3)_2$ |
| Ia.4879 | H | n-$C_4H_9$ | $CH_2$—CO—$N(CH_3)_2$ |
| Ia.4880 | F | n-$C_4H_9$ | $CH_2$—CO—$N(CH_3)_2$ |
| Ia.4881 | Cl | n-$C_4H_9$ | $CH_2$—CO—$N(CH_3)_2$ |
| Ia.4882 | H | $CH_2$—CH=$CH_2$ | $CH_2$—CO—$N(CH_3)_2$ |
| Ia.4883 | F | $CH_2$—CH=$CH_2$ | $CH_2$—CO—$N(CH_3)_2$ |
| Ia.4884 | Cl | $CH_2$—CH=$CH_2$ | $CH_2$—CO—$N(CH_3)_2$ |
| Ia.4885 | H | $CH_2$—C≡CH | $CH_2$—CO—$N(CH_3)_2$ |
| Ia.4886 | F | $CH_2$—C≡CH | $CH_2$—CO—$N(CH_3)_2$ |
| Ia.4887 | Cl | $CH_2$—C≡CH | $CH_2$—CO—$N(CH_3)_2$ |
| Ia.4888 | H | $CH_2$—CO—$OCH_3$ | $CH_2$—CO—$N(CH_3)_2$ |
| Ia.4889 | F | $CH_2$—CO—$OCH_3$ | $CH_2$—CO—$N(CH_3)_2$ |
| Ia.4890 | Cl | $CH_2$—CO—$OCH_3$ | $CH_2$—CO—$N(CH_3)_2$ |
| Ia.4891 | H | $CH_2$-phenyl | $CH_2$—CO—$N(CH_3)_2$ |
| Ia.4892 | F | $CH_2$-phenyl | $CH_2$—CO—$N(CH_3)_2$ |
| Ia.4893 | Cl | $CH_2$-phenyl | $CH_2$—CO—$N(CH_3)_2$ |
| Ia.4894 | H | $CH_3$ | $CH(CH_3)$—CO—$N(CH_3)_2$ |
| Ia.4895 | F | $CH_3$ | $CH(CH_3)$—CO—$N(CH_3)_2$ |
| Ia.4896 | Cl | $CH_3$ | $CH(CH_3)$—CO—$N(CH_3)_2$ |
| Ia.4897 | H | $C_2H_5$ | $CH(CH_3)$—CO—$N(CH_3)_2$ |
| Ia.4898 | F | $C_2H_5$ | $CH(CH_3)$—CO—$N(CH_3)_2$ |
| Ia.4899 | Cl | $C_2H_5$ | $CH(CH_3)$—CO—$N(CH_3)_2$ |
| Ia.4900 | H | n-$C_3H_7$ | $CH(CH_3)$—CO—$N(CH_3)_2$ |
| Ia.4901 | F | n-$C_3H_7$ | $CH(CH_3)$—CO—$N(CH_3)_2$ |
| Ia.4902 | Cl | n-$C_3H_7$ | $CH(CH_3)$—CO—$N(CH_3)_2$ |
| Ia.4903 | H | n-$C_4H_9$ | $CH(CH_3)$—CO—$N(CH_3)_2$ |
| Ia.4904 | F | n-$C_4H_9$ | $CH(CH_3)$—CO—$N(CH_3)_2$ |
| Ia.4905 | Cl | n-$C_4H_9$ | $CH(CH_3)$—CO—$N(CH_3)_2$ |
| Ia.4906 | H | $CH_2$—CH=$CH_2$ | $CH(CH_3)$—CO—$N(CH_3)_2$ |
| Ia.4907 | F | $CH_2$—CH=$CH_2$ | $CH(CH_3)$—CO—$N(CH_3)_2$ |
| Ia.4908 | Cl | $CH_2$—CH=$CH_2$ | $CH(CH_3)$—CO—$N(CH_3)_2$ |
| Ia.4909 | H | $CH_2$—C≡CH | $CH(CH_3)$—CO—$N(CH_3)_2$ |
| Ia.4910 | F | $CH_2$—C≡CH | $CH(CH_3)$—CO—$N(CH_3)_2$ |
| Ia.4911 | Cl | $CH_2$—C≡CH | $CH(CH_3)$—CO—$N(CH_3)_2$ |
| Ia.4912 | H | $CH_2$—CO—$OCH_3$ | $CH(CH_3)$—CO—$N(CH_3)_2$ |
| Ia.4913 | F | $CH_2$—CO—$OCH_3$ | $CH(CH_3)$—CO—$N(CH_3)_2$ |
| Ia.4914 | Cl | $CH_2$—CO—$OCH_3$ | $CH(CH_3)$—CO—$N(CH_3)_2$ |
| Ia.4915 | H | $CH_2$-phenyl | $CH(CH_3)$—CO—$N(CH_3)_2$ |
| Ia.4916 | F | $CH_2$-phenyl | $CH(CH_3)$—CO—$N(CH_3)_2$ |
| Ia.4917 | Cl | $CH_2$-phenyl | $CH(CH_3)$—CO—$N(CH_3)_2$ |
| Ia.4918 | H | $CH_3$ | $CH(C_2H_5)$—CO—$N(CH_3)_2$ |
| Ia.4919 | F | $CH_3$ | $CH(C_2H_5)$—CO—$N(CH_3)_2$ |
| Ia.4920 | Cl | $CH_3$ | $CH(C_2H_5)$—CO—$N(CH_3)_2$ |
| Ia.4921 | H | $C_2H_5$ | $CH(C_2H_5)$—CO—$N(CH_3)_2$ |
| Ia.4922 | F | $C_2H_5$ | $CH(C_2H_5)$—CO—$N(CH_3)_2$ |
| Ia.4923 | Cl | $C_2H_5$ | $CH(C_2H_5)$—CO—$N(CH_3)_2$ |
| Ia.4924 | H | n-$C_3H_7$ | $CH(C_2H_5)$—CO—$N(CH_3)_2$ |
| Ia.4925 | F | n-$C_3H_7$ | $CH(C_2H_5)$—CO—$N(CH_3)_2$ |
| Ia.4926 | Cl | n-$C_3H_7$ | $CH(C_2H_5)$—CO—$N(CH_3)_2$ |
| Ia.4927 | H | n-$C_4H_9$ | $CH(C_2H_5)$—CO—$N(CH_3)_2$ |
| Ia.4928 | F | n-$C_4H_9$ | $CH(C_2H_5)$—CO—$N(CH_3)_2$ |
| Ia.4929 | Cl | n-$C_4H_9$ | $CH(C_2H_5)$—CO—$N(CH_3)_2$ |
| Ia.4930 | H | $CH_2$—CH=$CH_2$ | $CH(C_2H_5)$—CO—$N(CH_3)_2$ |

TABLE 1-continued

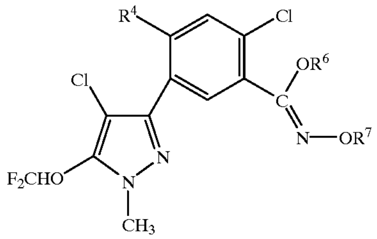

I

| No. | $R^4$ | $R^6$ | $R^7$ |
|---|---|---|---|
| Ia.4931 | F | $CH_2—CH═CH_2$ | $CH(C_2H_5)—CO—N(CH_3)_2$ |
| Ia.4932 | Cl | $CH_2—CH═CH_2$ | $CH(C_2H_5)—CO—N(CH_3)_2$ |
| Ia.4933 | H | $CH_2—C≡CH$ | $CH(C_2H_5)—CO—N(CH_3)_2$ |
| Ia.4934 | F | $CH_2—C≡CH$ | $CH(C_2H_5)—CO—N(CH_3)_2$ |
| Ia.4935 | Cl | $CH_2—C≡CH$ | $CH(C_2H_5)—CO—N(CH_3)_2$ |
| Ia.4936 | H | $CH_2—CO—OCH_3$ | $CH(C_2H_5)—CO—N(CH_3)_2$ |
| Ia.4937 | F | $CH_2—CO—OCH_3$ | $CH(C_2H_5)—CO—N(CH_3)_2$ |
| Ia.4938 | Cl | $CH_2—CO—OCH_3$ | $CH(C_2H_5)—CO—N(CH_3)_2$ |
| Ia.4939 | H | $CH_2$-phenyl | $CH(C_2H_5)—CO—N(CH_3)_2$ |
| Ia.4940 | F | $CH_2$-phenyl | $CH(C_2H_5)—CO—N(CH_3)_2$ |
| Ia.4941 | Cl | $CH_2$-phenyl | $CH(C_2H_5)—CO—N(CH_3)_2$ |
| Ia.4942 | H | $CH_3$ | cyclopentyl |
| Ia.4943 | F | $CH_3$ | cyclopentyl |
| Ia.4944 | Cl | $CH_3$ | cyclopentyl |
| Ia.4945 | H | $C_2H_5$ | cyclopentyl |
| Ia.4946 | F | $C_2H_5$ | cyclopentyl |
| Ia.4947 | Cl | $C_2H_5$ | cyclopentyl |
| Ia.4948 | H | n-$C_3H_7$ | cyclopentyl |
| Ia.4949 | F | n-$C_3H_7$ | cyclopentyl |
| Ia.4950 | Cl | n-$C_3H_7$ | cyclopentyl |
| Ia.4951 | H | n-$C_4H_9$ | cyclopentyl |
| Ia.4952 | F | n-$C_4H_9$ | cyclopentyl |
| Ia.4953 | Cl | n-$C_4H_9$ | cyclopentyl |
| Ia.4954 | H | $CH_2—CH═CH_2$ | cyclopentyl |
| Ia.4955 | F | $CH_2—CH═CH_2$ | cyclopentyl |
| Ia.4956 | Cl | $CH_2—CH═CH_2$ | cyclopentyl |
| Ia.4957 | H | $CH_2—C≡CH$ | cyclopentyl |
| Ia.4958 | F | $CH_2—C≡CH$ | cyclopentyl |
| Ia.4959 | Cl | $CH_2—C≡CH$ | cyclopentyl |
| Ia.4960 | H | $CH_2—CO—OCH_3$ | cyclopentyl |
| Ia.4961 | F | $CH_2—CO—OCH_3$ | cyclopentyl |
| Ia.4962 | Cl | $CH_2—CO—OCH_3$ | cyclopentyl |
| Ia.4963 | H | $CH_2$-phenyl | cyclopentyl |
| Ia.4964 | F | $CH_2$-phenyl | cyclopentyl |
| Ia.4965 | Cl | $CH_2$-phenyl | cyclopentyl |
| Ia.4966 | H | $CH_3$ | cyclohexyl |
| Ia.4967 | F | $CH_3$ | cyclohexyl |
| Ia.4968 | Cl | $CH_3$ | cyclohexyl |
| Ia.4969 | H | $C_2H_5$ | cyclohexyl |
| Ia.4970 | F | $C_2H_5$ | cyclohexyl |
| Ia.4971 | Cl | $C_2H_5$ | cyclohexyl |
| Ia.4972 | H | n-$C_3H_7$ | cyclohexyl |
| Ia.4973 | F | n-$C_3H_7$ | cyclohexyl |
| Ia.4974 | Cl | n-$C_3H_7$ | cyclohexyl |
| Ia.4975 | H | n-$C_4H_9$ | cyclohexyl |
| Ia.4976 | F | n-$C_4H_9$ | cyclohexyl |
| Ia.4977 | Cl | n-$C_4H_9$ | cyclohexyl |
| Ia.4978 | H | $CH_2—CH═CH_2$ | cyclohexyl |
| Ia.4979 | F | $CH_2—CH═CH_2$ | cyclohexyl |
| Ia.4980 | Cl | $CH_2—CH═CH_2$ | cyclohexyl |
| Ia.4981 | H | $CH_2—C≡CH$ | cyclohexyl |
| Ia.4982 | F | $CH_2—C≡CH$ | cyclohexyl |
| Ia.4983 | Cl | $CH_2—C≡CH$ | cyclohexyl |
| Ia.4984 | H | $CH_2—CO—OCH_3$ | cyclohexyl |
| Ia.4985 | F | $CH_2—CO—OCH_3$ | cyclohexyl |
| Ia.4986 | Cl | $CH_2—CO—OCH_3$ | cyclohexyl |
| Ia.4987 | H | $CH_2$-phenyl | cyclohexyl |
| Ia.4988 | F | $CH_2$-phenyl | cyclohexyl |
| Ia.4989 | Cl | $CH_2$-phenyl | cyclohexyl |
| Ia.4990 | H | $CH_3$ | phenyl |
| Ia.4991 | F | $CH_3$ | phenyl |
| Ia.4992 | Cl | $CH_3$ | phenyl |
| Ia.4993 | H | $C_2H_5$ | phenyl |

TABLE 1-continued

I

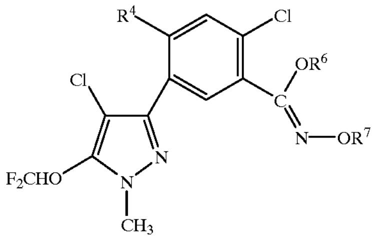

| No. | $R^4$ | $R^6$ | $R^7$ |
|---|---|---|---|
| Ia.4994 | F | $C_2H_5$ | phenyl |
| Ia.4995 | Cl | $C_2H_5$ | phenyl |
| Ia.4996 | H | n-$C_3H_7$ | phenyl |
| Ia.4997 | F | n-$C_3H_7$ | phenyl |
| Ia.4998 | Cl | n-$C_3H_7$ | phenyl |
| Ia.4999 | H | n-$C_4H_9$ | phenyl |
| Ia.5000 | F | n-$C_4H_9$ | phenyl |
| Ia.5001 | Cl | n-$C_4H_9$ | phenyl |
| Ia.5002 | H | $CH_2$—CH═$CH_2$ | phenyl |
| Ia.5003 | F | $CH_2$—CH═$CH_2$ | phenyl |
| Ia.5004 | Cl | $CH_2$—CH═$CH_2$ | phenyl |
| Ia.5005 | H | $CH_2$—C≡CH | phenyl |
| Ia.5006 | F | $CH_2$—C≡CH | phenyl |
| Ia.5007 | Cl | $CH_2$—C≡CH | phenyl |
| Ia.5008 | H | $CH_2$—CO—$OCH_3$ | phenyl |
| Ia.5009 | F | $CH_2$—CO—$OCH_3$ | phenyl |
| Ia.5010 | Cl | $CH_2$—CO—$OCH_3$ | phenyl |
| Ia.5011 | H | $CH_2$-phenyl | phenyl |
| Ia.5012 | F | $CH_2$-phenyl | phenyl |
| Ia.5013 | Cl | $CH_2$-phenyl | phenyl |
| Ia.5014 | H | $CH_3$ | $CH_2$-cyclopentyl |
| Ia.5015 | F | $CH_3$ | $CH_2$-cyclopentyl |
| Ia.5016 | Cl | $CH_3$ | $CH_2$-cyclopentyl |
| Ia.5017 | H | $C_2H_5$ | $CH_2$-cyclopentyl |
| Ia.5018 | F | $C_2H_5$ | $CH_2$-cyclopentyl |
| Ia.5019 | Cl | $C_2H_5$ | $CH_2$-cyclopentyl |
| Ia.5020 | H | n-$C_3H_7$ | $CH_2$-cyclopentyl |
| Ia.5021 | F | n-$C_3H_7$ | $CH_2$-cyclopentyl |
| Ia.5022 | Cl | n-$C_3H_7$ | $CH_2$-cyclopentyl |
| Ia.5023 | H | n-$C_4H_9$ | $CH_2$-cyclopentyl |
| Ia.5024 | F | n-$C_4H_9$ | $CH_2$-cyclopentyl |
| Ia.5025 | Cl | n-$C_4H_9$ | $CH_2$-cyclopentyl |
| Ia.5026 | H | $CH_2$—CH═$CH_2$ | $CH_2$-cyclopentyl |
| Ia.5027 | F | $CH_2$—CH═$CH_2$ | $CH_2$-cyclopentyl |
| Ia.5028 | Cl | $CH_2$—CH═$CH_2$ | $CH_2$-cyclopentyl |
| Ia.5029 | H | $CH_2$—C≡CH | $CH_2$-cyclopentyl |
| Ia.5030 | F | $CH_2$—C≡CH | $CH_2$-cyclopentyl |
| Ia.5031 | Cl | $CH_2$—C≡CH | $CH_2$-cyclopentyl |
| Ia.5032 | H | $CH_2$—CO—$OCH_3$ | $CH_2$-cyclopentyl |
| Ia.5033 | F | $CH_2$—CO—$OCH_3$ | $CH_2$-cyclopentyl |
| Ia.5034 | Cl | $CH_2$—CO—$OCH_3$ | $CH_2$-cyclopentyl |
| Ia.5035 | H | $CH_2$-phenyl | $CH_2$-cyclopentyl |
| Ia.5036 | F | $CH_2$-phenyl | $CH_2$-cyclopentyl |
| Ia.5037 | Cl | $CH_2$-phenyl | $CH_2$-cyclopentyl |
| Ia.5038 | H | $CH_3$ | $CH_2$-cyclohexyl |
| Ia.5039 | F | $CH_3$ | $CH_2$-cyclohexyl |
| Ia.5040 | Cl | $CH_3$ | $CH_2$-cyclohexyl |
| Ia.5041 | H | $C_2H_5$ | $CH_2$-cyclohexyl |
| Ia.5042 | F | $C_2H_5$ | $CH_2$-cyclohexyl |
| Ia.5043 | Cl | $C_2H_5$ | $CH_2$-cyclohexyl |
| Ia.5044 | H | n-$C_3H_7$ | $CH_2$-cyclohexyl |
| Ia.5045 | F | n-$C_3H_7$ | $CH_2$-cyclohexyl |
| Ia.5046 | Cl | n-$C_3H_7$ | $CH_2$-cyclohexyl |
| Ia.5047 | H | n-$C_4H_9$ | $CH_2$-cyclohexyl |
| Ia.5048 | F | n-$C_4H_9$ | $CH_2$-cyclohexyl |
| Ia.5049 | Cl | n-$C_4H_9$ | $CH_2$-cyclohexyl |
| Ia.5050 | H | $CH_2$—CH═$CH_2$ | $CH_2$-cyclohexyl |
| Ia.5051 | F | $CH_2$—CH═$CH_2$ | $CH_2$-cyclohexyl |
| Ia.5052 | Cl | $CH_2$—CH═$CH_2$ | $CH_2$-cyclohexyl |
| Ia.5053 | H | $CH_2$—C≡CH | $CH_2$-cyclohexyl |
| Ia.5054 | F | $CH_2$—C≡CH | $CH_2$-cyclohexyl |
| Ia.5055 | Cl | $CH_2$—C≡CH | $CH_2$-cyclohexyl |
| Ia.5056 | H | $CH_2$—CO—$OCH_3$ | $CH_2$-cyclohexyl |

TABLE 1-continued

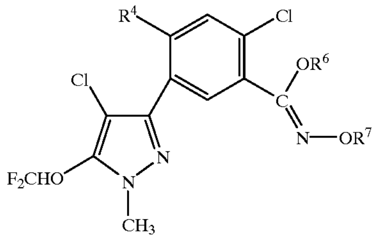

I

| No. | $R^4$ | $R^6$ | $R^7$ |
|---|---|---|---|
| Ia.5057 | F | $CH_2$—CO—$OCH_3$ | $CH_2$-cyclohexyl |
| Ia.5058 | Cl | $CH_2$—CO—$OCH_3$ | $CH_2$-cyclohexyl |
| Ia.5059 | H | $CH_2$-phenyl | $CH_2$-cyclohexyl |
| Ia.5060 | F | $CH_2$-phenyl | $CH_2$-cyclohexyl |
| Ia.5061 | Cl | $CH_2$-phenyl | $CH_2$-cyclohexyl |
| Ia.5062 | H | $CH_3$ | $CH_2$-phenyl |
| Ia.5063 | F | $CH_3$ | $CH_2$-phenyl |
| Ia.5064 | Cl | $CH_3$ | $CH_2$-phenyl |
| Ia.5065 | H | $C_2H_5$ | $CH_2$-phenyl |
| Ia.5066 | F | $C_2H_5$ | $CH_2$-phenyl |
| Ia.5067 | Cl | $C_2H_5$ | $CH_2$-phenyl |
| Ia.5068 | H | n-$C_3H_7$ | $CH_2$-phenyl |
| Ia.5069 | F | n-$C_3H_7$ | $CH_2$-phenyl |
| Ia.5070 | Cl | n-$C_3H_7$ | $CH_2$-phenyl |
| Ia.5071 | H | n-$C_4H_9$ | $CH_2$-phenyl |
| Ia.5072 | F | n-$C_4H_9$ | $CH_2$-phenyl |
| Ia.5073 | Cl | n-$C_4H_9$ | $CH_2$-phenyl |
| Ia.5074 | H | $CH_3$ | $CH_2$-(oxiran-2-yl) |
| Ia.5075 | F | $CH_3$ | $CH_2$-(oxiran-2-yl) |
| Ia.5076 | Cl | $CH_3$ | $CH_2$-(oxiran-2-yl) |
| Ia.5077 | H | $C_2H_5$ | $CH_2$-(oxiran-2-yl) |
| Ia.5078 | F | $C_2H_5$ | $CH_2$-(oxiran-2-yl) |
| Ia.5079 | Cl | $C_2H_5$ | $CH_2$-(oxiran-2-yl) |
| Ia.5080 | H | n-$C_3H_7$ | $CH_2$-(oxiran-2-yl) |
| Ia.5081 | F | n-$C_3H_7$ | $CH_2$-(oxiran-2-yl) |
| Ia.5082 | Cl | n-$C_3H_7$ | $CH_2$-(oxiran-2-yl) |
| Ia.5083 | H | n-$C_4H_9$ | $CH_2$-(oxiran-2-yl) |
| Ia.5084 | F | n-$C_4H_9$ | $CH_2$-(oxiran-2-yl) |
| Ia.5085 | Cl | n-$C_4H_9$ | $CH_2$-(oxiran-2-yl) |
| Ia.5086 | H | $CH_2$—CH═$CH_2$ | $CH_2$-(oxiran-2-yl) |
| Ia.5087 | F | $CH_2$—CH═$CH_2$ | $CH_2$-(oxiran-2-yl) |
| Ia.5088 | Cl | $CH_2$—CH═$CH_2$ | $CH_2$-(oxiran-2-yl) |
| Ia.5089 | H | $CH_2$—C≡CH | $CH_2$-(oxiran-2-yl) |
| Ia.5090 | F | $CH_2$—C≡CH | $CH_2$-(oxiran-2-yl) |
| Ia.5091 | Cl | $CH_2$—C≡CH | $CH_2$-(oxiran-2-yl) |
| Ia.5092 | H | $CH_2$—CO—$OCH_3$ | $CH_2$-(oxiran-2-yl) |
| Ia.5093 | F | $CH_2$—CO—$OCH_3$ | $CH_2$-(oxiran-2-yl) |
| Ia.5094 | Cl | $CH_2$—CO—$OCH_3$ | $CH_2$-(oxiran-2-yl) |
| Ia.5095 | H | $CH_2$-phenyl | $CH_2$-(oxiran-2-yl) |
| Ia.5096 | F | $CH_2$-phenyl | $CH_2$-(oxiran-2-yl) |
| Ia.5097 | Cl | $CH_2$-phenyl | $CH_2$-(oxiran-2-yl) |
| Ia.5098 | H | $CH_3$ | $CH_2$-(oxetan-3-yl) |
| Ia.5099 | F | $CH_3$ | $CH_2$-(oxetan-3-yl) |
| Ia.5100 | Cl | $CH_3$ | $CH_2$-(oxetan-3-yl) |
| Ia.5101 | H | $C_2H_5$ | $CH_2$-(oxetan-3-yl) |
| Ia.5102 | F | $C_2H_5$ | $CH_2$-(oxetan-3-yl) |
| Ia.5103 | Cl | $C_2H_5$ | $CH_2$-(oxetan-3-yl) |
| Ia.5104 | H | n-$C_3H_7$ | $CH_2$-(oxetan-3-yl) |
| Ia.5105 | F | n-$C_3H_7$ | $CH_2$-(oxetan-3-yl) |
| Ia.5106 | Cl | n-$C_3H_7$ | $CH_2$-(oxetan-3-yl) |
| Ia.5107 | H | n-$C_4H_9$ | $CH_2$-(oxetan-3-yl) |
| Ia.5108 | F | n-$C_4H_9$ | $CH_2$-(oxetan-3-yl) |
| Ia.5109 | Cl | n-$C_4H_9$ | $CH_2$-(oxetan-3-yl) |
| Ia.5110 | H | $CH_2$—CH═$CH_2$ | $CH_2$-(oxetan-3-yl) |
| Ia.5111 | F | $CH_2$—CH═$CH_2$ | $CH_2$-(oxetan-3-yl) |
| Ia.5112 | Cl | $CH_2$—CH═$CH_2$ | $CH_2$-(oxetan-3-yl) |
| Ia.5113 | H | $CH_2$—C≡CH | $CH_2$-(oxetan-3-yl) |
| Ia.5114 | F | $CH_2$—C≡CH | $CH_2$-(oxetan-3-yl) |
| Ia.5115 | Cl | $CH_2$—C≡CH | $CH_2$-(oxetan-3-yl) |
| Ia.5116 | H | $CH_2$—CO—$OCH_3$ | $CH_2$-(oxetan-3-yl) |
| Ia.5117 | F | $CH_2$—CO—$OCH_3$ | $CH_2$-(oxetan-3-yl) |
| Ia.5118 | Cl | $CH_2$—CO—$OCH_3$ | $CH_2$-(oxetan-3-yl) |
| Ia.5119 | H | $CH_2$-phenyl | $CH_2$-(oxetan-3-yl) |

TABLE 1-continued

I

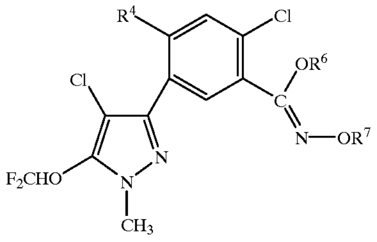

| No. | $R^4$ | $R^6$ | $R^7$ |
|---|---|---|---|
| Ia.5120 | F | $CH_2$-phenyl | $CH_2$-(oxetan-3-yl) |
| Ia.5121 | Cl | $CH_2$-phenyl | $CH_2$-(oxetan-3-yl) |
| Ia.5122 | H | $CH_3$ | $CH_2$—$CH_2$-(pyrrolidin-1-yl) |
| Ia.5123 | F | $CH_3$ | $CH_2$—$CH_2$-(pyrrolidin-1-yl) |
| Ia.5124 | Cl | $CH_3$ | $CH_2$—$CH_2$-(pyrrolidin-1-yl) |
| Ia.5125 | H | $C_2H_5$ | $CH_2$—$CH_2$-(pyrrolidin-1-yl) |
| Ia.5126 | F | $C_2H_5$ | $CH_2$—$CH_2$-(pyrrolidin-1-yl) |
| Ia.5127 | Cl | $C_2H_5$ | $CH_2$—$CH_2$-(pyrrolidin-1-yl) |
| Ia.5128 | H | n-$C_3H_7$ | $CH_2$—$CH_2$-(pyrrolidin-1-yl) |
| Ia.5129 | F | n-$C_3H_7$ | $CH_2$—$CH_2$-(pyrrolidin-1-yl) |
| Ia.5130 | Cl | n-$C_3H_7$ | $CH_2$—$CH_2$-(pyrrolidin-1-yl) |
| Ia.5131 | H | n-$C_4H_9$ | $CH_2$—$CH_2$-(pyrrolidin-1-yl) |
| Ia.5132 | F | n-$C_4H_9$ | $CH_2$—$CH_2$-(pyrrolidin-1-yl) |
| Ia.5133 | Cl | n-$C_4H_9$ | $CH_2$—$CH_2$-(pyrrolidin-1-yl) |
| Ia.5134 | H | $CH_2$—CH═$CH_2$ | $CH_2$—$CH_2$-(pyrrolidin-1-yl) |
| Ia.5135 | F | $CH_2$—CH═$CH_2$ | $CH_2$—$CH_2$-(pyrrolidin-1-yl) |
| Ia.5136 | Cl | $CH_2$—CH═$CH_2$ | $CH_2$—$CH_2$-(pyrrolidin-1-yl) |
| Ia.5137 | H | $CH_2$—C≡CH | $CH_2$—$CH_2$-(pyrrolidin-1-yl) |
| Ia.5138 | F | $CH_2$—C≡CH | $CH_2$—$CH_2$-(pyrrolidin-1-yl) |
| Ia.5139 | Cl | $CH_2$—C≡CH | $CH_2$—$CH_2$-(pyrrolidin-1-yl) |
| Ia.5140 | H | $CH_2$—CO—$OCH_3$ | $CH_2$—$CH_2$-(pyrrolidin-1-yl) |
| Ia.5141 | F | $CH_2$—CO—$OCH_3$ | $CH_2$—$CH_2$-(pyrrolidin-1-yl) |
| Ia.5142 | Cl | $CH_2$—CO—$OCH_3$ | $CH_2$—$CH_2$-(pyrrolidin-1-yl) |
| Ia.5143 | H | $CH_2$-phenyl | $CH_2$—$CH_2$-(pyrrolidin-1-yl) |
| Ia.5144 | F | $CH_2$-phenyl | $CH_2$—$CH_2$-(pyrrolidin-1-yl) |
| Ia.5145 | Cl | $CH_2$-phenyl | $CH_2$—$CH_2$-(pyrrolidin-1-yl) |
| Ia.5146 | H | $CH_3$ | $CH_2$-(pyridin-2-yl) |
| Ia.5147 | F | $CH_3$ | $CH_2$-(pyridin-2-yl) |
| Ia.5148 | Cl | $CH_3$ | $CH_2$-(pyridin-2-yl) |
| Ia.5149 | H | $C_2H_5$ | $CH_2$-(pyridin-2-yl) |
| Ia.5150 | F | $C_2H_5$ | $CH_2$-(pyridin-2-yl) |
| Ia.5151 | Cl | $C_2H_5$ | $CH_2$-(pyridin-2-yl) |
| Ia.5152 | H | n-$C_3H_7$ | $CH_2$-(pyridin-2-yl) |
| Ia.5153 | F | n-$C_3H_7$ | $CH_2$-(pyridin-2-yl) |
| Ia.5154 | Cl | n-$C_3H_7$ | $CH_2$-(pyridin-2-yl) |
| Ia.5155 | H | n-$C_4H_9$ | $CH_2$-(pyridin-2-yl) |
| Ia.5156 | F | n-$C_4H_9$ | $CH_2$-(pyridin-2-yl) |
| Ia.5157 | Cl | n-$C_4H_9$ | $CH_2$-(pyridin-2-yl) |
| Ia.5158 | H | $CH_2$—CH═$CH_2$ | $CH_2$-(pyridin-2-yl) |
| Ia.5159 | F | $CH_2$—CH═$CH_2$ | $CH_2$-(pyridin-2-yl) |
| Ia.5160 | Cl | $CH_2$—CH═$CH_2$ | $CH_2$-(pyridin-2-yl) |
| Ia.5161 | H | $CH_2$—C≡CH | $CH_2$-(pyridin-2-yl) |
| Ia.5162 | F | $CH_2$—C≡CH | $CH_2$-(pyridin-2-yl) |
| Ia.5163 | Cl | $CH_2$—C≡CH | $CH_2$-(pyridin-2-yl) |
| Ia.5164 | H | $CH_2$—CO—$OCH_3$ | $CH_2$-(pyridin-2-yl) |
| Ia.5165 | F | $CH_2$—CO—$OCH_3$ | $CH_2$-(pyridin-2-yl) |
| Ia.5166 | Cl | $CH_2$—CO—$OCH_3$ | $CH_2$-(pyridin-2-yl) |
| Ia.5167 | H | $CH_2$-phenyl | $CH_2$-(pyridin-2-yl) |
| Ia.5168 | F | $CH_2$-phenyl | $CH_2$-(pyridin-2-yl) |
| Ia.5169 | Cl | $CH_2$-phenyl | $CH_2$-(pyridin-2-yl) |

Furthermore, very especially preferred are the substituted 3-phenylpyrazoles of the formulae Ib to Iu below, in particular the compounds Ib.1–Ib.3060, which differ from the corresponding compounds Ia.1–Ia.3060 only by the fact that $R^3$ is fluorine:

Ib

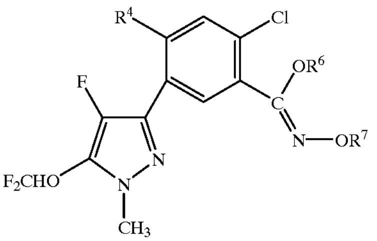

the compounds Ic.1–Ic.3060, which differ from the corresponding compounds Ia.1–Ia. 3060 only by the fact that $R^3$ is trifluoromethyl:

Ic

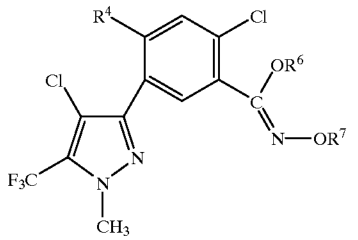

the compounds Id.1–Id.3060, which differ form the corresponding compounds Ia.1–Ia.3060 only by the fact that $R^2$ is trifluoromethyl and $R^3$ is fluorine:

Id

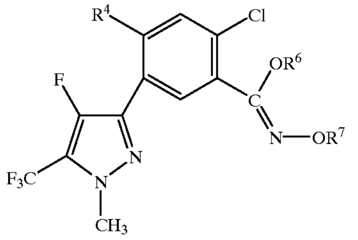

the compounds Ie.1–Ie.3060, which differ form the corresponding compounds Ia.1–Ia.3060 only by the fact that $R^2$ is methylsulfonyl:

Ie

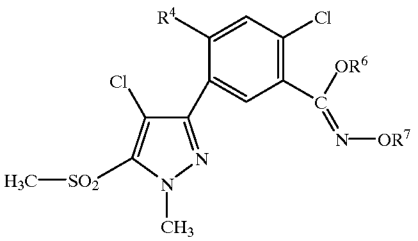

the compounds If.1–If.3060, which differ from the corresponding compounds Ia.1–Ia.3060 only by the fact that $R^2$ is methylsulfonyl and $R^3$ is fluorine:

If

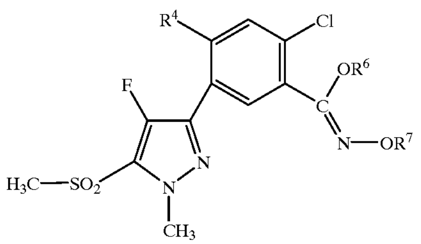

the compounds Ig.1–Ig.3060, which differ from the corresponding compounds Ia.1–Ia.3060 only by the fact that X is the group —CH═C(Cl)—:

Ig

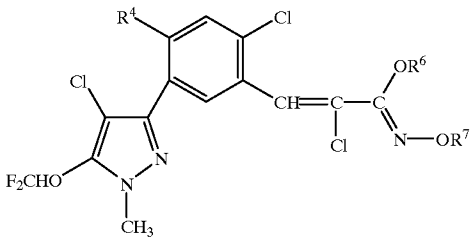

the compounds Ih.1–Ih.3060, which differ from the corresponding compounds Ia.1–Ia.3060 only by the fact that X is the group —CH═C(Cl)— and $R^3$ is fluorine:

Ih

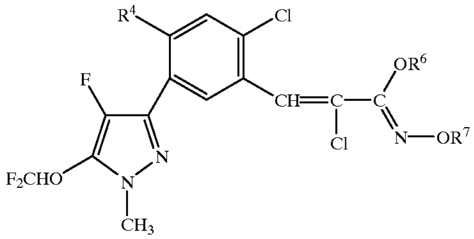

the compounds Ik.1–Ik.3060, which differ from the corresponding compounds Ia.1–Ia.3060 only by the fact that X is the group —CH═C(Cl)— and $R^2$ is trifluoromethyl:

Ik

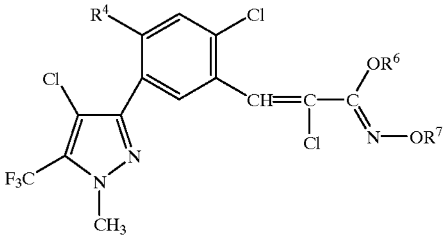

the compounds Im.1–Im.3060, which differ from the corresponding compounds Ia.1–Ia.3060 only by the fact that X is the group —CH═C(Cl)—, $R^2$ is trifluoromethyl and $R^3$ is Im

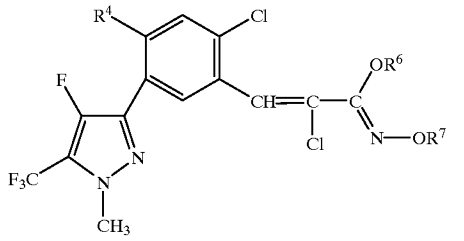

the compounds In.1–In. 3060, which differ from the corresponding compounds Ia.1–Ia.3060 only the fact that X is the group —CH═C(Cl)— and $R^2$ is methylsulfonyl:

In

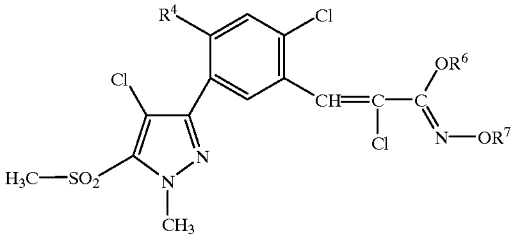

the compounds Io.1–Io.3060, which differ from the corresponding compounds Ia.1–Ia.3060 only by the fact that X is the group —CH═C(Cl)—, $R^2$ is methylsulfonyl and $R^3$ is fluorine:

Io

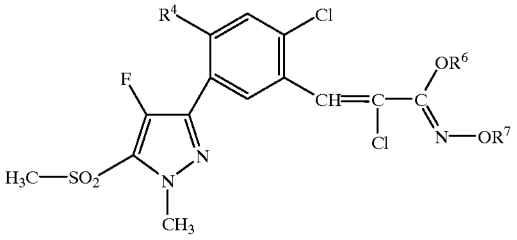

the compounds Ip.1–Ip.3060, which differ from the corresponding compounds Ia.1–Ia.3060 only by the fact that X is the 1,2-ethynediyl group:

Ip

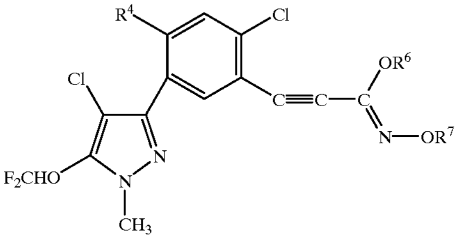

the compounds Iq.1–Iq.3060, which differ from the corresponding compounds Ia.1–Ia.3060 only by the fact that X is the 1,2-ethynediyl group and $R^3$ is fluorine:

Iq

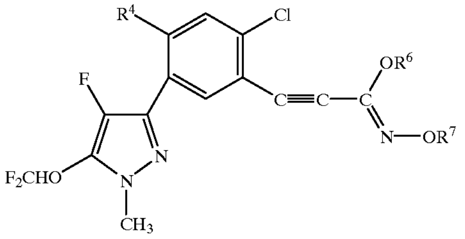

the compounds Ir.1–Ir.3060, which differ from the corresponding compounds Ia.1–Ia.3060 only by the fact that X is the 1,2-ethynediyl group and $R^2$ is trifluoromethyl:

Ir

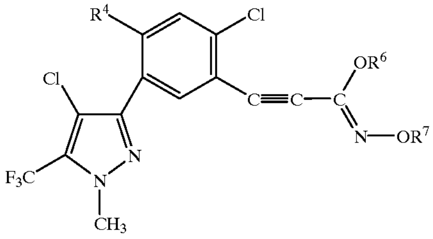

the compounds Is.1–Is.3060, which differ from the corresponding compounds Ia.1–Ia.3060 only by the fact that X is the 1,2-ethynediyl group, $R^2$ is trifluoromethyl and $R^3$ is fluorine:

Is

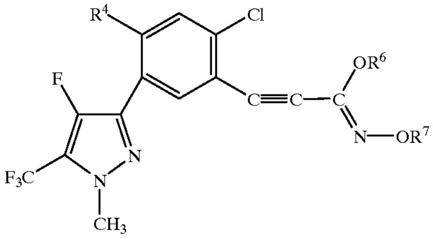

the compounds It.1–It.3060, which differ from the corresponding compounds Ia.1–Ia.3060 only by the fact that X is the 1,2-ethynediyl group and $R^2$ is methylsulfonyl:

It

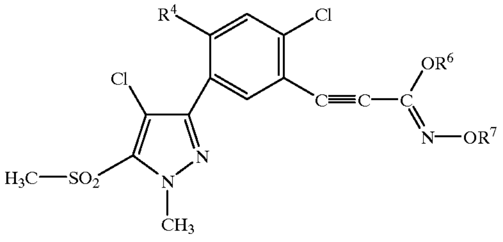

the compounds Iu.1–Iu.3060, which differ from the corresponding compounds Ia.1–Ia.3060 only by the fact that X is the 1,2-ethynediyl group, $R^2$ is methylsulfonyl and $R^3$ is fluorine:

Iu

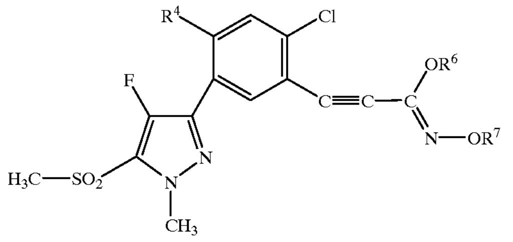

The substituted 3-phenylpyrazoles of the formula I are accessible in various ways, in particular by one of the processes below:

A) conversion of a 3-pyrazolylphenylcarboxylic acid II into the corresponding alkoxyamide III followed by alkylation or acylation in a manner known per se {see, for example, Houben-Weyl, Methoden der organischen Chemie [Methods in organic chemistry], Vol. E5, Georg Thieme Verlag, Stuttgart 1985, p. 587 et seq., 826 et seq. and 1141 et seq.}:

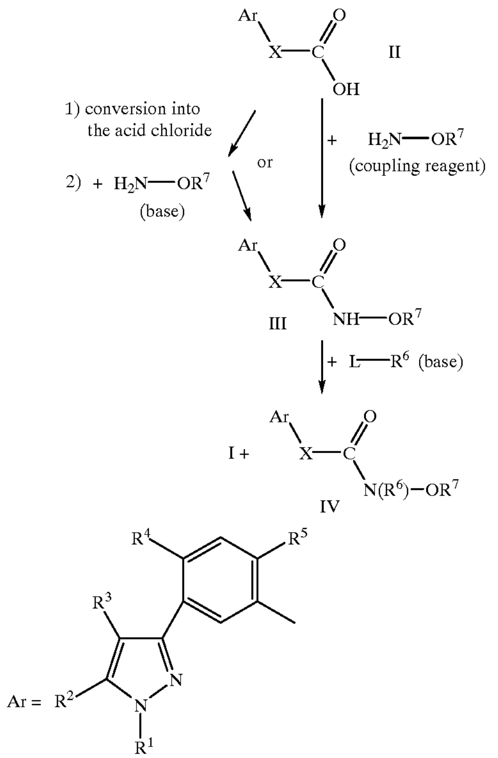

L is a customary leaving group, such as halogen, methylsulfonyloxy, trifluoromethylsulfonyloxy or p-tolylsulfonyloxy.

The conversion of II into III can be effected in two ways:

One embodiment consists in first preparing, form II, the corresponding acid chloride and then reacting the latter with an alkxoyamine $H_2N$—$OR^7$ in the presence of a base—eg. an amine such as triethylamine or pyridine, an alkali metal carbonate such as potassium carbonate, an alkali metal hydride such as sodium hydride or an alkali metal hydroxide such as sodium hydroxide and potassium hydroxide.

Examples of suitable chlorinating agents are phosgene, oxalyl chloride, phosphorus oxychloride and thionyl chloride. As a rule, the chlorination is effected in an inert organic solvent, suitable substances being, for example, aliphatic or aromatic hydrocarbons such as n-hexane and toluene, halo-hydrocarbons such as dichloromethane, ethers such as diethyl ether and tetrahydrofuran, and aprotic solvents such as dimethylformamide and acetonitrile.

In general, the abovementioned solvents and mixtures of these with water are generally also suitable for reacting the acid chloride with $H_2N$—$OR^7$.

A second embodiment consists in reacting II directly with the alkoxyamine $H_2N$—$OR^7$ in one of the organic solvents mentioned above. The process is preferably carried out in the presence of a coupling reagent, such as carbonyldiimidazole and dicyclohexylcarbodiimide.

The alkoxyamide III is subsequently alkylated or acylated with an alkylating, or acylating, agent L-$R^6$. The process is normally carried out in the presence of a base, eg. an amine such as triethylamine and pyridine, an alkali metal carbonate such as potassium carbonate, an alkali metal hydride such as sodium hydride or an alkali metal hydroxide such as sodium hydroxide and potassium hydroxide.

Examples of suitable solvents are aliphatic or aromatic hydrocarbons such as n-hexane and toluene, halohydrocarbons such as dichloromethane, ethers such as diethyl ether and tetrahydrofuran, aprotic solvents such as dimethylformamide and acetonitrile, and mixtures of these.

The reaction may give the isomer IV as a secondary product; it can be removed in the customary manner, eg. by means of extraction, crystallization, distillation, or chromatography.

All the abovementioned reactions are carried out between the melting and the boiling point of the solvent, in particular at from 0° to 100° C. The reactants are preferably employed in approximate equimolar amounts or in an excess of approximately up to ten times the molar amount, based on the amount of carboxylic acid II, its acid chloride or the alkoxy amide III.

B) Wittig reaction of a 3-pyrazolylbenzaldehyde V with an ylide VI or a phosphonate VII in the presence of a base {cf., for examples, Houben-Weyl, Methoden der organischen Chemie [Methods in organic chemistry], Vol. 5/lb, Georg Thieme Verlag, Stuttgart 1972, p. 383 et seq.}:

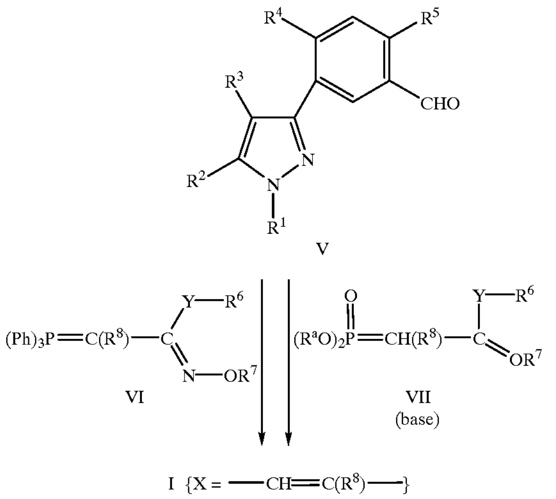

V, VI, VII

Ph represents the substituents on the phosphorus which are conventionally used in Wittig reagents, in particular phenyl; $R^a$ is, in particular, lower alkyl such as methyl or ethyl.

The reaction with VII is generally carried out in the presence of a base, eg. an alkali metal hydride such as sodium hydride, an alkali metal hydroxide such as sodium hydroxide and potassium hydroxide, an alkoxide such as potassium tertbutoxide, or butyllithium.

Examples of suitable solvents are aliphatic or aromatic hydrocarbons such as n-hexane and toluene, halohydrocarbons such as dichloromethane, ethers such as diethyl ether and tetrahydrofuran, aprotic solvents such as dimethylformamide and acetonitrile.

The reaction temperature is normally between the melting and boiling point of the reaction mixture, preferably at from 0° to 100° C.

Base and reactant VI or VII are generally employed in approximate equimolar amounts or in an excess of up to approximately ten times the molar amount, based on the amount of V.

Other possibilities for the preparation of various compounds I from the 3-pyrazolylbenzaldehydes V include the aldol condensation reaction which is known per se {conditions suitable for this purpose can be found in, for example, Nielsen, Org. React. 16 (1968), 1 et seq.}, and Knoevenagel or Perkin condensation reactions. Suitable reaction conditions are described, for example, in Org. React. 15 (1967), 204 et seq. {method of Knoevenagel} and Johnson, Org. React. 1 (1942), 210 et seq. {method of Perkin}.

C) Diazotization of a 3-pyrazolylaniline VIII and arylation of the resulting diazonium compound by the method of Meerwein {see, in this context, for example Org. Reactions 11 (1960), 189–260 and J. Org. Chem. 42 (1977), 2431}:

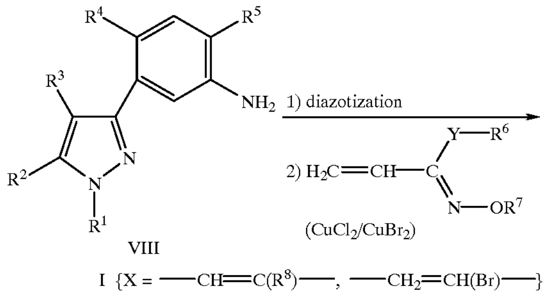

VIII

The diazonium salt can be obtained advantageously in a manner known per se by reacting a 3-pyrazolylaniline VIII with a nitrite such as sodium nitrite and potassium nitrite in an aqeous solution of an acid, eg. in hydrochloric acid, hydrobromic acid or sulfuric acid.

However, it is also possible to carry out the process under anhydrous conditions, eg. in hydrogen chloride-containing glacial acetic acid, in absolute alcohol, in dioxane or tetrahydrofuran, in acetonitrile or in acetone, in which case the aniline VIII is reacted with a nitrose ester, such as tert-butyl nitrite and isopentyl nitrite.

The subsequent Meerwein reaction of the diazonium salt with an olefin or alkyne in the presence of a copper salt, preferably a copper halide such as copper(I) chloride, copper(II) chloride, copper(I) bromide and copper(II) bromide, can be carried out, for example, in water, in a ketone such as acetone, diethyl ketone and methyl ethyl ketone, in a nitrile such as acetonitrile, in an ether such as dioxane and tetrahydrofuran or in an alcohol such as methanol and ethanol.

Diazotization and arylation can be carried out at from (−30) to +50° C. The reactants in the diazotization reaction are normally employed in an approximately stoichiometric ratio, but an excess of one or the other reactant may be advantageous.

In general, the olefins to be arylated are employed in a large excess; however, it is also possible to employ only a small excess or a stoichiometric or substoichiometric amount.

The copper halide is normally employed in an approximately stoichiometric amount based on the diazonium salt or, if the latter has not been isolated, based on the aniline VIII, but an excess or substoichiometric amount is also possible.

Diazotization and arylation can also be carried out in one step. In this case, the diazotization is effected in the presence of the olefin or alkyne component and of the copper halide.

D) Basic elimination of hydrogen halide from 3-phenylpyrazoles of formula I in which X represents $—CH_2—CH(halogen)—$ or $—CH{=}C(halogen)—$:

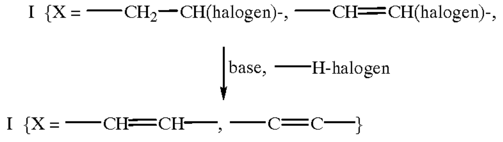

Examples of bases which are suitable for this purpose are amines such as triethylamine and pyridine, alkali metal hydroxides such as sodium hydroxide, alkali metal carbonates such as sodium carbonate and potassium carbonate, or alkali metal hydrides such as sodium hydride.

Examples of suitable solvents are aliphatic or aromatic hydrocarbons such as n-hexane and toluene, halogenated hydrocarbons such as dichloromethane, ethers such as diethyl ether and tetrahydrofuran, aprotic solvents such as dimethylformamide and acetonitrile, and mixtures of these.

If appropriate, the reaction can proceed simultaneously with other base-catalyzed reactions—as described above under A) to C)—, for example when I is formed from III (process A), when III is formed from II via the acid chloride route (process A), when I is formed from V (process B) or else when I is formed from VIII (process C).

Those 3-pyrazolylphenylcarboxylic acids II, 3-pyrazolylbenzaldehydes V and 3-pyrazolylanilines VIII which are mentioned as precursors in processes A) to C) are generally known or can be obtained by methods similar to known processes. Those starting materials II, V and VIII where $R^3$ is fluorine are accessible, for example, by fluorinating the corresponding compounds where $R^3$=hydrogen:

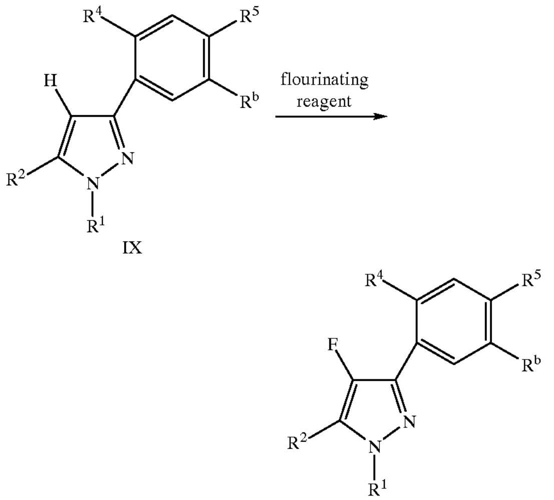

IX

X $R^b$ is hydrogen, halogen or a group which is inert to fluorination, such as $C_1$–$C_4$-alkyl and ($C_1$–$C_4$-alkoxy) carbonyl.

Examples of suitable fluorinating reagents are fluorine, sulfur tetrafluoride, N-fluoro-2-pyridone, N-fluoropyridinium fluoride, N-fluoro-N-methyltoluenesulfonamide, nitrogen trifluoride, SELECTFLUOR® {1-chloromethyl-4-fluoro-1,4-diazabicyclo[2.2.2]octaine bis(tetrafluoroborate)}, N-fluoro-benzenesulfonimide, 1-fluoroquinuclidinium triflate, acetyl hypofluorite or other conventionally used fluorinating agents {see, for example, D. T. Meshri, ACS Monogr. 187 (1995), 25}.

Particularly suitable as solvents are aliphatic or aromatic hydrocarbons which may be partially or fully fluorinated or chlorinated, such as n-hexane, toluene, dichloromethane and fluorotrichloromethane, ethers such as diethyl ether and tetrahydrofuran, nitriles such as acetonitrile, and mixtures of these.

The process products of the formula X can subsequently be converted into the compounds of the formula II, V or VIII (where in each case $R^3$=fluorine) by processes known per se as they are described, for example, in WO 97/02251.

Unless otherwise specified, all the above-described processes are expediently carried out under atmospheric pressure or under the inherent pressure of the reaction mixture in question.

The substituted 3-phenylpyrazoles I can normally be prepared by one of the synthesis methods mentioned above. However, for reasons of economy or process engineering, it may be more expedient to prepare some compounds I from similar 3-phenylpyrazoles which, however, differ in particular with regard to the meaning of the radical $R^6$ or $R^7$, the preparation being carried out in a manner known per se, eg. by alkylation, acetal hydrolysis, acetalization, amidation, ester hydroysis, condensation reaction, oxidation, Peterson olefination, reduction, etherification, electrification or Wittig reaction.

Those starting compounds for the individual processes which are not already known can be obtained in a manner known per se or by a method similar to one of the processes described.

The reaction mixtures are generally worked up by methods known per se, for example by diluting the reaction solution with water followed by isolation of the product by means of filtration, crystallization or solvent extraction, or removing the solvent, partitioning the residue in a mixture of water and a suitable organic solvent and working up the organic phase to give the product.

The substituted 3-phenylpyrazoles I may be obtained from the preparation in the form of isomer mixtures, but, if desired, the latter can be separated into the essentially pure isomers by the methods conventionally used for this purpose, such as crystallization or chromatography, also on an optically active adsorbate. Pure optically active isomers may be prepared advantageously from corresponding optically active starting materials.

Agriculturally useful salts of the compounds I can be formed by reacting them with a base of the corresponding cation, preferably an alkali metal hydroxide or alkali metal hydride, or by reacting them with an acid of the corresponding anion, preferably of hydrochloric acid, hydrobromic acid, sulfuric acid, phosphoric acid or nitric acid.

Salts of I whose metal ion is not an alkali metal ion can also be prepared by double decomposition of the corresponding alkali metal salt in the customary manner, and ammonium, phosphonium, sulfonium and sulfoxonium salts by means of ammonia, phosphonium hydroxide, sulfonium hydroxide, or sulfoxonium hydroxide.

The compounds I and their agriculturally useful salts, as isomer mixtures and also in the form of the pure isomers, are suitable as herbicides. The herbicidal compositions comprising I effect very good control of vegetation on non-crop areas, especially at high rates of application. In crops such as wheat, rice, maize, soybeans and cotton, they act against broad-leaved weeds and grass weeds without damaging the crop plants substantially. This effect is observed especially at low rates of application.

Depending on the application method in question, the compounds I, or the herbicidal compositions comprising them, can additionally be employed in a further number of crop plants for eliminating undesirable plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica npaus* var. *napus, Brassica napus* var. *napobrassica, Brassica rapa* var. *silvestris, Camellia sinensis, Carthamus tinctorius, Carya illionoiensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Iopmoea batatas, Juglans regia, Lens culinaris, Linum usitatissiumum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I can also be used in crops which tolerate the action of herbicides due to breeding, including genetic engineering methods.

The compounds I, or the herbicidal compositions comprising them, can be applied, for example, in the form of directly sprayable aqueous solutions, powders, suspensions, also highly-concentrated aqueous, oily or other suspensions or dispersion, emulsions, oil dispersions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

Suitable inert auxiliaries are essentially:

Mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substances, as such or dissolved in an oil or solvent, can be homogenized in water by means of wetting agent, tackifier, dispersant or emulsifier. Alternatively, it is possible to prepare concentrates from active substance, wetting agent, tackifier, dispersant or emulsifier and, if desired, solvent or oil, and these concentrates are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalene-sulfonic acid, and of fatty acids, of alkyl- and alkylarylsulfonates, of alkyl sulfates, lauryl ether sulfates and fatty alcohol sulfates, and the salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or polyglycol ether, alkylaryl polyether alcohols, isotridecyl alcohol, fatty alcohol/ethylene oxide condensates, ethoxylated castor oil, polyoxyethylene alkyl ether or polyoxypropylene alkyl ether, lauryl alcohol polyglycol ether acetate, sorbitol esters, lignin-sulfite waste liquors or methylcellulose.

Powders, materials for spreading and dusts can be prepared by mixing or concomitant grinding of the active substances with a solid carrier.

Granules, eg. coated granules, impregnated granules and homogenous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers.

The concentrations of the active ingredients I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples which follow illustrate the preparation of such products:

I. 20 parts by weight of the compound No. Ia.2 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. Ia.689 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. Ia.1322 are dissolved in a mixture composed of 25 parts by weight of cyclohexanone, 65 parts by weight of a mineral oil fraction of boiling point 210° to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. Ia.1331 are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill.

Finely distributing the mixture in 20,000 parts by weight of water gives a spray mixture which comprises 0.1% by weight of the active ingredient.

V. 3 parts by weight of the active ingredient No. Ig.1310 are mixed with 97 parts by weight of finely divided kaolin. This gives a dust which comprises 3% by weight of the active ingredient.

VI. 20 parts by weight of the active ingredient No. Ia.1334 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oil dispersion.

VIII. 1 part by weight of the active ingredient No. Ia.2270 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the active ingredient No. Ik.1310 is dissolved in a mixture composed of 80 parts by weight of cyclohexanone and 20 parts by weight of Wettol® EM 31 (=non-ionic emulsifier based on ethoxylated castor oil; BASF AG). This gives a stable emulsions concentrate.

The active ingredients I, or the herbicidal compositions, can be applied pre- or post-emergence. If the active ingredients are less well tolerated by certain crop plants, it is possible to use application techniques in which the herbicidal compositions are sprayed, with the aid of the spraying equipment, in such a way that they come into as little contact as possible, if any, with the leaves of the sensitive crop plants while reaching the leaves of undersirable plants which grow underneath, or the bare soil surface (post-directed, lay-by).

Depending on the intended aim, the season, the target plant and the growth stage, the rates of application of active ingredient I are from 0.001 to 3.0, preferably 0.01 to 1.0, kg of active substance (a.s.)/ha.

To widen the spectrum of action and to achieve synergistic effects, the substituted 3-phenylpyrazoles I may be mixed, and applied jointly, with a large number of representatives of other groups of herbicidally or growth-regulating active ingredients. Suitable examples of components in mixtures are 1,2,4-thiadiazoles, 1,3,4-thiadiazoles, amides, aminophosphoric acid and its derivatives, aminotriazoles, anilides, aryloxy/hetaryloxyalkanoic acids and their derivatives, benzoic acid and its derivatives, benzothiadiazinones, 2-(hetaroyl/aroyl)-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenoles, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds I, alone or in combination with other herbicides, in the form of a mixture with even further crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates may also be added.

PREPARATION EXAMPLES

Example 1

Methyl N-methoxy-2-chloro-5-(4-chloro-5-difluoromethoxy-1-methyl-1H-pyrazol-3-yl)-4-fluorobenzimidate (No. Ia.2)

A solution of 1 g (2.6 mmol) of N-methoxy-2-chloro-5-(4-chloro-5-difluoromethoxy-1-methyl-1H-pyrazol-3-yl)-4-fluorobenzamide in 50 ml of acetone was treated with 0.43 g (3.1 mmol) of potassium carbonate and 0.39 g (3.1 mmol) of dimethyl sulfate. After 3 days, the mixture was concentrated. The residue was treated with water, whereupon the mixture was extracted twice using ethyl acetate. The combined organic phases were washed with water and saturated aqueous sodium chloride solution, dried over magnesium sulfate and finally concentrated. The crude product was purified by means of column chromatography on silica gel (eluent:hexane/ethyl acetate=2:1). Yield: 0.2 g.

$^1H$ NMR (270 MHz, in $CDCl_3$): δ [ppm]=3.73 (s,3H), 3.85 (s,3H), 3.90 (s,3H), 6.71 (t,1H), 7.32 (d,1H), 7.68 (d,1H).

Precursor 1.1

2-Chloro-5-(4-chloro-5-difluoromethoxy-1-methyl-1H-pyrazol-3-yl)-4-fluorobenzoyl chloride A solution of 8 g (22 mmol) of 2-chloro-5-(4-chloro-5-difluoromethoxy-1-methyl-1H-pyrazol-3-yl)-4-fluorobenzoic acid in 100 ml of toluene was treated with 1 drop of dimethylformamide and 8.6 g (67 mmol) of oxalyl chloride. After the mixture had been stirred for 30 minutes at reflux temperature, it was cooled and concentrated. Yield: quantitative.

Precursor 1.2

N-Methoxy-2-chloro-5-(4-chloro-5-difluoromethoxy-1-methyl-1H-pyrazol-3-yl)-4-fluorobenzamide A solution of 8.4 g (22 mmol) of 2-chloro-5-(4-chloro-5-difluoromethoxy-1-methyl-1H-pyrazol-3-yl)-4-fluorobenzoyl chloride in 150 ml of toluene was treated with 34 g (0.24 mol) of potassium carbonate, and 16 g (48 mmol) of a 25% strength aqueous methoxyamine hydrochloride solution was subsequently added dropwise. After the reaction mixture had been stirred for 4 hours, it was diluted with 0.5 l of water. The organic phase was then separated off, washed with saturated aqueous sodium chloride solution, dried over magnesium sulfate and finally concentrated. Yield: 8.3 g.

$^1H$ NMR (270 MHz, in $CDCl_3$): δ [ppm]=3.83 (s,3H), 3.90 (s,3H), 6.71 (t,1H), 7.25 (d,1H), 7.79 (d,1H), 9.20 (s,1H).

Example 2

N-Methoxy-2-chloro-5-(4-chloro-5-difluoromethoxy-1-methyl-1H-pyrazol-3-yl)-4-fluorobenzimidic acetic anhydride (No. Ia.686)

0.26 g (2.6 mmol) of triethylamine and 0.23 g (2.9 mmol) of acetyl chloride were added dropwise in succession to a solution of 1 g (2.6 mmol) of N-2-chloro-5-(4-chloro-5-difluoromethoxy-1-methyl-1H-pyrazol-3-yl)-4-fluoro (methoxy)benzamide in 46 ml of dichloromethane. After the reaction mixture had been stirred for 16 hours, it was treated with water. The organic phase was subsequently separated off, dried over magnesium sulfate and finally concentrated.

The crude product was purified by means of silica gel chromatography (eluent:hexane/ethyl acetate=1:2). Yield: 0.3 g.

Example 3

Allyl N-methoxy-2-chloro-5-(4-chloro-1-methyl-5-trifluoromethyl-1H-pyrazol-3-yl)-4-fluorobenzimidate (No. Ic.590)

A solution of 1.5 g (3.9 mmol) of N-methoxy-2-chloro-5-(4-chloro-1-methyl-5-trifluoromethyl-1H-pyrazol-3-yl)-4-fluorobenzamide in 50 ml of acetone was treated with 0.6 g (4.6 mmol) of potassium carbonate and 0.6 g (4.6 mmol) of allyl bromide. After the mixture had been stirred for 16 hours, it was concentrated. The residue was treated with water. The product of value was subsequently extracted twice using ethyl acetate. The combined organic phases were washed with water and saturated aqueous sodium chloride solution, dried over magnesium sulfate and finally concentrated. The crude product was purified by column chromatography on silica gel (eluent:hexane/ethyl acetate=2:1). Yield: 0.3 g.

Precursor 3.1

2-Chloro-5-(4-chloro-1-methyl-5-trifluoromethyl-1H-pyrazol-3-yl)-4-fluorobenzoyl chloride 14 g (39 mmol) of 2-chloro-5-(4-chloro-1-methyl-5-trifluoromethyl-1H-pyrazol-3-yl)-4-fluorobenzoic acid were reacted by a method similar to the one given for precursor 1.1. Yield: 13.3 g.

Precursor 3.2

N-Methoxy-2-chloro-5-(4-chloro-1-methyl-5-trifluoromethyl-1H-pyrazol-3-yl)-4-fluorobenzamide 13.7 g (36 mmol) of 2-chloro-5-(4-chloro-1-methyl-5-trifluoromethyl-1H-pyrazol-3-yl)-4-fluorobenzoyl chloride were reacted by a method similar to the one described for precursor 1.2. Yield: 14 g.

$^1H$ NMR (270 MHz, in $CDCl_3$): δ [ppm]=3.90 (s,3H), 4.06 (s,3H), 7.27 (d,1H), 7.79 (d,1H), 9.05 (s,1H).

Example 4

Methyl N-methoxy-2-chloro-3-(2-chloro-5-(4-chloro-5-difluoromethoxy-1-methyl-1H-pyrazol-3-yl)-4-fluorophenyl)acrylimidate (No. Ig.2)

A solution of 1 g of N-Methoxy-2-chloro-3-(2-chloro-5-(4-chloro-5-difluoromethoxy-1-methyl-1H-pyrazol-3-yl)-4-fluorophenyl)acrylamide (2.3 mmol) in 30 ml of acetone was treated with 0.4 g (2.7 mmol) of pulverulent potassium carbonate and 0.35 g (2.5 mmol) of methyl iodide. After the mixture had been stirred for 16 hours, it was concentrated. The residue was treated with water and ethyl acetate. The organic phase was dried over magnesium sulfate and then concentrated. The residue was purified by means of column chromatography on silica gel (eluent:hexane/ethyl acetate=4:1). Yield: 0.2 g.

Precursor 4.1 tert-Butyl 2-chloro-3-(2-chloro-5-(4-chloro-5-dilfuoromethoxy-1-methyl-1H-pyrazol-3-yl)-4-fluorophenyl)acrylate A solution of 32 g of 2-chloro-5-(4-chloro-5-difluoromethoxy-1-methyl-1H-pyrazol-3-yl)-4-fluorobenzaldehyde (94 mmol) in 200 ml of toluene was treated with 72 g (0.14 mol) of tertbutoxycarbonyl(chloro)methylene(triphenyl)phosphorane. After the mixture had been stirred for 16 hours, it was concentrated. The residue was treated with ethyl acetate. The mixture was then heated at reflux temperature and filtered while hot. The solids removed were washed repeatedly with ethyl acetate. The filtrate was treated with approximately twice the volume of hexane, whereupon the mixture was refiltered. Finally, the filtrate was concentrated. The crude product which remained was purified from residual triphenylphosphine oxide by dissolving it in hexane/ethyl acetate (4:1) followed by filtration through a silica gel bed. Yield: 44 g.

$^1H$ NMR (250 MHz, in $CDCl_3$): δ [ppm]=1.58 (s,9H), 3.84 (s,3H), 6.73 (t,1H), 7.32 (d,1H), 8.03 (s,1H), 8.24 (d,1H).

Precursor 4.2

2-Chloro-3-(2-chloro-5-(4-chloro-5-difluoromethoxy-1-methyl-1H-pyrazol-3-yl)-4-fluorophenyl)acrylic acid A solution of 44 g of tert-butyl 2-chloro-3-(2-chloro-5-(4-chloro-5-difluoromethoxy-1-methyl-1H-pyrazol-3-yl)-4-fluorophenyl)acrylate (93 mmol) in 200 ml of dichloromethane was treated with 200 ml of trifluoroacetic acid. After the mixture had been stirred for 16 hours, it was concentrated. The residue was recrystallized from hexane/ethyl acetate (2:1). Yield: 23 g; a further 4 g by concentrating the mother liquor.

$^1H$ NMR (270 MHz, in $CDCl_3$): δ [ppm]=3.87 (s,3H), 6.72 (t,1H), 7.34 (d,1H), 8.26 (s,1H), 8.31 (d,1H).

Precursor 4.3

2-Chloro-3-(2-chloro-5-(4-chloro-5-difluoromethoxy-1-methyl-1H-pyrazol-3-yl)-4-fluorophenyl)acryloyl chloride A solution of 27 g of 2-chloro-3-(2-chloro-5-(4-chloro-5-difluoromethoxy-1-methyl-1H-pyrazol-3-yl)-4-fluorophenyl)acrylic acid (64 mmol) in 200 ml of toluene was treated with 3 drops of dimethylformamide and 33 g (0.26 mol) of oxalyl chloride. The mixture was subsequently stirred at 90° C. until the vigorous evolution of gas had ceased (after approximately 2.5 hours). The reaction mixture was then concentrated. Yield: 26 g of crude product which was further reacted without purification.

Precursor 4.4

N-Methoxy-2-chloro-3-(2-chloro-5-(4-chloro-5-difluoromethoxy-1-methyl-1H-pyrazol-3-yl)-4-fluorophenyl)acrylamide A solution of 4.5 g (10 mmol) of 2-chloro-3-(2-chloro-5-(4-chloro-5-difluoromethoxy-1-methyl-1H-pyrazol-3-yl)-4-fluorophenyl)acryloyl chloride in 25 ml of toluene was treated with 25 ml of water, 14.4 g (0.1 mol) of potassium carbonate and 1.7 g (20 mmol) of methoxyamine hydrochloride. After the mixture had been stirred for 16 hours at approximately 20° C., it was heated for a further 2 hours at 40° C. The reaction mixture was subsequently diluted with 200 ml of toluene and 200 ml of water. The solids were then filtered off. The organic phase was dried over magnesium sulfate and finally concentrated. Yield: 3.1 g.

$^1H$ NMR (270 MHz, in $CDCl_3$): δ [ppm]=3.85 (s,3H), 3.90 (s,3H), 6.73 (t,1H), 7.33 (d,1H), 8.04 (d,1H), 8.20 (s,1H), 9.33 (s,1H).

Example 5

Methoxycarbonylmethyl N-methoxy-2-chloro-3-[2-chloro-5-(4-chloro-1-methyl-5-trifluoromethyl-1H-pyrazol-3-yl)-4-fluorophenyl]acrylimide (No. Ik.1310)

A solution of 1.2 g (2.6 mmol) of N-methoxy-2-chloro-3-(2-chloro-5-(4-chloro-1-methyl-5-trifluoromethyl-1H-pyrazol-3-yl)-4-fluorophenyl)acrylamide in 50 ml of acetone was treated with 0.4 g (3 mmol) of potassium carbonate and 0.4 g (2.9 mmol) of methyl bromoacetate. After the mixture had been stirred for 16 hours, it was concentrated. The residue was treated with water. The product was then extracted with diethyl ether. The organic phase was dried over magnesium sulfate and subsequently concentrated. The crude product is purified by means of silica gel chromatography (eluent:hexane/ethyl acetate=4:1). Yield: 0.6 g.

Precursor 5.1 tert-Butyl 2-chloro-3-[2-chloro-5-(4-chloro-1-methyl-5-trifluoromethyl-1H-pyrazol-3-yl)-4-fluorophenyl]acrylate 6 g (18 mmol) of 2-chloro-5-(4-chloro-1-methyl-5-trifluoromethyl-1H-pyrazol-3-yl)-4-fluorobenzaldehyde were reacted by a method similar to the one described for precursor 4.1. Yield: 6.4 g.

$^1$H NMR (270 MHz, in $CDCl_3$): δ [ppm]=1.58 (s,9H), 4.07 (s,3H), 7.33 (d,1H), 8.03 (s,1H), 8.20 (d,1H).

Precursor 5.2

2-Chloro-3-[2-chloro-5-(4-chloro-1-methyl-5-trifluoromethyl-1H-pyrazol-3-yl)-4-fluorophenyl]acrylic acid 4.8 g (10 mmol) of 2-chloro-3-[2-chloro-5-(4-chloro-1-methyl-5-trifluoromethyl-1H-pyrazol-3-yl)-4-fluorophenyl] acrylic acid were treated by a method similar to the one described for precursor 4.2. Yield: 2.4 g. M.p.: 195–196° C.

Precursor 5.3

2-Chloro-3-[2-chloro-5-(4-chloro-1-methyl-5-trifluoromethyl-1H-pyrazol-3-yl)-4-fluorophenyl]acryloyl chloride 1.7 g (4 mmol) of 2-chloro-3-[2-chloro-5-(4-chloro-1-methyl-5-trifluoromethyl-1H-pyrazol-3-yl)-4-fluorophenyl] acrylic acid were reacted by a method similar to the one described for precursor 4.3. Yield: 1.7 g.

Precursor 5.4

N-Methoxy-2-chloro-3-[2-chloro-5-(4-chloro-1-methyl-5-trifluoromethyl-1H-pyrazol-3-yl)-4-fluorophenyl] acrylamide 1.7 g (3.9 mmol) of 2-chloro-3-[2-chloro-5-(4-chloro-1-methyl-5-trifluoromethyl-1H-pyrazol-3-yl)-4-fluorophenyl] acryloyl chloride were reacted by a method similar to the one described for precursor 4.4. Yield: 1.2 g.

$^1$H NMR (270 MHz, in $CDCl_3$): δ [ppm]=3.90 (s,3H), 4.08 (s,3H), 7.34 (d,1H), 8.00 (d,1H), 8.21 (s,1H), 9.36 (s,1H).

Example 6

Methyl N-methoxy-2-chloro-5-(4-chloro-1-methyl-5-methylsulfonyl-1H-pyrazol-3-yl)-4-fluorobenzamidate (No. Ie.2)

Using 1.4 g (3.5 mmol) of N-methoxy-2-chloro-5-(4-chloro-1-methyl-5-methylsulfonyl-1H-pyrazol-3-yl)-4-fluorobenzamide, 0.58 g (4.2 mmol) of potassium carbonate and 0.53 g (4.2 mmol) of dimethyl sulfate and following the procedure described in Example 1, 0.2 g of the product of value was obtained.

Precursor 6.1

2-Chloro-5-(4-chloro-5-(4-chloro-1-methyl-5-methylsulfonyl-1H-pyrazol-3-yl)-4-fluorobenzoic acid were reacted in a manner similar to precursor 1.1. Yield: quantitative.

Precursor 6.2

N-methoxy-2-chloro-5-(4-chloro-1-methyl-5-methylsulfonyl-1H-pyrazol-3-yl)-4-fluorobenzamide 5 g (13 mmol) of 2-chloro-5-(4-chloro-1-methyl-5-methylsulfonyl-1H-pyrazol-3-yl)-4-fluorobenzoyl chloride were reacted in a manner similar to precursor 1.2. Yield: 2.8 g.

$^1$H NMR (250 MHz, in $CDCl_3$): δ [ppm]=3.30 (s,3H), 3.91 (s,3H), 4.15 (s,3H), 7.29 (d,1H), 7.82 (d,1H), 8.95 (s,1H).

Example 7

2-Methoxyimino)ethyl N-methoxy-3-[2-chloro-5-(4-chloro-5-difluoromethoxy-1-methyl-1H-pyrazol-3-yl)-4-fluorophenyl]propiolimide (No. Ip.1094)

0.4 g (2.7 mmol) of potassium carbonate and 0.27 g (2.5 mmol) of O-methyl chloroacetaldehyde oxime were added to a solution of 1 g (2.3 mmol) of N-methoxy-2-chloro-3-[2-chloro-5-(4-chloro-5-difluoromethoxy-1-methyl-1H-pyrazol-3-yl)-4-fluorophenyl]acrylamide in 50 ml of acetone. After the mixture had been stirred for 3 days, it was concentrated. The residue was treated with 50 ml of dimethylformamide. The mixture was subsequently heated for 4 more hours at 100° C. and then reconcentrated. Then, the residue was treated with 20 ml of ethyl acetate. The resulting organic phase was washed with water, dried over magnesium sulfate and finally concentrated. The crude product was purified by means of silica gel chromatography (eluent:hexane/ethyl acetate=2:1). Yield: 0.2 g.

Example 8

Methyl N-methoxy-2,4-dichloro-5-(5-difluoromethoxy-4-fluoro-1-methyl-1H-pyrazol-3-yl)benzimidate (No. Ib.3)

Using 0.5 g (1.3 mmol) of N-methoxy-2,4-dichloro-5-(5-difluoromethoxy-4-fluoro-1-methyl-1H-pyrazol-3-yl) benzamide, 0.21 g (1.6 mmol) of potassium carbonate and 0.20 g (1.6 mmol) of dimethyl sulfate and following the procedure described in Example 1, 0.17 g of the desired produce of value was obtained.

Precursor 8.1

3-(2,4-Dichloro-5-methylphenyl)-5-difluoromethoxy-4-fluoro-1-methyl-1H-pyrazole 46.3 g (131 mmol) of Selectfluor™ were added to a solution of 40.2 g (131 mmol) of 3-(2,4-dichloro-5-methylphenyl)-5-difluoromethoxy-1-methyl-1H-pyrazole in 0.5 l of acetonitrile. After the mixture had been stirred for 12 hours at room temperature, it was heated for a further hour at reflux temperature. Thereafter, three batches of 6.9 g (20 mmol) of Selectfluor™ were added to the reaction mixture, a little at a time, and the mixture was heated in each case for one hour at reflux temperature. The resulting mixture was subsequently treated with 0.5 l of methyl tert-butyl ether. The organic phase was washed with water, saturated aqueous sodium hydrogen carbonate solution and again with water, then dried over magnesium sulfate and finally concentrated. The crude product was purified by means of silica gel chromatography (eluent:hexane/ethyl acetate=9:1). Yield: 20.3 g.

$^1$H NMR (400 MHz, in $CDCl_3$): δ [ppm]=2.36 (s,3H), 3.78 (s,3H), 6.66 (t,1H), 7.37 (s,1H), 7.46 (s,1H).

Precursor 8.2

2,4-Dichloro-5-(5-difluoromethoxy-4-fluoro-1-methyl-1H-pyrazol-3-yl)benzaldehyde A solution of 20.3 g (62 mmol) of 3-(2,4-dichloro-5-methylphenyl)-5-difluoromethoxy-4-fluoro-1-methyl-1H-pyrazole and 11.1 g (62 mmol) of N-bromosuccinimide in 0.27 l of tetrachloromethane was heated for two hours at reflux temperature while exposed to a UV lamp. Then, two portions of 2.2 g (12 mmol) of N-bromosuccinimide were added to the reaction mixture, a little at a time, whereupon in each case the mixture was heated to reflux temperature while being exposed again. The mixture was then allowed to cool, and the solids were filtered off. The filtrate was concentrated.

14.2 g (120 mmol) of N-methylmorpholin-N-oxide were subsequently added to the above substance, dissolved in 500 ml of acetonitrile. The mixture was stirred for 3 hours and then concentrated. The residue was treated with 500 ml of water and 500 ml of dichloromethane. To isolate the product, the organic phase was separated off, washed three times with water, then dried over magnesium sulfate and finally concentrated. The residue was purified by means of MPLC on silica gel (eluent:cyclohexane/ethyl acetate=9.1). Yield: 7.4 g.

$^1$H NMR (270 MHz, in $CDCl_3$): δ [ppm]=3.8 (s,3H), 6.67 (t,1H), 7.63 (s,1H), 8.09 (s,1H), 10.43 (s,1H).

Precursor 8.3

2,4-Dichloro-5-(5-difluoromethoxy-4-fluoro-1-methyl-1H-pyrazol-3-yl)benzoic acid First, a solution of 0.85 g (5.5 mmol) of sodium dihydrogen phosphate dihydrate in 10 ml of water and then 2.7 ml of a 30% strength aqueous hydrogen peroxide solution were added dropwise to a solution of 7.4 g (22 mmol) of 2,4-dichloro-5-(5-difluoromethoxy-4-fluoro-1-methyl-1H-pyrazol-3-yl)benzaldehyde in 200 ml of acetonitrile. A solution of 2.9 g (33 mmol) of sodium chloride in 25 ml of water was then added dropwise to the reaction mixture in the course of 20 minutes. After the solution had been stirred for one hour, the resulting mixture was acidified with dilute hydrochloric acid. Finally, the solid product of value which had formed was filtered off and dried. Yield: 6.3 g.

$^1$H NMR (250 MHz, in $CDCl_3$): δ [ppm]=3.83 (s,3H), 6.67 (t,1H), 7.64 (s,1H), 8.21 (s,1H).

Precursor 8.4

2,4-Dichloro-5-(5-fluoromethoxy-4-fluoro-1-methyl-1H-pyrazol-3-yl)benzoyl chloride 5.8 g (16 mmol) of 2,4-dichloro-5-(5-difluoromethoxy-4-fluoro-1-methyl-1H-pyrazol-3-yl)benzoic acid and 10.4 g (82 mmol) of oxalyl chloride were reacted in the manner described for Precursor 1.1. Yield: 5.2 g.

Precursor 8.5

N-methoxy-2,4-dichloro-5-(5-difluoromethoxy-4-fluoro-1-methyl-1H-pyrazol-3-yl)benzamide Using 5.2 g (14 mmol) of 2,4-dichloro-5-(5-difluoromethoxy-4-fluoro-1-methyl-1H-pyrazol-3-yl) benzoyl chloride, 19.2 g (0.14 mol) of potassium carbonate and 9.2 g (28 mmol) of a 25% strength aqueous methoxyamine hydrochloride solution and following the procedure described for Precursor 1.2, a crude product was obtained whose purification by means of silica gel chromatography (eluent:hexane/ethyl acetate=4:1) gave 1.5 g of the desired product of value.

$^1$H NMR (250 MHz, in $CDCl_3$): δ [ppm]=3.79 (s,3H), 3.90 (s,3H), 6.66 (t,1H), 7.55 (s,1H), 7.74 (s,1H), 9.00 (s,1H).

In addition to above-described active ingredients, Table 2 below lists further substituted 3-phenylpyrazoles I which were, or can be, prepared by a method similar to the one described above:

TABLE 2

I

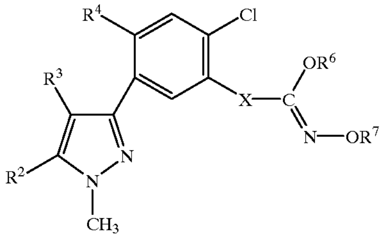

{$R^1$ = $CH_3$, $R^5$ = Cl, Y = O}

| No. | $R^2$ | $R^3$ | $R^4$ | $R^6$ | $R^7$ | X | M.p./$^1$H NMR [ppm]/MS [m/z] |
|---|---|---|---|---|---|---|---|
| Ia.2 | $OCHF_2$ | Cl | F | $CH_3$ | $CH_3$ | Bond | 107–108° C. |
| Ia.3 | $OCHF_2$ | Cl | Cl | $CH_3$ | $CH_3$ | Bond | 3.74(s, 3H), 3.85(s, 3H), 3.90(s, 3H), 6.71(t, 1H), 7.53(s, 1H), 7.62(s, 1H) |
| Ia.5 | $OCHF_2$ | Cl | F | $C_2H_5$ | $CH_3$ | Bond | 1.34(t, 3H), 3.84(s, 3H), 3.90(s, 3H), 3.96(q, 2H), 6.70(t, 1H), 7.30(d, 1H), 7.68(d, 1H) |
| Ia.32 | $OCHF_2$ | Cl | F | $CH_3$ | $C_2H_5$ | Bond | 96–97° C. |
| Ia.35 | $OCHF_2$ | Cl | F | $C_2H_5$ | $C_2H_5$ | Bond | 87–88° C. |
| Ia.446 | $OCHF_2$ | Cl | F | $CH_2—CH_2—OCH_3$ | $CH_3$ | Bond | 3.35(s, 3H), 3.65(t, 2H), 3.84(s, 3H), 3.89(s, 3H), 4.11(t, 2H), 6.72(t, 1H), 7.29(d, 1H), 7.72(d, 1H) |
| Ia.461 | $OCHF_2$ | Cl | F | $CH_2—CH_2—OCH_3$ | $CH_2—C≡CH$ | Bond | 2.47(s, 1H), 3.38(s, 3H), 3.64(t, 2H), 3.83(s, 3H), 4.65(s, 2H), 4.13(t, 2H), 4.68(d, 2H), 6.69(t, 1H), 7.29(d, 1H), 7.72(d, 1H) |
| Ia.590 | $OCHF_2$ | Cl | F | $CH_2—CH=CH_2$ | $CH_3$ | Bond | 54–56° C. |
| Ia.593 | $OCHF_2$ | Cl | F | $CH_2—CH=CH_2$ | $C_2H_5$ | Bond | 1.32(t, 3H), 3.85(s, 3H), 4.15(q, 2H), 4.49(d, 2H), 5.12(d, 1H), 5.29(d, 1H), 5.92(m, 1H), 6.72(t, 1H), 7.30(d, 1H), 7.68(d, 1H) |
| Ia.602 | $OCHF_2$ | Cl | F | $CH_2—CH=CH_2$ | $CH_2—CH=CH_2$ | Bond | 75–77° C. |
| Ia.686 | $OCHF_2$ | Cl | F | $CO—CH_3$ | $CH_3$ | Bond | 2.27(s, 3H), 3.85(s, 3H), 3.99(s, 3H), 6.70(t, 1H), 7.28(d, 1H), 7.85(d, 1H) |
| Ia.689 | $OCHF_2$ | Cl | F | $CO—CH_3$ | $C_2H_5$ | Bond | 1.32(t, 3H), 2.28(s, 3H), 3.85(s, 3H), 4.23(q, 2H), 6.72(t, 1H), 7.28(d, 1H), 7.85(d, 1H) |
| Ia.698 | $OCHF_2$ | Cl | F | $CO—CH_3$ | $CH_2—CH=CH_2$ | Bond | 2.28(s, 3H), 3.84(s, 3H), 4.68(d, 2H), |

TABLE 2-continued

I

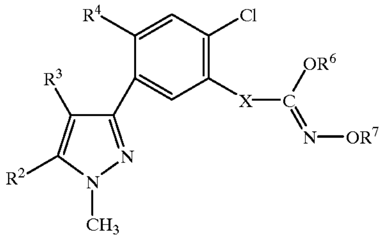

{$R^1 = CH_3$, $R^5 = Cl$, Y = O}

| No. | $R^2$ | $R^3$ | $R^4$ | $R^6$ | $R^7$ | X | M.p./$^1$H NMR [ppm]/MS [m/z] |
|---|---|---|---|---|---|---|---|
| | | | | | | | 5.25(dd, 1H), 5.34(dd, 1H), 6.01(m, 1H), 6.71(t, 1H), 7.28(d, 1H), 7.85(d, 1H) |
| Ia.782 | $OCHF_2$ | Cl | F | $CO—OCH_3$ | $CH_3$ | Bond | 3.84(s, 3H), 3.89(s, 3H), 4.01(s, 3H), 6.70(t, 1H), 7.29(d, 1H), 7.85(d, 1H) |
| Ia.830 | $OCHF_2$ | Cl | F | $CO—N(CH_3)_2$ | $CH_3$ | Bond | 2.93(s, 3H), 3.08(s, 3H), 3.81(s, 3H), 3.97(s, 3H), 6.72(t, 1H), 7.28(d, 1H), 7.90(d, 1H) |
| Ia.1001 | $OCHF_2$ | Cl | F | $CH_2$—CO-cyclopropyl | $C_2H_5$ | Bond | 0.95(m, 2H), 1.10(m, 2H), 1.32(t, 3H), 2.09(m, 1H), 3.84(s, 3H), 4.15(q, 2H), 4.75(s, 2H), 6.71(t, 1H), 7.29(d, 1H), 7.72(d, 1H) |
| Ia.1094 | $OCHF_2$ | Cl | F | $CH_2—CH{=}N—OCH_3$ | $CH_3$ | Bond | 3.83(m, 6H), 3.92(m, 3H), 4.62 and 4.78(2d, together 2H), 6.73(t, 1H), 6.97 and 7.49(2t, together 1H), 7.32(d, 1H), 7.71(d, 1H) |
| Ia.1097 | $OCHF_2$ | Cl | F | $CH_2—CH{=}N—OCH_3$ | $C_2H_5$ | Bond | 1.33(t, 3H), 3.84(m, 6H), 4.14(q, 2H), 4.63 and 4.80(2d, together 2H), 6.71(t, 1H), 698 and 7.50(2t, together 1H), 7.30(d, 1H), 7.69(d, 1H) |
| Ia.1214 | $OCHF_2$ | Cl | F | $CH_2—C({=}N—OCH_3)—CO—OCH_3$ | $CH_3$ | Bond | 3.85(s, 3H), 3.87(s, 3H), 3.89(s, 3H), 4.09(s, 3H), 4.92(s, 2H), 6.72(t, 1H), 7.30(d, 1H), 7.73(d, 1H) |
| Ia.1217 | $OCHF_2$ | Cl | F | $CH_2—C({=}N—OCH_3)—CO—OCH_3$ | $C_2H_5$ | Bond | 1.30(t, 3H), 3.85(s, 3H), 3.87(s, 3H), 4.06(s, 3H), 4.12(q, 2H), 4.95(s, 2H), 6.72(t, 1H), 7.29(d, 1H), 7.72(d, 1H) |
| Ia.1238 | $OCHF_2$ | Cl | F | $CH_2—COOH$ | $CH_3$ | Bond | 3.74(s, 3H), 3.85(s, 3H), 4.83(s, 2H), 6.70(t, 1H), 7.29(d, 1H), 7.73(d, 1H) |
| Ia.1310 | $OCHF_2$ | Cl | F | $CH_2—CO—OCH_3$ | $CH_3$ | Bond | 3.74(s, 3H), 3.85(s, 3H), 3.91(s, 3H), 4.63(s, 2H), 6.70(t, 1H), 7.29(d, 1H), 7.73(d, 1H) |
| Ia.1313 | $OCHF_2$ | Cl | F | $CH_2—CO—OCH_3$ | $C_2H_5$ | Bond | 98–100° C. |
| Ia.1322 | $OCHF_2$ | Cl | F | $CH_2—CO—OCH_3$ | $CH_2—CH{=}CH_2$ | Bond | 3.72(s, 3H), 3.84(s, 3H), 4.60(d, 2H), 4.68(s, 2H), 5.26(dd, 1H), 5.35(dd, 1H), 6.04(m, 1H), 6.71(t, 1H), 7.29(d, 1H), 7.74(d, 1H) |
| Ia.1325 | $OCHF_2$ | Cl | F | $CH_2—CO—OCH_3$ | $CH_2—C{\equiv}CH$ | Bond | 2.49(t, 1H), 3.75(s, 3H), 3.83(s, 3H), 4.65(s, 2H), 4.69(d, 2H), 6.70(t, 1H), 7.29(d, 1H), 7.76(d, 1H) |
| Ia.1331 | $OCHF_2$ | Cl | F | $CH_2—CO—OCH_3$ | $CH_2$-phenyl | Bond | 3.63(s, 3H), 3.81(s, 3H), 4.67(d, 2H), 5.11(s, 2H), 6.69(t, 1H), 7.20–7.45(m, 6H), 7.72(d, 1H) |
| Ia.1334 | $OCHF_2$ | Cl | F | $CH(CH_3)—CO—OCH_3$ | $CH_3$ | Bond | 1.61(d, 3H), 3.73(s, 3H), 3.85(s, 3H), 3.88(s, 3H), 4.77(q, 1H), 6.79(t, 1H), 7.30(d, 1H), 7.73(d, 1H) |
| Ia.1358 | $OCHF_2$ | Cl | F | $CH(C_2H_5)—CO—OCH_3$ | $CH_3$ | Bond | 1.08(t, 3H), 1.95(quint., 2H), 3.72(s, 3H), 3.84(s, 3H), 3.89(s, 3H), 4.63(t, 1H), 6.72(t, 1H), 7.28(d, 1H), 7.70(d, 1H) |
| Ia.1382 | $OCHF_2$ | Cl | F | $CH_2—CO—OC_2H_5$ | $CH_3$ | Bond | 1.28(t, 3H), 3.84(s, 3H), 3.92(s, 3H), 4.19(q, 2H), 4.60(s, 2H), 6.70(t, 1H), 7.9(d, 1H), 7.73(d, 1H) |
| Ia.1454 | $OCHF_2$ | Cl | F | $CH_2—CO—OC(CH_3)_3$ | $CH_3$ | Bond | 1.41(s, 9H), 3.83(s, 3H), 3.92(s, 3H), 4.45(s, 2H), 6.69(t, 1H), 7.29(d, 1H), 7.75(d, 1H) |
| Ia.1694 | $OCHF_2$ | Cl | F | $CH_2—CO—N(CH_3)_2$ | $CH_3$ | Bond | 468$[M]^+$, 424$[M—N(CH_3)_2]^+$ |
| Ia.1877 | $OCHF_2$ | Cl | F | $CH_2$-phenyl | $CH_2—C{\equiv}CH$ | Bond | 2.48(t, 1H), 3.81(s, 3H), 4.68(d, 2H), 5.03(s, 2H), 6.69(t, 1H), 7.20–7.35(m, 6H), 7.52(d, 1H) |
| Ia.1883 | $OCHF_2$ | Cl | F | $CH_2$-phenyl | $CH_2$-phenyl | Bond | 3.82(s, 3H), 5.05(s, 2H), 5.14(s, 2H), 6.69(t, 1H), 7.20–7.50(m, 12H) |
| Ia.2270 | $OCHF_2$ | Cl | F | $CH_3$ | $CH_2—CH{=}CH_2$ | Bond | 88–89° C. |
| Ia.2330 | $OCHF_2$ | Cl | F | $CH_3$ | $CH_2—C{\equiv}CH$ | Bond | 2.49(t, 1H), 3.74(s, 3H), 3.84(s, 3H), |

TABLE 2-continued

I

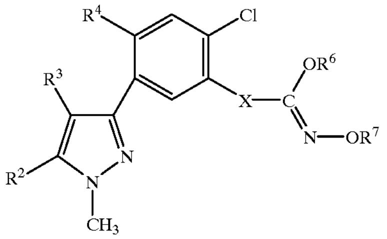

{$R^1 = CH_3$, $R^5 = Cl$, Y = O}

| No. | $R^2$ | $R^3$ | $R^4$ | $R^6$ | $R^7$ | X | M.p./$^1$H NMR [ppm]/MS [m/z] |
|---|---|---|---|---|---|---|---|
| | | | | | | | 4.68(d, 2H), 6.71(t, 1H), 7.32(d, 1H), 7.68(d, 1H) |
| Ia.2534 | $OCHF_2$ | Cl | F | $CH_3$ | $CH_2$—CO—$OCH_3$ | Bond | 455[M]$^+$ |
| Ia.2666 | $OCHF_2$ | Cl | F | $CH_3$ | $CH_2$—CO—$OC(CH_3)_3$ | Bond | 1.48(s, 9H), 3.78(s, 3H), 3.84(s, 3H), 4.51(s, 2H), 6.70(t, 1H), 7.31(d, 1H), 7.68(d, 1H) |
| Ia.2954 | $OCHF_2$ | Cl | F | $CH_3$ | $CH_2$-phenyl | Bond | 3.74(s, 3H), 3.84(s, 3H), 4.12(s, 2H), 6.70(t, 1H), 7.25–7.45(m, 6H), 7.66(d, 1H) |
| Ib.3 | $OCHF_2$ | F | Cl | $CH_3$ | $CH_3$ | Bond | 3.73(s, 3H), 3.79(s, 3H), 3.89(s, 3H), 6.67(t, 1H), 7.60(s, 1H), 7.63(s, 1H) |
| Ib.1311 | $OCHF_2$ | F | Cl | $CH_2$—CO—$OCH_3$ | $CH_3$ | Bond | 3.75(s, 3H), 3.79(s, 3H), 3.91(s, 3H), 4.63(s, 2H), 6.67(t, 1H), 7.56(s, 1H), 7.67(s, 1H) |
| Ic.2 | $CF_3$ | Cl | F | $CH_3$ | $CH_3$ | Bond | 3.84(s, 3H), 3.91(s, 3H), 4.08(s, 3H), 7.34(d, 1H), 7.65(d, 1H) |
| Ic.5 | $CF_3$ | Cl | F | $C_2H_5$ | $CH_3$ | Bond | 1.34(t, 3H), 3.90(s, 3H), 3.99(q, 2H), 4.06(s, 3H), 7.32(d, 1H), 7.64(d, 1H) |
| Ic.590 | $CF_3$ | Cl | F | $CH_2$—CH=$CH_2$ | $CH_3$ | Bond | 3.91(s, 3H), 4.08(s, 3H), 4.47(d, 2H), 5.23(dd, 1H), 5.29(dd, 1H), 5.90(m, 1H), 7.31(d, 1H), 7.63(d, 1H) |
| Ic.686 | $CF_3$ | Cl | F | CO—$CH_3$ | $CH_3$ | Bond | 2.27(s, 3H), 3.98(s, 3H), 4.07(s, 3H), 7.29(d, 1H), 3.82(d, 1H) |
| Ic.1310 | $CF_3$ | Cl | F | $CH_2$—CO—$OCH_3$ | $CH_3$ | Bond | 3.84(s, 3H), 3.91(s, 3H), 4.07(s, 3H), 4.66(s, 2H), 7.30(d, 1H), 7.72(d, 1H) |
| Ie.2 | $SO_2$—$CH_3$ | Cl | F | $CH_3$ | $CH_3$ | Bond | 3.32(s, 3H), 3.75(s, 3H), 390(s, 3H), 4.16(s, 2H), 7.37(d, 1H), 7.68(d, 1H) |
| Ie.662 | $SO_2$—$CH_3$ | Cl | F | $CH_2$—C≡CH | $CH_3$ | Bond | 2.54(t, 1H), 3.30(s, 3H), 3.91(s, 3H), 4.15(s, 3H), 4.71(d, 2H), 7.34(d, 1H), 7.73(d, 1H) |
| Ie.1310 | $SO_2$—$CH_3$ | Cl | F | $CH_2$—CO—$OCH_3$ | $CH_3$ | Bond | 3.32(s, 3H), 3.74(s, 3H), 3.92(s, 3H), 4.15(s, 3H), 4.66(s, 2H), 7.32(d, 1H), 7.73(d, 1H) |
| Ig.2 | $OCHF_2$ | Cl | F | $CH_3$ | $CH_3$ | —CH=C(Cl)— | 3.85(s, 3H), 3.96(s, 3H), 4.00(s, 3H), 6.72(t, 1H), 7.30(d, 1H), 7.44(s, 1H), 8.12(d, 1H) |
| Ig.5 | $OCHF_2$ | Cl | F | $C_2H_5$ | $CH_3$ | —CH=C(Cl)— | 1.42(t, 3H), 3.85(s, 3H), 3.95(s, 3H), 4.33(q, 2H), 6.72(t, 1H), 7.29(d, 1H), 7.49(s, 1H), 8.11(d, 1H) |
| Ig.590 | $OCHF_2$ | Cl | F | $CH_2$—CH=$CH_2$ | $CH_3$ | —CH=C(Cl)— | 3.86(s, 3H), 3.97(s, 3H), 4.75(d, 2H), 5.31(d, 1H), 5.40(d, 1H), 6.05(m, 1H), 6.71(t, 1H), 7.30(d, 1H), 7.51(s, 1H), 8.12(d, 1H) |
| Ig.686 | $OCHF_2$ | Cl | F | CO—$CH_3$ | $CH_3$ | —CH=C(Cl)— | 2.34(s, 3H), 3.84(s, 3H), 4.00(s, 3H), 6.72(t, 1H), 7.29(d, 1H), 7.37(s, 1H), 8.15(d, 1H) |
| Ig.998 | $OCHF_2$ | Cl | F | $CH_2$—CO-cyclopropyl | $CH_3$ | —CH=C(Cl)— | 1.00(m, 2H), 1.16(m, 2H), 2.15(m, 1H), 3.84(s, 3H), 3.92(s, 3H), 4.98(s, 2H), 6.72(t, 1H), 7.28(d, 1H), 7.63(s, 1H), 8.11(d, 1H) |
| Ig.1310 | $OCHF_2$ | Cl | F | $CH_2$—CO—$OCH_3$ | $CH_3$ | —CH=C(Cl)— | 105–107° C. |
| Ik.1310 | $CF_3$ | Cl | F | $CH_2$—CO—$OCH_3$ | $CH_3$ | —CH=C(Cl)— | 3.82(s, 3H), 3.95(s, 3H), 4.08(s, 3H), 4.90(s, 2H), 7.32(d, 1H), 7.72(s, 1H), 8.09(d, 1H) |
| Ip.1094 | $OCHF_2$ | Cl | F | $CH_2$—CH=N—$OCH_3$ | $CH_3$ | —C≡C— | 3.80–3.95(m, 9H), 4.93 and 5.15(2d, together 2H), 6.72(t, 1H), 6.96 and 7.55(2t, together 1H), 7.31(d, 1H), 7.70 and 7.74(2d, together 1H) |

Use Examples

The herbicidal activity of the substituted 3-phenylpyrazoles I was demonstrated by the following greenhouse experiments:

The culture containers used were plastic flowerpots containing loamy sand with approximately 3.0% of humus as substrate. The seeds of the test plant were sown separately for each species.

For the pre-emergence treatment, the active ingredients, suspended or emulsified in water, were applied directly after sowing by means of finely distributing nozzles. The contains were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were grown to a plant height of from 3 to 15 cm, depending on the plant habit, and only then treated with the active ingredient which had been suspended or emulsified in water. To this end, the test plants were either sown directly and grown in the same containers, or they were first grown separately as seedlings and transplanted into the test containers a few days prior to treatment. The rate of application for the post-emergence treatment was 3.9 or 1.9 g/ha of a.s. (active substance).

Depending on the species, the plants were kept at from 10 to 25° C., or 20–35° C., respectively. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage, or normal course of growth.

The plants used in the greenhouse experiments belonged to the following species:

| Scientific name | Common name |
|---|---|
| *Abutilon theophrasti* | velvet leaf |
| *Amaranthus retroflexus* | redroot pigweed |
| *Galium aparine* | catchweed bedstraw |
| *Sinapis alba* | white mustard |
| *Solanum nigrum* | black nightshade |

At application rates of 3.9 and 1.9 g of a.s./ha post-emergence, the compounds No. Ig.1310 and Ik.1310 showed a very good herbicidal activity against the abovementioned broad-leaved plants.

We claim:

1. A 3-phenylpyrazole of formula I

I

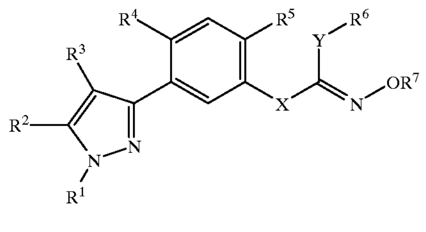

in which the variables have the following meanings:

$R^1$ is $C_1$–$C_4$-alkyl or $C_1$–$C_4$-haloalkyl;

$R^2$ is cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl, or $C_1$–$C_4$-haloalkylsulfonyl;

$R^3$ is hydrogen, cyano, halogen, $C_1$–$C_4$-alkyl or $C_1$–$C_4$-haloalkyl;

$R^4$ is hydrogen or halogen;

$R^5$ is cyano, halogen, $C_1$–$C_4$-alkyl, $C_1$–$C_4$-haloalkyl, $C_1$–$C_4$-alkoxy or $C_1$–$C_4$-haloalkoxy;

$R^6$, $R^7$ independently of one another are $C_1$–$C_6$-alkyl, $C_1$–$C_6$-haloalkyl, hydroxy-$C_1$–$C_4$-alkyl, cyano-$C_1$–$C_4$-alkyl, $C_1$–$C_4$-alkoxy-$C_1$–$C_4$-alkyl, $C_1$–$C_4$-haloalkoxy-$C_1$–$C_4$-alkyl, $C_3$–$C_4$-alkenyloxy-$C_1$–$C_4$-alkyl, $C_3$–$C_4$-alkynyloxy-$C_1$–$C_4$-alkyl, $C_3$–$C_8$-cycloalkoxy-$C_1$–$C_4$-alkyl, amino-$C_1$–$C_4$-alkyl, $C_1$–$C_4$-alkylamino-$C_1$–$C_4$-alkyl, di($C_1$–$C_4$-alkyl)amino-$C_1$–$C_4$-alkyl, $C_1$–$C_4$-alkylthio-$C_1$–$C_4$-alkyl, $C_1$–$C_4$-haloalkylthio-$C_1$–$C_4$-alkyl, $C_3$–$C_4$-alkenylthio-$C_1$–$C_4$-alkyl, $C_3$–$C_4$-alkynylthio-$C_1$–$C_4$-alkyl, $C_1$–$C_4$-alkylsulfinyl-$C_1$–$C_4$-alkyl, $C_1$–$C_4$-haloalkylsulfinyl-$C_1$–$C_4$-alkyl, $C_3$–$C_4$-alkenylsulfinyl-$C_1$–$C_4$-alkyl, $C_3$–$C_4$-alkynylsulfinyl-$C_1$–$C_4$-alkyl, $C_1$–$C_4$-alkylsulfonyl-$C_1$–$C_4$-alkyl, $C_1$–$C_4$-haloalkylsulfonyl-$C_1$–$C_4$-alkyl, $C_3$–$C_4$-alkenylsulfonyl-$C_1$–$C_4$-alkyl, $C_3$–$C_4$-alkynylsulfonyl-$C_1$–$C_4$-alkyl, $C_3$–$C_6$-alkenyl, cyano-$C_3$–$C_6$-alkenyl, $C_3$–$C_6$-haloalkenyl, $C_3$–$C_6$-alkynyl, cyano-$C_3$–$C_6$-alkynyl, $C_3$-$C_6$-haloalkynyl, ($C_1$–$C_4$-alkyl)carbonyl, ($C_1$–$C_4$-haloalkyl)carbonyl, ($C_1$–$C_4$-alkoxy)carbonyl, aminocarbonyl, ($C_1$–$C_4$-alkyl)aminocarbonyl, di($C_1$–$C_4$-alkyl)aminocarbonyl, ($C_1$–$C_4$-alkoxy-$C_1$–$C_4$-alkyl)carbonyl, $C_1$–$C_4$-alkylsulfonyl, $C_1$–$C_4$-haloalkylsulfonyl, ($C_1$–$C_4$-alkyl)carbonyl-$C_1$–$C_4$-alkyl, ($C_1$–$C_4$-haloalkyl)carbonyl-$C_1$–$C_4$-alkyl, ($C_3$–$C_8$-cycloalkyl)carbonyl-$C_1$–$C_4$-alkyl, ($C_1$–$C_4$-alkoxy)imino-$C_1$–$C_4$-alkyl, ($C_3$–$C_4$-alkenyloxy)imino-$C_1$–$C_4$-alkyl, hydroxycarbonyl-$C_1$–$C_4$-alkyl, ($C_1$–$C_4$-alkoxy)carbonyl-$C_1$–$C_4$-alkyl which is unsubstituted or substituted by a ($C_1$–$C_4$-alkoxy)imino group, ($C_1$–$C_4$-haloalkoxy)carbonyl-$C_1$–$C_4$-alkyl, ($C_1$–$C_4$-alkylthio)carbonyl-$C_1$–$C_4$-alkyl, aminocarbonyl-$C_1$–$C_4$-alkyl, ($C_1$–$C_4$-alkylamino)carbonyl-$C_1$–$C_4$-alkyl, di($C_1$–$C_4$-alkylamino)carbonyl-$C_1$–$C_4$-alkyl, $C_3$–$C_8$-cycloalkyl, $C_3$–$C_8$-cycloalkyl-$C_1$–$C_4$-alkyl, phenyl, phenyl-$C_1$–$C_4$-alkyl or 3- or 7-membered heterocyclyl or heterocyclyl-$C_1$–$C_4$-alkyl, wherein one of the ring members of the cycloalkyl rings and heterocycles optionally is a carbonyl or thiocarbonyl ring member; and wherein the cycloalkyl, phenyl and heterocyclyl rings are unsubstituted or carry from one to four substituents selected from the group consisting of: cyano, nitro, amino, hydroxyl, carboxyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, ($C_1$–$C_4$-alkoxy)carbonyl, ($C_1$–$C_4$-alkyl)carbonyl, ($C_1$–$C_4$-haloalkyl)carbonyl, ($C_1$–$C_4$-alkyl)carbonyloxy, ($C_1$–$C_4$-haloalkyl)carbonyloxy and di($C_1$–$C_4$-alkyl)amino;

X is a chemical bond, a 1,2-ethynediyl group or a group *—$CH_2$—$CH(R^8)$— or *—CH═$C(R^8)$— which is bonded to the phenyl ring via the bond characterized with an asterisk, and wherein $R^8$ is hydrogen, cyano, nitro, halogen, $C_1$–$C_4$-alkyl or $C_1$–$C_4$-haloalkyl;

Y is oxygen or sulfur;

or an agriculturally useful salt thereof.

2. The 3-phenylpyrazole defined in claim 1, or its agriculturally useful salt, wherein $R^1$ is $C_1$–$C_4$-alkyl.

3. The 3-phenylpyrazole defined in claim 1, or its agriculturally useful salt, wherein $R^1$ is methyl.

4. The 3-phenylpyrazole defined in claim 1, or its agriculturally useful salt, wherein $R^2$ is trifluoromethyl, difluoromethoxy or methylsulfonyl.

5. The 3-phenylpyrazole defined in claim 1, or its agriculturally useful salt, wherein $R^2$ is difluoromethoxy.

6. The 3-phenylpyrazole defined in claim 1, or its agriculturally useful salt, wherein $R^3$ is cyano or halogen.

7. The 3-phenylpyrazole defined in claim 1, or its agriculturally useful salt, wherein $R^3$ is chlorine.

8. The 3-phenylpyrazole defined in claim 1, or its agriculturally useful salt, wherein $R^4$ is fluorine or chlorine.

9. The 3-phenylpyrazole defined in claim 1, or its agriculturally useful salt, wherein $R^5$ is chlorine.

10. The 3-phenylpyrazole defined in claim 1, or its agriculturally useful salt, wherein $R^6$ is $C_1$–$C_6$-alkyl, $C_1$–$C_6$-haloalkyl, cyano-$C_1$–$C_4$-alkyl, $C_1$–$C_4$-alkoxy-$C_1$–$C_4$-alkyl, $C_1$–$C_4$-alkylthio-$C_1$–$C_4$-alkyl, $C_1$–$C_4$-alkylsulfonyl-$C_1$–$C_4$-alkyl, $C_3$–$C_6$-alkenyl, $C_3$–$C_6$-haloalkenyl, $C_3$–$C_6$-alkynyl, ($C_1$–$C_4$-alkyl)carbonyl, ($C_1$–$C_4$-haloalkyl)carbonyl, ($C_1$–$C_4$-alkoxy)carbonyl, di($C_1$–$C_4$-alkyl)aminocarbonyl, ($C_1$–$C_4$-alkyl)carbonyl-$C_1$–$C_4$-alkyl, ($C_3$–$C_8$-cycloalkyl)carbonyl-$C_1$–$C_4$-alkyl, ($C_1$–$C_4$-alkoxy)imino-$C_1$–$C_4$-alkyl, hydroxycarbonyl-$C_1$–$C_4$-alkyl, ($C_1$–$C_4$-alkoxy)carbonyl-$C_1$–$C_4$-alkyl which is unsubstituted or substituted by a ($C_1$–$C_4$-alkoxy)imino group, di($C_1$–$C_4$-alkyl)aminocarbonyl-$C_1$–$C_4$-alkyl, $C_3$–$C_8$-cycloalkyl, $C_3$–$C_8$-cycloalkyl-$C_1$–$C_4$-alkyl or phenyl-$C_1$–$C_4$-alkyl.

11. The 3-phenylpyrazole defined in claim 1, or its agriculturally useful salt, wherein $R^6$ is a $C_1$–$C_6$-alkyl, $C_3$–$C_6$-alkenyl, $C_3$–$C_6$-alkynyl, ($C_1$–$C_4$-alkyl)carbonyl, ($C_1$–$C_4$-alkoxy)carbonyl, di($C_1$–$C_4$-alkyl)aminocarbonyl, ($C_1$–$C_4$-alkoxy)carbonyl-$C_1$–$C_4$-alkyl or di($C_1$–$C_4$-alkyl)aminocarbonyl-$C_1$–$C_4$-alkyl.

12. The 3-phenylpyrazole defined in claim 1, or its agriculturally useful salt, wherein $R^7$ is $C_1$–$C_6$-alkyl, $C_3$–$C_6$-alkenyl, $C_3$–$C_6$-alkynyl, ($C_1$–$C_4$-alkoxy)carbonyl-$C_1$–$C_4$-alkyl or phenyl-$C_1$–$C_4$-alkyl.

13. The 3-phenylpyrazole defined in claim 1, or its agriculturally useful salt, wherein X is a chemical bond, a 1,2-ethynediyl group or a group *—CH=C($R^8$)—, wherein $R^8$ is hydrogen, cyano, chlorine, bromine or methyl.

14. The 3-phenylpyrazole defined in claim 13, or its agriculturally useful salt, wherein $R^8$ is chlorine.

15. The 3-phenylpyrazole defined in claim 1, or its agriculturally useful salt, wherein X is a chemical bond.

16. The 3-phenylpyrazole defined in claim 1, or its agriculturally useful salt, wherein Y is oxygen.

17. A herbicidal composition comprising a herbicidally active amount of at least one 3-phenylpyrazole as defined in claim 1 or of an agriculturally useful salt thereof and at least one liquid or solid carrier.

18. The composition defined in claim 17, further comprising at least one surfactant.

19. A process for the preparation of the 3-phenylpyrazole defined in claim 1, which comprises reacting an alkoxyamide of formula III

III

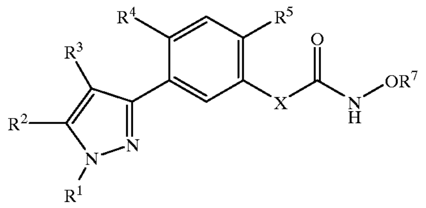

with an alkylating or acrylating agent L-$R^6$, wherein L is a leaving group, in the presence of a base.

20. A method of controlling undesirable vegetation, which comprises treating plants, their environment or seeds with a herbicidically active amount of at least one 3-phenylpyrazole as defined in claim 1 or of an agriculturally useful salt thereof.

* * * * *